US012403200B2

(12) United States Patent
Gillard et al.

(10) Patent No.: US 12,403,200 B2
(45) Date of Patent: *Sep. 2, 2025

(54) METHODS AND COMPOSITIONS FOR TREATING AUTOIMMUNE DISEASES

(71) Applicant: Vor Biopharma Inc., Cambridge, MA (US)

(72) Inventors: Geoffrey O. Gillard, Harvard, MA (US); Jennifer Lynn Proctor, Medford, MA (US); Anthony Boitano, Newton, MA (US); Michael Cooke, Boston, MA (US)

(73) Assignee: Vor Biopharma Inc., Cambridge, MA (US)

( * ) Notice: Subject to any disclaimer, the term of this patent is extended or adjusted under 35 U.S.C. 154(b) by 695 days.

This patent is subject to a terminal disclaimer.

(21) Appl. No.: 17/457,583

(22) Filed: Dec. 3, 2021

(65) Prior Publication Data

US 2022/0273811 A1 Sep. 1, 2022

Related U.S. Application Data

(63) Continuation of application No. PCT/US2020/036177, filed on Jun. 4, 2020.

(60) Provisional application No. 63/030,860, filed on May 27, 2020, provisional application No. 62/968,870, filed on Jan. 31, 2020, provisional application No. 62/944,988, filed on Dec. 6, 2019, provisional application No. 62/933,279, filed on Nov. 8, 2019, provisional application No. 62/882,310, filed on Aug. 2, 2019, provisional application No. 62/863,141, filed on Jun. 18, 2019, provisional application No. 62/857,232, filed on Jun. 4, 2019.

(51) Int. Cl.

| | |
|---|---|
| *A61K 47/68* | (2017.01) |
| *A61K 35/28* | (2015.01) |
| *A61P 37/06* | (2006.01) |

(52) U.S. Cl.

CPC .......... *A61K 47/6831* (2017.08); *A61K 35/28* (2013.01); *A61K 47/68035* (2023.08); *A61K 47/6817* (2017.08); *A61K 47/6819* (2017.08); *A61K 47/6829* (2017.08); *A61K 47/6849* (2017.08); *A61P 37/06* (2018.01)

(58) Field of Classification Search

None

See application file for complete search history.

(56) References Cited

U.S. PATENT DOCUMENTS

| | | | |
|---|---|---|---|
| 2003/0232009 | A1 | 12/2003 | Babcook et al. |
| 2017/0226209 | A1 | 8/2017 | Guillonneau et al. |
| 2019/0153114 | A1 | 5/2019 | Pearse et al. |

FOREIGN PATENT DOCUMENTS

| | | | | |
|---|---|---|---|---|
| WO | WO-2016164502 A1 | 10/2016 | | |
| WO | WO-2017219025 A1 | * 12/2017 | ......... A61K 31/4745 | |
| WO | WO-2018116178 A1 | 6/2018 | | |

OTHER PUBLICATIONS

Martires K. et al., Sclerotic-type chronic GVHD of the skin: clinical risk factors, laboratory markers, and burden of disease, blood, vol. 118, pp. 4250-4257, published on Sep. 3, 2012.

Zanotti G, et al., Synthesis of analogues of amaninamide, an amatoxin from the white Amanita virosa mushroom. Int J Pept Protein Res. Oct. 1987;30(4):450-9.

* cited by examiner

*Primary Examiner* — Brian Gangle

(74) *Attorney, Agent, or Firm* — Womble Bond Dickinson (US) LLP; Cristin Howley Cowles; Colleen McKiernan

(57) ABSTRACT

Disclosed are methods and compositions relating to the treatment of autoimmune diseases using anti-CD45 antibody drug conjugates (ADCs).

24 Claims, 51 Drawing Sheets

Specification includes a Sequence Listing.

SEQUENCE LISTING

```
<160> NUMBER OF SEQ ID NOS: 39

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Asp Arg Val Gln Pro Gly Arg
1               5                   10                  15

Ser Leu Thr Leu Ser Cys Val Thr Ser Gly Phe Thr Phe Asn Asn Tyr
            20                  25                  30

Trp Met Thr Trp Ile Arg Gln Val Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Thr Tyr Tyr Cys
                85                  90                  95

Ala Arg Asp Glu Arg Trp Ala Gly Ala Met Asp Ala Trp Gly Gln Gly
            100                 105                 110

Thr Ser Val Thr Val Ser Ser
        115


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Asn Asn Tyr Trp Met Thr
1               5


<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Ser Ser Ser Gly Gly Ser Ile Tyr Tyr Pro Asp Ser Val Lys
1               5                   10                  15

Gly
```

```
<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Arg Asp Glu Arg Trp Ala Gly Ala Met Asp Ala
1               5                   10


<210> SEQ ID NO 5
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Ile
        35                  40                  45

Tyr Glu Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln His Asn Ser Arg Phe Thr
                85                  90                  95

Phe Gly Ser Gly Thr Lys Leu Glu Ile Lys
            100                 105


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Gln Asn Ile Asn Lys Asn Leu Asp
1               5                   10


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Thr Asn Asn Leu Gln Thr
1               5


<210> SEQ ID NO 8
<211> LENGTH: 8
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 8

Tyr Gln His Asn Ser Arg Phe Thr
1 5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Glu Val Gln Leu Val Glu Ser Gly Gly Asp Leu Val Gln Pro Gly Arg
1 5 10 15

Ser Leu Lys Leu Ser Cys Ile Ala Ser Gly Phe Thr Phe Thr Asn Phe
20 25 30

Trp Met Thr Trp Ile Arg Gln Val Ser Gly Lys Gly Leu Glu Trp Val
35 40 45

Ala Ser Ile Ser Ser Ser Gly Gly Ser Ile Tyr Tyr Pro Asp Ser Val
50 55 60

Lys Asp Arg Phe Thr Ile Ser Arg Asp Asn Ala Lys Asn Thr Leu Tyr
65 70 75 80

Leu Gln Met Asn Ser Leu Arg Ser Glu Asp Thr Ala Thr Tyr Tyr Cys
85 90 95

Val Lys Leu His Tyr Tyr Ser Gly Gly Gly Asp Ala Trp Gly Gln Gly
100 105 110

Thr Ser Val Thr Val Ser Ser
115

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Phe Thr Phe Thr Asn Phe Trp Met Thr
1 5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Ile Ser Ser Ser Gly Gly Ser Ile Tyr Tyr Pro Asp Ser Val Lys
1 5 10 15

Asp

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Lys Leu His Tyr Tyr Ser Gly Gly Gly Asp Ala
1               5                   10

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Phe Leu Ser Ala Ser Val Gly
1               5                   10                  15

Asp Arg Val Thr Ile Asn Cys Lys Ala Ser Gln Asn Ile Asn Lys Tyr
            20                  25                  30

Leu Asp Trp Tyr Gln Gln Lys His Gly Glu Ala Pro Lys Leu Leu Ile
        35                  40                  45

His Tyr Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Ser Ser Arg Trp Thr
                85                  90                  95

Phe Gly Gly Gly Thr Lys Leu Glu Leu Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ala Ser Gln Asn Ile Asn Lys Tyr Leu Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Thr Asn Asn Leu His Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Leu Gln His Ser Ser Arg Trp Thr
1               5


<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Asp Leu Val Gln Pro Gly Arg
1               5                   10                  15

Ser Leu Lys Leu Ser Cys Val Ala Ser Gly Phe Thr Phe Asn Asn Tyr
            20                  25                  30

Trp Met Thr Trp Ile Arg Gln Val Pro Gly Lys Gly Leu Glu Trp Val
        35                  40                  45

Ala Ser Ile Ser Ser Ser Gly Gly Ser Ile Tyr Tyr Pro Asp Ser Val
    50                  55                  60

Lys Asp Arg Phe Thr Ile Ser Arg Asp Asn Ala Lys Asn Thr Leu Phe
65                  70                  75                  80

Leu Gln Met Asn Ser Leu Arg Ser Glu Asp Thr Ala Thr Tyr Tyr Cys
                85                  90                  95

Ala Arg Leu Tyr Tyr Tyr Ser Gly Gly Gly Asp Ala Trp Gly Gln Gly
            100                 105                 110

Thr Ser Val Thr Val Ser Ser
        115


<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Thr Phe Asn Asn Tyr Trp Met Thr
1               5


<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ile Ser Ser Ser Gly Gly Ser Ile Tyr Tyr Pro Asp Ser Val Lys
1               5                   10                  15

Asp


<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

```
Ala Arg Leu Tyr Tyr Tyr Ser Gly Gly Gly Asp Ala
1               5                   10


<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Phe Leu Ser Ala Ser Val Gly
1               5                   10                  15

Asp Arg Val Thr Ile Ile Cys Lys Ala Ser Gln Asp Ile Asn Lys Tyr
            20                  25                  30

Leu Asp Trp Tyr Gln Gln Lys Leu Gly Glu Ala Pro Lys Leu Leu Ile
        35                  40                  45

Tyr Asn Thr Asn Asn Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Leu Gln His Ile Ser Arg Trp Thr
                85                  90                  95

Phe Gly Gly Gly Thr Lys Leu Glu Leu Lys
            100                 105


<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Ser Gln Asp Ile Asn Lys Tyr Leu Asp
1               5                   10


<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn Thr Asn Asn Leu His Thr
1               5


<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln His Ile Ser Arg Trp Thr
1               5
```

<210> SEQ ID NO 25
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
gacatccaga tgacccagtc tccacctgtg ctgtctgcat ctgtaggaga cagagtcacc 60
ctttcatgca aggcaagtca gaatattaac aaaaatttag actggtatca gcagaaacat 120
ggggaagccc ctaagctcct gatctatgag acaaataatt tgcaaacggg gatcccatca 180
aggttcagtg gcagtggatc tgggacagat tacactctca ccatcagcag tctgcaacct 240
gaagatgtgg caacttacta ctgttaccag cacaactcca gattcacttt tggctcaggg 300
accaagctgg agatcaaa 318

<210> SEQ ID NO 26
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
gaagtgcagc tggtggagtc tgggggagac agggtacagc ctggcaggtc cctgacactc 60
tcctgtgtaa catctggatt cacctttaac aactattgga tgacctggat ccggcaagta 120
ccagggaagg gcctggagtg ggtcgcttct attagttcca gtggcggtag catatattat 180
cccgactctg tgaagggccg attcaccatc tccagagaca acgccaagaa caccctgtat 240
ctgcaaatga acagtctgag atccgaggac acggcgacct actactgcgc aagagacgaa 300
agatgggctg gcgctatgga cgcctggggg caagggacct ccgtcaccgt ctcctca 357

<210> SEQ ID NO 27
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27
gacatccaga tgacccagtc tccatccttc ctgtctgcat ctgtaggaga cagagtcacc 60
atcaactgca aggcgagtca gaacattaat aaatatttag attggtatca gcagaaacat 120
ggggaggccc ctaagctcct gatccattac accaataatt tgcacacagg gataccatca 180
aggttcagtg gaagtggatc tgggacagat tacactttga ccatcagcag cctgcagcct 240
gaagatgttg caacatattt ctgtctgcaa cattccagca ggtggacctt cggcggaggg 300
accaagcttg agctgaaa 318

<210> SEQ ID NO 28
<211> LENGTH: 234
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28

-continued

```
gggaagggcc tggagtgggt cgctagcatt agttctagtg gaggtagcat atattatccc     60

gactctgtga aggaccgatt caccatctcc agagacaacg ccaagaacac actgtatctg    120

caaatgaaca gtctgagatc cgaggacacg gcgacatact actgcgttaa gcttcactac    180

tattccggag ggggtgatgc ttggggccaa ggaacctccg tcaccgtctc ctca          234


<210> SEQ ID NO 29
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

gacatccaga tgacccagtc tccatccttc ctgtctgcat ctgtaggaga cagagtcacc     60

atcatctgca aggcgagtca ggacattaac aagtatttag actggtatca gcagaaattg    120

ggggaagccc ctaagctcct gatctacaat acaaataatt tgcacacagg gataccatca    180

aggttcagtg gaagtggatc tgggacagat tacactttga ccatcagcag cctgcagcct    240

gaagatgtcg caacatattt ttgtctgcag cacattagca gatggacctt cggcggaggg    300

accaagctgg agctgaaa                                                  318


<210> SEQ ID NO 30
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

gaagtgcagc tggtggagtc tgggggagat ttggtacagc ctggcaggtc cctgaaactc     60

tcctgtgttg cctctggatt cacctttaat aactattgga tgacatggat tcggcaagtt    120

ccagggaagg gcctggagtg ggtcgcttcc attagtagta gtggtggtag catatattat    180

cccgactctg tgaaggatcg attcaccatc tccagagaca acgccaagaa cacactgttt    240

ctgcaaatga acagtctgag atctgaggac acggcgacat actactgcgc gagactgtat    300

tactattctg gtggtggcga tgcgtggggc caaggaacct ccgtcaccgt ctcctca       357


<210> SEQ ID NO 31
<211> LENGTH: 1211
<212> TYPE: PRT
<213> ORGANISM: Homo sapiens

<400> SEQUENCE: 31

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95
```

-continued

```
Asn Thr Thr Asp Ala Tyr Leu Asn Ala Ser Glu Thr Thr Thr Leu Ser
            100                 105                 110

Pro Ser Gly Ser Ala Val Ile Ser Thr Thr Thr Ile Ala Thr Thr Pro
        115                 120                 125

Ser Lys Pro Thr Cys Asp Glu Lys Tyr Ala Asn Ile Thr Val Asp Tyr
    130                 135                 140

Leu Tyr Asn Lys Glu Thr Lys Leu Phe Thr Ala Lys Leu Asn Val Asn
145                 150                 155                 160

Glu Asn Val Glu Cys Gly Asn Asn Thr Cys Thr Asn Asn Glu Val His
                165                 170                 175

Asn Leu Thr Glu Cys Lys Asn Ala Ser Val Ser Ile Ser His Asn Ser
            180                 185                 190

Cys Thr Ala Pro Asp Lys Thr Leu Ile Leu Asp Val Pro Pro Gly Val
        195                 200                 205

Glu Lys Phe Gln Leu His Asp Cys Thr Gln Val Glu Lys Ala Asp Thr
    210                 215                 220

Thr Ile Cys Leu Lys Trp Lys Asn Ile Glu Thr Phe Thr Cys Asp Thr
225                 230                 235                 240

Gln Asn Ile Thr Tyr Arg Phe Gln Cys Gly Asn Met Ile Phe Asp Asn
                245                 250                 255

Lys Glu Ile Lys Leu Glu Asn Leu Glu Pro Glu His Glu Tyr Lys Cys
            260                 265                 270

Asp Ser Glu Ile Leu Tyr Asn Asn His Lys Phe Thr Asn Ala Ser Lys
        275                 280                 285

Ile Ile Lys Thr Asp Phe Gly Ser Pro Gly Glu Pro Gln Ile Ile Phe
    290                 295                 300

Cys Arg Ser Glu Ala Ala His Gln Gly Val Ile Thr Trp Asn Pro Pro
305                 310                 315                 320

Gln Arg Ser Phe His Asn Phe Thr Leu Cys Tyr Ile Lys Glu Thr Glu
                325                 330                 335

Lys Asp Cys Leu Asn Leu Asp Lys Asn Leu Ile Lys Tyr Asp Leu Gln
            340                 345                 350

Asn Leu Lys Pro Tyr Thr Lys Tyr Val Leu Ser Leu His Ala Tyr Ile
        355                 360                 365

Ile Ala Lys Val Gln Arg Asn Gly Ser Ala Ala Met Cys His Phe Thr
    370                 375                 380

Thr Lys Ser Ala Pro Pro Ser Gln Val Trp Asn Met Thr Val Ser Met
385                 390                 395                 400

Thr Ser Asp Asn Ser Met His Val Lys Cys Arg Pro Pro Arg Asp Arg
                405                 410                 415

Asn Gly Pro His Glu Arg Tyr His Leu Glu Val Glu Ala Gly Asn Thr
            420                 425                 430

Leu Val Arg Asn Glu Ser His Lys Asn Cys Asp Phe Arg Val Lys Asp
        435                 440                 445

Leu Gln Tyr Ser Thr Asp Tyr Thr Phe Lys Ala Tyr Phe His Asn Gly
    450                 455                 460

Asp Tyr Pro Gly Glu Pro Phe Ile Leu His His Ser Thr Ser Tyr Asn
465                 470                 475                 480

Ser Lys Ala Leu Ile Ala Phe Leu Ala Phe Leu Ile Ile Val Thr Ser
                485                 490                 495

Ile Ala Leu Leu Val Val Leu Tyr Lys Ile Tyr Asp Leu His Lys Lys
            500                 505                 510
```

-continued

```
Arg Ser Cys Asn Leu Asp Glu Gln Gln Glu Leu Val Glu Arg Asp Asp
        515                 520                 525

Glu Lys Gln Leu Met Asn Val Glu Pro Ile His Ala Asp Ile Leu Leu
    530                 535                 540

Glu Thr Tyr Lys Arg Lys Ile Ala Asp Glu Gly Arg Leu Phe Leu Ala
545                 550                 555                 560

Glu Phe Gln Ser Ile Pro Arg Val Phe Ser Lys Phe Pro Ile Lys Glu
                565                 570                 575

Ala Arg Lys Pro Phe Asn Gln Asn Lys Asn Arg Tyr Val Asp Ile Leu
            580                 585                 590

Pro Tyr Asp Tyr Asn Arg Val Glu Leu Ser Glu Ile Asn Gly Asp Ala
        595                 600                 605

Gly Ser Asn Tyr Ile Asn Ala Ser Tyr Ile Asp Gly Phe Lys Glu Pro
    610                 615                 620

Arg Lys Tyr Ile Ala Ala Gln Gly Pro Arg Asp Glu Thr Val Asp Asp
625                 630                 635                 640

Phe Trp Arg Met Ile Trp Glu Gln Lys Ala Thr Val Ile Val Met Val
                645                 650                 655

Thr Arg Cys Glu Glu Gly Asn Arg Asn Lys Cys Ala Glu Tyr Trp Pro
            660                 665                 670

Ser Met Glu Glu Gly Thr Arg Ala Phe Gly Asp Val Val Val Lys Ile
        675                 680                 685

Asn Gln His Lys Arg Cys Pro Asp Tyr Ile Ile Gln Lys Leu Asn Ile
    690                 695                 700

Val Asn Lys Lys Glu Lys Ala Thr Gly Arg Glu Val Thr His Ile Gln
705                 710                 715                 720

Phe Thr Ser Trp Pro Asp His Gly Val Pro Glu Asp Pro His Leu Leu
                725                 730                 735

Leu Lys Leu Arg Arg Arg Val Asn Ala Phe Ser Asn Phe Phe Ser Gly
            740                 745                 750

Pro Ile Val Val His Cys Ser Ala Gly Val Gly Arg Thr Gly Thr Tyr
        755                 760                 765

Ile Gly Ile Asp Ala Met Leu Glu Gly Leu Glu Ala Glu Asn Lys Val
    770                 775                 780

Asp Val Tyr Gly Tyr Val Val Lys Leu Arg Arg Gln Arg Cys Leu Met
785                 790                 795                 800

Val Gln Val Glu Ala Gln Tyr Ile Leu Ile His Gln Ala Leu Val Glu
                805                 810                 815

Tyr Asn Gln Phe Gly Glu Thr Glu Val Asn Leu Ser Glu Leu His Pro
            820                 825                 830

Tyr Leu His Asn Met Lys Lys Arg Asp Pro Pro Ser Glu Pro Ser Pro
        835                 840                 845

Leu Glu Ala Glu Phe Gln Arg Leu Pro Ser Tyr Arg Ser Trp Arg Thr
    850                 855                 860

Gln His Ile Gly Asn Gln Glu Glu Asn Lys Ser Lys Asn Arg Asn Ser
865                 870                 875                 880

Asn Val Ile Pro Tyr Asp Tyr Asn Arg Val Pro Leu Lys His Glu Leu
                885                 890                 895

Glu Met Ser Lys Glu Ser Glu His Asp Ser Asp Glu Ser Ser Asp Asp
            900                 905                 910

Asp Ser Asp Ser Glu Glu Pro Ser Lys Tyr Ile Asn Ala Ser Phe Ile
        915                 920                 925

Met Ser Tyr Trp Lys Pro Glu Val Met Ile Ala Ala Gln Gly Pro Leu
```

930 935 940

Lys Glu Thr Ile Gly Asp Phe Trp Gln Met Ile Phe Gln Arg Lys Val
945 950 955 960

Lys Val Ile Val Met Leu Thr Glu Leu Lys His Gly Asp Gln Glu Ile
965 970 975

Cys Ala Gln Tyr Trp Gly Glu Gly Lys Gln Thr Tyr Gly Asp Ile Glu
980 985 990

Val Asp Leu Lys Asp Thr Asp Lys Ser Ser Thr Tyr Thr Leu Arg Val
995 1000 1005

Phe Glu Leu Arg His Ser Lys Arg Lys Asp Ser Arg Thr Val Tyr
1010 1015 1020

Gln Tyr Gln Tyr Thr Asn Trp Ser Val Glu Gln Leu Pro Ala Glu
1025 1030 1035

Pro Lys Glu Leu Ile Ser Met Ile Gln Val Val Lys Gln Lys Leu
1040 1045 1050

Pro Gln Lys Asn Ser Ser Glu Gly Asn Lys His His Lys Ser Thr
1055 1060 1065

Pro Leu Leu Ile His Cys Arg Asp Gly Ser Gln Gln Thr Gly Ile
1070 1075 1080

Phe Cys Ala Leu Leu Asn Leu Leu Glu Ser Ala Glu Thr Glu Glu
1085 1090 1095

Val Val Asp Ile Phe Gln Val Val Lys Ala Leu Arg Lys Ala Arg
1100 1105 1110

Pro Gly Met Val Ser Thr Phe Glu Gln Tyr Gln Phe Leu Tyr Asp
1115 1120 1125

Val Ile Ala Ser Thr Tyr Pro Ala Gln Asn Gly Gln Val Lys Lys
1130 1135 1140

Asn Asn His Gln Glu Asp Lys Ile Glu Phe Asp Asn Glu Val Asp
1145 1150 1155

Lys Val Lys Gln Asp Ala Asn Cys Val Asn Pro Leu Gly Ala Pro
1160 1165 1170

Glu Lys Leu Pro Glu Ala Lys Glu Gln Ala Glu Gly Ser Glu Pro
1175 1180 1185

Thr Ser Gly Thr Glu Gly Pro Glu His Ser Val Asn Gly Pro Ala
1190 1195 1200

Ser Pro Ala Leu Asn Gln Gly Ser
1205 1210

<210> SEQ ID NO 32
<211> LENGTH: 1145
<212> TYPE: PRT
<213> ORGANISM: Homo sapiens

<400> SEQUENCE: 32

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Asp Ala Tyr Leu Asn Ala Ser Glu Thr Thr Thr Leu Ser Pro Ser
35 40 45

Gly Ser Ala Val Ile Ser Thr Thr Thr Ile Ala Thr Thr Pro Ser Lys
50 55 60

Pro Thr Cys Asp Glu Lys Tyr Ala Asn Ile Thr Val Asp Tyr Leu Tyr
65 70 75 80

-continued

```
Asn Lys Glu Thr Lys Leu Phe Thr Ala Lys Leu Asn Val Asn Glu Asn
                85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125

Ala Pro Asp Lys Thr Leu Ile Leu Asp Val Pro Pro Gly Val Glu Lys
    130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175

Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
    210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
    290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
        355                 360                 365

Arg Asn Glu Ser His Lys Asn Cys Asp Phe Arg Val Lys Asp Leu Gln
    370                 375                 380

Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
                405                 410                 415

Ala Leu Ile Ala Phe Leu Ala Phe Leu Ile Ile Val Thr Ser Ile Ala
            420                 425                 430

Leu Leu Val Val Leu Tyr Lys Ile Tyr Asp Leu His Lys Lys Arg Ser
        435                 440                 445

Cys Asn Leu Asp Glu Gln Gln Glu Leu Val Glu Arg Asp Asp Glu Lys
    450                 455                 460

Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
                485                 490                 495

Gln Ser Ile Pro Arg Val Phe Ser Lys Phe Pro Ile Lys Glu Ala Arg
```

```
            500                 505                 510

Lys Pro Phe Asn Gln Asn Lys Asn Arg Tyr Val Asp Ile Leu Pro Tyr
        515                 520                 525

Asp Tyr Asn Arg Val Glu Leu Ser Glu Ile Asn Gly Asp Ala Gly Ser
    530                 535                 540

Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
                565                 570                 575

Arg Met Ile Trp Glu Gln Lys Ala Thr Val Ile Val Met Val Thr Arg
            580                 585                 590

Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Val Lys Ile Asn Gln
    610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
                645                 650                 655

Ser Trp Pro Asp His Gly Val Pro Glu Asp Pro His Leu Leu Leu Lys
            660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
    690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
                725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
    770                 775                 780

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
            820                 825                 830

Ser Lys Glu Ser Glu His Asp Ser Asp Glu Ser Ser Asp Asp Asp Ser
        835                 840                 845

Asp Ser Glu Glu Pro Ser Lys Tyr Ile Asn Ala Ser Phe Ile Met Ser
    850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925
```

Leu Lys Asp Thr Asp Lys Ser Ser Thr Tyr Thr Leu Arg Val Phe Glu
    930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
                965                 970                 975

Ile Ser Met Ile Gln Val Val Lys Gln Lys Leu Pro Gln Lys Asn Ser
            980                 985                 990

Ser Glu Gly Asn Lys His His Lys  Ser Thr Pro Leu Leu  Ile His Cys
        995                 1000                1005

Arg Asp  Gly Ser Gln Gln Thr  Gly Ile Phe Cys Ala  Leu Leu Asn
    1010                1015                1020

Leu Leu  Glu Ser Ala Glu Thr  Glu Glu Val Val Asp  Ile Phe Gln
    1025                1030                1035

Val Val  Lys Ala Leu Arg Lys  Ala Arg Pro Gly Met  Val Ser Thr
    1040                1045                1050

Phe Glu  Gln Tyr Gln Phe Leu  Tyr Asp Val Ile Ala  Ser Thr Tyr
    1055                1060                1065

Pro Ala  Gln Asn Gly Gln Val  Lys Lys Asn Asn His  Gln Glu Asp
    1070                1075                1080

Lys Ile  Glu Phe Asp Asn Glu  Val Asp Lys Val Lys  Gln Asp Ala
    1085                1090                1095

Asn Cys  Val Asn Pro Leu Gly  Ala Pro Glu Lys Leu  Pro Glu Ala
    1100                1105                1110

Lys Glu  Gln Ala Glu Gly Ser  Glu Pro Thr Ser Gly  Thr Glu Gly
    1115                1120                1125

Pro Glu  His Ser Val Asn Gly  Pro Ala Ser Pro Ala  Leu Asn Gln
    1130                1135                1140

Gly Ser
    1145

<210> SEQ ID NO 33
<211> LENGTH: 1192
<212> TYPE: PRT
<213> ORGANISM: Homo sapiens

<400> SEQUENCE: 33

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80

Asp Ala Tyr Leu Asn Ala Ser Glu Thr Thr Thr Leu Ser Pro Ser Gly
                85                  90                  95

Ser Ala Val Ile Ser Thr Thr Thr Ile Ala Thr Thr Pro Ser Lys Pro
            100                 105                 110

Thr Cys Asp Glu Lys Tyr Ala Asn Ile Thr Val Asp Tyr Leu Tyr Asn
        115                 120                 125

Lys Glu Thr Lys Leu Phe Thr Ala Lys Leu Asn Val Asn Glu Asn Val

-continued

```
    130                 135                 140

Glu Cys Gly Asn Asn Thr Cys Thr Asn Asn Glu Val His Asn Leu Thr
145                 150                 155                 160

Glu Cys Lys Asn Ala Ser Val Ser Ile Ser His Asn Ser Cys Thr Ala
                165                 170                 175

Pro Asp Lys Thr Leu Ile Leu Asp Val Pro Pro Gly Val Glu Lys Phe
            180                 185                 190

Gln Leu His Asp Cys Thr Gln Val Glu Lys Ala Asp Thr Thr Ile Cys
        195                 200                 205

Leu Lys Trp Lys Asn Ile Glu Thr Phe Thr Cys Asp Thr Gln Asn Ile
    210                 215                 220

Thr Tyr Arg Phe Gln Cys Gly Asn Met Ile Phe Asp Asn Lys Glu Ile
225                 230                 235                 240

Lys Leu Glu Asn Leu Glu Pro Glu His Glu Tyr Lys Cys Asp Ser Glu
                245                 250                 255

Ile Leu Tyr Asn Asn His Lys Phe Thr Asn Ala Ser Lys Ile Ile Lys
            260                 265                 270

Thr Asp Phe Gly Ser Pro Gly Glu Pro Gln Ile Ile Phe Cys Arg Ser
        275                 280                 285

Glu Ala Ala His Gln Gly Val Ile Thr Trp Asn Pro Pro Gln Arg Ser
    290                 295                 300

Phe His Asn Phe Thr Leu Cys Tyr Ile Lys Glu Thr Glu Lys Asp Cys
305                 310                 315                 320

Leu Asn Leu Asp Lys Asn Leu Ile Lys Tyr Asp Leu Gln Asn Leu Lys
                325                 330                 335

Pro Tyr Thr Lys Tyr Val Leu Ser Leu His Ala Tyr Ile Ile Ala Lys
            340                 345                 350

Val Gln Arg Asn Gly Ser Ala Ala Met Cys His Phe Thr Thr Lys Ser
        355                 360                 365

Ala Pro Pro Ser Gln Val Trp Asn Met Thr Val Ser Met Thr Ser Asp
    370                 375                 380

Asn Ser Met His Val Lys Cys Arg Pro Pro Arg Asp Arg Asn Gly Pro
385                 390                 395                 400

His Glu Arg Tyr His Leu Glu Val Glu Ala Gly Asn Thr Leu Val Arg
                405                 410                 415

Asn Glu Ser His Lys Asn Cys Asp Phe Arg Val Lys Asp Leu Gln Tyr
            420                 425                 430

Ser Thr Asp Tyr Thr Phe Lys Ala Tyr Phe His Asn Gly Asp Tyr Pro
        435                 440                 445

Gly Glu Pro Phe Ile Leu His His Ser Thr Ser Tyr Asn Ser Lys Ala
    450                 455                 460

Leu Ile Ala Phe Leu Ala Phe Leu Ile Ile Val Thr Ser Ile Ala Leu
465                 470                 475                 480

Leu Val Val Leu Tyr Lys Ile Tyr Asp Leu His Lys Lys Arg Ser Cys
                485                 490                 495

Asn Leu Asp Glu Gln Gln Glu Leu Val Glu Arg Asp Asp Glu Lys Gln
            500                 505                 510

Leu Met Asn Val Glu Pro Ile His Ala Asp Ile Leu Leu Glu Thr Tyr
        515                 520                 525

Lys Arg Lys Ile Ala Asp Glu Gly Arg Leu Phe Leu Ala Glu Phe Gln
    530                 535                 540

Ser Ile Pro Arg Val Phe Ser Lys Phe Pro Ile Lys Glu Ala Arg Lys
545                 550                 555                 560
```

-continued

```
Pro Phe Asn Gln Asn Lys Asn Arg Tyr Val Asp Ile Leu Pro Tyr Asp
                565                 570                 575

Tyr Asn Arg Val Glu Leu Ser Glu Ile Asn Gly Asp Ala Gly Ser Asn
            580                 585                 590

Tyr Ile Asn Ala Ser Tyr Ile Asp Gly Phe Lys Glu Pro Arg Lys Tyr
        595                 600                 605

Ile Ala Ala Gln Gly Pro Arg Asp Glu Thr Val Asp Asp Phe Trp Arg
    610                 615                 620

Met Ile Trp Glu Gln Lys Ala Thr Val Ile Val Met Val Thr Arg Cys
625                 630                 635                 640

Glu Glu Gly Asn Arg Asn Lys Cys Ala Glu Tyr Trp Pro Ser Met Glu
                645                 650                 655

Glu Gly Thr Arg Ala Phe Gly Asp Val Val Val Lys Ile Asn Gln His
            660                 665                 670

Lys Arg Cys Pro Asp Tyr Ile Ile Gln Lys Leu Asn Ile Val Asn Lys
        675                 680                 685

Lys Glu Lys Ala Thr Gly Arg Glu Val Thr His Ile Gln Phe Thr Ser
    690                 695                 700

Trp Pro Asp His Gly Val Pro Glu Asp Pro His Leu Leu Leu Lys Leu
705                 710                 715                 720

Arg Arg Arg Val Asn Ala Phe Ser Asn Phe Phe Ser Gly Pro Ile Val
                725                 730                 735

Val His Cys Ser Ala Gly Val Gly Arg Thr Gly Thr Tyr Ile Gly Ile
            740                 745                 750

Asp Ala Met Leu Glu Gly Leu Glu Ala Glu Asn Lys Val Asp Val Tyr
        755                 760                 765

Gly Tyr Val Val Lys Leu Arg Arg Gln Arg Cys Leu Met Val Gln Val
    770                 775                 780

Glu Ala Gln Tyr Ile Leu Ile His Gln Ala Leu Val Glu Tyr Asn Gln
785                 790                 795                 800

Phe Gly Glu Thr Glu Val Asn Leu Ser Glu Leu His Pro Tyr Leu His
                805                 810                 815

Asn Met Lys Lys Arg Asp Pro Pro Ser Glu Pro Ser Pro Leu Glu Ala
            820                 825                 830

Glu Phe Gln Arg Leu Pro Ser Tyr Arg Ser Trp Arg Thr Gln His Ile
        835                 840                 845

Gly Asn Gln Glu Glu Asn Lys Ser Lys Asn Arg Asn Ser Asn Val Ile
    850                 855                 860

Pro Tyr Asp Tyr Asn Arg Val Pro Leu Lys His Glu Leu Glu Met Ser
865                 870                 875                 880

Lys Glu Ser Glu His Asp Ser Asp Glu Ser Ser Asp Asp Asp Ser Asp
                885                 890                 895

Ser Glu Glu Pro Ser Lys Tyr Ile Asn Ala Ser Phe Ile Met Ser Tyr
            900                 905                 910

Trp Lys Pro Glu Val Met Ile Ala Ala Gln Gly Pro Leu Lys Glu Thr
        915                 920                 925

Ile Gly Asp Phe Trp Gln Met Ile Phe Gln Arg Lys Val Lys Val Ile
    930                 935                 940

Val Met Leu Thr Glu Leu Lys His Gly Asp Gln Glu Ile Cys Ala Gln
945                 950                 955                 960

Tyr Trp Gly Glu Gly Lys Gln Thr Tyr Gly Asp Ile Glu Val Asp Leu
                965                 970                 975
```

```
Lys Asp Thr Asp Lys Ser Ser Thr Tyr Thr Leu Arg Val Phe Glu Leu
            980                 985                 990

Arg His Ser Lys Arg Lys Asp Ser  Arg Thr Val Tyr Gln  Tyr Gln Tyr
        995                 1000                 1005

Thr Asn  Trp Ser Val Glu Gln  Leu Pro Ala Glu Pro  Lys Glu Leu
    1010                 1015                 1020

Ile Ser  Met Ile Gln Val Val  Lys Gln Lys Leu Pro  Gln Lys Asn
    1025                 1030                 1035

Ser Ser  Glu Gly Asn Lys His  His Lys Ser Thr Pro  Leu Leu Ile
    1040                 1045                 1050

His Cys  Arg Asp Gly Ser Gln  Gln Thr Gly Ile Phe  Cys Ala Leu
    1055                 1060                 1065

Leu Asn  Leu Leu Glu Ser Ala  Glu Thr Glu Glu Val  Val Asp Ile
    1070                 1075                 1080

Phe Gln  Val Val Lys Ala Leu  Arg Lys Ala Arg Pro  Gly Met Val
    1085                 1090                 1095

Ser Thr  Phe Glu Gln Tyr Gln  Phe Leu Tyr Asp Val  Ile Ala Ser
    1100                 1105                 1110

Thr Tyr  Pro Ala Gln Asn Gly  Gln Val Lys Lys Asn  Asn His Gln
    1115                 1120                 1125

Glu Asp  Lys Ile Glu Phe Asp  Asn Glu Val Asp Lys  Val Lys Gln
    1130                 1135                 1140

Asp Ala  Asn Cys Val Asn Pro  Leu Gly Ala Pro Glu  Lys Leu Pro
    1145                 1150                 1155

Glu Ala  Lys Glu Gln Ala Glu  Gly Ser Glu Pro Thr  Ser Gly Thr
    1160                 1165                 1170

Glu Gly  Pro Glu His Ser Val  Asn Gly Pro Ala Ser  Pro Ala Leu
    1175                 1180                 1185

Asn Gln  Gly Ser
    1190
```

<210> SEQ ID NO 34
<211> LENGTH: 1258
<212> TYPE: PRT
<213> ORGANISM: Homo sapiens

<400> SEQUENCE: 34

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140
```

-continued

```
Ile Ser Asp Ala Tyr Leu Asn Ala Ser Glu Thr Thr Thr Leu Ser Pro
145                 150                 155                 160

Ser Gly Ser Ala Val Ile Ser Thr Thr Thr Ile Ala Thr Thr Pro Ser
                165                 170                 175

Lys Pro Thr Cys Asp Glu Lys Tyr Ala Asn Ile Thr Val Asp Tyr Leu
            180                 185                 190

Tyr Asn Lys Glu Thr Lys Leu Phe Thr Ala Lys Leu Asn Val Asn Glu
        195                 200                 205

Asn Val Glu Cys Gly Asn Asn Thr Cys Thr Asn Asn Glu Val His Asn
    210                 215                 220

Leu Thr Glu Cys Lys Asn Ala Ser Val Ser Ile Ser His Asn Ser Cys
225                 230                 235                 240

Thr Ala Pro Asp Lys Thr Leu Ile Leu Asp Val Pro Pro Gly Val Glu
                245                 250                 255

Lys Phe Gln Leu His Asp Cys Thr Gln Val Glu Lys Ala Asp Thr Thr
            260                 265                 270

Ile Cys Leu Lys Trp Lys Asn Ile Glu Thr Phe Thr Cys Asp Thr Gln
        275                 280                 285

Asn Ile Thr Tyr Arg Phe Gln Cys Gly Asn Met Ile Phe Asp Asn Lys
    290                 295                 300

Glu Ile Lys Leu Glu Asn Leu Glu Pro Glu His Glu Tyr Lys Cys Asp
305                 310                 315                 320

Ser Glu Ile Leu Tyr Asn Asn His Lys Phe Thr Asn Ala Ser Lys Ile
                325                 330                 335

Ile Lys Thr Asp Phe Gly Ser Pro Gly Glu Pro Gln Ile Ile Phe Cys
            340                 345                 350

Arg Ser Glu Ala Ala His Gln Gly Val Ile Thr Trp Asn Pro Pro Gln
        355                 360                 365

Arg Ser Phe His Asn Phe Thr Leu Cys Tyr Ile Lys Glu Thr Glu Lys
    370                 375                 380

Asp Cys Leu Asn Leu Asp Lys Asn Leu Ile Lys Tyr Asp Leu Gln Asn
385                 390                 395                 400

Leu Lys Pro Tyr Thr Lys Tyr Val Leu Ser Leu His Ala Tyr Ile Ile
                405                 410                 415

Ala Lys Val Gln Arg Asn Gly Ser Ala Ala Met Cys His Phe Thr Thr
            420                 425                 430

Lys Ser Ala Pro Pro Ser Gln Val Trp Asn Met Thr Val Ser Met Thr
        435                 440                 445

Ser Asp Asn Ser Met His Val Lys Cys Arg Pro Pro Arg Asp Arg Asn
    450                 455                 460

Gly Pro His Glu Arg Tyr His Leu Glu Val Glu Ala Gly Asn Thr Leu
465                 470                 475                 480

Val Arg Asn Glu Ser His Lys Asn Cys Asp Phe Arg Val Lys Asp Leu
                485                 490                 495

Gln Tyr Ser Thr Asp Tyr Thr Phe Lys Ala Tyr Phe His Asn Gly Asp
            500                 505                 510

Tyr Pro Gly Glu Pro Phe Ile Leu His His Ser Thr Ser Tyr Asn Ser
        515                 520                 525

Lys Ala Leu Ile Ala Phe Leu Ala Phe Leu Ile Ile Val Thr Ser Ile
    530                 535                 540

Ala Leu Leu Val Val Leu Tyr Lys Ile Tyr Asp Leu His Lys Lys Arg
545                 550                 555                 560
```

-continued

```
Ser Cys Asn Leu Asp Glu Gln Gln Glu Leu Val Glu Arg Asp Asp Glu
                565                 570                 575

Lys Gln Leu Met Asn Val Glu Pro Ile His Ala Asp Ile Leu Leu Glu
            580                 585                 590

Thr Tyr Lys Arg Lys Ile Ala Asp Glu Gly Arg Leu Phe Leu Ala Glu
        595                 600                 605

Phe Gln Ser Ile Pro Arg Val Phe Ser Lys Phe Pro Ile Lys Glu Ala
    610                 615                 620

Arg Lys Pro Phe Asn Gln Asn Lys Asn Arg Tyr Val Asp Ile Leu Pro
625                 630                 635                 640

Tyr Asp Tyr Asn Arg Val Glu Leu Ser Glu Ile Asn Gly Asp Ala Gly
                645                 650                 655

Ser Asn Tyr Ile Asn Ala Ser Tyr Ile Asp Gly Phe Lys Glu Pro Arg
            660                 665                 670

Lys Tyr Ile Ala Ala Gln Gly Pro Arg Asp Glu Thr Val Asp Asp Phe
        675                 680                 685

Trp Arg Met Ile Trp Glu Gln Lys Ala Thr Val Ile Val Met Val Thr
    690                 695                 700

Arg Cys Glu Glu Gly Asn Arg Asn Lys Cys Ala Glu Tyr Trp Pro Ser
705                 710                 715                 720

Met Glu Glu Gly Thr Arg Ala Phe Gly Asp Val Val Val Lys Ile Asn
                725                 730                 735

Gln His Lys Arg Cys Pro Asp Tyr Ile Ile Gln Lys Leu Asn Ile Val
            740                 745                 750

Asn Lys Lys Glu Lys Ala Thr Gly Arg Glu Val Thr His Ile Gln Phe
        755                 760                 765

Thr Ser Trp Pro Asp His Gly Val Pro Glu Asp Pro His Leu Leu Leu
    770                 775                 780

Lys Leu Arg Arg Arg Val Asn Ala Phe Ser Asn Phe Phe Ser Gly Pro
785                 790                 795                 800

Ile Val Val His Cys Ser Ala Gly Val Gly Arg Thr Gly Thr Tyr Ile
                805                 810                 815

Gly Ile Asp Ala Met Leu Glu Gly Leu Glu Ala Glu Asn Lys Val Asp
            820                 825                 830

Val Tyr Gly Tyr Val Val Lys Leu Arg Arg Gln Arg Cys Leu Met Val
        835                 840                 845

Gln Val Glu Ala Gln Tyr Ile Leu Ile His Gln Ala Leu Val Glu Tyr
    850                 855                 860

Asn Gln Phe Gly Glu Thr Glu Val Asn Leu Ser Glu Leu His Pro Tyr
865                 870                 875                 880

Leu His Asn Met Lys Lys Arg Asp Pro Pro Ser Glu Pro Ser Pro Leu
                885                 890                 895

Glu Ala Glu Phe Gln Arg Leu Pro Ser Tyr Arg Ser Trp Arg Thr Gln
            900                 905                 910

His Ile Gly Asn Gln Glu Glu Asn Lys Ser Lys Asn Arg Asn Ser Asn
        915                 920                 925

Val Ile Pro Tyr Asp Tyr Asn Arg Val Pro Leu Lys His Glu Leu Glu
    930                 935                 940

Met Ser Lys Glu Ser Glu His Asp Ser Asp Glu Ser Ser Asp Asp Asp
945                 950                 955                 960

Ser Asp Ser Glu Glu Pro Ser Lys Tyr Ile Asn Ala Ser Phe Ile Met
                965                 970                 975

Ser Tyr Trp Lys Pro Glu Val Met Ile Ala Ala Gln Gly Pro Leu Lys
```

```
            980                 985                 990

Glu Thr Ile Gly Asp Phe Trp Gln  Met Ile Phe Gln Arg  Lys Val Lys
        995                 1000                1005

Val Ile  Val Met Leu Thr Glu  Leu Lys His Gly Asp  Gln Glu Ile
    1010                 1015                1020

Cys Ala  Gln Tyr Trp Gly Glu  Gly Lys Gln Thr Tyr  Gly Asp Ile
    1025                 1030                1035

Glu Val  Asp Leu Lys Asp Thr  Asp Lys Ser Ser Thr  Tyr Thr Leu
    1040                 1045                1050

Arg Val  Phe Glu Leu Arg His  Ser Lys Arg Lys Asp  Ser Arg Thr
    1055                 1060                1065

Val Tyr  Gln Tyr Gln Tyr Thr  Asn Trp Ser Val Glu  Gln Leu Pro
    1070                 1075                1080

Ala Glu  Pro Lys Glu Leu Ile  Ser Met Ile Gln Val  Val Lys Gln
    1085                 1090                1095

Lys Leu  Pro Gln Lys Asn Ser  Ser Glu Gly Asn Lys  His His Lys
    1100                 1105                1110

Ser Thr  Pro Leu Leu Ile His  Cys Arg Asp Gly Ser  Gln Gln Thr
    1115                 1120                1125

Gly Ile  Phe Cys Ala Leu Leu  Asn Leu Leu Glu Ser  Ala Glu Thr
    1130                 1135                1140

Glu Glu  Val Val Asp Ile Phe  Gln Val Val Lys Ala  Leu Arg Lys
    1145                 1150                1155

Ala Arg  Pro Gly Met Val Ser  Thr Phe Glu Gln Tyr  Gln Phe Leu
    1160                 1165                1170

Tyr Asp  Val Ile Ala Ser Thr  Tyr Pro Ala Gln Asn  Gly Gln Val
    1175                 1180                1185

Lys Lys  Asn Asn His Gln Glu  Asp Lys Ile Glu Phe  Asp Asn Glu
    1190                 1195                1200

Val Asp  Lys Val Lys Gln Asp  Ala Asn Cys Val Asn  Pro Leu Gly
    1205                 1210                1215

Ala Pro  Glu Lys Leu Pro Glu  Ala Lys Glu Gln Ala  Glu Gly Ser
    1220                 1225                1230

Glu Pro  Thr Ser Gly Thr Glu  Gly Pro Glu His Ser  Val Asn Gly
    1235                 1240                1245

Pro Ala  Ser Pro Ala Leu Asn  Gln Gly Ser
    1250                 1255


<210> SEQ ID NO 35
<211> LENGTH: 1240
<212> TYPE: PRT
<213> ORGANISM: Homo sapiens

<400> SEQUENCE: 35

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Val Ser Ser Val Gln Thr Pro His Leu Pro Thr His Ala Asp
        35                  40                  45

Ser Gln Thr Pro Ser Ala Gly Thr Asp Thr Gln Thr Phe Ser Gly Ser
    50                  55                  60

Ala Ala Asn Ala Lys Leu Asn Pro Thr Pro Gly Ser Asn Ala Ile Ser
65                  70                  75                  80
```

-continued

```
Asp Val Pro Gly Glu Arg Ser Thr Ala Ser Thr Phe Pro Thr Asp Pro
                85                  90                  95

Val Ser Pro Leu Thr Thr Thr Leu Ser Leu Ala His His Ser Ser Ala
            100                 105                 110

Ala Leu Pro Ala Arg Thr Ser Asn Thr Thr Ile Thr Ala Asn Thr Ser
        115                 120                 125

Asp Ala Tyr Leu Asn Ala Ser Glu Thr Thr Thr Leu Ser Pro Ser Gly
    130                 135                 140

Ser Ala Val Ile Ser Thr Thr Thr Ile Ala Thr Thr Pro Ser Lys Pro
145                 150                 155                 160

Thr Cys Asp Glu Lys Tyr Ala Asn Ile Thr Val Asp Tyr Leu Tyr Asn
                165                 170                 175

Lys Glu Thr Lys Leu Phe Thr Ala Lys Leu Asn Val Asn Glu Asn Val
            180                 185                 190

Glu Cys Gly Asn Asn Thr Cys Thr Asn Asn Glu Val His Asn Leu Thr
        195                 200                 205

Glu Cys Lys Asn Ala Ser Val Ser Ile Ser His Asn Ser Cys Thr Ala
    210                 215                 220

Pro Asp Lys Thr Leu Ile Leu Asp Val Pro Pro Gly Val Glu Lys Phe
225                 230                 235                 240

Gln Leu His Asp Cys Thr Gln Val Glu Lys Ala Asp Thr Thr Ile Cys
                245                 250                 255

Leu Lys Trp Lys Asn Ile Glu Thr Phe Thr Cys Asp Thr Gln Asn Ile
            260                 265                 270

Thr Tyr Arg Phe Gln Cys Gly Asn Met Ile Phe Asp Asn Lys Glu Ile
        275                 280                 285

Lys Leu Glu Asn Leu Glu Pro Glu His Glu Tyr Lys Cys Asp Ser Glu
    290                 295                 300

Ile Leu Tyr Asn Asn His Lys Phe Thr Asn Ala Ser Lys Ile Ile Lys
305                 310                 315                 320

Thr Asp Phe Gly Ser Pro Gly Glu Pro Gln Ile Ile Phe Cys Arg Ser
                325                 330                 335

Glu Ala Ala His Gln Gly Val Ile Thr Trp Asn Pro Pro Gln Arg Ser
            340                 345                 350

Phe His Asn Phe Thr Leu Cys Tyr Ile Lys Glu Thr Glu Lys Asp Cys
        355                 360                 365

Leu Asn Leu Asp Lys Asn Leu Ile Lys Tyr Asp Leu Gln Asn Leu Lys
    370                 375                 380

Pro Tyr Thr Lys Tyr Val Leu Ser Leu His Ala Tyr Ile Ile Ala Lys
385                 390                 395                 400

Val Gln Arg Asn Gly Ser Ala Ala Met Cys His Phe Thr Thr Lys Ser
                405                 410                 415

Ala Pro Pro Ser Gln Val Trp Asn Met Thr Val Ser Met Thr Ser Asp
            420                 425                 430

Asn Ser Met His Val Lys Cys Arg Pro Pro Arg Asp Arg Asn Gly Pro
        435                 440                 445

His Glu Arg Tyr His Leu Glu Val Glu Ala Gly Asn Thr Leu Val Arg
    450                 455                 460

Asn Glu Ser His Lys Asn Cys Asp Phe Arg Val Lys Asp Leu Gln Tyr
465                 470                 475                 480

Ser Thr Asp Tyr Thr Phe Lys Ala Tyr Phe His Asn Gly Asp Tyr Pro
                485                 490                 495

Gly Glu Pro Phe Ile Leu His His Ser Thr Ser Tyr Asn Ser Lys Ala
```

-continued

```
            500                 505                 510

Leu Ile Ala Phe Leu Ala Phe Leu Ile Ile Val Thr Ser Ile Ala Leu
        515                 520                 525

Leu Val Val Leu Tyr Lys Ile Tyr Asp Leu His Lys Lys Arg Ser Cys
    530                 535                 540

Asn Leu Asp Glu Gln Gln Glu Leu Val Glu Arg Asp Asp Glu Lys Gln
545                 550                 555                 560

Leu Met Asn Val Glu Pro Ile His Ala Asp Ile Leu Leu Glu Thr Tyr
                565                 570                 575

Lys Arg Lys Ile Ala Asp Glu Gly Arg Leu Phe Leu Ala Glu Phe Gln
            580                 585                 590

Ser Ile Pro Arg Val Phe Ser Lys Phe Pro Ile Lys Glu Ala Arg Lys
        595                 600                 605

Pro Phe Asn Gln Asn Lys Asn Arg Tyr Val Asp Ile Leu Pro Tyr Asp
    610                 615                 620

Tyr Asn Arg Val Glu Leu Ser Glu Ile Asn Gly Asp Ala Gly Ser Asn
625                 630                 635                 640

Tyr Ile Asn Ala Ser Tyr Ile Asp Gly Phe Lys Glu Pro Arg Lys Tyr
                645                 650                 655

Ile Ala Ala Gln Gly Pro Arg Asp Glu Thr Val Asp Asp Phe Trp Arg
            660                 665                 670

Met Ile Trp Glu Gln Lys Ala Thr Val Ile Val Met Val Thr Arg Cys
        675                 680                 685

Glu Glu Gly Asn Arg Asn Lys Cys Ala Glu Tyr Trp Pro Ser Met Glu
    690                 695                 700

Glu Gly Thr Arg Ala Phe Gly Asp Val Val Val Lys Ile Asn Gln His
705                 710                 715                 720

Lys Arg Cys Pro Asp Tyr Ile Ile Gln Lys Leu Asn Ile Val Asn Lys
                725                 730                 735

Lys Glu Lys Ala Thr Gly Arg Glu Val Thr His Ile Gln Phe Thr Ser
            740                 745                 750

Trp Pro Asp His Gly Val Pro Glu Asp Pro His Leu Leu Leu Lys Leu
        755                 760                 765

Arg Arg Arg Val Asn Ala Phe Ser Asn Phe Phe Ser Gly Pro Ile Val
    770                 775                 780

Val His Cys Ser Ala Gly Val Gly Arg Thr Gly Thr Tyr Ile Gly Ile
785                 790                 795                 800

Asp Ala Met Leu Glu Gly Leu Glu Ala Glu Asn Lys Val Asp Val Tyr
                805                 810                 815

Gly Tyr Val Val Lys Leu Arg Arg Gln Arg Cys Leu Met Val Gln Val
            820                 825                 830

Glu Ala Gln Tyr Ile Leu Ile His Gln Ala Leu Val Glu Tyr Asn Gln
        835                 840                 845

Phe Gly Glu Thr Glu Val Asn Leu Ser Glu Leu His Pro Tyr Leu His
    850                 855                 860

Asn Met Lys Lys Arg Asp Pro Pro Ser Glu Pro Ser Pro Leu Glu Ala
865                 870                 875                 880

Glu Phe Gln Arg Leu Pro Ser Tyr Arg Ser Trp Arg Thr Gln His Ile
                885                 890                 895

Gly Asn Gln Glu Glu Asn Lys Ser Lys Asn Arg Asn Ser Asn Val Ile
            900                 905                 910

Pro Tyr Asp Tyr Asn Arg Val Pro Leu Lys His Glu Leu Glu Met Ser
        915                 920                 925
```

```
Lys Glu Ser Glu His Asp Ser Asp Glu Ser Ser Asp Asp Asp Ser Asp
    930                 935                 940

Ser Glu Glu Pro Ser Lys Tyr Ile Asn Ala Ser Phe Ile Met Ser Tyr
945                 950                 955                 960

Trp Lys Pro Glu Val Met Ile Ala Ala Gln Gly Pro Leu Lys Glu Thr
                965                 970                 975

Ile Gly Asp Phe Trp Gln Met Ile Phe Gln Arg Lys Val Lys Val Ile
            980                 985                 990

Val Met Leu Thr Glu Leu Lys His  Gly Asp Gln Glu Ile  Cys Ala Gln
        995                 1000                1005

Tyr Trp  Gly Glu Gly Lys Gln  Thr Tyr Gly Asp Ile  Glu Val Asp
    1010                 1015                 1020

Leu Lys  Asp Thr Asp Lys Ser  Ser Thr Tyr Thr Leu  Arg Val Phe
    1025                 1030                 1035

Glu Leu  Arg His Ser Lys Arg  Lys Asp Ser Arg Thr  Val Tyr Gln
    1040                 1045                 1050

Tyr Gln  Tyr Thr Asn Trp Ser  Val Glu Gln Leu Pro  Ala Glu Pro
    1055                 1060                 1065

Lys Glu  Leu Ile Ser Met Ile  Gln Val Val Lys Gln  Lys Leu Pro
    1070                 1075                 1080

Gln Lys  Asn Ser Ser Glu Gly  Asn Lys His His Lys  Ser Thr Pro
    1085                 1090                 1095

Leu Leu  Ile His Cys Arg Asp  Gly Ser Gln Gln Thr  Gly Ile Phe
    1100                 1105                 1110

Cys Ala  Leu Leu Asn Leu Leu  Glu Ser Ala Glu Thr  Glu Glu Val
    1115                 1120                 1125

Val Asp  Ile Phe Gln Val Val  Lys Ala Leu Arg Lys  Ala Arg Pro
    1130                 1135                 1140

Gly Met  Val Ser Thr Phe Glu  Gln Tyr Gln Phe Leu  Tyr Asp Val
    1145                 1150                 1155

Ile Ala  Ser Thr Tyr Pro Ala  Gln Asn Gly Gln Val  Lys Lys Asn
    1160                 1165                 1170

Asn His  Gln Glu Asp Lys Ile  Glu Phe Asp Asn Glu  Val Asp Lys
    1175                 1180                 1185

Val Lys  Gln Asp Ala Asn Cys  Val Asn Pro Leu Gly  Ala Pro Glu
    1190                 1195                 1200

Lys Leu  Pro Glu Ala Lys Glu  Gln Ala Glu Gly Ser  Glu Pro Thr
    1205                 1210                 1215

Ser Gly  Thr Glu Gly Pro Glu  His Ser Val Asn Gly  Pro Ala Ser
    1220                 1225                 1230

Pro Ala  Leu Asn Gln Gly Ser
    1235                 1240


<210> SEQ ID NO 36
<211> LENGTH: 1306
<212> TYPE: PRT
<213> ORGANISM: Homo sapiens

<400> SEQUENCE: 36

Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Gly Leu Thr Thr Ala Lys Met Pro Ser Val Pro Leu Ser Ser Asp
```

-continued

```
        35                  40                  45

Pro Leu Pro Thr His Thr Thr Ala Phe Ser Pro Ala Ser Thr Phe Glu
    50                  55                  60

Arg Glu Asn Asp Phe Ser Glu Thr Thr Thr Ser Leu Ser Pro Asp Asn
65                  70                  75                  80

Thr Ser Thr Gln Val Ser Pro Asp Ser Leu Asp Asn Ala Ser Ala Phe
                85                  90                  95

Asn Thr Thr Gly Val Ser Ser Val Gln Thr Pro His Leu Pro Thr His
            100                 105                 110

Ala Asp Ser Gln Thr Pro Ser Ala Gly Thr Asp Thr Gln Thr Phe Ser
        115                 120                 125

Gly Ser Ala Ala Asn Ala Lys Leu Asn Pro Thr Pro Gly Ser Asn Ala
    130                 135                 140

Ile Ser Asp Val Pro Gly Glu Arg Ser Thr Ala Ser Thr Phe Pro Thr
145                 150                 155                 160

Asp Pro Val Ser Pro Leu Thr Thr Thr Leu Ser Leu Ala His His Ser
                165                 170                 175

Ser Ala Ala Leu Pro Ala Arg Thr Ser Asn Thr Thr Ile Thr Ala Asn
            180                 185                 190

Thr Ser Asp Ala Tyr Leu Asn Ala Ser Glu Thr Thr Thr Leu Ser Pro
        195                 200                 205

Ser Gly Ser Ala Val Ile Ser Thr Thr Thr Ile Ala Thr Thr Pro Ser
    210                 215                 220

Lys Pro Thr Cys Asp Glu Lys Tyr Ala Asn Ile Thr Val Asp Tyr Leu
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
    370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
    450                 455                 460
```

-continued

```
Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
    530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
                565                 570                 575

Lys Ala Leu Ile Ala Phe Leu Ala Phe Leu Ile Ile Val Thr Ser Ile
            580                 585                 590

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
    610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655

Phe Gln Ser Ile Pro Arg Val Phe Ser Lys Phe Pro Ile Lys Glu Ala
            660                 665                 670

Arg Lys Pro Phe Asn Gln Asn Lys Asn Arg Tyr Val Asp Ile Leu Pro
        675                 680                 685

Tyr Asp Tyr Asn Arg Val Glu Leu Ser Glu Ile Asn Gly Asp Ala Gly
    690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
            740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Val Lys Ile Asn
    770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
        835                 840                 845

Ile Val Val His Cys Ser Ala Gly Val Gly Arg Thr Gly Thr Tyr Ile
    850                 855                 860

Gly Ile Asp Ala Met Leu Glu Gly Leu Glu Ala Glu Asn Lys Val Asp
865                 870                 875                 880
```

-continued

Val Tyr Gly Tyr Val Val Lys Leu Arg Arg Gln Arg Cys Leu Met Val
885 890 895

Gln Val Glu Ala Gln Tyr Ile Leu Ile His Gln Ala Leu Val Glu Tyr
900 905 910

Asn Gln Phe Gly Glu Thr Glu Val Asn Leu Ser Glu Leu His Pro Tyr
915 920 925

Leu His Asn Met Lys Lys Arg Asp Pro Pro Ser Glu Pro Ser Pro Leu
930 935 940

Glu Ala Glu Phe Gln Arg Leu Pro Ser Tyr Arg Ser Trp Arg Thr Gln
945 950 955 960

His Ile Gly Asn Gln Glu Glu Asn Lys Ser Lys Asn Arg Asn Ser Asn
965 970 975

Val Ile Pro Tyr Asp Tyr Asn Arg Val Pro Leu Lys His Glu Leu Glu
980 985 990

Met Ser Lys Glu Ser Glu His Asp Ser Asp Glu Ser Ser Asp Asp Asp
995 1000 1005

Ser Asp Ser Glu Glu Pro Ser Lys Tyr Ile Asn Ala Ser Phe Ile
1010 1015 1020

Met Ser Tyr Trp Lys Pro Glu Val Met Ile Ala Ala Gln Gly Pro
1025 1030 1035

Leu Lys Glu Thr Ile Gly Asp Phe Trp Gln Met Ile Phe Gln Arg
1040 1045 1050

Lys Val Lys Val Ile Val Met Leu Thr Glu Leu Lys His Gly Asp
1055 1060 1065

Gln Glu Ile Cys Ala Gln Tyr Trp Gly Glu Gly Lys Gln Thr Tyr
1070 1075 1080

Gly Asp Ile Glu Val Asp Leu Lys Asp Thr Asp Lys Ser Ser Thr
1085 1090 1095

Tyr Thr Leu Arg Val Phe Glu Leu Arg His Ser Lys Arg Lys Asp
1100 1105 1110

Ser Arg Thr Val Tyr Gln Tyr Gln Tyr Thr Asn Trp Ser Val Glu
1115 1120 1125

Gln Leu Pro Ala Glu Pro Lys Glu Leu Ile Ser Met Ile Gln Val
1130 1135 1140

Val Lys Gln Lys Leu Pro Gln Lys Asn Ser Ser Glu Gly Asn Lys
1145 1150 1155

His His Lys Ser Thr Pro Leu Leu Ile His Cys Arg Asp Gly Ser
1160 1165 1170

Gln Gln Thr Gly Ile Phe Cys Ala Leu Leu Asn Leu Leu Glu Ser
1175 1180 1185

Ala Glu Thr Glu Glu Val Val Asp Ile Phe Gln Val Val Lys Ala
1190 1195 1200

Leu Arg Lys Ala Arg Pro Gly Met Val Ser Thr Phe Glu Gln Tyr
1205 1210 1215

Gln Phe Leu Tyr Asp Val Ile Ala Ser Thr Tyr Pro Ala Gln Asn
1220 1225 1230

Gly Gln Val Lys Lys Asn Asn His Gln Glu Asp Lys Ile Glu Phe
1235 1240 1245

Asp Asn Glu Val Asp Lys Val Lys Gln Asp Ala Asn Cys Val Asn
1250 1255 1260

Pro Leu Gly Ala Pro Glu Lys Leu Pro Glu Ala Lys Glu Gln Ala
1265 1270 1275

Glu Gly Ser Glu Pro Thr Ser Gly Thr Glu Gly Pro Glu His Ser

```
    1280                1285                1290

Val Asn  Gly Pro Ala Ser Pro  Ala Leu Asn Gln Gly  Ser
    1295                1300                1305


<210> SEQ ID NO 37
<211> LENGTH: 552
<212> TYPE: PRT
<213> ORGANISM: Homo sapiens

<400> SEQUENCE: 37

Gln Ser Pro Thr Pro Ser Pro Thr Gly Leu Thr Thr Ala Lys Met Pro
1               5                   10                  15

Ser Val Pro Leu Ser Ser Asp Pro Leu Pro Thr His Thr Thr Ala Phe
            20                  25                  30

Ser Pro Ala Ser Thr Phe Glu Arg Glu Asn Asp Phe Ser Glu Thr Thr
        35                  40                  45

Thr Ser Leu Ser Pro Asp Asn Thr Ser Thr Gln Val Ser Pro Asp Ser
    50                  55                  60

Leu Asp Asn Ala Ser Ala Phe Asn Thr Thr Gly Val Ser Ser Val Gln
65                  70                  75                  80

Thr Pro His Leu Pro Thr His Ala Asp Ser Gln Thr Pro Ser Ala Gly
                85                  90                  95

Thr Asp Thr Gln Thr Phe Ser Gly Ser Ala Ala Asn Ala Lys Leu Asn
            100                 105                 110

Pro Thr Pro Gly Ser Asn Ala Ile Ser Asp Val Pro Gly Glu Arg Ser
        115                 120                 125

Thr Ala Ser Thr Phe Pro Thr Asp Pro Val Ser Pro Leu Thr Thr Thr
    130                 135                 140

Leu Ser Leu Ala His His Ser Ser Ala Ala Leu Pro Ala Arg Thr Ser
145                 150                 155                 160

Asn Thr Thr Ile Thr Ala Asn Thr Ser Asp Ala Tyr Leu Asn Ala Ser
                165                 170                 175

Glu Thr Thr Thr Leu Ser Pro Ser Gly Ser Ala Val Ile Ser Thr Thr
            180                 185                 190

Thr Ile Ala Thr Thr Pro Ser Lys Pro Thr Cys Asp Glu Lys Tyr Ala
        195                 200                 205

Asn Ile Thr Val Asp Tyr Leu Tyr Asn Lys Glu Thr Lys Leu Phe Thr
    210                 215                 220

Ala Lys Leu Asn Val Asn Glu Asn Val Glu Cys Gly Asn Asn Thr Cys
225                 230                 235                 240

Thr Asn Asn Glu Val His Asn Leu Thr Glu Cys Lys Asn Ala Ser Val
                245                 250                 255

Ser Ile Ser His Asn Ser Cys Thr Ala Pro Asp Lys Thr Leu Ile Leu
            260                 265                 270

Asp Val Pro Pro Gly Val Glu Lys Phe Gln Leu His Asp Cys Thr Gln
        275                 280                 285

Val Glu Lys Ala Asp Thr Thr Ile Cys Leu Lys Trp Lys Asn Ile Glu
    290                 295                 300

Thr Phe Thr Cys Asp Thr Gln Asn Ile Thr Tyr Arg Phe Gln Cys Gly
305                 310                 315                 320

Asn Met Ile Phe Asp Asn Lys Glu Ile Lys Leu Glu Asn Leu Glu Pro
                325                 330                 335

Glu His Glu Tyr Lys Cys Asp Ser Glu Ile Leu Tyr Asn Asn His Lys
            340                 345                 350
```

Phe Thr Asn Ala Ser Lys Ile Ile Lys Thr Asp Phe Gly Ser Pro Gly
355 360 365

Glu Pro Gln Ile Ile Phe Cys Arg Ser Glu Ala Ala His Gln Gly Val
370 375 380

Ile Thr Trp Asn Pro Pro Gln Arg Ser Phe His Asn Phe Thr Leu Cys
385 390 395 400

Tyr Ile Lys Glu Thr Glu Lys Asp Cys Leu Asn Leu Asp Lys Asn Leu
405 410 415

Ile Lys Tyr Asp Leu Gln Asn Leu Lys Pro Tyr Thr Lys Tyr Val Leu
420 425 430

Ser Leu His Ala Tyr Ile Ile Ala Lys Val Gln Arg Asn Gly Ser Ala
435 440 445

Ala Met Cys His Phe Thr Thr Lys Ser Ala Pro Pro Ser Gln Val Trp
450 455 460

Asn Met Thr Val Ser Met Thr Ser Asp Asn Ser Met His Val Lys Cys
465 470 475 480

Arg Pro Pro Arg Asp Arg Asn Gly Pro His Glu Arg Tyr His Leu Glu
485 490 495

Val Glu Ala Gly Asn Thr Leu Val Arg Asn Glu Ser His Lys Asn Cys
500 505 510

Asp Phe Arg Val Lys Asp Leu Gln Tyr Ser Thr Asp Tyr Thr Phe Lys
515 520 525

Ala Tyr Phe His Asn Gly Asp Tyr Pro Gly Glu Pro Phe Ile Leu His
530 535 540

His Ser Thr Ser Tyr Asn Ser Lys
545 550

<210> SEQ ID NO 38
<211> LENGTH: 17
<212> TYPE: PRT
<213> ORGANISM: Homo sapiens

<400> SEQUENCE: 38

Arg Asn Gly Pro His Glu Arg Tyr His Leu Glu Val Glu Ala Gly Asn
1 5 10 15

Thr

<210> SEQ ID NO 39
<211> LENGTH: 31
<212> TYPE: PRT
<213> ORGANISM: Homo sapiens

<400> SEQUENCE: 39

Cys Arg Pro Pro Arg Asp Arg Asn Gly Pro His Glu Arg Tyr His Leu
1 5 10 15

Glu Val Glu Ala Gly Asn Thr Leu Val Arg Asn Glu Ser His Lys
20 25 30

METHODS AND COMPOSITIONS FOR TREATING AUTOIMMUNE DISEASES

CROSS REFERENCE TO RELATED APPLICATIONS

This application is a continuation of International Application No. PCT/US2020/036177, filed on Jun. 4, 2020, which claims priority to U.S. Provisional Application No. 62/857,232, filed on Jun. 4, 2019; U.S. Provisional Application No. 62/863,141, filed on Jun. 18, 2019; U.S. Provisional Application No. 62,882,310, filed on Aug. 2, 2019; U.S. Provisional Application No. 62/933,279, filed on Nov. 8, 2019; U.S. Provisional Application No. 62/944,988, filed on Dec. 6, 2019; U.S. Provisional Application No. 62/968,870, filed on Jan. 31, 2020; and U.S. Provisional Application No. 63/030,860, filed on May 27, 2020, each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Dec. 3, 2021, is named M103034_2180US_C1_SL.txt and is 83,947 bytes in size.

FIELD

The present invention relates to the field of treating autoimmune diseases.

BACKGROUND

Autologous hematopoietic stem cell transplant (autoHSCT) is a highly effective treatment in selected patients with autoimmune diseases. AutoHSCT can induce long-term remission (up to 15 years) with 70-80% progression free survival in patients with relapsed refractory and secondary progressive multiple sclerosis subtypes (Muraro 2017) that is superior to standard of care agents in a randomized study (Burt 2019). Likewise, use of autoHSCT in patients with scleroderma achieved superior outcomes in two randomized studies (Tyndall 2014, Sullivan 2018). These results are achieved by eradication of autoreactive immune cells and re-establishment of a self-tolerant immune system, i.e., immune system reset. However, only a small fraction of eligible patients undergo autoHSCT, in part due to toxicity associated with current conditioning protocols.

SUMMARY

Described herein are methods and compositions for improving autologous hematopoietic stem cell transplant (autoHSCT). Provided herein are methods and compositions for addressing challenges known in the field of autoHSCT, including antibodies and/or antibody drug conjugates (ADCs) that selectively target CD45 to eradicate autoimmune cells and enable autoHSCT as a potentially one-time curative treatment for patients with autoimmune disease. This approach for conditioning prior to autoHSCT could increase the number of autoimmune patients eligible for transplant and significantly reduce the side effects associated with current conditioning protocols.

Accordingly, in one aspect, the invention provides a method of depleting a population of CD45+ cells in a human patient having an autoimmune disease, the method comprising administering to the patient having the autoimmune disease an effective amount of an anti-CD45 antibody, or an antigen binding portion thereof. In another aspect, the invention provides a method of depleting a population of CD45+ cells in a human patient having an autoimmune disease, the method comprising administering to the patient having the autoimmune disease an effective amount of an antibody drug conjugate (ADC) comprising an anti-CD45 antibody, or an antigen binding portion thereof.

In another aspect, the invention provides a method of conditioning a human patient having an autoimmune disease for receiving a hematopoietic stem cell (HSC) transplant, the method comprising administering to the human patient having the autoimmune disease an anti-CD45 antibody, or an antigen binding portion thereof. In another aspect, the invention provides a method of conditioning a human patient having an autoimmune disease for receiving a hematopoietic stem cell (HSC) transplant, the method comprising administering to the human patient having the autoimmune disease an antibody drug conjugate (ADC) comprising an anti-CD45 antibody, or an antigen binding portion thereof.

In some embodiments, the autoimmune disease is an inflammatory arthritis (for example, rheumatoid arthritis), autoimmune encephalitis, scleroderma, multiple sclerosis, type 1 diabetes, or systemic sclerosis.

In some embodiments, the method further comprises administering a transplant comprising hematopoietic stem cells (HSCs) to the patient. In certain embodiments, the HSC transplant is an autologous HSC transplant (autoHSCT).

In some embodiments, the anti-CD45 ADC is administered to the patient as a single dose.

In some embodiments, the patient does not require treatment (e.g., chronic treatment) for the autoimmune disease following transplantation. For example, in some embodiments, the patient has multiple sclerosis and the patient does not require treatment with natalizumab, dimethyl fumarate, or monomethyl fumarate following transplantation. In other embodiments, the patient has arthritis and the patient does not require treatment with a TNF inhibitor (e.g., anti-TNFα antibody, such as etanercept, infliximab, adalimumab, certolizumab pegol, or golimumab) following transplantation.

In some embodiments, the patient enters remission for at least 1 year following transplantation. In some embodiments, the patient enters remission for at least 2 years following transplantation. In some embodiments, the patient enters remission for at least 5 years following transplantation. In some embodiments, the patient enters remission for at least 1 year, at least 2 years, at least 3 years, at least 4 years, at least 5 years, at least 6 years, at least 7 years, at least 8 years, at least 9 years, or at least 10 years. In some embodiments, the patient enters remission for at least 1-3 years, at least 3-5 years, at least 5-7 years, at least 7-9 years, or at least 8-10 years. In some embodiments, the remission is clinical remission. In other embodiments, the remission is biochemical remission. In yet further embodiments, the remission is histologic remission.

In some embodiments, the anti-CD45 ADC is administered to the patient about three days prior to the patient receiving the transplant comprising HSCs.

In some embodiments, the HSC transplant is administered to the patient after the anti-CD45 ADC has substantially cleared from the blood of the human patient.

In another aspect, provided herein is a method of treating a patient having scleroderma, also known as systemic sclerosis, said method comprising administering an anti-CD45 antibody drug conjugate (ADC) to the patient having scleroderma, such that the scleroderma is treated, wherein the anti-CD45 ADC comprises an anti-CD45 antibody, or fragment thereof, conjugated to a cytotoxin via a linker.

In some embodiments of any of the preceding aspects, the anti-CD45 antibody is a chimeric antibody or a humanized antibody.

In some embodiments, the anti-CD45 antibody is a human antibody.

In some embodiments, the anti-CD45 antibody is intact.

In some embodiments, the anti-CD45 antibody or antigen-binding portion thereof is selected from the group consisting of a monoclonal antibody or antigen-binding portion thereof, a polyclonal antibody or antigen-binding portion thereof, a bispecific antibody or antigen-binding portion thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, and a tandem di-scFv.

In some embodiments, the anti-CD45 antibody has an isotype selected from the group consisting of IgG, IgA, IgM, IgD, and IgE. In certain embodiments, the anti-CD45 antibody contains a human IgG1, IgG2, IgG3, or IgG4 isotype Fc domain.

In some embodiments, the anti-CD45 antibody, or antigen binding portion thereof, comprises an Fc domain, and wherein the anti-CD45 antibody, or antigen binding portion thereof, is conjugated to the cytotoxin by way of a cysteine residue in the Fc domain. In certain embodiments, the cysteine residue is introduced by way of an amino acid substitution in the Fc domain. In particular embodiments, the amino acid substitution is D265C (EU numbering).

In some embodiments of any of the preceding aspects, the anti-CD45 antibody, or antigen binding portion thereof, is conjugated to a cytotoxin. In some embodiments, the cytotoxin is selected from the group consisting of an pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer.

In some embodiments, the cytotoxin is an auristatin. In certain embodiments, the auristatin is MMAE or MMAF.

In some embodiments, the cytotoxin is a pyrrolobenzodiazepine or a pyrrolobenzodiazepine dimer.

In some embodiments, the cytotoxin is an RNA polymerase inhibitor. In some embodiments, the RNA polymerase inhibitor is an amatoxin.

In certain embodiments, the amatoxin is represented by formula (IA)

(IA)

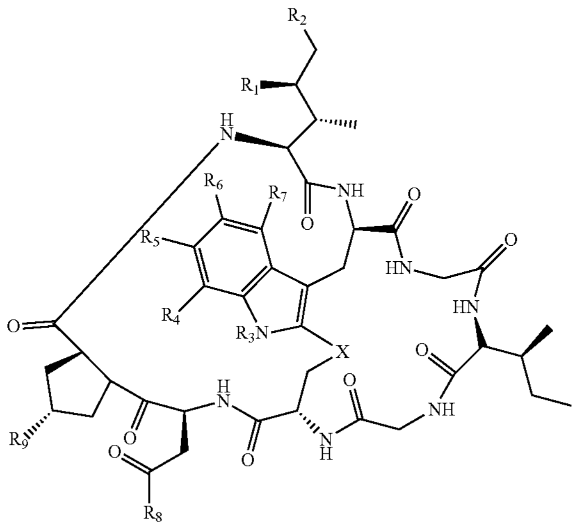

wherein $R_1$ is H, OH, $OR_A$, or $OR_C$;

$R_2$ is H, OH, $OR_B$, or $OR_C$;

$R_A$ and $R_B$, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, ORD, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ heteroalkenylene, optionally substituted $C_2$-$C_6$ alkynylene, optionally substituted $C_2$-$C_6$ heteroalkynylene, optionally substituted cycloalkylene, optionally substituted heterocycloalkylene, optionally substituted arylene, or optionally substituted heteroarylene; and Z is a chemical moiety formed from a coupling reaction between a reactive substituent present on L and a reactive substituent present within the antibody or antigen-binding fragment thereof, wherein Am comprises exactly one $R_C$ substituent.

In some embodiments, the anti-CD45 ADC has a formula of

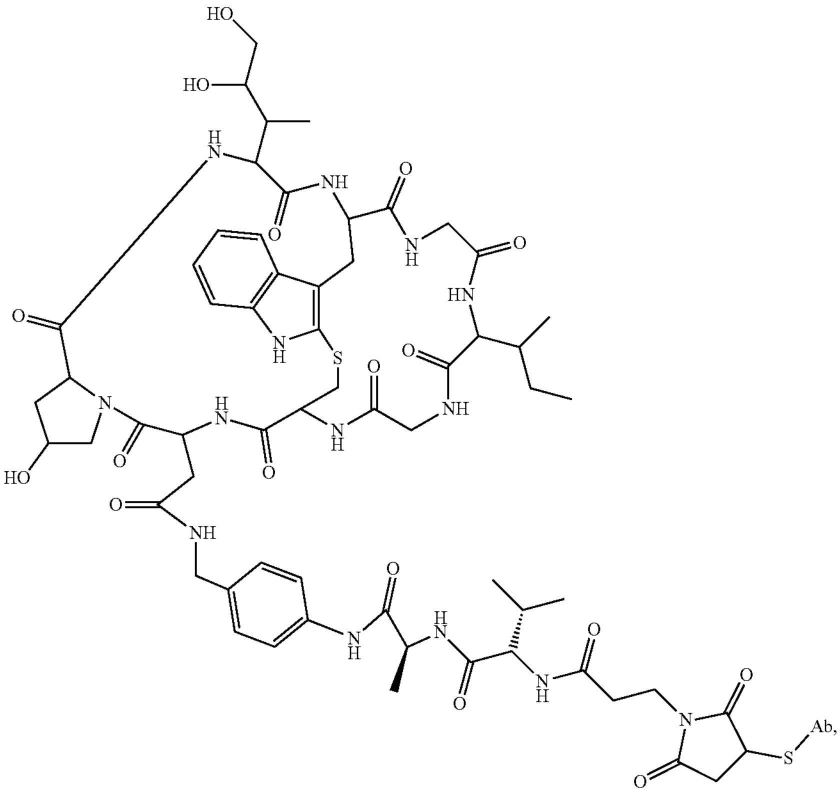
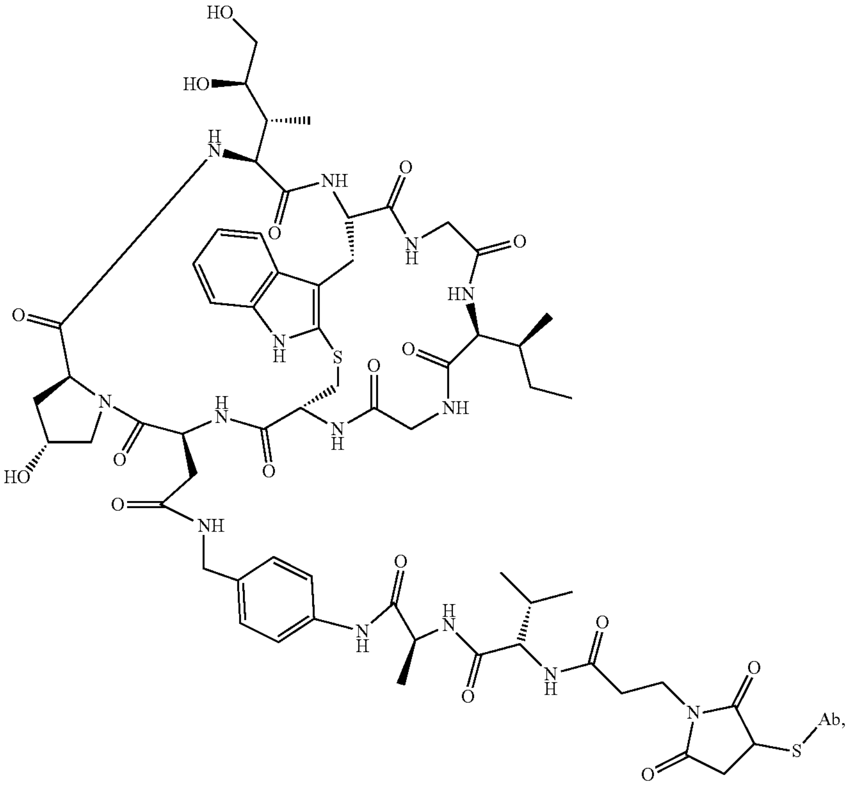
or

-continued

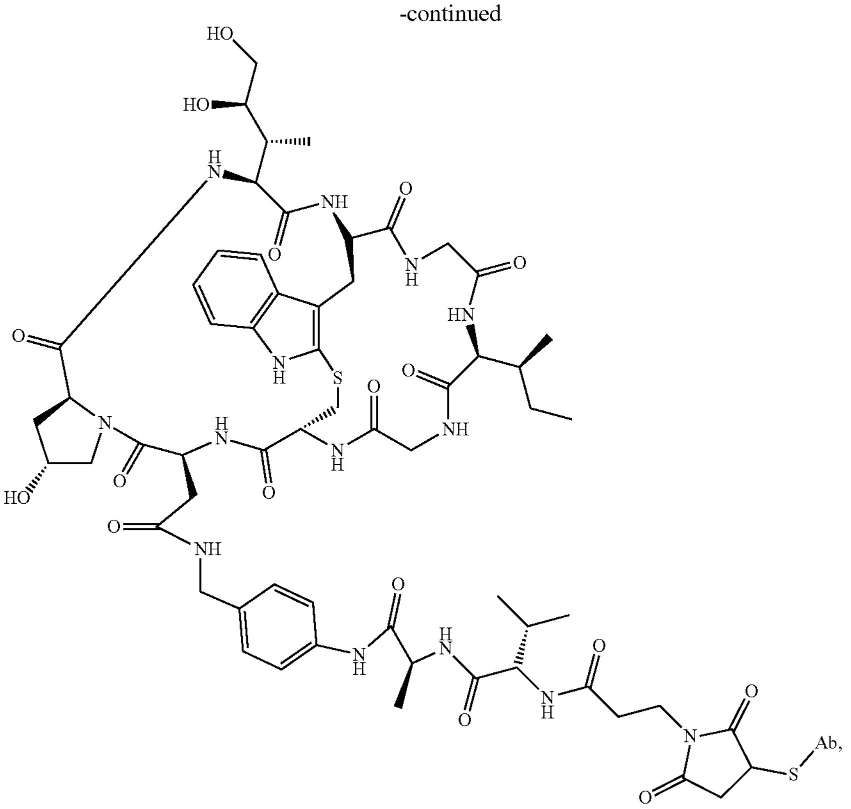

wherein Ab represents the anti-CD45 antibody.

In some embodiments, the anti-CD45 ADC has a formula of

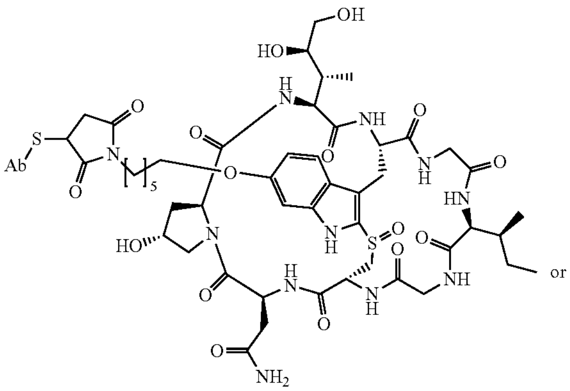

or

-continued

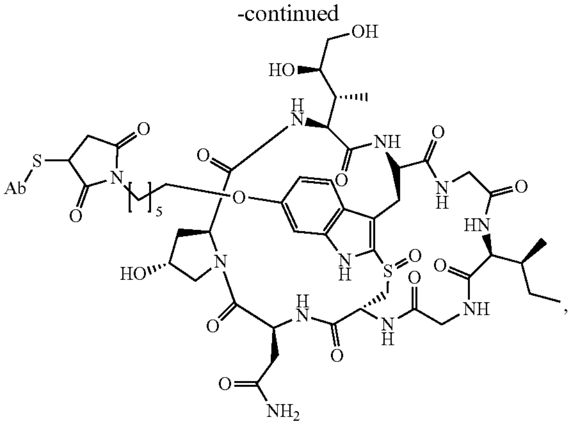

, wherein Ab represents the anti-CD45 antibody.

In some embodiments, the RNA polymerase inhibitor is an amanitin.

Also provided are methods of depleting a population of CD45+ cells in a human patient having an autoimmune disease, the methods comprising administering to the patient having the autoimmune disease an effective amount of an engineered toxin body targeting CD45. In some embodiments, the engineered toxin body comprises an antibody, or antigen binding fragment thereof, that specifically binds to CD45. In some embodiments, the engineered toxin body comprises an scFv that specifically binds to CD45. In some embodiments, the engineered toxin body comprises a protein-based toxin. In some embodiments, the protein-based toxin is a protein synthesis inhibitor, e.g., a ribosome inactivating protein. In some embodiments, the protein-based toxin is selected from the group consisting of Shiga toxin, Shiga-like toxin A subunit, saporin, ricin, and mutants, fragments, and derivatives thereof.

In some embodiments of any of the preceding aspects, the anti-CD45 antibody, or antigen binding portion thereof, is conjugated to a cytotoxin via a linker.

In some embodiments of any of the preceding aspects, the anti-CD45 antibody is a bispecific or biparatopic antibody.

In some embodiments of any of the preceding aspects, the anti-CD45 antibody, or antigen binding portion thereof, is administered to the patient in combination with a second therapeutic agent. In some embodiments, the second therapeutic agent comprises an antibody, or an antigen binding portion thereof.

BRIEF DESCRIPTION OF THE DRAWINGS

FIG. 1A is a schematic depicting the in vivo design of the study in which C57BL/6 (CD45.2) mice were conditioned with a single intravenous dose administration of anti-mouse CD45-ADC (0.3, 1, or 3 mg/kg) or Isotype-ADC (3 mg/kg) 48 h prior to transplant. FIG. 1B graphically depicts the percentage of donor chimerism in the peripheral blood of mice from each treatment group at the indicated time points (i.e., week 0, week 4, week 8, week 12 and week 16). FIGS. 1C-1E graphically depicts the percentage of donor myeloid cells (FIG. 1C), B-cells (FIG. 1D), and T-cells (FIG. 1E) in mice from each treatment group at the indicated time points (i.e., week 0, week 4, week 8, week 12 and week 16).

FIG. 2B) are shown as a function of the indicated ADC concentration (anti-mouse anti-CD45 ADC or isotype-ADC).

FIG. 3A is a schematic depicting the design of the in vivo study in which Balb/c (CD45.1) mice were conditioned with 6.5 Gy TBI 24 h prior to allogenic (Allo) adoptive cell transfer of DBA/2 (CD45.2) splenocytes. Host animals (CD45.1+) were treated with a single intravenous dose (3 mg/kg) administration of anti-mouse CD45-ADC, or isotype-ADC 7 days post initiation of scGvHD (CD45.2+ cells). FIGS. 3B and 3C depict flow cytometry analyses of spleen (FIG. 3B) or peripheral blood (FIG. 3C) harvested from mice administered isotype-ADC or anti-CD45-ADC and analyzed for allogenic cells, T-cells, and proliferating T cells. FIGS. 3D and 3E graphically depict results of the number and percentage of allogeneic T cells (total T cells and proliferating Ki-67+ T cells) in spleen (FIG. 3D) or peripheral blood (FIG. 3E) harvested from mice administered isotype-ADC or anti-CD45-ADC.

FIG. 4A graphically depicts EAE clinical score as a function of days-post induction in the indicated treatment conditions (no BMT, day 9 BMT, or day 14 BMT). FIG. 4B graphically depicts the percentage of donor chimerism in the peripheral blood of mice from the indicated treatment groups (PBS control, day 9 BMT, or day 14 BMT) harvested at the indicated time points (4 weeks post-transplant and 8 weeks post-transplant). FIGS. 4C and 4D graphically depict a comparison of host and donor cells in the peripheral blood (FIG. 4C) and lymph node (FIG. 4D) harvested from control (no transplant) vs treated (day 9 BMT) mice.

FIGS. 5A-5G describe the results of an in vivo study showing that administration of CD45-ADC enables autologous hematopoietic stem cell transplant (autoHSCT) and substantially reduces pathology in a murine experimental autoimmune encephalitis (EAE) model. FIG. 5A is a schematic depicting the study design, in which EAE was initiated in C57BL/6 ("B6") mice via immunization with $MOG_{35-55}$ peptide in complete Freund's adjuvant (CFA) on day 0 with pertussis toxin ("PTX") on days 0 and 1. FIG. 5B graphically depicts the degree of overall donor chimerism, myeloid chimerism, and T cell chimerism in transplant recipients in the indicated treatment groups. FIGS. 5C and 5D graphically depict the relative number of splenic T cells (FIG. 5C) and relative number of splenic IL-1A+ T-cells (i.e., splenic IL-17A-producing effector cells) (FIG. 5D). Groups of immunized mice were conditioned ("Tx") with 3 mg/kg of CD45-ADC on day 5 (FIG. 5E) or day 10 (FIG. 5F) post-immunization followed by congenic bone marrow transplant ("BMT"; $2\times10^7$ BM cells from B6.SJL ($CD45.1^+$)). All animals were scored daily starting at 5 days post-immunization. Vehicle and FTY-720-treated groups are shown as comparators. FIGS. 5E and 5F graphically depicts the EAE clinical score overtime (from day 0 through day 56 post-immunization) in mice that received treatment with an CD45-ADC on day 5 (FIG. 5E) or day 10 (FIG. 5F). FIG. 5G graphically depicts the EAE clinical score from day 0 through day 28 post-immunization in mice that received treatment with an CD45-ADC on day 5, with the results obtained in mice treated with a naked CD45 Ab (3 mg/kg, single dose) or an isotype-ADC plus BMT also shown for comparison. FIG. 5H graphically depicts the results of an in vitro study comparing human anti-CD45-ADC mediated killing of PBMCs from MS patients and healthy donors.

FIGS. 6A-6C graphically depict the results of an in vitro killing assay showing the degree of human PBMC killing (FIG. 6A), cyno PBMC killing (FIG. 6B), or human CD34+ CD90+ cell killing (FIG. 6C and FIG. 6D) as a function of the indicated ADC concentration (anti-human anti-CD45 ADC or isotype-ADC). Corresponding EC50 values are summarized in Table 4. FIG. 6E graphically depicts the percentage of human hematopoietic cells (human $\beta_2M$+ cells) in the peripheral blood of mice treated with PBS, an isotype-ADC (3 mg/kg), or an anti-human CD45 ADC (1 mg/kg, 3 mg/kg, or 6 mg/kg) at Day 0, Day 7, or Day 14 post-treatment. FIGS. 6F and 6G graphically depict the percentage of human CD34+ cells (FIG. 6F) and number of human CD34+ cells (FIG. 6G) in the bone marrow of mice 14 days after administration of PBS, an isotype-ADC (3 mg/kg), or an anti-human CD45 ADC (1 mg/kg, 3 mg/kg, or 6 mg/kg). FIGS. 6H and 6I graphically depict the results of a similar study, in which the CD45 ADC is administered at 1 mg/kg, 2 mg/kg, or 3 mg/kg.

FIG. 7A depicts a flow cytometry analysis of peripheral blood harvested from peripheral blood of NHPs 72 hours following administration of the anti-CD45-ADC at 0.5 mg/kg, 1 mg/kg or 2 mg/kg and analyzed for myeloid cells, T cells, B cells, or lymphocytes. FIG. 7B graphically depicts the level of peripheral lymphocytes in NHP three days after administration of the anti-CD45-ADC at 0.5 mg/kg, 1 mg/kg or 2 mg/kg. FIG. 7C depicts a flow cytometry analysis of bone marrow harvested from bone marrow of NHPs 6 days post-administration of the anti-CD45-ADC at 0.5 mg/kg, 1 mg/kg or 2 mg/kg and analyzed for HSCs. FIG. 7D graphically depicts the level of white blood cells (WBC), HSCs, and lymphocytes in NHPs 6 days post-administration of the anti-CD45-ADC at 0.5 mg/kg, 1 mg/kg or 2 mg/kg and analyzed for HSCs. FIGS. 7E and 7F graphically depicts the level of ALT, bilirubin, AST, and/or ALP in NHPs as a function of days post-administration of the CD45-ADC at 2 mg/kg. FIG. 7G graphically depicts the level of peripheral lymphocytes in NHP after administration of anti-CD45-ADC at 0.5 mg/kg, 1 mg/kg or 2 mg/kg. FIG. 7H graphically depicts the level of CD34+CD90+CD45RA− HSCs in NHP after administration of anti-CD45-ADC at 0.5 mg/kg, 1 mg/kg or 2 mg/kg.

FIG. 9A is a schematic showing the study design, in which Balb/c mice (CD45.2+) were given 3 immunizations (study day 0, 21, and 42) with recombinant human core G1 aggrecan (60 μg in 2 mg DDA). FIG. 9B graphically depicts the degree of total donor chimerism, neutrophil chimerism, B cell chimerism, and T cell chimerism in the peripheral blood of transplant recipients in the indicated treatment groups at three weeks post-transplant. FIG. 9C graphically depicts the degree of total donor chimerism and donor HSCs in the bone marrow of transplant-recipients in the indicated treatment groups at three weeks post-transplant. FIG. 9D shows images of mice treated with a control or CD45-ADC. FIG. 9E graphically depicts cumulative arthritis score as a function of days post final immunization in the indicated treatment groups.

FIG. 10A graphically depicts the percentage of human hematopoietic cells (human $\beta_2$M+ cells) in the peripheral blood in mice treated with PBS, an isotype-ADC (3 mg/kg), or an anti-human CD45 ADC (1 mg/kg or 3 mg/kg) at Day 0, Day 7, or Day 14 post-treatment. FIG. 10B graphically depicts the number of human hematopoietic cells (human $\beta_2$M+ cells)/femur in the bone marrow of mice treated with PBS, an isotype-ADC (3 mg/kg), or an anti-human CD45 ADC (1 mg/kg or 3 mg/kg). FIG. 10C graphically depicts the number of human CD34+ CD38$^{neg}$ cells/Femur in the bone marrow of mice treated with PBS, an isotype-ADC (3 mg/kg), or an anti-human CD45 ADC (1 mg/kg or 3 mg/kg). FIG. 10D shows an image of mice treated with either an isotype-ADC or an anti-human CD45-targeting ADC before treatment (pre-ADC) and 14 days post-administration of the ADC. FIG. 10E graphically depicts the clinical GVHD score (based on the size and presentation of skin lesions) as a function of days post-ADC administration for mice treated with an isotype-ADC or anti-CD45 ADC. FIG. 10F graphically depicts the degree of peripheral human T cell depletion at Day 0, Day 7, Day 14, and Day 62 in animals treated with the anti-human CD45 ADC.

FIG. 11A depicts the adoptive transfer of OT-I and OT-II into RIP-OVA mice. FIG. 11B graphically depicts the diabetes incidence of mice in the indicated treatment groups.

DETAILED DESCRIPTION

Figure 1A:
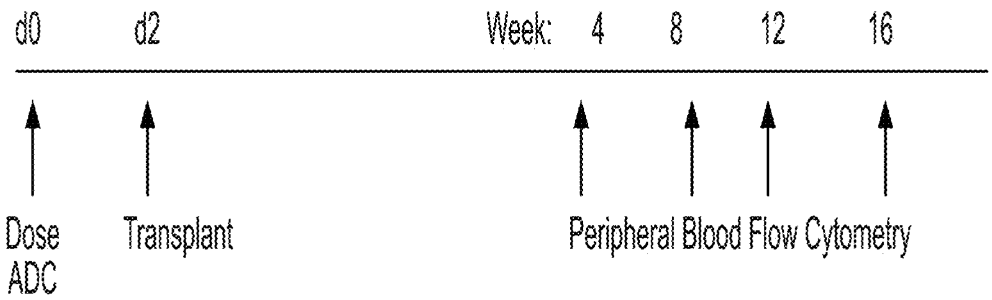
FIGS. 1A-1E depict results of an in vivo study demonstrating that an anti-CD45 ADC successfully conditions mice for congenic transplant.

Disclosed herein are methods and compositions relating to anti-CD45 antibody drug conjugates (ADCs) that are useful as therapeutic agents, e.g., in treating autoimmune disorders or acting as a conditioning agent for transplantation. Accordingly, included herein are anti-hematopoietic cell antibodies (anti-CD45 antibodies) are useful in hematopoietic stem cell therapies. For example, the antibodies or ADCs herein are useful in conditioning procedures, in which a patient is prepared for receipt of a transplant including hematopoietic stem cells. Such procedures promote the engraftment of a hematopoietic stem cell transplant. According to the methods described herein, a patient may be conditioned for hematopoietic stem cell transplant therapy by administration to the patient of an anti-CD45 ADC, antibody or antigen-binding fragment thereof capable of binding CD45 (e.g., CD45 expressed by hematopoietic cells (e.g., hematopoietic stem cells or mature immune cells (e.g., T cells)). As described herein, the anti-CD45 antibody may be covalently conjugated to a cytotoxin so as to form an antibody drug conjugate (ADC). Administration of an ADC capable of binding CD45 to a patient having an autoimmune disease can promote the engraftment of a hematopoietic stem cell transplant.

The sections that follow provide a description of anti-CD45 ADCs that can be administered to a patient, such as a patient suffering from an autoimmune disease, in order to promote engraftment of hematopoietic stem cell transplant, as well as methods of administering such therapeutics to a patient (e.g., prior to hematopoietic stem cell transplantation). The methods described herein provide a means for eradicating autoreactive immune cells (CD45+ cells) and re-establishing a self-tolerant immune system, i.e., immune system reset. The methods described herein provide a conditioning therapy for undergoing autoHSCT.

Definitions

Unless stated otherwise, the following terms and phrases as used herein are intended to have the following meanings.

As used herein, the term "about" refers to a value that is within 5% above or below the value being described.

As used herein, the term "allogeneic", when used in the context of transplantation, is used to define cells (or tissue or an organ) that are transplanted from a donor to a recipient of the same species.

As used herein, the term "autologous" refers to cells or a graft where the donor and recipient are the same subject.

As used herein, the term "xenogeneic" refers to cells where the donor and recipient species are different.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In some embodiments, natural killer cells include cell lines, such as NK-92 cells. Further examples of NK cell lines include NKG, YT, NK-YS, HANK-1, YTS cells, and NKL cells. An immune cell can be allogeneic or autologous.

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), and antibody fragments so long as they exhibit the desired antigen-binding activity.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. In some aspects, the CDRs are defined in accordance with Kabat, Chothia, AbM, Contact, or IMGT. See, e.g., Dondelinger et al., "Understanding the Significance and Implications of Antibody Numbering and Antigen-Binding Surface/Residue Definition," Front. Immunol. 9: 2278 (15 pages) (2018), which is herein incorporated by reference in its entirety. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the term "bispecific antibody" refers to an antibody, including but not limited to a monoclonal, e.g., a de-immunized or humanized antibody, that is capable of binding two different epitopes that can be on the same or different antigens. For instance, the first epitope to which the bispecific antibody binds may be located on a first cell surface antigen that is expressed by a hematopoietic stem cell, such as CD45, and the second epitope to which the bispecific antibody binds may be located on a second cell surface antigen, where the first cell surface antigen and the second cell surface antigen are different. In some embodiments, the second cell surface antigen may be expressed by a hematopoietic cell, such as a hematopoietic stem cell, a hematopoietic progenitor cell, or a mature hematopoietic cell. In some embodiments, the binding specificities can be directed towards unique, non-overlapping epitopes on the same target antigen (i.e., a biparatopic antibody).

The term "antigen-binding fragment," as used herein, refers to one or more portions of an antibody that retain the ability to specifically bind to a target antigen. The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')2 fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment that consists of a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

An "intact" or "full length" antibody, as used herein, refers to an antibody having two heavy (H) chain polypeptides and two light (L) chain polypeptides interconnected by disulfide bonds.

The term "specifically binds", as used herein, refers to the ability of an antibody (or ADC) to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. If an antibody specifically binds to SEQ ID NO: "A," then the antibody can bind to all of or some of (i.e., a portion of) the residues in SEQ ID NO: "A." By way of example, an antibody "binds specifically" to a target if the antibody, when labeled, can be competed away from its target by the corresponding non-labeled antibody. In some embodiments, an antibody specifically binds to a target, e.g., an antigen expressed by hematopoietic stem cells, such as CD45; if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In some embodiments, $K_D$ is determined according to standard bio-layer interferometry (BLI). It shall be understood, however, that the antibody may be capable of specifically binding to two or more antigens which are related in sequence. For example, in some embodiments, an antibody can specifically bind to both human and a non-human (e.g., mouse or non-human primate) orthologs of an antigen, e.g., CD45.

In some embodiments, the term "specific binding to CD45" or "specifically binds to CD45," as used herein, refers to an antibody or that binds to CD45 and has a dissociation constant ($K_D$) of $1.0\times10^{-7}$ M or less, as determined by surface plasmon resonance. In some embodiments, $K_D$ (M) is determined according to standard bio-layer interferometry (BLI). In some embodiments, $K_{off}$ (1/s) is determined according to standard bio-layer interferometry (BLI). It shall be understood, however, that the antibody may be capable of specifically binding to two or more antigens which are related in sequence. For example, in some embodiments, an antibody can specifically bind to both human and a non-human (e.g., mouse or non-human primate) orthologs of CD45. Thus, as used herein, an antibody that "specifically binds to human CD45" is intended to refer to an antibody that binds to human CD45 (and possibly CD45 from one or more non-human species) but does not substantially bind to non-CD45 proteins. Preferably, the antibody binds to human CD45 with a $K_D$ of $1\times10^{-7}$ M or less, a $K_D$ of $5\times10^{-8}$ M or less, a $K_D$ of $3\times10^{-8}$ M or less, a $K_D$ of $1\times10^{-8}$ M or less, or a $K_D$ of $5\times10^{-9}$ M or less.

The term "monoclonal antibody" as used herein refers to an antibody that is derived from a single clone and is not limited to antibodies produced through hybridoma technology. Monoclonal antibodies useful with the present disclosure can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

The terms "Fc region," "Fc domain," and "Fc domain" as used herein refer to the portion of an immunoglobulin, e.g., an IgG molecule, that correlates to a crystallizable fragment obtained by papain digestion of an IgG molecule. The Fc region can be an isotype selected from the group consisting of IgG, IgA, IgM, IgD, and IgE. The Fc region comprises the C-terminal half of two heavy chains (e.g., of an IgG molecule) that are linked by disulfide bonds. It has no antigen binding activity but contains the carbohydrate moiety and binding sites for complement and Fc receptors, including the FcRn receptor (see below). For example, an Fc domain contains the entire second constant domain CH2 (residues at EU positions 231-340 of IgG1) and the third constant domain CH3 (residues at EU positions 341-447 of human IgG1). As used herein, the Fc domain includes the "lower hinge region" (residues at EU positions 233-239 of IgG1). Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "modified Fc region" or "variant Fc region" as used herein refers to an IgG Fc domain comprising one or more amino acid substitutions, deletions, insertions or modifications introduced at any position within the Fc domain. In certain aspects a variant IgG Fc domain comprises one or more amino acid substitutions resulting in decreased or ablated binding affinity for an Fc gamma R and/or Clq as compared to the wild type Fc domain not comprising the one or more amino acid substitutions. Further, Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a variant Fc domain (e.g., an antibody, fusion protein or conjugate) can exhibit altered binding affinity for at least one or more Fc ligands (e.g., Fc gamma Rs) relative to a corresponding antibody otherwise having the same amino acid sequence but not comprising the one or more amino acid substitution, deletion, insertion or modifications such as, for example, an unmodified Fc region containing naturally occurring amino acid residues at the corresponding position in the Fc region.

Variant Fc domains are defined according to the amino acid modifications that compose them. For all amino acid substitutions discussed herein in regard to the Fc region, numbering is always according to the EU index as in Kabat. Thus, for example, D265C is an Fc variant with the aspartic acid (D) at EU position 265 substituted with cysteine (C) relative to the parent Fc domain. It is noted that the order in which substitutions are provided is arbitrary.

The terms "Fc gamma receptor" or "Fc gamma R" as used herein refer to any member of the family of proteins that bind the IgG antibody Fc region and are encoded by the FcgammaR genes. In humans this family includes but is not limited to FcgammaRI (CD64), including isoforms FcgammaRIa, FcgammaRIb, and FcgammaRIc; FcgammaRII (CD32), including isoforms FcgammaRIIa (including allotypes H131 and R131), FcgammaRIIb (including FcgammaRIIb-1 and FcgammaRIIb-2), and FcgammaRIIc; and FcgammaRIII (CD16), including isoforms FcgammaRIIIa (including allotypes V158 and F158) and FcgammaRIIIb (including allotypes FcgammaRIIIb-NA1 and FcgammaRIIIb-NA2), as well as any undiscovered human FcgammaRs or FcgammaR isoforms or allotypes. An FcgammaR can be from any organism, including but not limited to humans, mice, rats, rabbits, and monkeys. Mouse FcgammaRs include but are not limited to FcgammaRI(CD64), FcgammaRII (CD32), FcgammaRIII(CD16), and FcgammaRIII-2 (CD16-2), as well as any undiscovered mouse FcgammaRs or FcgammaR isoforms or allotypes.

The term "effector function" as used herein refers to a biochemical event that results from the interaction of an Fc domain with an Fc receptor. Effector functions include but are not limited to ADCC, ADCP, and CDC. By "effector cell" as used herein is meant a cell of the immune system that expresses or one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and gamma delta T cells, and can be from any organism included but not limited to humans, mice, rats, rabbits, and monkeys.

The term "silent", "silenced", or "silencing" as used herein refers to an antibody having a modified Fc region described herein that has decreased binding to an Fc gamma receptor (FcγR) relative to binding of an identical antibody comprising an unmodified Fc region to the FcγR (e.g., a decrease in binding to a FcγR by at least 70%, at least 80%, at least 90%, at least 95%, at least 98%, at least 99%, or 100% relative to binding of the identical antibody comprising an unmodified Fc region to the FcγR as measured by, e.g., BLI). In some embodiments, the Fc silenced antibody has no detectable binding to an FcγR. Binding of an antibody having a modified Fc region to an FcγR can be determined using a variety of techniques known in the art, for example but not limited to, equilibrium methods (e.g., enzyme-linked immunosorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or OCTET® analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

As used herein, the term "identical antibody comprising an unmodified Fc region" refers to an antibody that lacks the recited amino acid substitutions (e.g., D265C, H435A), but otherwise has the same amino acid sequence as the Fc modified antibody to which it is being compared.

The terms "antibody-dependent cell-mediated cytotoxicity" or "ADCC" refer to a form of cytotoxicity in which a polypeptide comprising an Fc domain, e.g., an antibody, bound onto Fc receptors (FcRs) present on certain cytotoxic cells (e.g., primarily NK cells, neutrophils, and macrophages) and enables these cytotoxic effector cells to bind specifically to an antigen-bearing "target cell" and subsequently kill the target cell with cytotoxins. (Hogarth et al., Nature review Drug Discovery 2012, 11:313) It is contemplated that, in addition to antibodies and fragments thereof, other polypeptides comprising Fc domains, e.g., Fc fusion proteins and Fc conjugate proteins, having the capacity to bind specifically to an antigen-bearing target cell will be able to effect cell-mediated cytotoxicity.

For simplicity, the cell-mediated cytotoxicity resulting from the activity of a polypeptide comprising an Fc domain is also referred to herein as ADCC activity. The ability of any particular polypeptide of the present disclosure to mediate lysis of the target cell by ADCC can be assayed. To assess ADCC activity, a polypeptide of interest (e.g., an antibody) is added to target cells in combination with immune effector cells, resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al., J. Exp. Med. 166:1351 (1987); Wilkinson et al., J. Immunol. Methods 258:183 (2001); Patel et al., J. Immunol. Methods 184:29 (1995). Alternatively, or additionally, ADCC activity of the antibody of interest can be assessed in vivo, e.g., in an animal model such as that disclosed in Clynes et al., Proc. Natl. Acad. Sci. USA 95:652 (1998).

As used herein, the terms "condition" and "conditioning" refer to processes by which a patient is prepared for receipt of a transplant, e.g., a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation). According to the methods described herein, a patient may be conditioned for hematopoietic stem cell transplant therapy by administration to the patient of an ADC, antibody, or antigen-binding fragment thereof capable of binding CD45 expressed by hematopoietic stem cells. As described herein, the antibody may be covalently conjugated to a cytotoxin so as to form a drug-antibody conjugate. Administration of an ADC, or antibody, or antigen-binding fragment thereof, capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "effective amount" or "therapeutically effective amount" refers to an amount of a therapeutic agent, e.g., an anti-CD45 ADC, that is sufficient to achieve the desired result or to have an effect on an autoimmune disease in a human patient.

As used herein, the term "half-life" refers to the time it takes for the plasma concentration of the antibody drug in the body to be reduced by one half or 50% in a subject, e.g., a human subject. This 50% reduction in serum concentration reflects the amount of drug circulating.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625,126; 5,633,425; 5,569,825; 5,661,016; 5,545,806; 5,814,318; 5,885,793; 5,916,771; and 5,939,598).

"Humanized" forms of non-human (e.g., murine or rat) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

Also provided are "conservative sequence modifications" of the sequences set forth in SEQ ID NOs described herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD73 antibody is preferably replaced with another amino acid residue from the same side chain family. Methods of identifying nucleotide and amino acid conservative substitutions that do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)).

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells). Such cells may include $CD34^+$ cells. $CD34^+$ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSCs are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self renewal potential (i.e., they survive throughout adulthood, and can be serially transplanted through successive recipients), whereas ST-HSCs have limited self renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, T cells and B cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the terms "subject" and "patient" refer to an organism, such as a human, that receives treatment for a particular disease or condition as described herein.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein "to treat" or "treatment", refer to any improvement of any consequence of disease, such as prolonged survival, less morbidity, and/or a lessening of side effects which are the byproducts of an alternative therapeutic modality; as is readily appreciated in the art, full eradication of disease is a preferred but not a requirement for a treatment act. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of autoimmune cells (e.g., CD45+ autoimmune lymphocytes, such as a CD45+ T-cell that expresses a T-cell receptor that cross-reacts with a self antigen). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, patients that are "in need of" a hematopoietic stem cell transplant include patients that have an autoimmune disease described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. In some embodiments, the subject has an autoimmune disease, such as rheumatoid arthritis (represented by proteoglycan-induced arthritis (PGIA) in a mouse model), autoimmune encephalitis, sclerodermatous graft-vs-host disease, scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety, and particularly as it pertains to pathologies that may be treated by administration of hematopoietic stem cell transplant therapy.

As used herein, the term "vector" includes a nucleic acid vector, such as a plasmid, a DNA vector, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "conjugate" or "antibody drug conjugate" or "ADC" refers to an antibody which is linked to a cytotoxin. An ADC is formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another, e.g., between an antibody and a cytotoxin. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, "drug-to-antibody ratio" or "DAR" refers to the number of drugs, e.g., amatoxin, attached to the antibody of a conjugate. The DAR of an ADC can range from 1 to 8, although higher loads are also possible depending on the number of linkage sites on an antibody. In certain embodiments, the conjugate has a DAR of 1, 2, 3, 4, 5, 6, 7, or 8.

As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art; vinca alkaloids, such as vinblastine, vinblastine sulfate, vincristine, vincristine sulfate, vindesine, and vinorelbine; taxanes, such as docetaxel and paclitaxel; macrolides, such as discodermolides, cochicine, and epothilones, and derivatives thereof, such as epothilone B or a derivative thereof.

As used herein, the term "amatoxin" refers to a member of the amatoxin family of peptides produced by *Amanita phalloides* mushrooms, or derivative thereof, such as a variant or derivative thereof capable of inhibiting RNA polymerase II activity. Amatoxins useful in conjunction with the compositions and methods described herein include compounds described herein, e.g., α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

The term "acyl" as used herein refers to —C(═O)R, wherein R is hydrogen ("aldehyde"), C1-C12 alkyl, C2-C12 alkenyl, C2-C12 alkynyl, C3-C7 carbocyclyl, C6-C20 aryl, 5-10 membered heteroaryl, or 5-10 membered heterocyclyl, as defined herein. Non-limiting examples include formyl, acetyl, propanoyl, benzoyl, and acryloyl.

The term "C1-C12 alkyl" as used herein refers to a straight chain or branched, saturated hydrocarbon having from 1 to 12 carbon atoms. Representative C1-C12 alkyl groups include, but are not limited to, -methyl, -ethyl, -n-propyl, -n-butyl, -n-pentyl, and -n-hexyl; while branched C1-C12 alkyls include, but are not limited to, -isopropyl, -sec-butyl, -isobutyl, -tert-butyl, -isopentyl, and 2-methylbutyl. A C1-C12 alkyl group can be unsubstituted or substituted.

The term "alkenyl" as used herein refers to C2-C12 hydrocarbon containing normal, secondary, or tertiary carbon atoms with at least one site of unsaturation, i.e., a carbon-carbon, sp2 double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a C2-C12 hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a C6-C20 carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroarylalkyl" as used herein refers to an acyclic alkyl radical in which one of the hydrogen atoms bonded to a carbon atom, typically a terminal or sp3 carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline.

Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Typical substituents include, but are not limited to, —X, —R, —OH, —OR, —SH, —SR, NH2, —NHR, —N(R)2, —N+(R)3, —CX3, —CN, —OCN, —SCN, —NCO, —NCS, —NO, —NO2, —N3, —NC(═O)H, —NC(═O)R, —C(═O)H, —C(═O)R, —C(═O)NH2, —C(═O)N(R)2, —SO3-, —SO3H, —S(═O)2R, —OS(═O)2OR, —S(═O)2NH2, —S(═O)2N(R)2, —S(═O)R, —OP(═O)(OH)2, —OP(═O)(OR)2, —P(═O)(OR)2, —PO3, —PO3H2, —C(═O)X, —C(═S)R, —CO2H, —CO2R, —CO2-, —C(═S)OR, —C(═O)SR, —C(═S)SR, —C(═O)NH2, —C(═O)N(R)2, —C(═S)NH2, —C(═S)N(R)2, —C(═NH)NH2, and —C(═NR)N(R)2; wherein each X is independently selected for each occasion from F, C, Br, and I; and each R is independently selected for each occasion from C1-C12 alkyl, C6-C20 aryl, C3-C14 heterocycloalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH2-, —CH2CH2-, —CH2CH(CH3)CH2-, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J. Chem. Educ. 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the invention of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, or carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. “Solvate” means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

Anti-CD45 Antibodies

The invention includes the use of an anti-CD45 antibody, or an antigen-binding portion thereof. Some embodiments include the use of an anti-CD45 ADC that comprises an anti-CD45 antibody, or an antigen-binding portion thereof. The present invention is based in part on the discovery that anti-CD45 antibodies and/or ADCs can be used as therapeutic agents to (i) treat autoimmune diseases characterized by CD45+ cells and (ii) promote the engraftment of transplanted hematopoietic stem cells in a patient in need of transplant therapy. These therapeutic activities can be caused, for instance, by the binding of an anti-CD45 antibody or ADC to endogenous cells expressing CD45 such that endogenous autoimmune cells are eradicated. In this way, transplanted hematopoietic stem cells may successfully engraft in a patient, such as human patient suffering from an autoimmune disease, as the patient will have targeted immune depletion resulting in the re-establishment of a self-tolerant system.

CD45 is a hematopoietic cell-specific transmembrane protein tyrosine phosphatase essential for T and B cell antigen receptor-mediated signaling. CD45 includes a large extracellular domain, and a phosphatase containing cytosolic domain. CD45 may act as both a positive and negative regulator depending on the nature of the stimulus and the cell type involved. Although there are a large number of permutations possible in the CD45 gene, only six isoforms are traditionally identified in humans. The isoforms are RA, RO, RB, RAB, RBC and RABC (Hermiston et al. 2003 “CD45: a critical regulator of signaling thresholds in immune cells.” *Annu Rev Immunol.* 2:107-137). CD45RA is expressed on naïve T cells, and CD45RO is expressed on activated and memory T cells, some B cell subsets, activated monocytes/macrophages, and granulocytes. CD45RB is expressed on peripheral B cells, naïve T cells, thymocytes, weakly on macrophages, and dendritic cells.

Antibodies and antigen-binding fragments capable of binding human CD45 (mRNA NCBI Reference Sequence: NM_080921.3, Protein NCBI Reference Sequence: NP_563578.2), including those capable of binding the isoform CD45RO, can be used in conjunction with the compositions and methods disclosed herein, such as to promote engraftment of hematopoietic stem cell grafts in a patient in need of hematopoietic stem cell transplant therapy. Multiple isoforms of CD45 arise from the alternative splicing of 34 exons in the primary transcript. Splicing of exons 4, 5, 6, and potentially 7 give rise to multiple CD45 variations.

Alternative splicing can result in individual exons or combinations of exons expressed in various isoforms of the CD45 protein (for example, CD45RA, CD45RAB, CD45RABC). In contrast, CD45RO lacks expression of exons 4-6 and is generated from a combination of exons 1-3 and 7-34. There is evidence that exon 7 can also be excluded from the protein, resulting in splicing together of exons 1-3 and 8-34. This protein, designated E3-8, has been detected at the mRNA level but has not been currently identified by flow cytometry.

CD45RO is currently the only known CD45 isoform expressed on hematopoietic stem cells. CD45RA and CD45RABC have not been detected or are excluded from the phenotype of hematopoietic stem cells. There is evidence from studies conducted in mice that CD45RB is expressed on fetal hematopoietic stem cells, but it is not present on adult bone marrow hematopoietic stem cells. Notably, CD45RC has a high rate of polymorphism in exon 6 found within Asian populations (a polymorphism at exon 6 in CD45RC is found in approximately 25% of the Japanese population). This polymorphism leads to high expression of CD45RO and decreased levels of CD45RA, CD45RB, and CD45RC. Additionally, CD45RA variants (such as CD45RAB and CD45RAC) exhibit a polymorphism in exon 4 that has been associated with autoimmune disease.

The presence of CD45RO on hematopoietic stem cells and its comparatively limited expression on other immune cells (such as T and B lymphocyte subsets and various myeloid cells) renders CD45RO a particularly well-suited target for conditioning therapy for patients in need of a hematopoietic stem cell transplant. As CD45RO only lacks expression of exons 4, 5, and 6, its use as an immunogen enables the screening of pan CD45 Abs and CD45RO-specific antibodies.

Anti-CD45 antibodies that can be used in conjunction with the patient conditioning methods described herein include anti-CD45 antibodies, and antigen-binding portions thereof. Antigen-binding portions of antibodies are well known in the art, and can readily be constructed based on the antigen-binding region of the antibody. In exemplary embodiments, the anti-CD45 antibody used in conjunction with the conditioning methods described herein can be a monoclonal antibody or antigen-binding fragment thereof, a polyclonal antibody or antigen-binding fragment thereof, a humanized antibody or antigen-binding fragment thereof, a fully human antibody or antigen-binding fragment thereof, a chimeric antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, or a tandem di-scFv. Exemplary anti-CD45 antibodies which may be used in whole or in part in the ADCs or methods described herein are provided below.

In some embodiments, the anti-CD45 antibody is or is derived from clone H130, which is commercially available from BIOLEGEND® (San Diego, CA), or a humanized variant thereof. Humanization of antibodies can be performed by replacing framework residues and constant region residues of a non-human antibody with those of a germline human antibody according to procedures known in the art (as described, for instance, in Example 7, below). Additional anti-CD45 antibodies that can be used in conjunction with the methods described herein include the anti-CD45 antibodies ab10558, EP322Y, MEM-28, ab10559, 0.N.125, F10-89-4, Hle-1, 2B11, YTH24.5, PD7/26/16, F10-89-4, 1B7, ab154885, B-A11, phosphor S1007, ab170444, EP350, Y321, GA90, D3/9, X1 6/99, and LT45, which are commercially available from ABCAM® (Cambridge, MA), as well as humanized variants thereof. Further anti-CD45 antibodies that may be used in conjunction with the patient conditioning procedures described herein include anti-CD45 antibody HPA000440, which is commercially available from SIGMA-ALDRICH® (St. Louis, MO), and humanized variants thereof. Additional anti-CD45 antibodies that can be used in conjunction with the patient conditioning methods described herein include murine monoclonal antibody BC8, which is described, for instance, in Matthews et al., Blood 78:1864-1874, 1991, the disclosure of which is incorporated herein by reference as it pertains to anti-CD45 antibodies, as well as humanized variants thereof. Further anti-CD45 antibodies that can be used in conjunction with the methods described herein include monoclonal antibody YAML568, which is described, for instance, in Glatting et al., J. Nucl. Med. 8:1335-1341, 2006, the disclosure of which is incorporated herein by reference as it pertains to anti-CD45 antibodies, as well as humanized variants thereof. Additional anti-CD45 antibodies that can be used in conjunction with the patient conditioning procedures described herein include monoclonal antibodies YTH54.12 and YTH25.4, which are described, for instance, in Brenner et al., Ann. N.Y. Acad. Sci. 996:80-88, 2003, the disclosure of which is incorporated herein by reference as it pertains to anti-CD45 antibodies, as well as humanized variants thereof. Additional anti-CD45 antibodies for use with the patient conditioning methods described herein include UCHL1, 2H4, SN130, MD4.3, MBI, and MT2, which are described, for instance, in Brown et al., Immunology 64:331-336, 1998, the disclosure of which is incorporated herein by reference as it pertains to anti-CD45 antibodies, as well as humanized variants thereof. Additional anti-CD45 antibodies that can be used in conjunction with the methods described herein include those produced and released from American Type Culture Collection (ATCC) Accession Nos. RA3-6132, RA3-2C2, and TIB122, as well as monoclonal antibodies C363.16A, and 13/2, which are described, for instance, in Johnson et al., J. Exp. Med. 169:1179-1184, 1989, the disclosure of which is incorporated herein by reference as it pertains to anti-CD45 antibodies, as well as humanized variants thereof. Further anti-CD45 antibodies that can be used in conjunction with the patient conditioning methods described herein include the monoclonal antibodies AHN-12.1, AHN-12, AHN-12.2, AHN-12.3, AHN-12.4, HLe-1, and KC56(T200), which are described, for instance, in Harvath et al., J. Immunol. 146:949-957, 1991, the disclosure of which is incorporated herein by reference as it pertains to anti-CD45 antibodies, as well as humanized variants thereof.

Additional anti-CD45 antibodies that can be used in conjunction with the patient conditioning methods described herein include those described, for example, in U.S. Pat. No. 7,265,212 (which describes, e.g., anti-CD45 antibodies 39E11, 16C9, and 1G10, among other clones); U.S. Pat. No. 7,160,987 (which describe, e.g., anti-CD45 antibodies produced and released by ATCC Accession No. HB-11873, such as monoclonal antibody 6G3); and U.S. Pat. No. 6,099,838 (which describes, e.g., anti-CD45 antibody MT3, as well as antibodies produced and released by ATCC Accession Nos. HB220 (also designated MB23G2) and HB223), as well as US 2004/0096901 and US 2008/0003224 (which describes, e.g., anti-CD45 antibodies produced and released by ATCC Accession No. PTA-7339, such as monoclonal antibody 17.1), the disclosures of each of which are incorporated herein by reference as they pertain to anti-CD45 antibodies.

Further anti-CD45 antibodies that can be used in conjunction with the patient conditioning methods described herein include antibodies produced and released from ATCC Accession Nos. MB4B4, MB23G2, 14.8, GAP 8.3, 74-9-3, I/24.D6, 9.4, 4B2, M1/9.3.4.HL.2, as well as humanized and/or affinity-matured variants thereof. Affinity maturation can be performed, for instance, using in vitro display techniques described herein or known in the art, such as phage display, as described in Example 6, below.

Additional anti-CD45 antibodies that can be used in conjunction with the patient conditioning methods described herein include anti-CD45 antibody T29/33, which is described, for instance, in Morikawa et al., Int. J. Hematol. 54:495-504, 1991, the disclosure of which is incorporated herein by reference as it pertains to anti-CD45 antibodies.

In certain embodiments, the anti-CD45 antibody is selected from apamistamab (also known 90Y-BC8, lomab-B, BC8; as described in, e.g., US20170326259, WO2017155937, and Orozco et al. *Blood.* 127.3 (2016): 352-359) or BC8-B10 (as described, e.g., in Li et al. *PloS one* 13.10 (2018): e0205135), each of which is incorporated by reference. Other anti-CD45 antibodies have been described, for example, in WO2003/048327, WO2016/016442, US2017/0226209, US2016/0152733, U.S. Pat. No. 9,701,756; US2011/0076270, or U.S. Pat. No. 7,825,222, each of which is incorporated by reference in its entirety.

In some embodiments, an anti-CD45 antibody, or antigen-binding fragment thereof, specifically binds to human CD45 at a region comprising the amino acid sequence RNGPHERYHLEVEAGNT (SEQ ID NO: 38). For example, in certain embodiments, the anti-CD45 antibody, or antigen-binding fragment thereof, specifically binds to human CD45 at amino acid residues 486R, 493Y, and 502T of SEQ ID NO: 37 (fragment of CD45 isoform corresponding to NP_002829.3), or at residues corresponding thereto in a region comprising the sequence RNGPHERYHLEVEAGNT (SEQ ID NO: 38; bold residues indicate binding site) in other human CD45 isoforms. In some embodiments, the anti-CD45 antibody, or antigen-binding fragment thereof, specifically binds to a fibronectin domain (e.g., fibronectin d4 domain) of human CD45.

In some embodiments, an isolated anti-CD45 antibody, or an antigen binding portion thereof, specifically binds to an epitope of human CD45 comprising residues 486R, 493Y, and 502T of SEQ ID NO: 37, and also binds to cynomolgous and/or rhesus CD45.

In some embodiments, an isolated anti-CD45 antibody, or an antigen binding portion thereof, specifically binds to an epitope of human CD45 comprising the amino acid sequence RNGPHERYHLEVEAGNT (SEQ ID NO: 38), and also binds to cynomolgous and rhesus CD45.

In some embodiments, an isolated anti-CD45 antibody, or an antigen binding portion thereof, specifically binds to an epitope of human CD45 comprising the amino acid sequence CRPPRDRNGPHERYHLEVEAGNTLVRNESHK (SEQ ID NO: 39), and binds to cynomolgous and rhesus CD45.

In some embodiments, an isolated anti-CD45 antibody, or an antigen binding portion thereof, specifically binds to an epitope of human CD45 comprising residues 486R, 493Y, and 502T of SEQ ID NO: 37; binds to at least one additional amino acid, at least two additional amino acids, at least three additional amino acids, at least four additional amino acids, or at least five additional amino acids in a peptide comprising RNGPHERYHLEVEAGNT (SEQ ID NO: 38), wherein the additional amino acid residues are not residues 486R, 493Y, and 502T of SEQ ID NO: 37; and also binds to cynomolgous and rhesus CD45.

In some embodiments, the invention provides an anti-CD45 antibody, or antigen-binding fragment thereof, comprising binding regions, e.g., CDRs, or variable regions, corresponding to those of AbA. The heavy chain variable region (VH) amino acid sequence of AbA is set forth in SEQ ID NO: 1. The VH CDR domain amino acid sequences of AbA are set forth in SEQ ID NO: 2 (VH CDR1); SEQ ID NO: 3 (VH CDR2), and SEQ ID NO: 4 (VH CDR3). The light chain variable region (VL) amino acid sequence of AbA is described in SEQ ID NO: 5. The VL CDR domain amino acid sequences of AbA are set forth in SEQ ID NO: 6 (VL CDR1); SEQ ID NO: 7 (VL CDR2), and SEQ ID NO: 8 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 1, and a light chain variable region comprising the amino acid sequence as set forth in SEQ ID NO: 5. In some embodiments, the anti-CD45 antibody comprises a heavy chain comprising a CDR1, CDR2 and CDR3 comprising the amino acid sequences set forth in SEQ ID NOs: 2, 3, and 4, and a light chain variable region comprising a CDR1, CDR2 and CDR3 comprising the amino acid sequences set forth in SEQ ID NOs: 6, 7, and 8.

In some embodiments, the invention provides an anti-CD45 antibody, or antigen-binding fragment thereof, comprising binding regions, e.g., CDRs, or variable regions, corresponding to those of AbB. The heavy chain variable region (VH) amino acid sequence of AbB is set forth in SEQ ID NO: 9. The VH CDR domain amino acid sequences of AbB are set forth in SEQ ID NO: 10 (VH CDR1); SEQ ID NO: 11 (VH CDR2), and SEQ ID NO: 12 (VH CDR3). The light chain variable region (VL) amino acid sequence of AbB is described in SEQ ID NO: 13. The VL CDR domain amino acid sequences of AbB are set forth in SEQ ID NO: 14 (VL CDR1); SEQ ID NO: 15 (VL CDR2), and SEQ ID NO: 16 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 9, and a light chain variable region comprising the amino acid sequence as set forth in SEQ ID NO: 13. In some embodiments, the anti-CD45 antibody comprises a heavy chain comprising a CDR1, CDR2 and CDR3 comprising the amino acid sequences set forth in SEQ ID NOs: 10, 11, and 12, and a light chain variable region comprising a CDR1, CDR2 and CDR3 comprising the amino acid sequences set forth in SEQ ID NOs: 14, 15, and 16.

In some embodiments, the invention provides an anti-CD45 antibody, or antigen-binding fragment thereof, comprising binding regions, e.g., CDRs, or variable regions, corresponding to those of AbC. The heavy chain variable region (VH) amino acid sequence of AbC is set forth in SEQ ID NO: 17 (see Table 6). The VH CDR domain amino acid sequences of AbC are set forth in SEQ ID NO: 18 (VH CDR1); SEQ ID NO: 19 (VH CDR2), and SEQ ID NO: 20 (VH CDR3). The light chain variable region (VL) amino acid sequence of AbC is described in SEQ ID NO: 21 (see Table 6). The VL CDR domain amino acid sequences of AbC are set forth in SEQ ID NO: 22 (VL CDR1); SEQ ID NO: 23 (VL CDR2), and SEQ ID NO: 24 (VL CDR3). Accordingly, in certain embodiments, the anti-CD45 antibody, or antigen-binding fragment thereof, provided herein comprises a heavy chain variable region comprising the amino acid sequence set forth in SEQ ID NO: 17, and a light chain variable region comprising the amino acid sequence as set forth in SEQ ID NO: 21. In some embodiments, the anti-CD45 antibody comprises a heavy chain comprising a CDR1, CDR2 and CDR3 comprising the amino acid sequences set forth in SEQ ID NOs: 18, 19, and 20, and a light chain variable region comprising a CDR1, CDR2 and CDR3 comprising the amino acid sequences set forth in SEQ ID NOs: 22, 23, and 24.

In certain embodiments, an antibody comprises a modified heavy chain (HC) variable region comprising a HC variable domain described in Table 6, or a variant of a HC variable region in Table 6, which variant (i) differs from a HC variable domain described in Table 6 in 1, 2, 3, 4 or 5 amino acids substitutions, additions or deletions; (ii) differs from a HC variable domain described in Table 6 in at most 5, 4, 3, 2, or 1 amino acids substitutions, additions or deletions; (iii) differs from a HC variable domain described in Table 6 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to a HC variable domain described in Table 6, wherein in any of (i)-(iv), an amino acid substitution may be a conservative amino acid substitution or a non-conservative amino acid substitution.

In certain embodiments, an antibody comprises a modified light chain (LC) variable region comprising a LC variable domain described in Table 6, or a variant thereof, which variant (i) differs from a LC variable domain described in Table 6 in 1, 2, 3, 4 or 5 amino acids substitutions, additions or deletions; (ii) differs from a LC variable domain described in Table 6 in at most 5, 4, 3, 2, or 1 amino acids substitutions, additions or deletions; (iii) differs from a LC variable domain described in Table 6 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to a LC variable domain described in Table 6, wherein in any of (i)-(iv), an amino acid substitution may be a conservative amino acid substitution or a non-conservative amino acid substitution.

In certain embodiments, an anti-CD45 antibody comprises the CDRs described herein in Table 6 wherein the CDR comprises a conservative amino acid substitution (or 2, 3, 4, or 5 amino acid substitutions) while retaining the CD45 binding specificity of the antibody (i.e., specificity similar to AbA, AbB, or AbC).

In certain embodiments, an anti-CD45 antibody is a de-immunized antibody based on AbA, AbB or AbC antibodies, or antigen binding portions thereof. A de-immunized antibody is one whose V regions have been chosen to lack T-cell epitopes or altered to remove T-cell epitopes, thereby minimizing or eliminating the potential for the antibody to be immunogenic. In certain embodiments, an anti-CD45 antibody is de-immunized by selecting or engineering framework domains to be without T-cell epitopes, which if present in the antibody sequence would enable the human subject to make a HAHA/HAMA response against the anti-CD45 antibody, resulting in an immune-mediated reaction that causes adverse events in human subjects or diminished treatment effectiveness. The antibodies disclosed herein (i.e., the AbA, AbB, and AbC variable and CDR sequences described herein) can serve as a parent sequence from which a de-immunized antibody can be derived.

Additional anti-CD45 antibodies are provided in International Patent Application Nos. PCT/US2019/058973 and PCT/US2019/058971, the entire contents of each of which are incorporated herein by reference.

Additional anti-CD45 antibodies, and antigen-binding portions thereof, can be generated using art recognized methods, including but not limited to the methods of identifying antibodies described herein (e.g., high throughput screening of antibody libraries, phage display, computational modeling, etc.).

The disclosures of each of the foregoing publications are incorporated herein by reference in their entirety.

The antibodies or antigen binding fragments thereof described herein and used in the ADCs described herein may include modifications and/or mutations that alter the properties of the antibodies and/or fragments, such as those that increase half-life, increase or decrease ADCC, etc., as is known in the art.

In some embodiments, the ADC comprises a bispecific antibody or antigen binding portion thereof, that specifically binds to CD45, and an additional target antigen. Some embodiments comprising bispecific binding agents that comprise an antigen binding moiety comprising an anti-CD45 antibody, or antigen binding portion thereof, e.g., a half-antibody, scFv, Fab, Fab', a Fab, a Fab', a di-scFv, a tandem di-scFv, a tri-scFv, a tandem tri-scFv, a Fv, a disulfide linked Fv, a DART, a single domain antibody (sdAb), a diabody, a tandem diabody, a triabody or a tandem triabody, or a portion thereof. In some embodiments, the anti-CD45 antibody, or antigen binding portion thereof, is a de-immunized anti-CD45 antibody, or antigen binding portion thereof. In some embodiments, the anti-CD45 antibody, or antigen binding portion thereof, is a chimeric anti-CD45 antibody, or antigen binding portion thereof. In other embodiments, the anti-CD45 antibody, or antigen binding portion thereof, is a humanized anti-CD45 antibody, or antigen binding portion thereof. In other embodiments, the anti-CD45 antibody, or antigen binding portion thereof, is a fully human anti-CD45 antibody, or antigen binding portion thereof. In some embodiments, an anti-CD45 binding agent, or portion thereof, described herein can be incorporated into an anti-CD45 bispicific binding agents. For example, in some embodiments, an anti-CD45 bispecific binding agent can comprise a heavy chain variable region sequence of SEQ ID NO:1, and a light chain variable region sequence of SEQ ID NO:5. In some embodiments, an anti-CD45 bispecific binding agent can comprise a heavy chain variable region comprising a CDR1, CDR2 and CDR3 comprising the amino acid sequences set forth in SEQ ID NOs: 2, 3, and 4, and a light chain variable region comprising a CDR1, CDR2 and CDR3 comprising the amino acid sequences set forth in SEQ ID NOs: 6, 7, and 8.

in some embodiments, an anti-CD45 bispecific binding agent can comprise a heavy chain variable region sequence of SEQ ID NO:9, and a light chain variable region sequence of SEQ ID NO:13. In some embodiments, an anti-CD45 bispecific binding agent can comprise a heavy chain variable region comprising a CDR1, CDR2 and CDR3 comprising the amino acid sequences set forth in SEQ ID NOs: 10, 11, and 12, and a light chain variable region comprising a CDR1, CDR2 and CDR3 comprising the amino acid sequences set forth in SEQ ID NOs: 14, 15, and 16. in some embodiments, an anti-CD45 bispecific binding agent can comprise a heavy chain variable region sequence of SEQ ID NO:17, and a light chain variable region sequence of SEQ ID NO:21. In some embodiments, an anti-CD45 bispecific binding agent can comprise a heavy chain variable region comprising a CDR1, CDR2 and CDR3 comprising the amino acid sequences set forth in SEQ ID NOs: 18, 19, and 20, and a light chain variable region comprising a CDR1, CDR2 and CDR3 comprising the amino acid sequences set forth in SEQ ID NOs: 22, 23, and 24.

Other anti-CD45 antibodies or binding agents known in the art or identified using the methods set forth herein can additionally or alternatively be used in the bispecific binding agents described herein.

Fc-Modified Antibodies

Antibodies and/or ADCs used in the invention may, in certain embodiments, comprise an anti-CD45 antibody, or antigen binding portion thereof having an Fc modification(s) that allows Fc silencing. The Fc-modified antibodies or ADCs herein not only allow for selective depletion of endogenous hematopoietic stem cells but also have reduced cytotoxic effects on the exogenous hematopoietic stem cell transplant, thereby further promoting engraftment of the hematopoietic stem cell graft.

The antibodies or binding fragments described herein may also include modifications and/or mutations that alter the properties of the antibodies and/or fragments, such as those that increase half-life, or increase or decrease ADCC.

In some embodiments, antibodies comprising one or more radiolabeled amino acids are provided. A radiolabeled antibody may be used for both diagnostic and therapeutic purposes (conjugation to radiolabeled molecules is another possible feature). Non-limiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

In some embodiments, an anti-CD45 ADC comprises an anti-CD45 antibody, or binding fragment thereof, comprising a modified Fc region, wherein said modified Fc region comprises at least one amino acid modification relative to a wild-type Fc region, such that said molecule has an altered affinity for or binding to an FcgammaR (FcγR). Certain amino acid positions within the Fc region are known through crystallography studies to make a direct contact with FcγR. Specifically, amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). The antibodies described herein may comprise variant Fc regions comprising modification of at least one residue that makes a direct contact with an FcγR based on structural and crystallographic analysis. In some embodiments, the Fc region of the anti-CD45 antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody. In some embodiments, the Fc region comprises a D265A mutation. In some embodiments, the Fc region comprises a D265C mutation. In some embodiments, the Fc region of the antibody (or fragment thereof) comprises an amino acid substitution at amino acid 234 according to the EU index as in Kabat.

In some embodiments, the Fc region comprises a mutation at an amino acid position of D265, V205, H435, I253, and/or H310. For example, specific mutations at these positions include D265C, V205C, H435A, I253A, and/or H310A.

In some embodiments, the Fc region comprises a L234A mutation. In some embodiments, the Fc region of the anti-CD45 antibody (or fragment thereof) comprises an amino acid substitution at amino acid 235 according to the EU index as in Kabat. In some embodiments, the Fc region comprises a L235A mutation. In yet another embodiment, the Fc region comprises a L234A and L235A mutation. In a further embodiment, the Fc region comprises a D265C, L234A, and L235A mutation. In yet a further embodiment, the Fc region comprises a D265C, L234A, L235A, and H435A mutation. In a further embodiment, the Fc region comprises a D265C and H435A mutation.

In some embodiments, the anti-CD45 antibody herein comprises an Fc region comprising one of the following modifications or combinations of modifications: D265A, D265C, D265C/H435A, D265C/LALA, D265C/LALA/H435A, D265C/N297G, D265C/N297G/H435A, D265C (IgG2*), D265C (IgG2)/H435A, D265C/N297Q/H435A, D265C/N297Q, EPLVLAdeIG/H435A, N297A, N297G, or N297Q.

Binding or affinity between a modified Fc region and a Fc gamma receptor can be determined using a variety of techniques known in the art, for example but not limited to, equilibrium methods (e.g., enzyme-linked immunosorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE® analysis or OCTET™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with the antibody of interest conjugated to a labeled compound in the presence of increasing amounts of an unlabeled second antibody.

In some embodiments, an antibody having the Fc modifications described herein (e.g., D265C, L234A, L235A, and/or H435A) has at least a 70% decrease, at least an 80% decrease, at least a 90% decrease, at least a 95% decrease, at least a 98% decrease, at least a 99% decrease, or a 100% decrease in binding to a Fc gamma receptor relative to binding of the identical antibody comprising an unmodified Fc region to the Fc gamma receptor (e.g., as assessed by biolayer interferometry (BLI)).

Fc region binding interactions with a Fc gamma receptor are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and/or a D265C mutation) has substantially reduced or abolished effector functions. Effector functions can be assayed using a variety of methods known in the art, e.g., by measuring cellular responses (e.g., mast cell degranulation or cytokine release) in response to the antibody of interest. For example, using standard methods in the art, the Fc-modified antibodies can be assayed for their ability to trigger mast cell degranulation or for their ability to trigger cytokine release, e.g. by human peripheral blood mononuclear cells.

Thus, in some embodiments, the Fc region comprises a mutation resulting in a decrease in half-life (e.g., relative to an antibody having an unmodified Fc region). An antibody having a short half-life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express a target antigen (e.g., CD45) but are not the target of the anti-CD45 antibody unlike the endogenous stem cells. In some embodiments, the Fc regions comprise a mutation at position 435 (EU index according to Kabat). In some embodiments, the mutation is an H435A mutation.

In some embodiments, the anti-CD45 described herein has a half-life (e.g., in humans) equal to or less than 24 hours, equal to or less than 23 hours, equal to or less than 22 hours, equal to or less than 21 hours, equal to or less than 20 hours, equal to or less than 19 hours, equal to or less than 18 hours, equal to or less than 17 hours, equal to or less than 16 hours, equal to or less than 15 hours, equal to or less than 14 hours, equal to or less than 13 hours, equal to or less than 12 hours, or equal to or less than 11 hours.

In some embodiments, the anti-CD45 antibody described herein has a half-life (e.g., in humans) 1-5 hours, 5-10 hours, 10-15 hours, 15-20 hours, or 20 to 25 hours.

In some aspects, the Fc region comprises two or more mutations that confer reduced half-life and reduce an effector function of the antibody. In some embodiments, the Fc region comprises a mutation resulting in a decrease in half-life and a mutation of at least one residue that can make direct contact with an FcγR (e.g., as based on structural and crystallographic analysis). In some embodiments, the Fc region comprises a H435A mutation, a L234A mutation, and a L235A mutation. In some embodiments, the Fc region comprises a H435A mutation and a D265C mutation. In some embodiments, the Fc region comprises a H435A mutation, a L234A mutation, a L235A mutation, and a D265C mutation.

In some embodiments, the antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In some embodiments, the Fc region of the anti-CD45 antibody (or fragment thereof) comprises an amino acid substitution at amino acid 265 according to the EU index as in Kabat. In some embodiments, the Fc region comprises a D265C mutation. In some embodiments, the Fc region comprises a D265C and H435A mutation. In some embodiments, the Fc region comprises a D265C, a L234A, and a L235A mutation. In some embodiments, the Fc region comprises a D265C, a L234A, a L235A, and a H435A mutation.

Notably, Fc amino acid positions are in reference to the EU numbering index unless otherwise indicated.

The disclosures of each of the foregoing publications are incorporated herein by reference as they pertain to Fc regions. Antibodies and antigen-binding fragments that may be used in conjunction with the compositions and methods described herein include the above-described antibodies and antigen-binding fragments thereof, as well as variants of those non-human antibodies and antigen-binding fragments described above and antibodies or antigen-binding fragments that bind the same epitope as those described above, as assessed, for instance, by way of a competitive antigen binding assay.

Methods of engineering antibodies to include any of the Fc modifications herein are well known in the art. These methods include, but are not limited to, preparation by site-directed (or oligonucleotide-mediated) mutagenesis, PCR mutagenesis, and cassette mutagenesis of a prepared DNA molecule encoding the antibody or at least the constant region of the antibody. Site-directed mutagenesis is well known in the art (see, e.g., Carter et al., Nucleic Acids Res., 13:4431-4443 (1985) and Kunkel et al., Proc. Natl. Acad. Sci. USA, 82:488 (1987)). PCR mutagenesis is also suitable for making amino acid sequence variants of the starting polypeptide. See Higuchi, in PCR Protocols, pp. 177-183 (Academic Press, 1990); and Vallette et al., Nuc. Acids Res. 17:723-733 (1989). Another method for preparing sequence variants, cassette mutagenesis, is based on the technique described by Wells et al., Gene, 34:315-323 (1985).

Methods of Identifying Antibodies

Methods for high throughput screening of antibody, or antibody fragment libraries capable of binding CD45 expressed by hematopoietic stem cells can be used to identify anti-CD45 antibodies useful for treating autoimmune diseases, and conditioning a patient (e.g., a human patient) in need of hematopoietic stem cell therapy as described herein. Such methods include in vitro display techniques known in the art, such as phage display, bacterial display, yeast display, mammalian cell display, ribosome display, mRNA display, and cDNA display, among others.

The use of phage display to isolate antibodies, or antigen-binding fragments, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348:552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). Human anti-CD45 antibodies can also be generated, for example, in the HUMAB-MOUSE® or XENOMOUSE™. These techniques, among others, can be used to identify and improve the affinity of antibodies, antibody or fragments, capable of binding CD45 expressed by hematopoietic stem cells in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies capable of binding an antigen (e.g., CD45) expressed by hematopoietic stem cells or immune cells. For example, using computational modeling techniques, one of skill in the art can screen libraries of antibodies, or antibody fragments, in silico for molecules capable of binding specific epitopes on an antigen expressed by hematopoietic stem cells or immune cells (e.g., CD45), such as extracellular epitopes of the antigen.

Additional techniques can be used to identify antibodies, or antibody fragments, capable of binding CD45 expressed by hematopoietic stem cells and that are internalized by the cell, for instance, by receptor-mediated endocytosis. For example, the in vitro display techniques described above can be adapted to screen for antibodies, or antibody fragments, that bind CD45 and that are subsequently internalized. Phage display represents one such technique that can be used in conjunction with this screening paradigm. To identify an anti-CD45 antibody, or antibody fragment, that can be internalized by hematopoietic stem cells or immune cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD45 for instance, by first incubating the phage library with blocking agents (such as, for instance, milk protein, bovine serum albumin, and/or IgG so as to remove phage encoding antibodies, or antibody fragments, that exhibit non-specific protein binding and phage that encode antibodies or fragments thereof that bind Fc domains, and then incubating the phage library with a population of cells, e.g., hematopoietic stem cells, which express CD45. The phage library can be incubated with the hematopoietic stem cells for a time sufficient to allow anti-CD45 antibodies, or antibody fragments, to bind the cognate cell-surface antigen and to subsequently be internalized by the hematopoietic stem cells (e.g., from 30 minutes to 6 hours at 4° C., such as 1 hour at 4° C.). Phage containing antibodies, or antibody fragments, that do not exhibit sufficient affinity for the CD45 so as to permit binding to, and internalization by, hematopoietic stem cells can subsequently be removed by washing the cells, for instance, with cold (4° C.) 0.1 M glycine buffer at pH 2.8. Phage bound to antibodies, or antibody fragments, that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or antibody fragments, inserted within the phage genome. The encoded antibodies, or antibody fragments, can subsequently be prepared de novo by chemical synthesis (for instance, of antibody fragments, such as scFv fragments) or by recombinant expression (for instance, of full-length antibodies).

The internalizing capacity of the prepared antibodies, or antibody fragments, can be assessed, for instance, using radionuclide internalization assays known in the art. For example, anti-CD45 antibodies, or antibody fragments, identified using in vitro display techniques described herein or known in the art can be functionalized by incorporation of a radioactive isotope, such as $^{18}F$, $^{75}Br$, $^{77}Br$, $^{122}I$, $^{123}I$, $^{124}I$, $^{125}I$, $^{129}I$, $^{131}I$, $^{211}At$, $^{67}Ga$, $^{111}In$, $^{99}Tc$, $^{169}Yb$, $^{186}Re$, $^{64}Cu$, $^{67}Cu$, $^{177}Lu$, $^{77}As$, $^{72}As$, $^{86}Y$, $^{90}Y$, $^{89}Zr$, $^{212}Bi$, $^{213}Bi$, or $^{225}Ac$. For instance, radioactive halogens, such as $^{18}F$, $^{75}Br$, $^{77}Br$, $^{122}I$, $^{123}I$, $^{124}I$, $^{125}I$, $^{129}I$, $^{131}I$, $^{211}At$, can be incorporated into antibodies, or antibody fragments, using beads, such as polystyrene beads, containing electrophilic halogen reagents (e.g., Iodination Beads, Thermo Fisher Scientific, Inc., Cambridge, MA). Radiolabeled antibodies, fragments thereof, or ADCs, can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof, (e.g., using cold (4° C.) 0.1 M glycine buffer at pH 2.8). Internalized antibodies, or antibody fragments, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibodies may be produced using recombinant methods and compositions, e.g., as described in U.S. Pat. No. 4,816,567. In some embodiments, isolated nucleic acid encoding an anti-CD45 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD45 antibody, a nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR− CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In some embodiments, the host cell is eukaryotic, e.g. a Chinese Hamster Ovary (CHO) cell or lymphoid cell (e.g., Y0, NS0, Sp20 cell).

In certain embodiments antigen binding proteins (the antigen targeting moiety), such as a ligand or functionally active fragment thereof, may be used in the conjugates or fusion proteins described herein. For example, stem cell factor (SCF) is a ligand for CD117, where SCF can be conjugated or fused to a toxin to achieve the conditioning methods disclosed herein.

In certain embodiments, an antibody mimetic is used as the antigen targeting moiety in the compositions and methods disclosed herein. Examples of antibody mimetics include, but are not limited to, an adnectins, an affibody, an afflins, an affimer, an affitin, and alphabody, and anticalin, an aptamer, an armadillo repeat protein-based scaffold, an atrimer, an avimer, a DARpin, a fynomer, a knottin, a Kunitz domain peptide, a monobody, and a nanofitin.

Antibody Drug Conjugates (ADCs)

Antibodies, or antigen-binding fragments thereof, described herein can be conjugated (linked) to a cytotoxin via a linker. In some embodiments, the cytotoxic molecule is conjugated to a cell internalizing antibody, or antigen-binding fragment thereof as disclosed herein such that following the cellular uptake of the antibody, or fragment thereof, the cytotoxin may access its intracellular target and mediate hematopoietic cell death.

Cytotoxins

Various cytotoxins can be conjugated to an anti-CD45 antibody via a linker for use in the therapies described herein. In particular, the anti-CD45 ADCs include an anti-CD45 antibody (or an antigen-binding fragment thereof) conjugated (i.e., covalently attached by a linker) to a cytotoxic moiety (or cytotoxin). In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate T cell death.

ADCs of the present invention therefore may be of the general formula Ab-(Z-L-D)$_n$, wherein an antibody or antigen-binding fragment thereof (Ab) is conjugated (covalently linked) to a linker (L), through a chemical moiety (Z), to a cytotoxic moiety ("drug," D).

Accordingly, the anti-CD45 antibody or antigen-binding fragment thereof may be conjugated to a number of drug moieties as indicated by integer n, which represents the average number of cytotoxins per antibody, which may range, e.g., from about 1 to about 20. In some embodiments, n is from 1 to 4. In some embodiments, n is 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some anti-CD45 ADCs, they may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading (DAR), e.g. n>5, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof, or another cytotoxic compound described herein or known in the art.

In some embodiments, the cytotoxin of the antibody-drug conjugate is an RNA polymerase inhibitor. In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

Additional details regarding cytotoxins that can be used in the anti-CD45 ADCs useful in the compositions and methods of the invention are described below.

Amatoxins

In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

In some embodiments, the cytotoxin of the antibody-drug conjugate is an RNA polymerase inhibitor. In some embodiments, the RNA polymerase inhibitor is an amatoxin or derivative thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. Structures of the various naturally occurring amatoxins are represented by formula III and accompanying Table 1, and are disclosed in, e.g., Zanotti et al., Int. J. Peptide Protein Res. 30, 1987, 450-459.

(III)

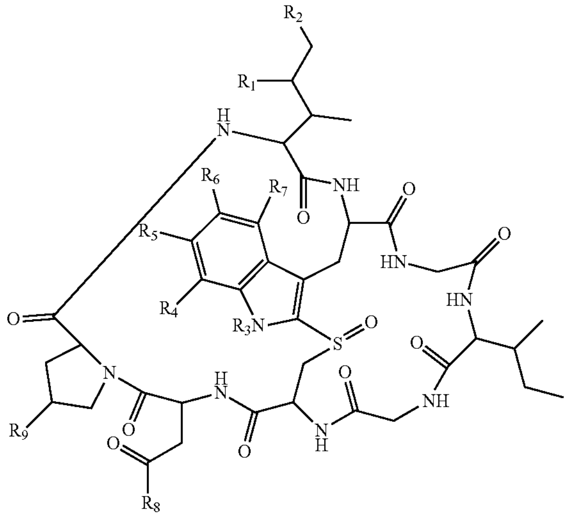

TABLE 1

| Natural Amatoxin structure table. | | | | | | | |
|---|---|---|---|---|---|---|---|
| Name | $R_1$ | $R_2$ | $R_3$, $R_4$ | $R_5$ | $R_6$, $R_7$ | $R_8$ | $R_9$ |
| α-amanitin | OH | OH | H | OH | H | $NH_2$ | OH |
| β-amanitin | OH | OH | H | OH | H | OH | OH |
| γ-amanitin | OH | H | H | OH | H | $NH_2$ | OH |
| ε-amanitin | OH | H | H | OH | H | OH | OH |
| Amanin | OH | OH | H | H | H | OH | OH |
| Amaninamide | OH | OH | H | H | H | $NH_2$ | OH |
| Amanullin | H | H | H | OH | H | $NH_2$ | OH |
| Amanullinic acid | H | H | H | OH | H | OH | OH |
| Proamanullin | H | H | H | OH | H | $NH_2$ | H |

Amatoxins may be isolated from a variety of mushroom species (e.g., *Amanita phalloides, Galerina marginata, Lepiota brunneo-incarnata*) or may be prepared semi-synthetically or synthetically. A member of this family, α-amanitin, is described in Wieland, Int. *J. Pept. Protein Res.* 1983, 22(3):257-276. A derivative of an amatoxin may be obtained by chemical modification of a naturally occurring compound ("semi-synthetic"), or may be obtained from an entirely synthetic source. Synthetic routes to various amatoxin derivatives are disclosed in, for example, U.S. Pat. No. 9,676,702 and in Perrin et al., J. Am. Chem. Soc. 2018, 140, p. 6513-6517, each of which is incorporated by reference herein in their entirety with respect to synthetic methods for preparing and derivatizing amatoxins.

Many positions on amatoxins or derivatives thereof can serve as the position to covalently bond the linking moiety L, and, hence the antibodies or antigen-binding fragments thereof. In some embodiments, the cytotoxin in the ADC's as disclosed herein is an amatoxin or derivative thereof represented by formula (IV):

(IV)

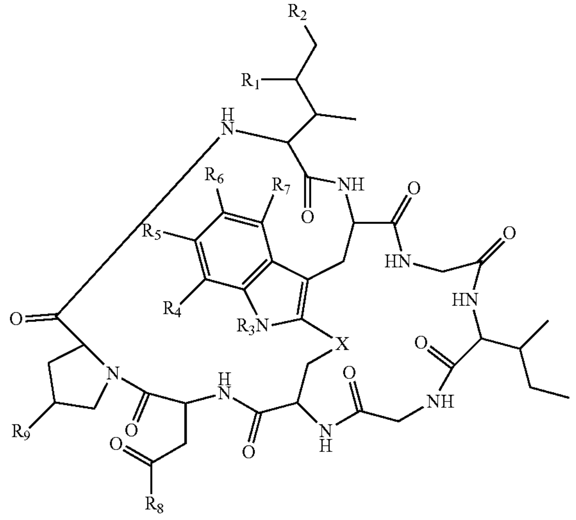

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, in one embodiment, amatoxins useful in conjunction with the compositions and methods described herein include compounds according to formula (IVA)

(IVA)

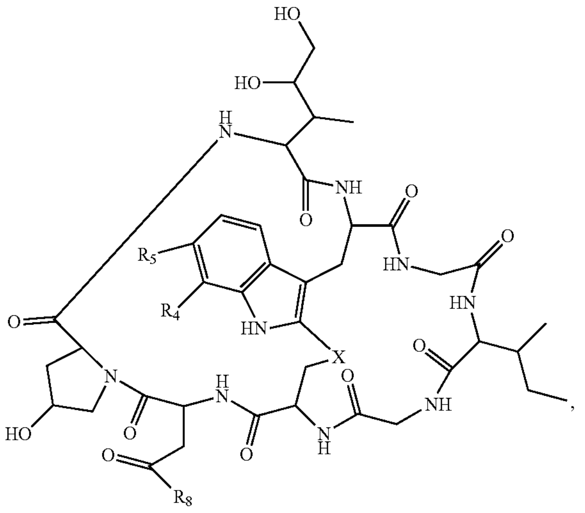

wherein $R_4$, $R_5$, X, and $R_8$ are each as defined above.

For instance, in one embodiment, amatoxins useful in conjunction with the compositions and methods described herein include compounds according to formula (IVB), below:

(IVB)

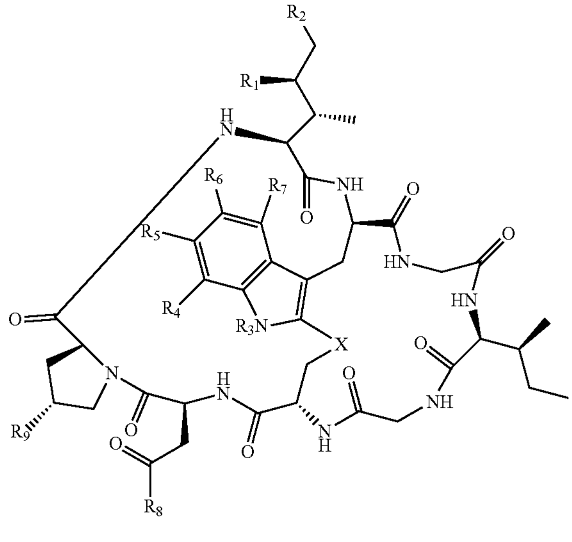

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

In one embodiment, amatoxins useful in conjunction with the compositions and methods described herein also include compounds according to formula (IVC), below:

(IVC)

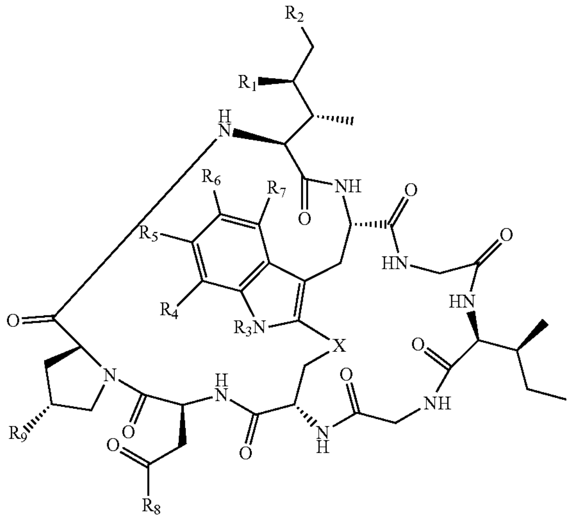

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocycloalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

As described herein, amatoxins may be conjugated to an antibody, or an antigen-binding fragment thereof, for instance, by way of a linker moiety. Exemplary methods of amatoxin conjugation and linkers useful for such processes are described in the section entitled "Linkers for chemical conjugation," as well as in Table 2, below. Exemplary linker-containing amatoxins useful for conjugation to an anti-CD45 antibody, or an antigen-binding fragment, in accordance with the compositions and methods described herein are shown in structural formulas (I), (IA), (IB), (II), (IIA), and (IIB), recited herein.

For instance, the antibodies, and antigen-binding fragments, described herein may be bound to an amatoxin so as to form a conjugate represented by the formula Ab-Z-L-Am, wherein Ab is the antibody, or antigen-binding fragment thereof, L is a linker, Z is a chemical moiety and Am is an amatoxin. Many positions on amatoxins or derivatives thereof can serve as the position to covalently bond the linking moiety L, and, hence the antibodies or antigen-binding fragments thereof. In some embodiments, Am-L-Z is represented by formula (I)

(I)

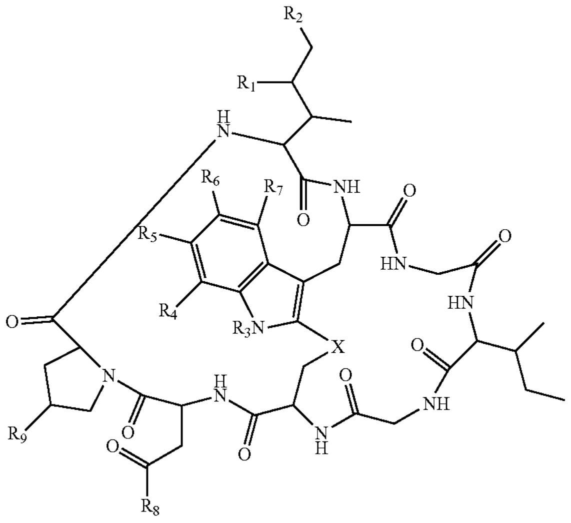

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide (e.g., a dipeptide), —(C═O)—, a disulfide, a hydrazone, a —$(CH_2CH_2O)_p$— group, wherein p is an integer from 1-6, a $((CH_2)_mO)_n(CH_2)_m$— group, where n and each m are each independently selected from 1, 2, 3, 4, 5, 6, 7, 8, 9, and 10; or a combination thereof; and and Z is a chemical moiety formed from a coupling reaction between a reactive substituent present on L and a reactive substituent Z' present within an antibody, or antigen-binding fragment thereof, that binds a target antigen (e.g., CD45).

In some embodiments, Am contains exactly one $R_C$ substituent.

In some embodiments, the linker-reactive substituent group, taken together as L-Z', prior to conjugation with the antibody or antigen binding fragment thereof, has the structure:

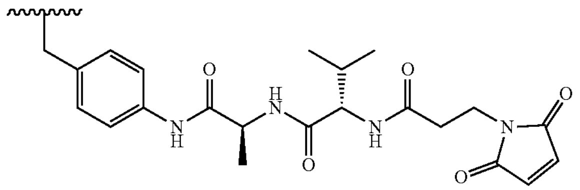 [SMILES: *Cc1ccc(NC(=O)[C@H](C)NC(=O)[C@@H](NC(=O)CCN2C(=O)C=CC2=O)C(C)C)cc1]

where the wavy line indicates the point of attachment to a substituent on the amatoxin. This linker-reactive substituent group L-Z' may alternatively be referred to as N-beta-maleimidopropyl-Val-Ala-para-aminobenzyl (BMP-Val-Ala-PAB). The wavy line at the linker terminus indicates the point of attachment to the amatoxin.

In some embodiments, the linker L and the chemical moiety Z, after conjugation to the antibody, taken together as L-Z-Ab, has the structure:

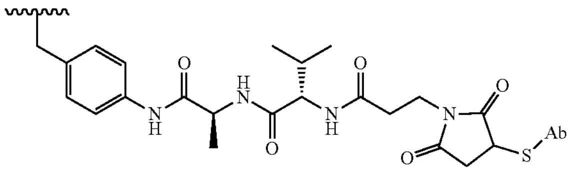

where S is a sulfur atom which represents the reactive substituent present within the CD45 antibody, or antigen-binding fragment thereof, (e.g., from the —SH group of a cysteine residue). The wavy line at the linker terminus indicates the point of attachment to the amatoxin.

In some embodiments, the conjugate is represented by one of formulas V, VA, or VB:

(V)

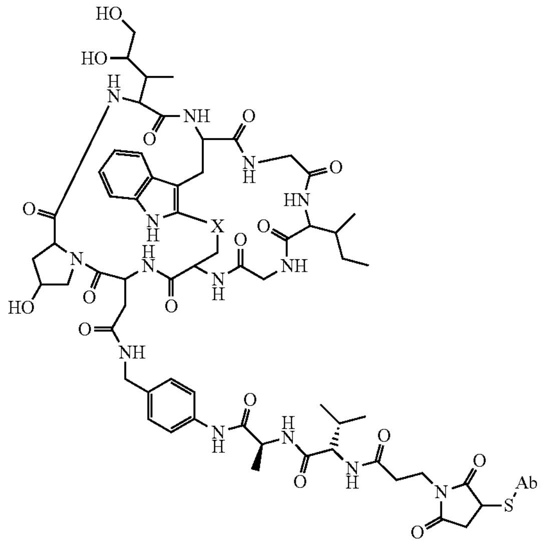

-continued (VA)

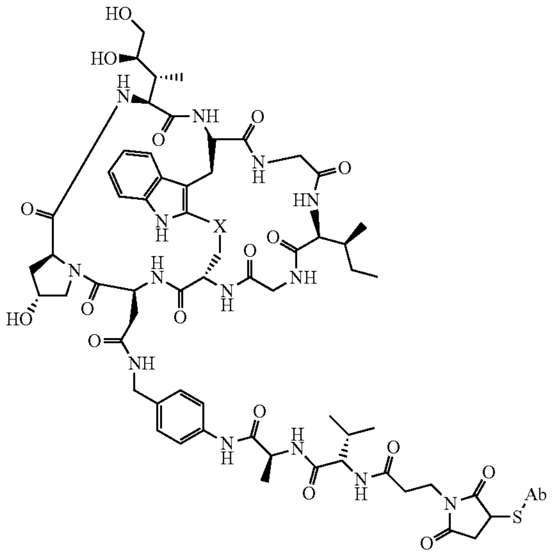

(VB)

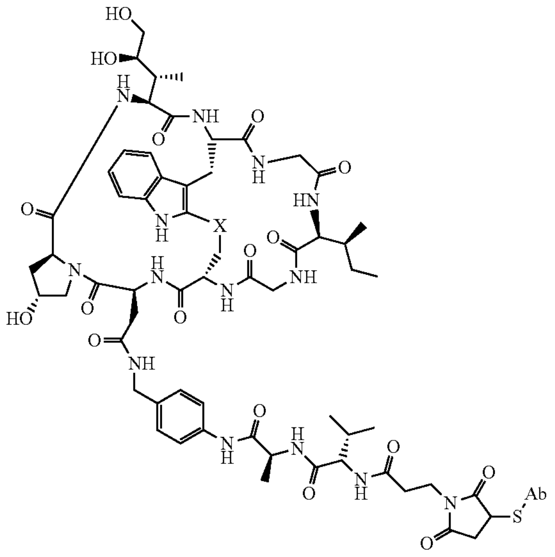

where X is S, SO or $SO_2$, and Ab is the antibody (e.g., anti-CD45 antibody).

In some embodiments, Am-L-Z-Ab is
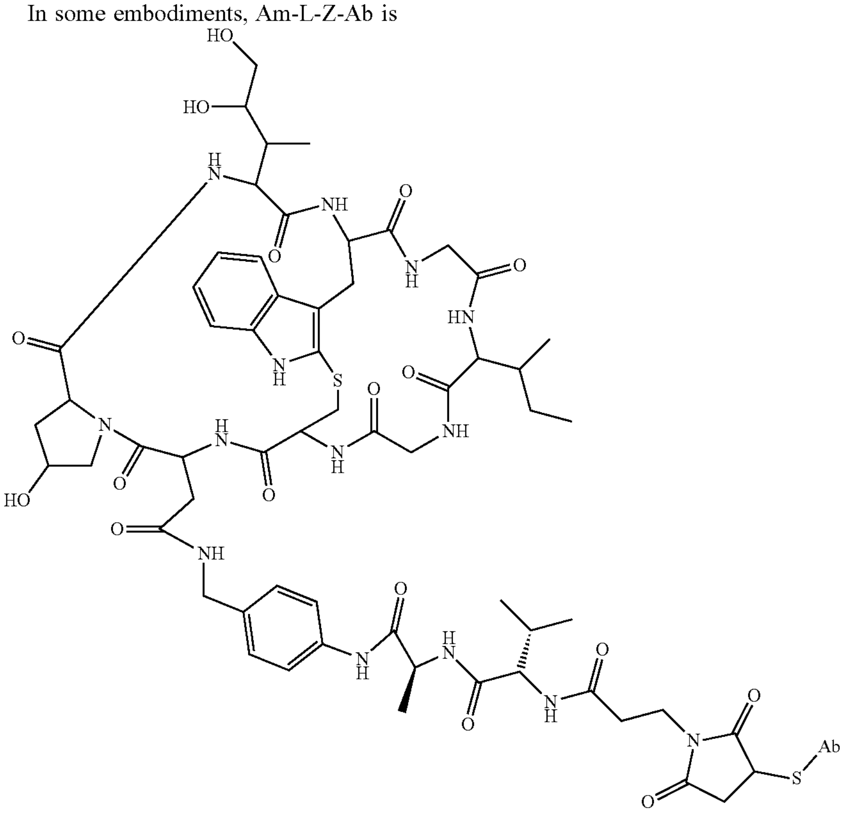
In some embodiments, Am-L-Z-Ab is
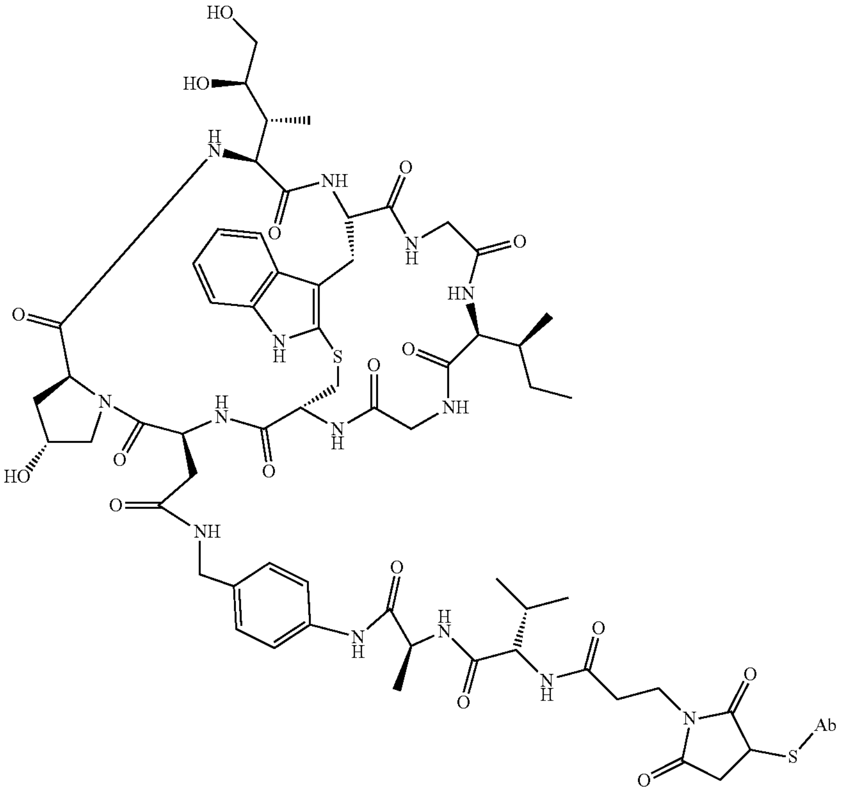

In some embodiments, Am-L-Z-Ab is
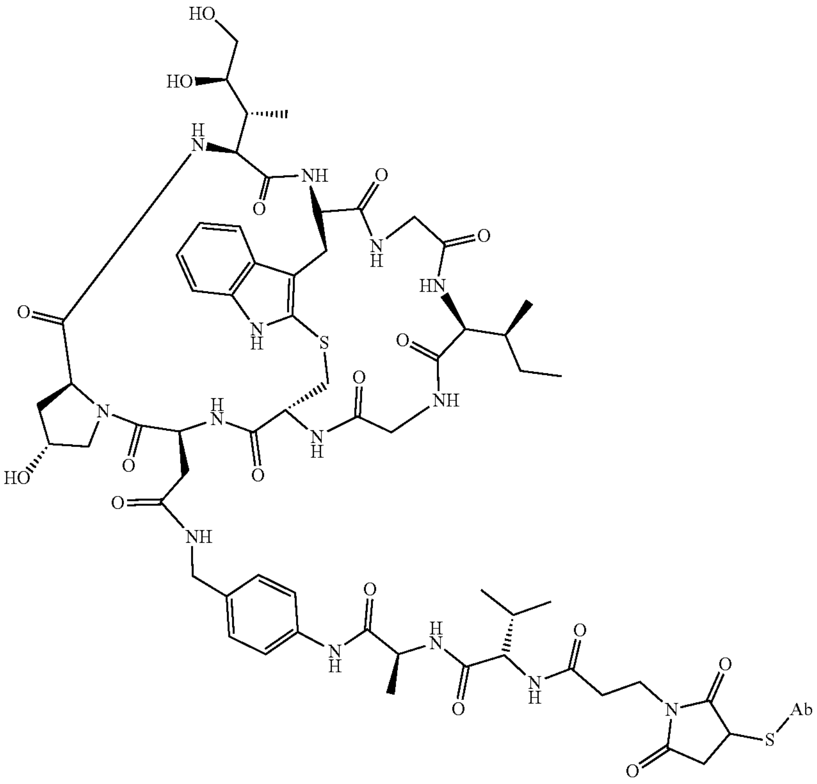
In some embodiments, the Am-L-Z precursor is
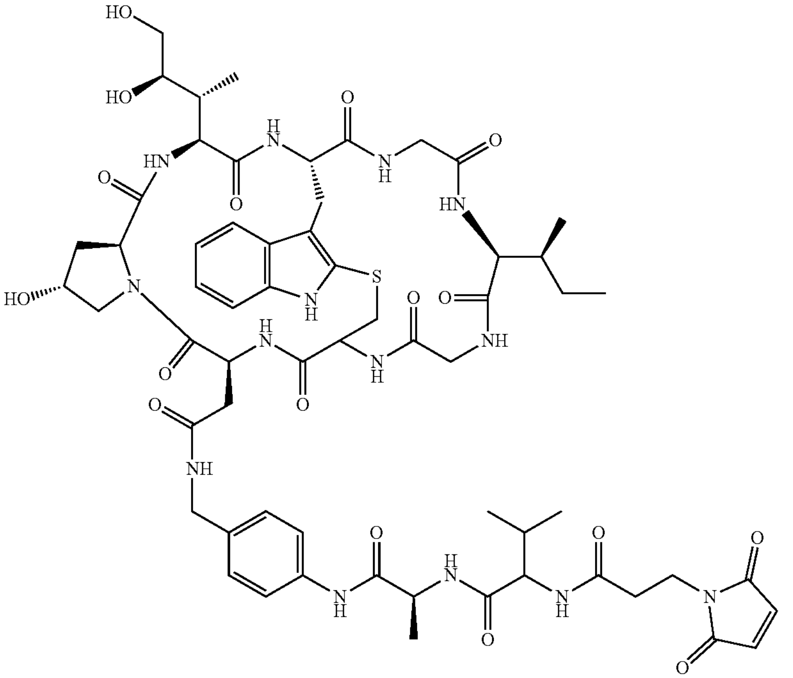 [SMILES: CC[C@H](C)[C@@H]1NC(=O)CNC(=O)[C@@H]2Cc3c([nH]c4ccccc34)SCC(NC(=O)CNC1=O)C(=O)N[C@@H](CC(=O)NCc1ccc(NC(=O)[C@H](C)NC(=O)C(NC(=O)CCN3C(=O)C=CC3=O)C(C)C)cc1)C(=O)N1C[C@H](O)C[C@H]1C(=O)N[C@@H]([C@@H](C)[C@@H](O)CO)C(=O)N2]
wherein the maleimide reacts with a thiol group found on a cysteine in the antibody.

In some embodiments, the Am-L-Z precursor is

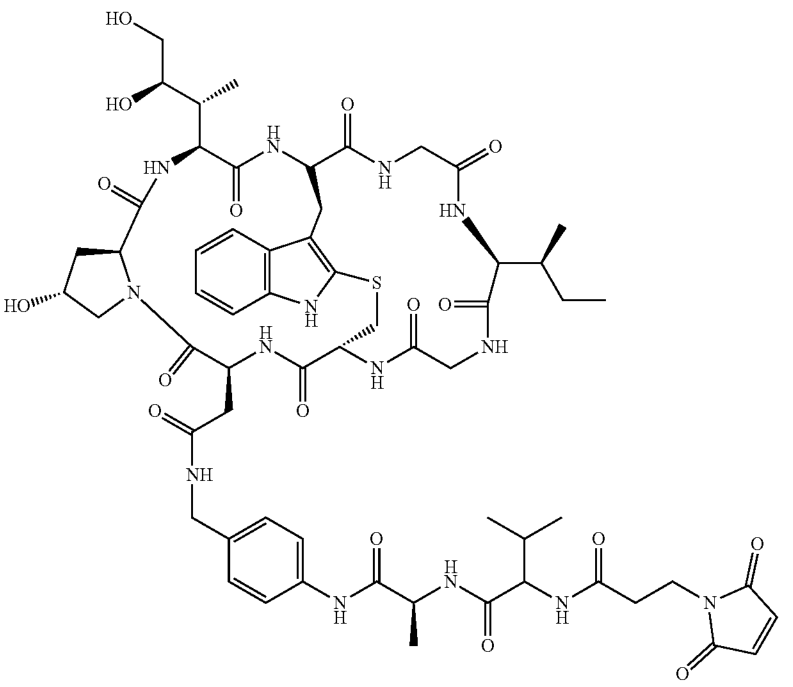

wherein the maleimide reacts with a thiol group found on a cysteine in the antibody.

In some embodiments, Am-L-Z is represented by formula (IA)

(IA)

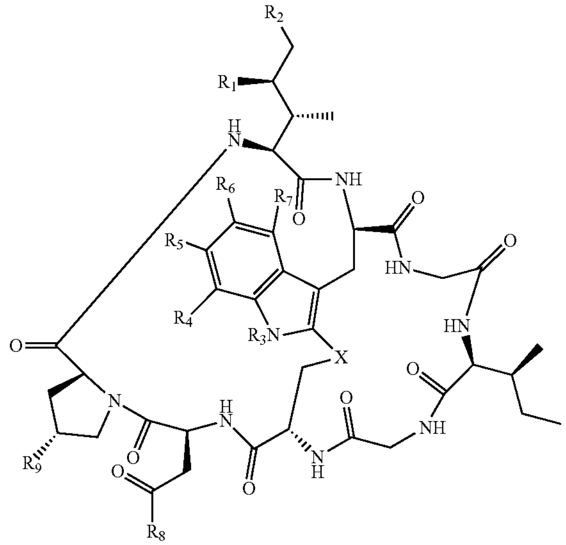

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—, or a combination thereof;

Z is a chemical moiety formed from a coupling reaction between a reactive substituent present on L and a reactive substituent present within an antibody, or antigen-binding fragment thereof, that binds CD45; and wherein Am contains exactly one $R_C$ substituent.

In some embodiments L-Z is

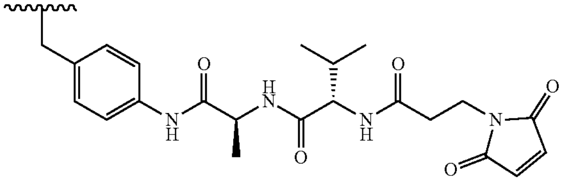 [SMILES: *Cc1ccc(NC(=O)[C@H](C)NC(=O)[C@@H](NC(=O)CCN2C(=O)C=CC2=O)C(C)C)cc1]

In some embodiments, Am-L-Z is represented by formula (IB)

(IB)

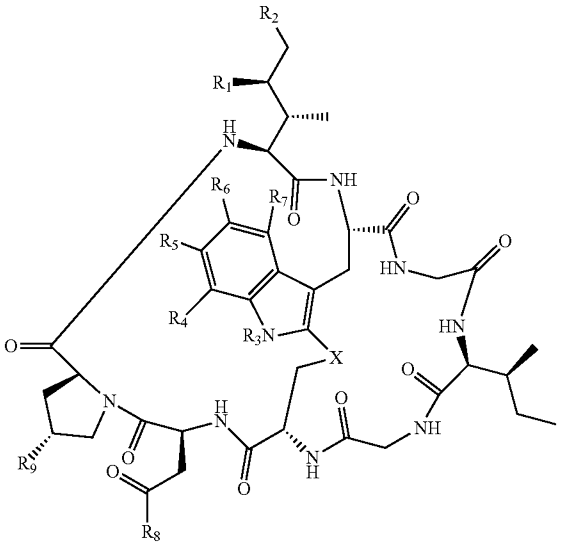

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_5$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a peptide, a dipeptide, —(C═O)—; a disulfide, a hydrazone, a —$(CH_2CH_2O)_p$— group, wherein p is an integer from 1-6, a $((CH_2)_mO)_n(CH_2)_m$— group, where n and each m are each independently selected from 1, 2, 3, 4, 5, 6, 7, and 10 or a combination thereof;

Z is a chemical moiety formed from a coupling reaction between a reactive substituent present on L and a reactive substituent Z' present within an antibody, or antigen-binding fragment thereof, that binds CD45; and wherein Am contains exactly one $R_C$ substituent.

In some embodiments, L-Z-Ab is

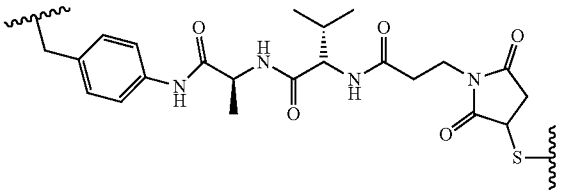

In some embodiments, $R_A$ and $R_B$, when present, together with the oxygen atoms to which they are bound, combine to form a 5-membered heterocycloalkyl group of formula:

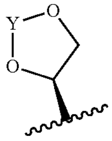

wherein Y is —(C═O)—, —(C═S)—, —(C═$NR_E$)—, or —($CR_ER_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB), wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form:

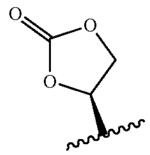 [SMILES: *[C@@H]1COC(=O)O1]

$R_3$ is H or $R_C$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, or $NHR_C$;

$R_9$ is H or OH;

X is —S—, —S(O)—, or —$SO_2$—; and wherein $R_C$ and $R_D$ are each as defined above.

In some embodiments, Am-L-Z is represented by formula (IA) or formula (IB), wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form:

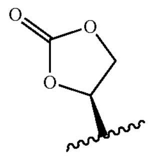 [SMILES: *[C@@H]1COC(=O)O1]

$R_3$ is H or $R_C$;

$R_4$ and $R_5$ are each independently H, OH, $OR_C$, $R_C$, or $OR_D$;

$R_6$ and $R_7$ are each H;

$R_8$ is OH, $NH_2$, $OR_C$, or $NHR_C$;

$R_9$ is H or OH;

X is —S—, —S(O)—, or —$SO_2$—; and wherein $R_C$ is as defined above.

In some embodiments, Am-L-Z is represented by formula (IA) or formula (IB), wherein $R_1$ is H, OH, or $OR_A$;

$R_2$ is H, OH, or $OR_B$;

$R_A$ and $R_B$, when present, together with the oxygen atoms to which they are bound, combine to form:

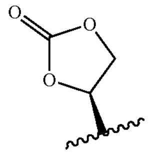 [SMILES: *[C@@H]1COC(=O)O1]

$R_3$, $R_4$, $R_6$, and $R_7$ are each H;

$R_5$ is $OR_C$;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2016/0002298, the disclosure of which is incorporated herein by reference in its entirety.

In some embodiments, Am-L-Z is represented by formula (IA) or formula (IB), wherein $R_1$ and $R_2$ are each independently H or OH;

$R_3$ is $R_C$;

$R_4$, $R_6$, and $R_7$ are each H;

$R_5$ is H, OH, or $OC_1$-$C_6$ alkyl;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H, OH, $OR_C$, or $R_C$;

$R_8$ is OH or $NH_2$;

$R_9$ is H or OH;

X is —S—, —S(O)—, or —$SO_2$—; and wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H or OH;

$R_8$ is OH, $NH_2$, $OR_C$, or $NHR_C$;

$R_9$ is H or OH;

X is —S—, —S(O)—, or —$SO_2$—; and wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

In some embodiments, Am-L-Z is

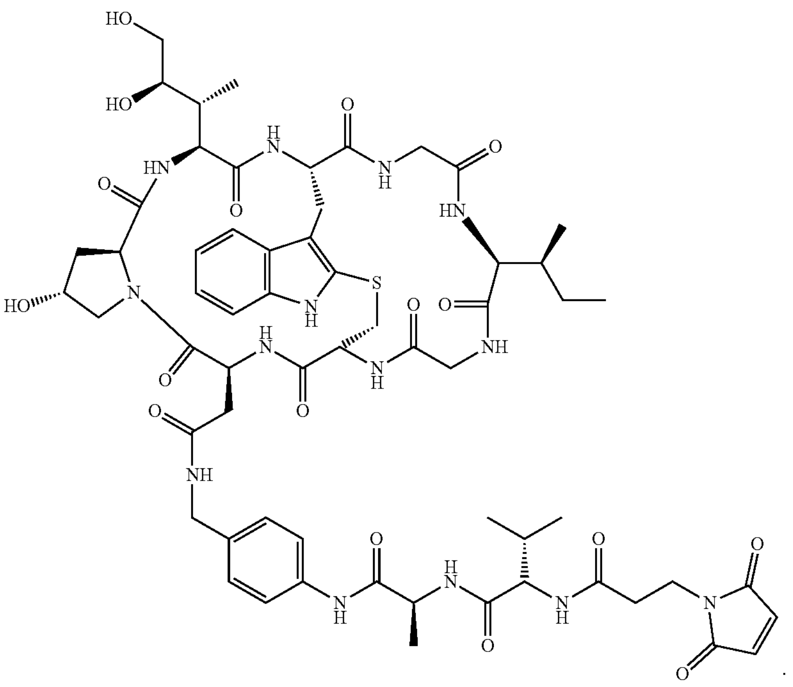

Additional amatoxins that may be used for conjugation to an antibody, or antigen-binding fragment thereof, in accordance with the compositions and methods described herein are described, for example, in WO 2016/142049; WO 2016/071856; WO 2017/149077; WO 2018/115466; and WO 2017/046658, the disclosures of which are incorporated herein by reference in their entirety.

In some embodiments, Am-L-Z is represented by formula (II), formula (IIA), or formula (IIB)

(II)

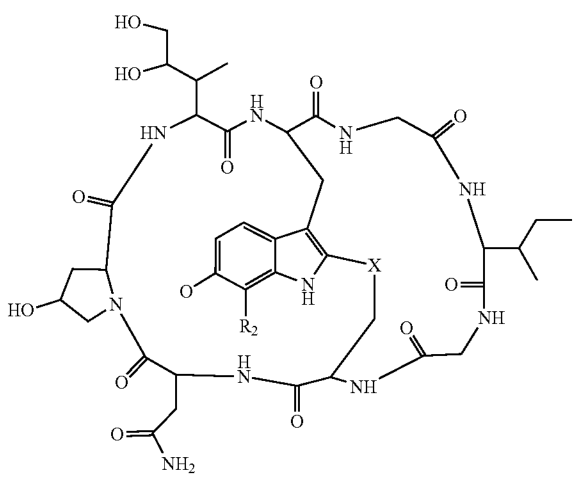

-continued (IIA)

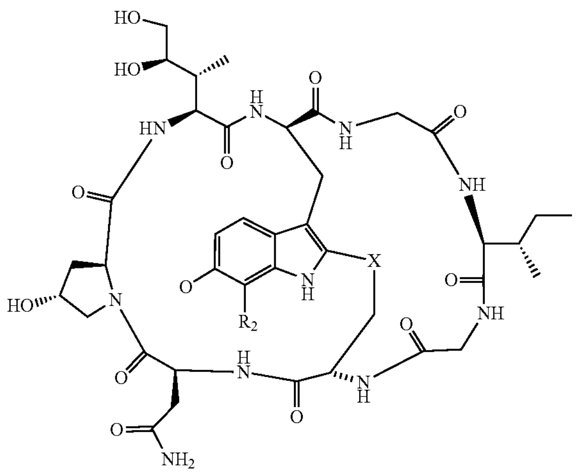

-continued (IIB)

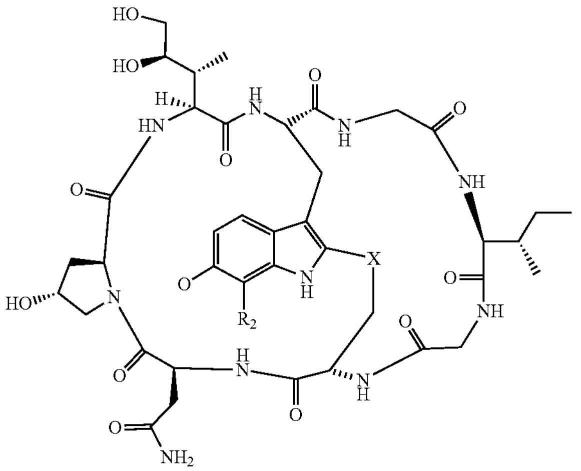

wherein X is S, SO, or $SO_2$; $R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; wherein when $R_1$ is H, $R_2$ is the linker, and when $R_2$ is H, $R_1$ is the linker.

In some embodiments, the linker-reactive substituent group, taken together as L-Z', prior to conjugation with the antibody or antigen binding fragment thereof, has the structure:

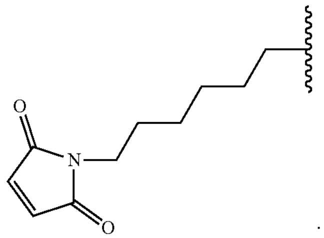 [SMILES: *CCCCCCN1C(=O)C=CC1=O]

This linker-reactive substituent group may alternatively be referred to as 1-n-hexyl-maleimide, which is a non-cleavable linker. The wavy line at the linker terminus indicates the point of attachment to the amatoxin. In some embodiments, the linker L and the chemical moiety Z, after conjugation to the antibody, taken together as L-Z, has the structure:

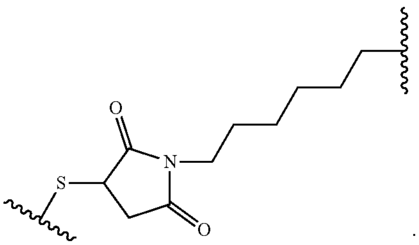

where S is a sulfur atom which represents the reactive substituent present within an antibody, or antigen-binding fragment thereof, that binds CD45 (e.g., from the —SH group of a cysteine residue).

In some embodiments, Am-L-Z-Ab is:

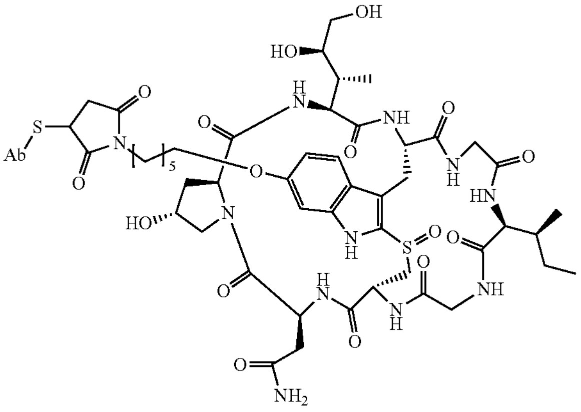

In some embodiments, Am-L-Z-Ab is:

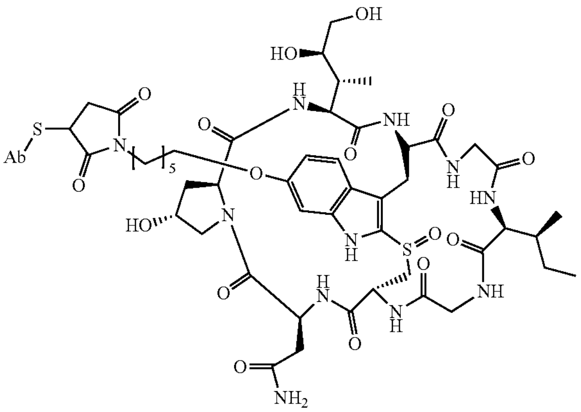

In some embodiments, the cytotoxin is an α-amanitin. In some embodiments, the α-amanitin is attached to an antibody (e.g., an anti-CD45 antibody) via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—. In some embodiments, the linker L and the chemical moiety Z, after conjugation to the CD45 antibody, taken together as L-Z-Ab, is

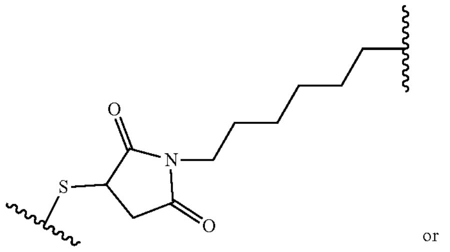

or

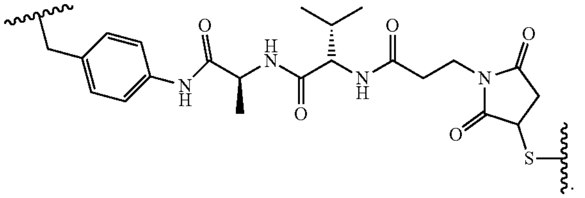

In some embodiments, the cytotoxin is a β-amanitin. In some embodiments, the β-amanitin is attached to an anti-CD45 antibody) via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—.

In some embodiments, the linker L and the chemical moiety Z, after conjugation to the CD45 antibody, taken together as L-Z-Ab, is

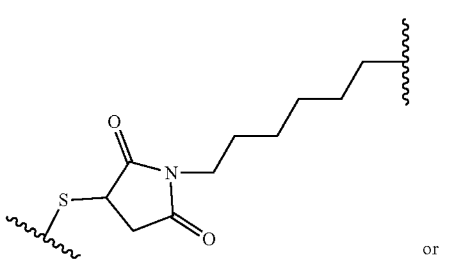

or

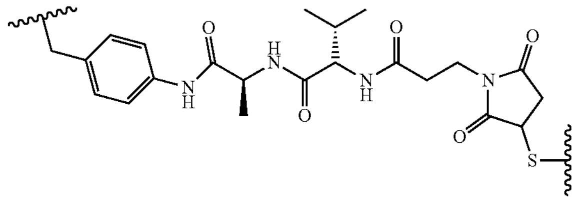

In some embodiments, the cytotoxin is a γ-amanitin. In some embodiments, the γ-amanitin is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$)—.

In some embodiments, the linker L and the chemical moiety Z, after conjugation to the CD45 antibody taken together as L-Z-Ab, is

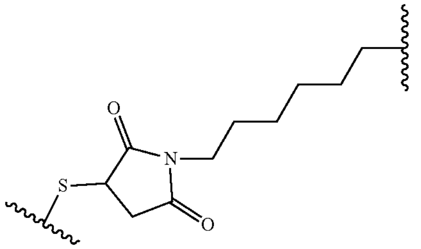

or

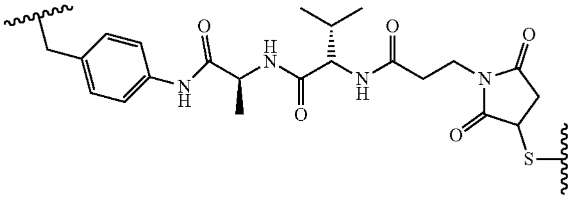

In some embodiments, the cytotoxin is a ε-amanitin. In some embodiments, the ε-amanitin is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—.

In some embodiments, the linker L and the chemical moiety Z, after conjugation to the antibody, taken together as L-Z-Ab, is

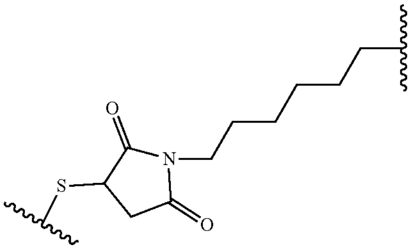

or

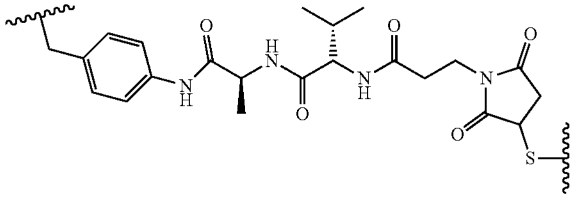

In some embodiments, the cytotoxin is an amanin. In some embodiments, the amanin is attached to an anti-CD45 antibody) via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—.

In some embodiments, the linker L and the chemical moiety Z, after conjugation to the antibody, taken together as L-Z-Ab, is

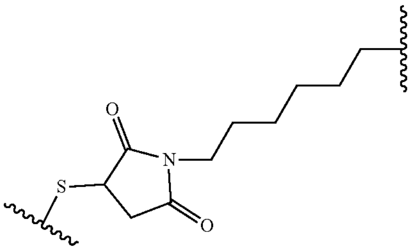

or

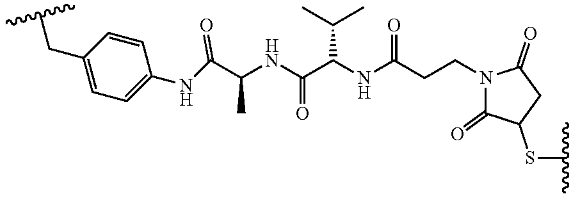

In some embodiments, the cytotoxin is an amaninamide. In some embodiments, the amaninamide is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —(C═O)$(CH_2)_n$— unit, wherein n is an integer from 1-6.

In some embodiments, the linker includes a —$(CH_2)_n$— unit, where n is an integer from 2-6. In some embodiments, the linker is -PAB-Cit-Val-(C═O)$(CH_2)_n$—. In some embodiments, the linker is -PAB-Ala-Val-(C═O)$(CH_2)_n$—.

In some embodiments, the linker L and the chemical moiety Z, after conjugation to the antibody, taken together as L-Z-Ab, is

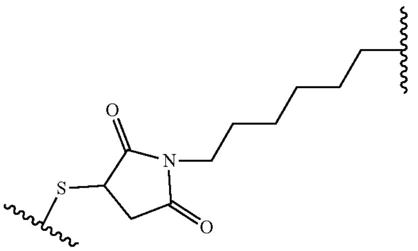

or

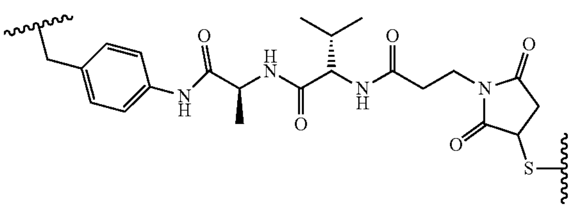

In some embodiments, the cytotoxin is an amanullin. In some embodiments, the amanullin is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C═O)$(CH_2)_n$)— unit, wherein n is an integer from 1-6.

In some embodiments, the linker includes a —$(CH_2)_n$— unit, where n is an integer from 2-6. In some embodiments, the linker is -PAB-Cit-Val-((C═O)$(CH_2)_n$)—. In some embodiments, the linker is -PAB-Ala-Val-((C═O)$(CH_2)_n$)—.

In some embodiments, the linker L and the chemical moiety Z, after conjugation to the antibody, taken together as L-Z-Ab, is

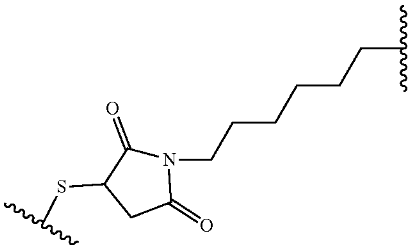

or

-continued

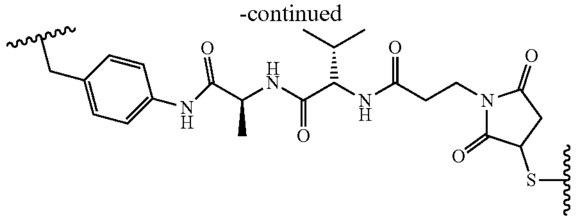

In some embodiments, the cytotoxin is an amanullinic acid. In some embodiments, the amanullinic acid is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a $-(CH_2)_n-$ unit, where n is an integer from 2-6. In some embodiments, the linker is -PAB-Cit-Val-$(C{=}O)(CH_2)_n-$. In some embodiments, the linker is -PAB-Ala-Val-$(C{=}O)(CH_2)_n-$.

In some embodiments, the linker L and the chemical moiety Z, after conjugation to the antibody, taken together as L-Z-Ab, is

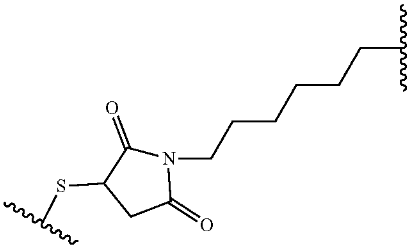

or

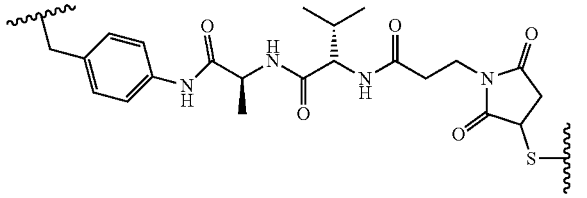

In some embodiments, the cytotoxin is a proamanullin. In some embodiments, the proamanullin is attached to an anti-CD45 antibody via a linker L. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a $-(C{=}O)(CH_2)_n-$ unit, wherein n is an integer from 1-6.

In some embodiments, the linker includes a $-(CH_2)_n-$ unit, where n is an integer from 2-6. In some embodiments, the linker is -PAB-Cit-Val-$(C{=}O)(CH_2)_n-$. In some embodiments, the linker is -PAB-Ala-Val-$(C{=}O)(CH_2)_n-$.

In some embodiments, the linker L and the chemical moiety Z, after conjugation to the antibody, taken together as L-Z-Ab, is

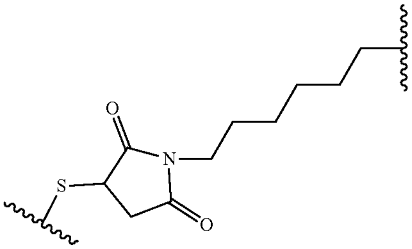

or

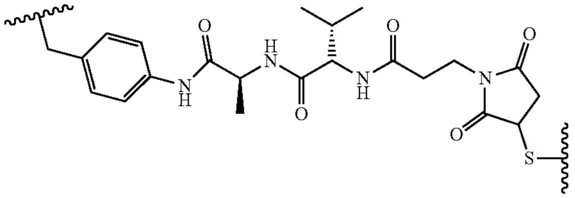

Synthetic methods of making amatoxin are described in U.S. Pat. No. 9,676,702, which is incorporated by reference herein.

Antibodies, and antigen-binding fragments, for use with the compositions and methods described herein can be conjugated to an amatoxin, such as α-amanitin or a variant thereof, using conjugation techniques known in the art or described herein. For instance, antibodies, and antigen-binding fragments thereof, that recognize and bind a target antigen (e.g., an anti-CD45 antibody) can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Auristatins

Antibodies and antigen-binding fragments thereof described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, (MMAE and MMAF, respectively), disclosed in Senter et al, Proceedings of the American Association for Cancer Research, Volume 45, Abstract Number 623, presented Mar. 28, 2004, the disclosure of which is herein incorporated by reference in its entirety.

An exemplary auristatin embodiment is MMAE, wherein the wavy line indicates the point of covalent attachment to the linker of an antibody-linker conjugate (-L-Z-Ab or -L-Z', as described herein),

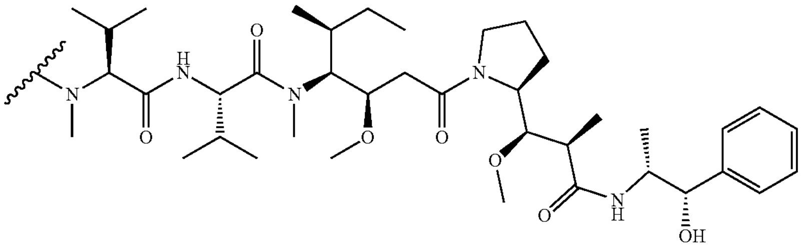 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

wherein the wavy line indicates the point of covalent attachment to the linker of an antibody-drug or drug-linker conjugate (-L-Z-Ab or -L-Z', as described herein).

Another exemplary auristatin embodiment is MMAF:

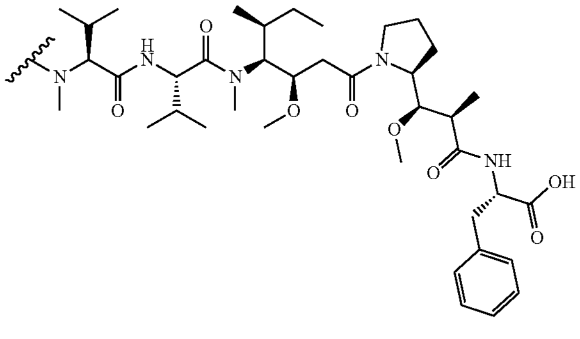 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

wherein the wavy line indicates the point of covalent attachment to the linker of an antibody-linker conjugate (-L-Z-Ab or -L-Z', as described herein), as disclosed in US 2005/0238649.

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Maytansinoids

Antibodies and antigen-binding fragments thereof described herein can be conjugated to a cytotoxin that is a microtubule binding agent. In some embodiments, the microtubule binding agent is a maytansine, a maytansinoid or a maytansinoid analog. Maytansinoids are mitotic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the antibody-drug conjugates (ADCs) of the present disclosure utilize the thiol-containing maytansinoid (DM1), formally termed N$^{2'}$-deacetyl-N$^{2'}$-(3-mercapto-1-oxopropyl)-maytansine, as the cytotoxic agent. DM1 is represented by the following structural formula VI:

(VI)

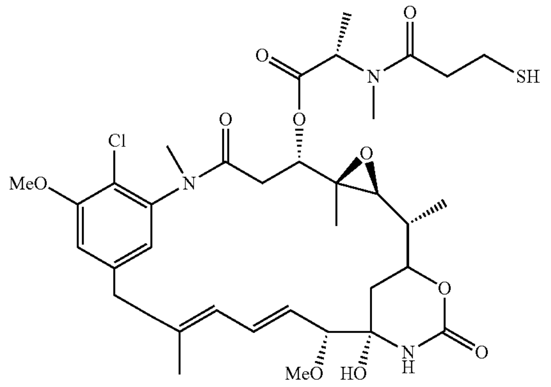

In another embodiment, the conjugates of the present invention utilize the thiol-containing maytansinoid N$^{2'}$-deacetyl-N$^{2'}$(4-methyl-4-mercapto-1-oxopentyl)-maytansine (e.g., DM4) as the cytotoxic agent. DM4 is represented by the following structural formula VII:

(VII)

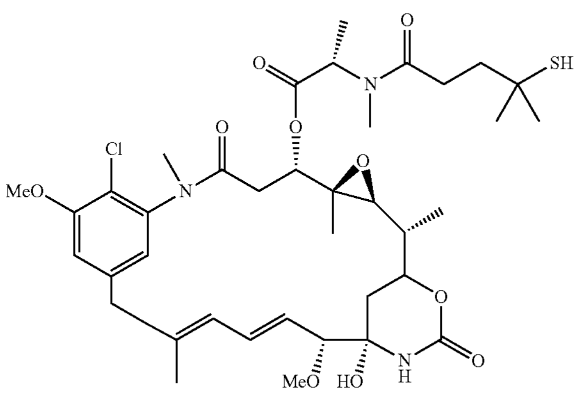

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula VII:

(VIII)

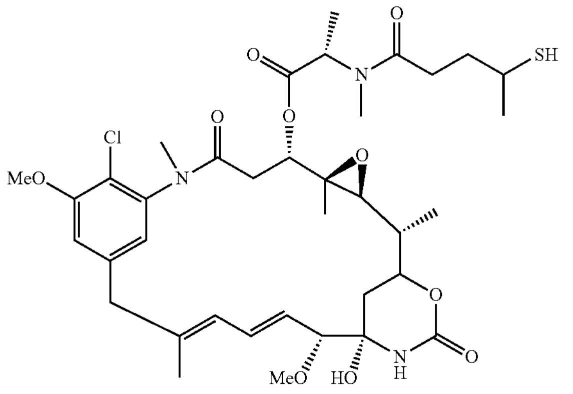

Each of the maytansinoids taught in U.S. Pat. Nos. 5,208,020 and 7,276,497, can also be used in the conjugates of the present disclosure. In this regard, the entire disclosure of U.S. Pat. Nos. 5,208,020 and 7,276,497 is incorporated herein by reference.

Many positions on maytansinoids can serve as the position to covalently bond the linking moiety and, hence the antibodies or antigen-binding fragments thereof (-L-Z-Ab or -L-Z', as described herein). For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to covalently bond the linker moiety, and in some particular embodiments, the C-3 position of maytansinol serves as the position to covalently bond the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020; 5,416,064; 6,333,410; 6,441,163; 6,716,821; and 7,368,565, each of which is incorporated herein in its entirety.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in Anthracycline Antibiotics In Cancer Therapy; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in Anthracycline: Current Status And New Developments p 11]. Commonly used anthracyclines include doxorubicin, epirubicin, idarubicin and daunomycin. In some embodiments, the cytotoxin is an anthracycline selected from the group consisting of daunorubicin, doxorubicin, epirubicin, and idarubicin. Representative examples of anthracyclines include, but are not limited to daunorubicin (Cerubidine; Bedford Laboratories), doxorubicin (ADRIAMYCIN®; Bedford Laboratories; also referred to as doxorubicin hydrochloride, hydroxy-daunorubicin, and RUBEX®), epirubicin (ELLENCE®; Pfizer), and idarubicin (IDAMYCIN®; Pfizer Inc.)

The anthracycline analog, doxorubicin (ADRIAMYCIN®) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

One non-limiting example of a suitable anthracycline for use herein is PNU-159682 ("PNU"). PNU exhibits greater than 3000-fold cytotoxicity relative to the parent nemorubicin (Quintieri et al., Clinical Cancer Research 2005, 11, 1608-1617). PNU is represented by structural formula:

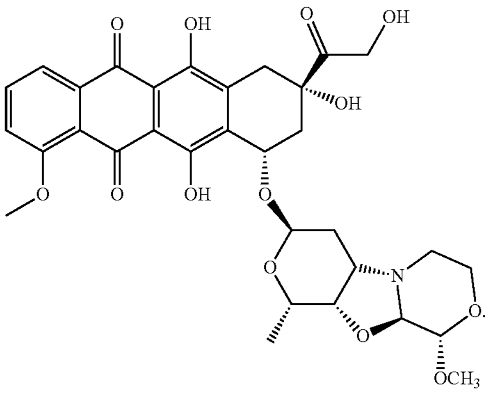

Multiple positions on anthracyclines such as PNU can serve as the position to covalently bond the linking moiety and, hence the bispecific binding agents as described herein. For example, linkers may be introduced through modifications to the hydroxymethyl ketone side chain.

In some embodiments, the cytotoxin is a PNU derivative represented by structural formula:

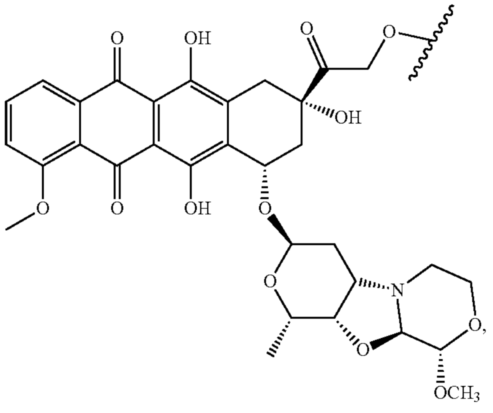

wherein the wavy line indicates the point of covalent attachment to the linker of the ADC as described herein.

In some embodiments, the cytotoxin is a PNU derivative represented by structural formula:

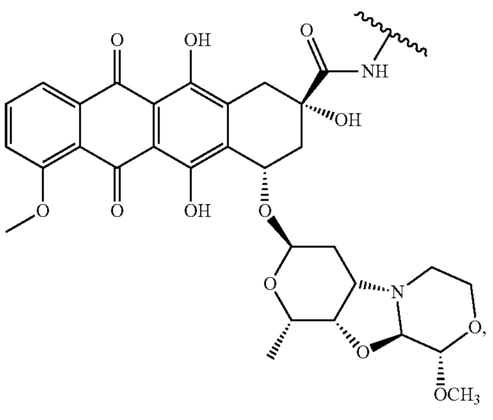

wherein the wavy line indicates the point of covalent attachment to the linker of the ADC as described herein.

Benzodiazepine Cytotoxins

Anti-CD45 antibodies, and antigen-binding fragments thereof, as described herein (including e.g., bispecific and biparatopic antibodies) can be conjugated to a cytotoxin comprising a benzodiazepine moiety, such as a PBD or an IGN, as described herein.

Pyrrolobenzodiazepines (PBDs)

PBDs are of the general structure:

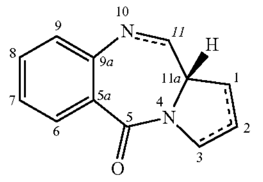

They differ in the number, type and position of substituents, in both their aromatic ("A") rings and pyrrolo ("C") rings, and in the degree of saturation of the C ring. In the diazepine B-ring there is either an imine (N═C), a carbinolamine (NH—CH(OH)), or a carbinolamine methyl ether (NH—CH(OMe)) at the N10-C11 position. This position is the electrophilic moiety responsible for DNA alkylation. All of the known natural product PBDs have an (S)-configuration at the chiral C11a position which provides them with a right-handed twist when viewed from the C ring towards the A ring. This provides the appropriate three-dimensional shape for isohelicity with the minor groove of B-form DNA, leading to a tight fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). The ability of PBDs to form adducts in the minor groove enables them to interfere with DNA processing, resulting in anti-tumor activity.

It has been previously disclosed that the biological activity of these molecules can be potentiated by joining two PBD units together through their C8-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions, such as the palindromic 5'-Pu-GATC-Py-3' inter-strand cross-link (Smellie, M., et al., *Biochemistry,* 42, 8232-8239 (2003); Martin, C., et al., *Biochemistry,* 44, 4135-4147) which is thought to be mainly responsible for their biological activity. An advantageous dimeric pyrrolobenzodiazepine compound has been described by Gregson et al. (*Chem. Commun.* 1999, 797-798; "compound 1", and by Gregson et al. (*J. Med. Chem.* 2001, 44, 1161-1174; "compound 4a"). This compound, also known as SG2000, is of the structural formula:

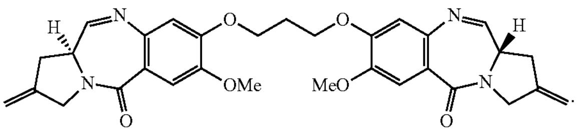

Generally, modifications to the pyrrolidine alkene moiety provide the handle with which to covalently bond the linking moiety and, hence the antibodies or antigen-binding fragments thereof (-L-Z' and -L-Z-Ab, respectively, as described herein). Alternatively, a linker may be attached at position N10.

In some embodiments, the cytotoxin is a pyrrolobenzodiazepine dimer represented by the structural formula:

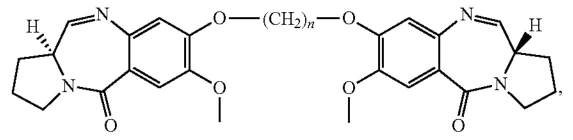

wherein n is an integer from 2 to 5. The compound of this formula wherein n is 3 is known as DSB-120 (Bose et al., J. Am. Chem. Soc. 1992, 114, 4939-4941).

In some embodiments, the cytotoxin is a pyrrolobenzodiazepine dimer represented by the structural formula:

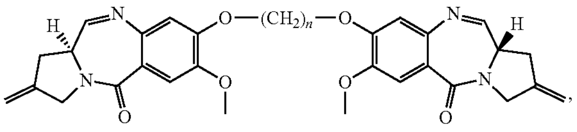

wherein n is an integer from 2 to 5. The compound of this formula wherein n is 3 is known as SJG-136 (Gregson et al., J. Med. Chem. 2001, 44, 737-748). The compound of this formula wherein n is 5 is known as DRG-16 (Gregson et al., Med. Chem. 2004; 47:1161-1174).

In some embodiments, the cytotoxin is a pyrrolobenzodiazepine dimer represented by the structural formula:

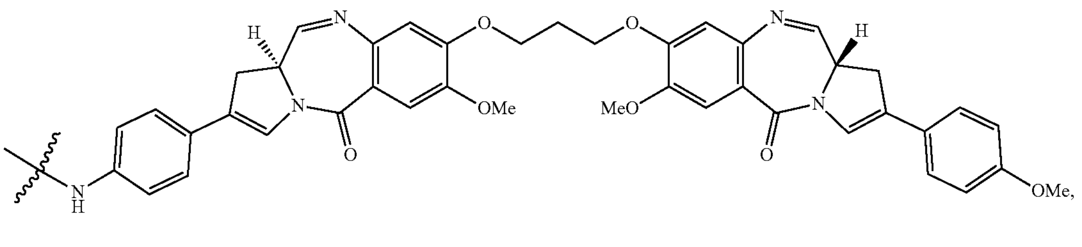 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the point of covalent attachment to the linker of the ADC as described herein. ADCs based on this PBD are disclosed in, for example, Sutherland et al., Blood 2013 122:1455-1463, which is incorporated by reference herein in its entirety.

In some embodiments, the cytotoxin is a PBD dimer represented by the structural formula:

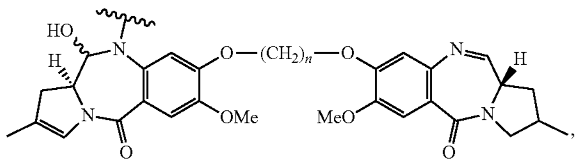

wherein n is 3 or 5, and wherein the wavy line indicates the point of covalent attachment to the linker of the ADC as described herein.

In some embodiments, the cytotoxin is a PBD dimer represented by the structural formula (I):

(I)

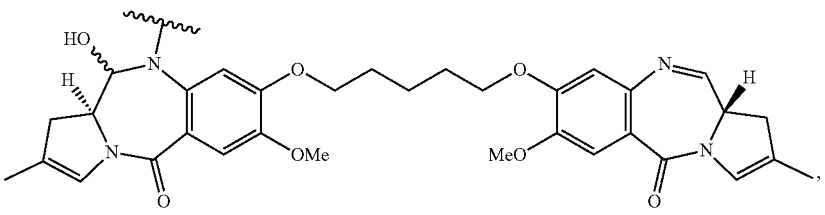

wherein the wavy line indicates the point of covalent attachment to the linker of the ADC as described herein.

Indolinobenzodiazepines (IGNs)

In some embodiments, the antibodies, or antigen-binding fragments thereof, that bind CD45 as described herein can be conjugated to a cytotoxin that is an indolinobenzodiazepine ("IGN") or a cytotoxin that comprises an IGN. In some embodiments, the IGN cytotoxin is an indolinobenzodiazepine dimer or an indolinobenzodiazepine pseudodimer.

Indolinobenzodiazepine dimers represent a relatively new chemical class of cytotoxins with high in vitro potency (low pM range $IC_{50}$ values) towards cancer cells. Similar to the PBD dimer SJG-136, IGN dimers bind to the minor groove of DNA, and covalently bind to guanine residues via the two imine functionalities in the dimer, resulting in crosslinking of the DNA. An IGN dimer (IGN 6; replacing the methylene groups of the PBD moiety with phenyl rings) demonstrated ~10-fold higher potency in vitro as compared to SJG-136, possibly due to faster rate of adduct formation with DNA IGN (see, e.g., Miller et al., "A New Class of Antibody-Drug Conjugates with Potent DNA Alkylating Activity" Mol. Cancer Ther. 2016, 15(8), 1870-1878). In contrast, IGN pseudodimers comprise a single reactive indolinobenzodiazepine imine; the second indolinobenzodiazepine in the dimeric cytotoxin is present in reduced (amine) form.

Accordingly, IGN pseudodimers alkylate DNA through the single imine moiety present in the dimer, and do not cross-link DNA.

In some embodiments, the cytotoxin is an IGN pseudodimer having a structure of formula:

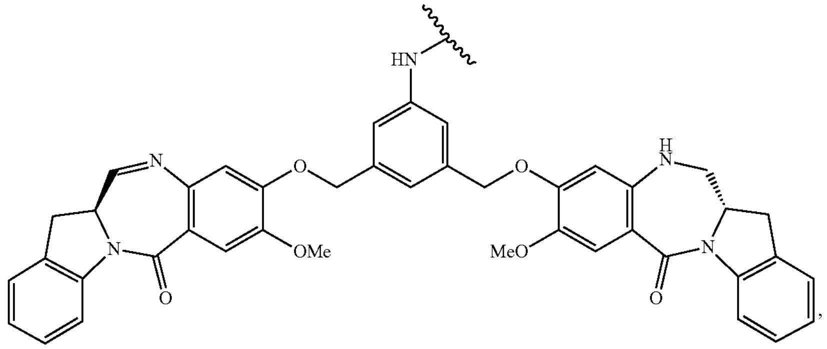 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker.

In some embodiments, the cytotoxin-linker conjugate, prior to conjugation to the antibody and including the reactive substituent Z', taken together as Cy-L-Z', has the structure:

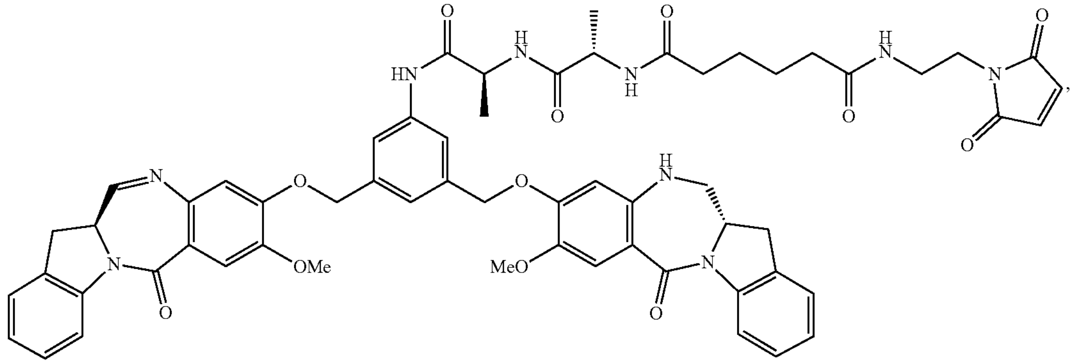 [SMILES: COc1cc2c(cc1OCc1cc(COc3cc4c(cc3OC)C(=O)N3c5ccccc5C[C@H]3CN4)cc(NC(=O)[C@H](C)NC(=O)[C@H](C)NC(=O)CCCCC(=O)NCCN3C(=O)C=CC3=O)c1)N=C[C@@H]1Cc3ccccc3N1C2=O]

This cytotoxin-linker conjugate is referred to herein as DGN549, and is present in the ADC IMGN632, both of which are disclosed in, for example, International Patent Application Publication No. WO2017004026, which is incorporated by reference herein.

In some embodiments, the cytotoxin is an indolinobenzodiazepine pseudodimer having a structure of formula:

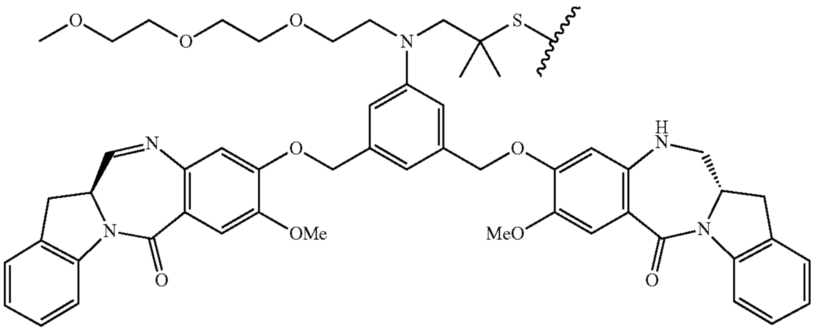 [SMILES: *SC(C)(C)CN(CCOCCOCCOC)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker. This IGN pseudodimer cytotoxin is referred to herein as DGN462, disclosed in, for example, U.S. Patent Application Publication No. 20170080102, which is incorporated by reference herein.

In some embodiments, the cytotoxin-linker conjugate, prior to conjugation to the antibody and including the chemical moiety Z, taken together as Cy-L-Z, has the structure:

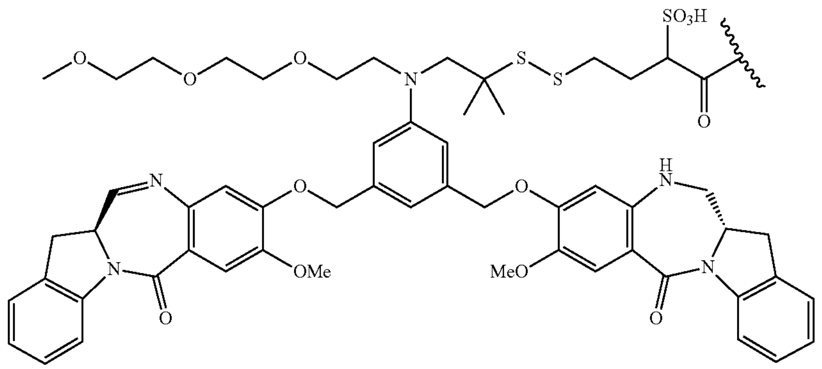 [SMILES: *C(=O)C(CCSSC(C)(C)CN(CCOCCOCCOC)c1cc(COc2cc3c(cc2OC)C(=O)N2c4ccccc4C[C@H]2C=N3)cc(COc2cc3c(cc2OC)C(=O)N2c4ccccc4C[C@H]2CN3)c1)S(=O)(=O)O]

wherein the wavy line indicates the point of attachment to the antibody (e.g., an anti-CD45 antibody or fragment thereof). This cytotoxin-linker conjugate is present in the ADC IMGN779, disclosed in, for example, U.S. Patent Application Publication No. 20170080102, previously incorporated by reference herein.

Calicheamicin

In other embodiments, the antibodies and antigen-binding fragments thereof described herein can be conjugated to a cytotoxin that is an enediyne antitumor antibiotic (e.g., calicheamicins, ozogamicin). The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

An exemplary calicheamicin is designated $\gamma_1$, which is herein referenced simply as gamma, and has the structural formula:

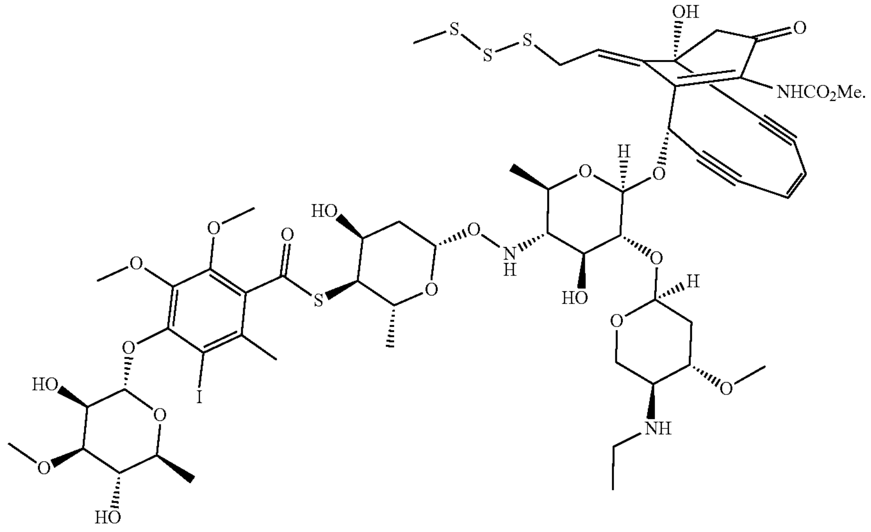

In some embodiments, the calicheamicin is a gamma-calicheamicin derivative or an N-acetyl gamma-calicheamicin derivative. Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents. Calicheamicins contain a methyltrisulfide moiety that can be reacted with appropriate thiols to form disulfides, at the same time introducing a functional group that is useful in attaching a calicheamicin derivative to a bispecific binding agent as described herein, via a linker. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

In some embodiments, the cytotoxin of the ADC as disclosed herein is a calicheamicin disulfide derivative represented by the formula:

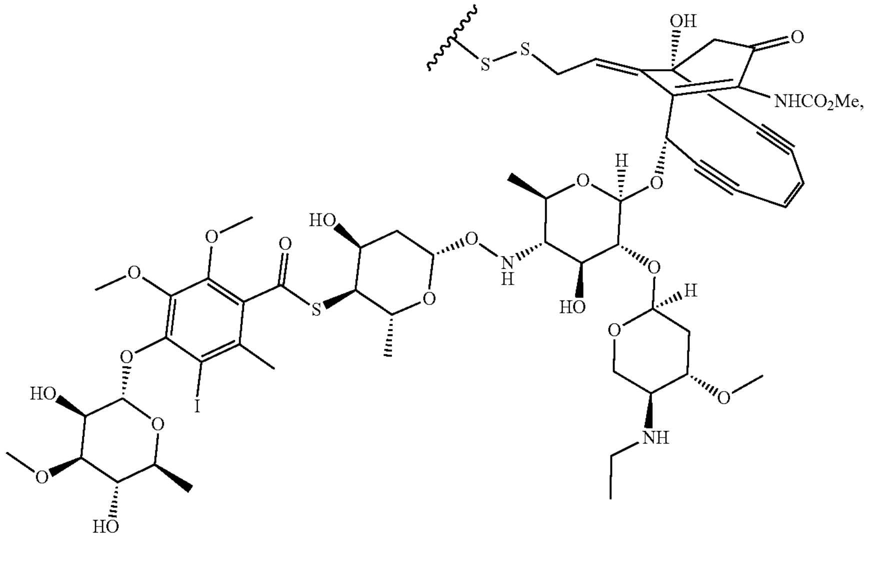

wherein the wavy line indicates the attachment point of the linker.

Additional Cytotoxins

In other embodiments, the antibodies and antigen-binding fragments thereof described herein can be conjugated to a cytotoxin other than or in addition to those cytotoxins disclosed herein above. Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, merbarone, meterelin, methioninase, metoclopramide, MIF inhibitor, mifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

In some embodiments, the cytotoxin to which the antibody, antibody fragment, or other antigen binding agent, e.g., a ligand such as stem cell factor, is attached is a protein-based toxin. An example of a protein based toxin is a shiga toxin. Thus, in some embodiments, the cytotoxin to which the antibody, antibody fragment, or other antigen binding agent, e.g., a ligand such as stem cell factor, is attached is a Shiga toxin, or a mutant, fragment or derivative thereof, for example Shiga-like toxin A subunit, and mutants, fragments, and derivatives thereof. In some embodiments, the cytotoxin to which the antibody, antibody fragment, or other antigen binding agent is conjugated is a Shiga-like toxin such as SLT I, SLT II, SLT IIV, LT toxin, or C3 toxin.

In certain embodiments, the cytotoxin is a part of a fusion protein comprising a protein-based toxin and an antigen binding protein. For example, a fusion protein in certain embodiments is an engineered toxin body comprising an antibody fragment, such as an scFv, and a protein-based toxin, e.g., a protein synthesis inhibitor, e.g., a ribosome inactivating protein, e.g., Shiga toxin, Shiga-like toxin A subunit, saporin, ricin, and mutants, fragments, and derivatives thereof, etc.

Linkers

The term “Linker” as used herein means a divalent chemical moiety comprising a covalent bond or a chain of atoms that covalently attaches an anti-CD45 antibody-drug conjugates (ADC) of formula I. Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term “linker” is used in describing the linker in conjugated form, one or both of the reactive termini will be absent (such as reactive moiety Z', having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, or antibody fragments described herein to a cytotoxic molecule. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio) propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety, and particularly as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference as it pertains to linkers suitable for covalent conjugation. In some embodiments, the linker includes a dipeptide selected from Val-Ala and Val-Cit.

Linkers suitable for conjugating the antibodies, or antibody fragments, described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety, and particularly as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

Linkers suitable for use herein further may include one or more groups selected from $C_1$-$C_8$ alkylene, $C_1$-$C_6$ heteroalkylene, $C_2$-$C_6$ alkenylene, $C_2$-$C_6$ heteroalkenylene, $C_2$-$C_6$alkynylene, $C_2$-$C_6$ heteroalkynylene, $C_3$-$C_6$cycloalkylene, heterocycloalkylene, arylene, heteroarylene, and combinations thereof, each of which may be optionally substituted. Non-limiting examples of such groups include $(CH_2)_p$, $(CH_2CH_2O)_p$, and —(C═O)(CH$_2$)$_p$— units, wherein p is an integer from 1-6, independently selected for each occasion.

Suitable linkers may contain groups having solubility enhancing properties. Linkers including the (CH$_2$CH$_2$O)$_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference as it pertains to linkers suitable for covalent conjugation.

Suitable linkers may contain groups having solubility enhancing properties. Linkers including the (CH$_2$CH$_2$O)$_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference as it pertains to linkers suitable for covalent conjugation. Further solubility enhancing groups include, for example, acyl and carbamoyl sulfamide groups, having the structure:

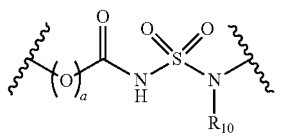

wherein a is 0 or 1; and $R^{10}$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted and/or optionally interrupted by one or more heteroatoms selected from O, S and $NR^{11}R^{12}$ wherein $R^{11}$ and $R^{12}$ are independently selected from the group consisting of hydrogen and $C_1$-$C_4$ alkyl groups; or $R^{10}$ is a cytotoxin, wherein the cytotoxin is optionally connected to N via a spacer moiety. Linkers containing such groups are described, for example, in U.S. Pat. No. 9,636,421 and U.S. Patent Application Publication No. 2017/0298145, the disclosures of which are incorporated herein by reference as they pertain to linkers suitable for covalent conjugation to cytotoxins and antibodies or antigen-binding fragments thereof.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, —(C═O)—, or —(CH$_2$CH$_2$O)$_p$— group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker L comprises the moiety *-$L_1L_2$-**, wherein:

$L_1$ is absent or is —(CH$_2$)$_m$NR$^{13}$C(═O)—, —(CH$_2$)$_m$NR$^{13}$—, —(CH$_2$)$_m$X$_3$(CH$_2$)$_m$—,

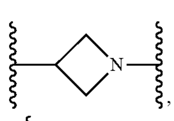,

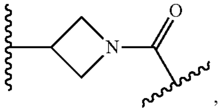,

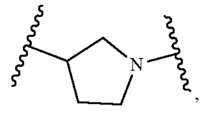,

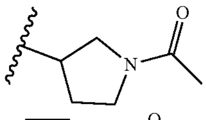,

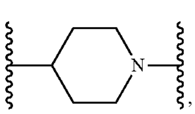,

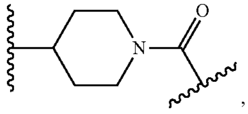, or

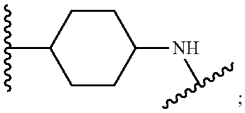;

$L_2$ is absent or is —(CH$_2$)$_m$—, —NR$^{13}$(CH$_2$)$_m$—, —(CH$_2$)$_m$NR$^{13}$C(═O)(CH$_2$)$_m$—, —X$_4$, —(CH$_2$)$_m$NR$^{13}$C(═O)X$_4$, —(CH$_2$)$_m$NR$^{13}$C(═O)—, —((CH$_2$)$_m$O)$_n$(CH$_2$)$_m$—, —((CH$_2$)$_m$O)$_n$(CH$_2$)$_m$X$_3$(CH$_2$)$_m$—, —NR$^{13}$((CH$_2$)$_m$O)$_n$X$_3$(CH$_2$)$_m$—, —NR$^{13}$((CH$_2$)$_m$O)$_n$(CH$_2$)$_m$X$_3$(CH$_2$)$_m$—, —X$_1$X$_2$C(═O)(CH$_2$)$_m$—, —(CH$_2$)$_m$(O(CH$_2$)$_m$)$_n$—, —(CH$_2$)$_m$NR$^{13}$(CH$_2$)$_m$—, —(CH$_2$)$_m$NR$^{13}$C(═O)(CH$_2$)$_m$X$_3$(CH$_2$)$_m$—, —(CH$_2$)$_m$C(═O)NR$^{13}$(CH$_2$)$_m$NR$^{13}$C(═O)(CH$_2$)$_m$—, —(CH$_2$)$_m$C(═O)—, —(CH$_2$)$_m$NR$^{13}$(CH$_2$)$_m$C(═O)X$_2$X$_1$C(═O)—, —(CH$_2$)$_m$X$_3$(CH$_2$)$_m$C(═O)X$_2$X$_1$C(═O)—, —(CH$_2$)$_m$C(═O)NR$^{13}$(CH$_2$)$_m$—, —(CH$_2$)$_m$C(═O)NR$^{13}$(CH$_2$)$_m$X$_3$(CH$_2$)$_m$—, —(CH$_2$)$_m$X$_3$(CH$_2$)$_m$NR$^{13}$C(═O)(CH$_2$)$_m$—, —(CH$_2$)$_m$X$_3$(CH$_2$)$_m$C(═O)NR$^{13}$(CH$_2$)$_m$—, —(CH$_2$)$_m$O)$_n$(CH$_2$)$_m$NR$^{13}$C(═O)(CH$_2$)$_m$—, —(CH$_2$)$_m$C(═O)NR$^{13}$(CH$_2$)$_m$(O(CH$_2$)$_m$)$_n$—, —(CH$_2$)$_m$(O(CH$_2$)$_m$)$_n$C(═O)—, —(CH$_2$)$_m$NR$^{13}$(CH$_2$)$_m$C(═O)—, —(CH$_2$)$_m$C(═O)NR$^{13}$(CH$_2$)$_m$NR$^{13}$C(═O)—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(═O)—, —(CH$_2$)$_m$C(═O)NR$^{13}$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{13}$C(═O)(CH$_2$)$_m$—, —(CH$_2$)$_m$X$_3$(CH$_2$)$_m$(O(CH$_2$)$_m$)$_n$C(═O)—, —(CH$_2$)$_m$X$_3$(CH$_2$)$_m$(O(CH$_2$)$_m$)$_n$—, —(CH$_2$)$_m$C(═O)NR$^{13}$(CH$_2$)$_m$C(═O)—, —(CH$_2$)$_m$C(═O)NR$^{13}$(CH$_2$)$_m$(O(CH$_2$)$_m$)$_n$C(═O)—, —((CH$_2$)$_m$O)$_n$(CH$_2$)$_m$NR$^{13}$C(═O)(CH$_2$)$_m$—, —(CH$_2$)$_m$C(═O)NR$^{13}$(CH$_2$)$_m$C(═O)NR$^{13}$(CH$_2$)$_m$—, —(CH$_2$)$_m$NR$^{13}$C(═O)(CH$_2$)$_m$NR$^{13}$C(═O)(CH$_2$)—(CH$_2$)$_m$X$_3$(CH$_2$)$_m$C(═O)NR$^{13}$—, —(CH$_2$)$_m$C(═O)NR$^{13}$—, —(CH$_2$)$_m$X$_3$—, —C(R$^{13}$)$_2$(CH$_2$)$_m$—, —(CH$_2$)$_m$C(R$^{13}$)$_2$NR$^{13}$—, —(CH$_2$)$_m$C(═O)NR$^{13}$(CH$_2$)$_m$NR$^{13}$—, —(CH$_2$)$_m$C(═O)NR$^{13}$(CH$_2$)$_m$NR$^{13}$C(═O)NR$^{13}$—, —(CH$_2$)$_m$C(═O)X$_2$X$_1$C(═O)—, —C(R$^{13}$)$_2$(CH$_2$)$_m$NR$^{13}$C(═O)(CH$_2$)$_m$—, —(CH$_2$)$_m$C(═O)NR$^{13}$(CH$_2$)$_m$C(R$^{13}$)$_2$NR$^{13}$—, —C(R$^{13}$)$_2$(CH$_2$)$_m$X$_3$(CH$_2$)$_m$—, —(CH$_2$)$_m$X$_3$(CH$_2$)$_m$C(R$^{13}$)$_2$NR$^{13}$—, —C(R$^{13}$)$_2$(CH$_2$)$_m$OC(═O)NR$^{13}$(CH$_2$)$_m$—, —(CH$_2$)$_m$NR$^{13}$C(═O)O(CH$_2$)$_m$C(R$^{13}$)$_2$NR$^{13}$—, —(CH$_2$)$_m$X$_3$(CH$_2$)$_m$NR$^{13}$, —(CH$_2$)$_m$X$_3$(CH$_2$)$_m$(O(CH$_2$)$_m$)$_n$NR$^{13}$—, —(CH$_2$)$_m$NR$^{13}$—, —(CH$_2$)$_m$C $(=O)NR^{13}(CH_2)_m(O(CH_2)_m)_nNR^{13}—$, $—(CH_2)_m(O(CH_2)_m)_nNR^{13}—$, $—(CH_2CH_2O)_n(CH_2)_m—$, $—(CH_2)_m(OCH_2CH_2)_n$, $—(CH_2)_mO(CH_2)_m—$, $—(CH_2)_mS(=O)_2—$, $—(CH_2)_mC(=O)NR^{13}(CH_2)_mS(=O)_2—$, $—(CH_2)_mX_3(CH_2)_mS(=O)_2—$, $—(CH_2)_mX_2X_1C(=O)—$, $—(CH_2)_m(O(CH_2)_m)_nC(=O)X_2X_1C(=O)—$, $—(CH_2)_m(O(CH_2)_m)_nX_2X_1C(=O)—$, $—(CH_2)_mX_3(CH_2)_mX_2X_1C(=O)—$, $—(CH_2)_mX_3(CH_2)_m(O(CH_2)_m)_nX_2X_1C(=O)—$, $—(CH_2)_mX_3(CH_2)_mC(=O)NR^{13}(CH_2)_mNR^{13}C(=O)—$, $—(CH_2)_mX_3(CH_2)_mC(=O)NR^{13}(CH_2)_mC(=O)—$, $—(CH_2)_mX_3(CH_2)_mC(=O)NR^{13}(CH_2)_m(O(CH_2)_m)_nC(=O)—$, $—(CH_2)_mC(=O)X_2X_1C(=O)NR^{13}(CH_2)_m—$, $—(CH_2)_mX_3(O(CH_2)_m)_nC(=O)—$, $—(CH_2)_mNR^{13}C(=O)((CH_2)_mO)_n(CH_2)_m—$, $—(CH_2)_m(O(CH_2)_m)_nC(=O)NR^{13}(CH_2)_m—$, $—(CH_2)_mNR^{13}C(=O)NR^{13}(CH_2)_m—$ or $—(CH_2)_mX_3(CH_2)_mNR^{13}C(=O)—$;

wherein $X_1$ is

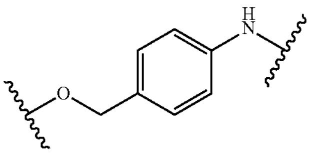

,

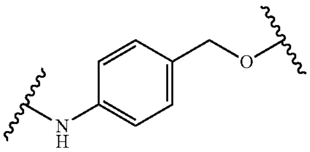

,

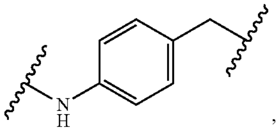

,

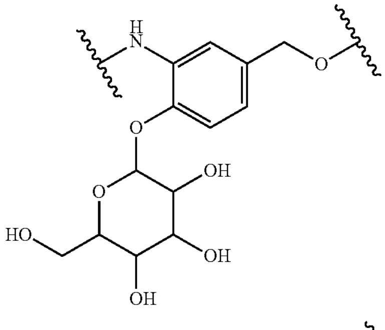

, or

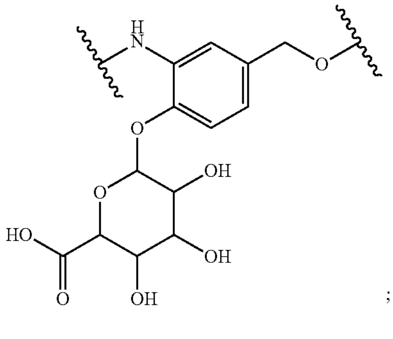

;

$X_2$ is

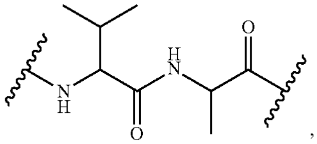

,

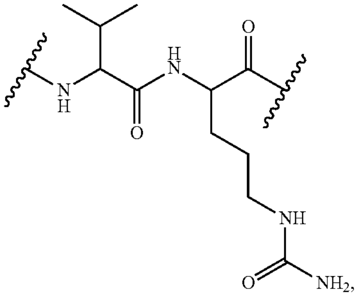

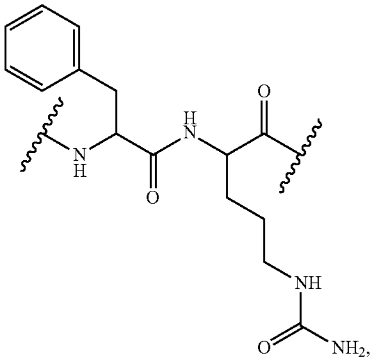

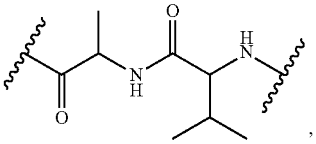

, or

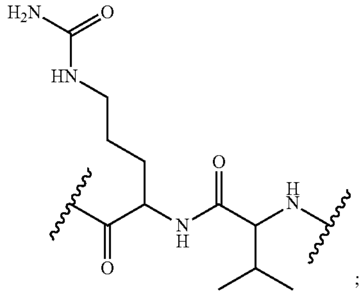

;

$X_3$ is

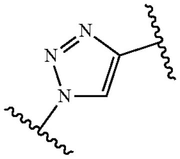

or

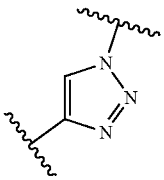

;

and $X_4$ is

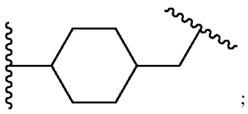

wherein $R^{13}$ is independently selected for each occasion from H and $C_1$-$C_6$ alkyl;

m is independently selected for each occasion from 1, 2, 3, 4, 5, 6, 7, 8, 9 and 10;

n is independently selected for each occasion from 1, 2, 3, 4, 5, 6, 7, 8, 9, 10, 11, 12, 13 and 14; and wherein the single asterisk (*) indicates the attachment point to the cytotoxin (e.g., an amatoxin), and the double asterisk (**) indicates the attachment point to the reactive substituent Z' or chemical moiety Z, with the proviso that $L_1$ and $L_2$ are not both absent.

In some embodiments, the linker includes a p-aminobenzyl group (PAB). In some embodiments, the p-aminobenzyl group is disposed between the cytotoxic drug and a protease cleavage site in the linker. In some embodiments, the p-aminobenzyl group is part of a p-aminobenzyloxycarbonyl unit. In some embodiments, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, $—(CH_2)_p—$, $—(CH_2CH_2O)_p—$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a $—(C{=}O)(CH_2)_p—$ unit, wherein p is an integer from 1-6.

In one specific embodiment, the linker comprises the structure:

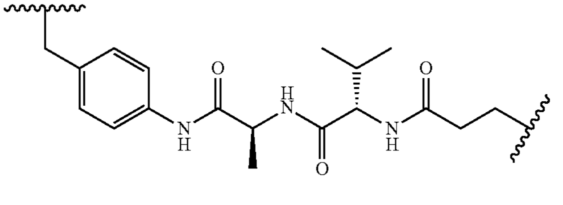 [SMILES: *CCC(=O)N[C@H](C(=O)N[C@@H](C)C(=O)Nc1ccc(C*)cc1)C(C)C]

wherein the wavy lines indicate attachment points to the cytotoxin and the reactive moiety Z'. In another specific embodiment, the linker comprises the structure:

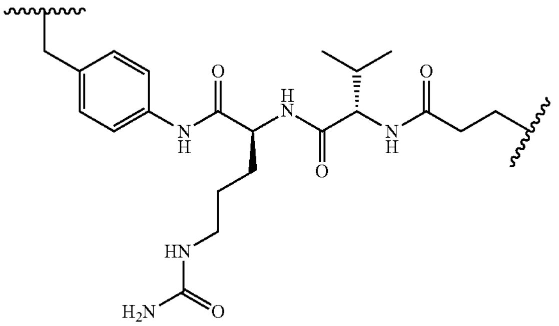 [SMILES: *CCC(=O)N[C@H](C(=O)N[C@@H](CCCNC(N)=O)C(=O)Nc1ccc(C*)cc1)C(C)C]

wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

In certain embodiments, the linker of the ADC is maleimidocaproyl-Val-Ala-para-aminobenzyl (mc-Val-Ala-PAB).

In certain embodiments, the linker of the ADC is maleimidocaproyl-Val-Cit-para-aminobenzyl (mc-vc-PAB).

In some embodiments, the linker comprises

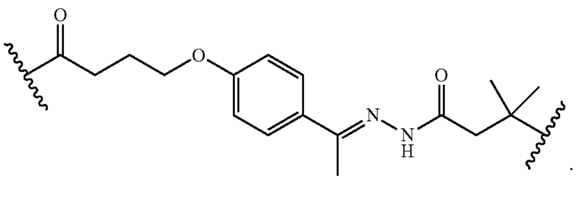 [SMILES: *C(=O)CCCOc1ccc(/C(C)=N/NC(=O)CC(*)(C)C)cc1]

In some embodiments, the linker comprises MCC (4-[N-maleimidomethyl]cyclohexane-1-carboxylate).

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, $—(C{=}O)—$, or $—(CH_2CH_2O)_p—$ group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In some embodiments, the p-aminobenzyl group is disposed between the cytotoxic drug and a protease cleavage site in the linker. In some embodiments, the p-aminobenzyl group is part of a p-aminobenzyloxycarbonyl unit. In some embodiments, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, $-(CH_2)_p-$, $-(CH_2CH_2O)_p-$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a $-(C{=}O)(CH_2)_p-$ unit, wherein p is an integer from 1-6.

In one specific embodiment, the linker comprises the structure

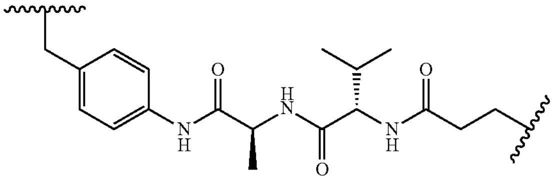 [SMILES: *CCC(=O)N[C@H](C(=O)N[C@@H](C)C(=O)Nc1ccc(C*)cc1)C(C)C]

wherein the wavy lines indicate attachment points to the cytotoxin and the reactive moiety Z'. In another specific embodiment, the linker comprises the structure

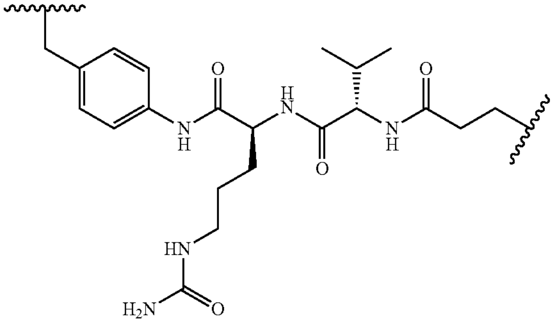 [SMILES: *CCC(=O)N[C@H](C(=O)N[C@@H](CCCNC(N)=O)C(=O)Nc1ccc(C*)cc1)C(C)C]

wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug. Such conjugation reactions will now be described more fully.

A number of different reactions are available for covalent attachment of linkers or drug-linker conjugates to the antibody or antigen-binding fragment thereof. Suitable attachment points on the antibody molecule include the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Linkers useful for conjugation to the antibodies or antigen-binding fragments as described herein include, without limitation, linkers containing chemical moieties Z formed by coupling reactions as depicted in Table 2, below. Wavy lines designate points of attachment to the antibody or antigen-binding fragment, or the cytotoxic molecule.

TABLE 2

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | 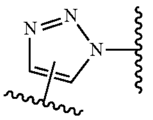 |

TABLE 2-continued
| Exemplary chemical moieties Z formed by coupling reactions in the formation of antibody-drug conjugates | |
|---|---|
| Exemplary Coupling Reactions | Chemical Moiety Z Formed by Coupling Reactions |
| [3 + 2] Cycloaddition | 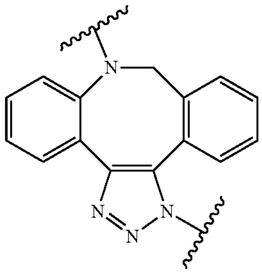 [SMILES: *N1Cc2ccccc2-c2c(nnn2*)-c2ccccc21] |
| [3 + 2] Cycloaddition, Esterification | 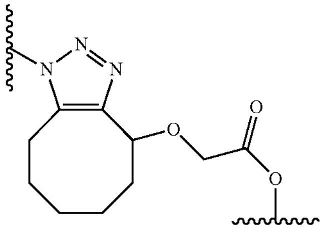 [SMILES: *OC(=O)COC1CCCCCc2c1nnn2*] |
| [3 + 2] Cycloaddition, Esterification | 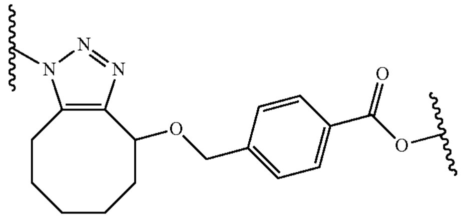 [SMILES: *OC(=O)c1ccc(COC2CCCCCc3c2nnn3*)cc1] |
| [3 + 2] Cycloaddition, Esterification | 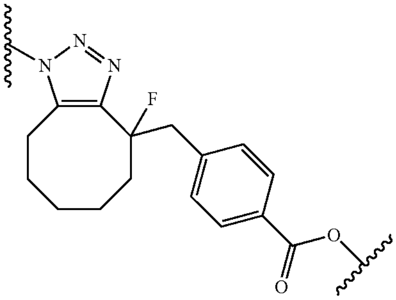 [SMILES: *OC(=O)c1ccc(CC2(F)CCCCCc3c2nnn3*)cc1] |
| [3 + 2] Cycloaddition, Esterification | 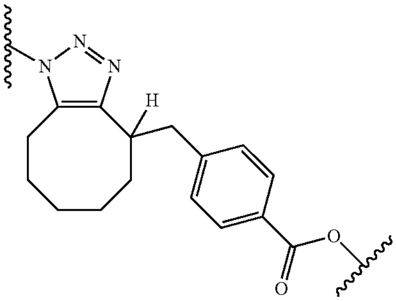 [SMILES: *OC(=O)c1ccc(CC2CCCCCc3c2nnn3*)cc1] |

TABLE 2-continued
| Exemplary chemical moieties Z formed by coupling reactions in the formation of antibody-drug conjugates | |
|---|---|
| Exemplary Coupling Reactions | Chemical Moiety Z Formed by Coupling Reactions |
| [3 + 2] Cycloaddition, Esterification | 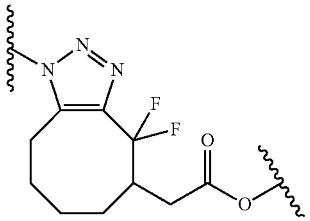 [SMILES: *OC(=O)CC1CCCCc2c(nnn2*)C1(F)F] |
| [3 + 2] Cycloaddition, Esterification | 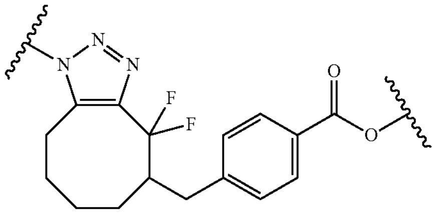 [SMILES: *OC(=O)c1ccc(CC2CCCCc3c(nnn3*)C2(F)F)cc1] |
| [3 + 2] Cycloaddition, Esterification | 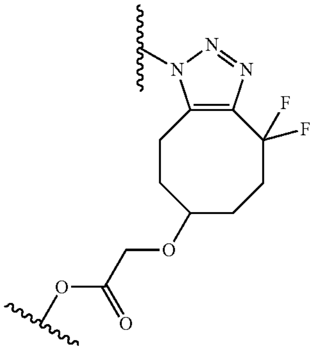 [SMILES: *OC(=O)COC1CCc2c(nnn2*)C(F)(F)CC1] |
| [3 + 2] Cycloaddition, Esterification | 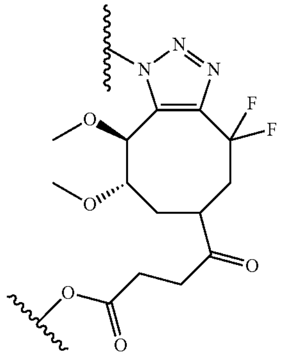 [SMILES: *OC(=O)CCC(=O)C1C[C@H](OC)[C@@H](OC)c2c(nnn2*)C(F)(F)C1] |

TABLE 2-continued
| Exemplary chemical moieties Z formed by coupling reactions in the formation of antibody-drug conjugates | |
|---|---|
| Exemplary Coupling Reactions | Chemical Moiety Z Formed by Coupling Reactions |
| [3 + 2] Cycloaddition, Esterification | 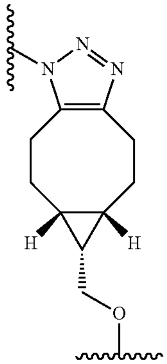 [SMILES: *OC[C@@H]1[C@@H]2CCc3c(nnn3*)CC[C@@H]21] |
| [3 + 2] Cycloaddition, Esterification | 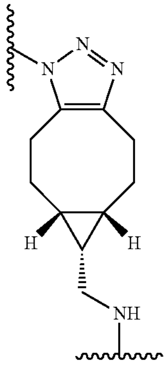 [SMILES: *NC[C@@H]1[C@@H]2CCc3c(nnn3*)CC[C@@H]21] |
| [3 + 2] Cycloaddition, Esterification | 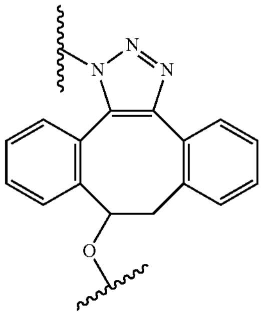 [SMILES: *OC1Cc2ccccc2-c2nnn(*)c2-c2ccccc21] |
| [3 + 2] Cycloaddition, Etherification | 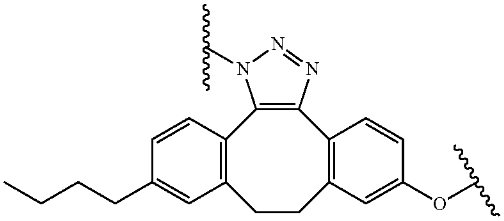 [SMILES: *Oc1ccc2c(c1)CCc1cc(CCCC)ccc1-c1c-2nnn1*] |

TABLE 2-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | 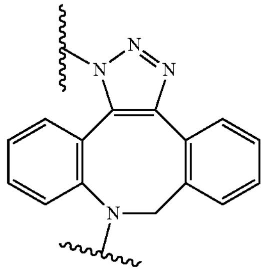 [SMILES: *N1Cc2ccccc2-c2nnn(*)c2-c2ccccc21] |
| Michael addition | 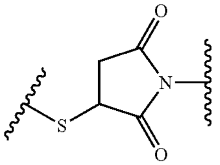 [SMILES: *SC1CC(=O)N(*)C1=O] |
| Michael addition | 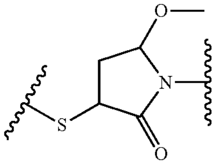 [SMILES: *SC1CC(OC)N(*)C1=O] |
| Imine condensation, Amidation | 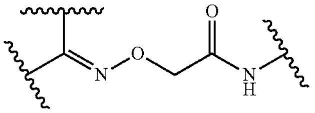 [SMILES: *NC(=O)CON=C(*)*] |
| Imine condensation | 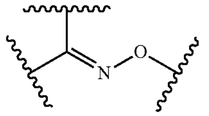 [SMILES: *ON=C(*)*] |
| Disulfide formation | 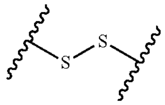 [SMILES: *SS*] |
| Thiol alkylation | 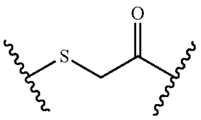 [SMILES: *SCC(*)=O] |
| Condensation, Michael addition | 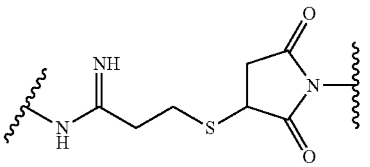 [SMILES: *NC(=N)CCSC1CC(=O)N(*)C1=O] |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive moiety Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

In some embodiments, Z' is $-NR^{13}C(=O)CH=CH_2$, $-N_3$, $-SH$, $-S(=O)_2(CH=CH_2)$, $-(CH_2)_2S(=O)_2(CH=CH_2)$, $-NR^{13}S(=O)_2(CH=CH_2)$, $-NR^{13}C(=O)CH_2R^{14}$, $-NR^{13}C(=O)CH_2Br$, $-NR^{13}C(=O)CH_2I$, $-NHC(=O)CH_2Br$, $-NHC(=O)CH_2I$, $-ONH_2$, $-C(O)NHNH_2$, $-CO_2H$, $-NH_2$, $-NH(C=O)$, $-NC(=S)$,
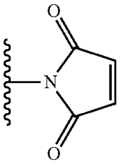, 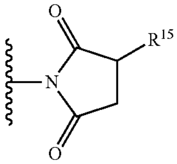, 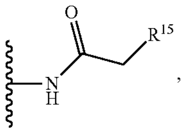, 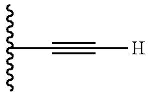, 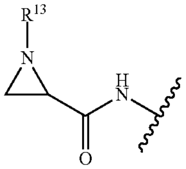,
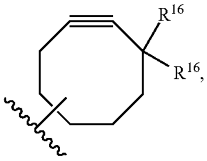, 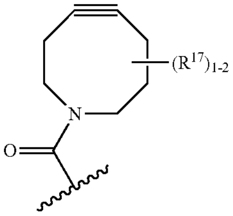, 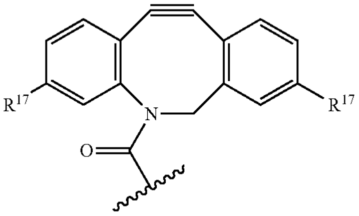,
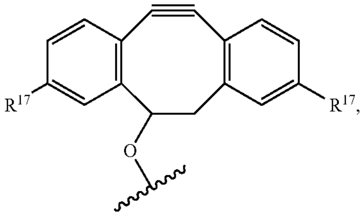, 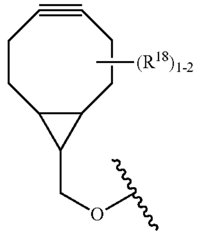, 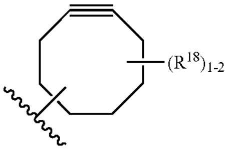,
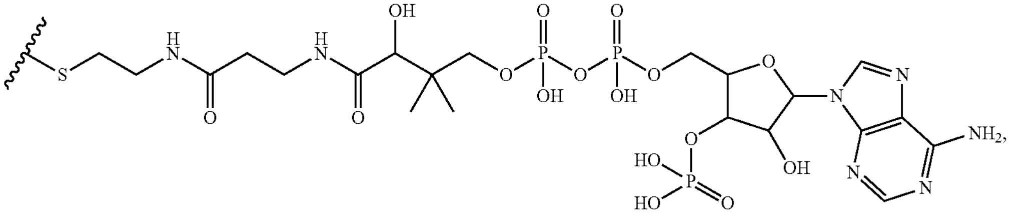,
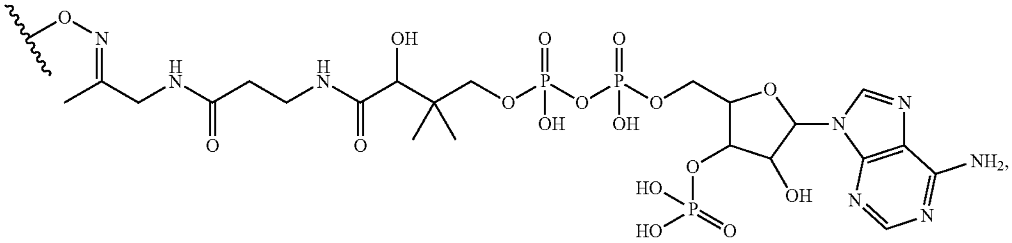,
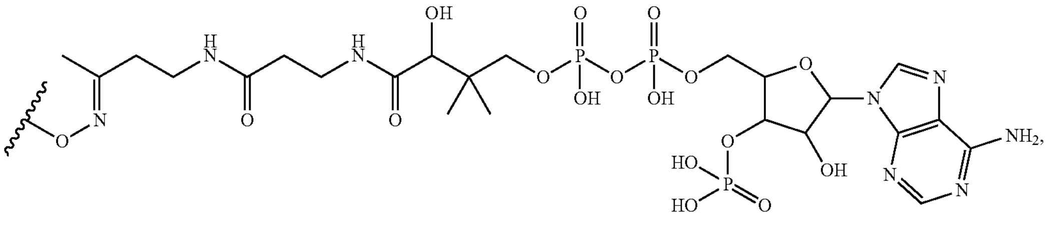,
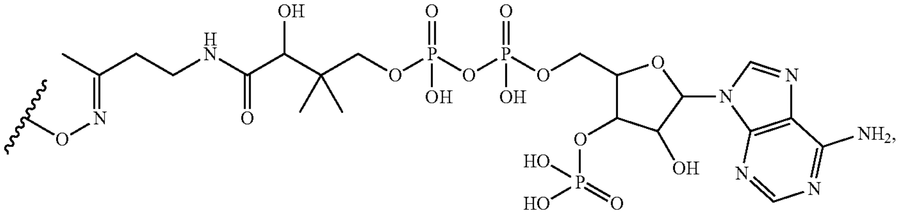, -continued

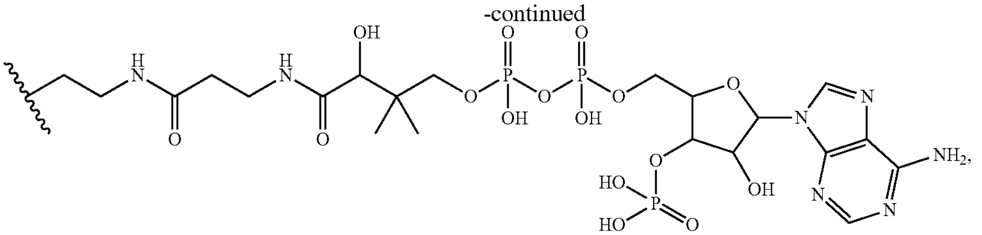

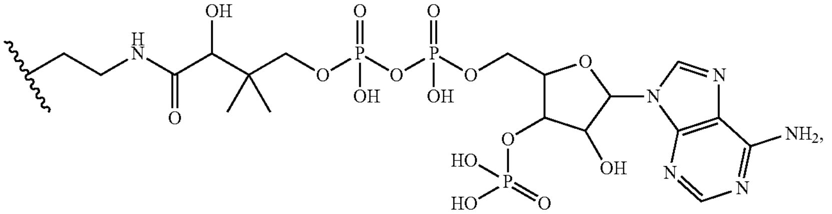

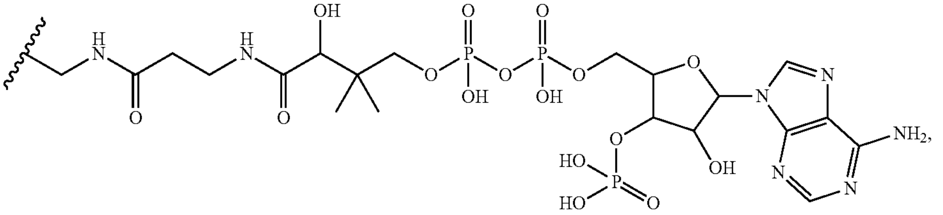

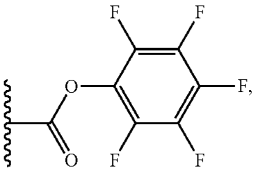
,
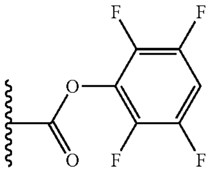
,
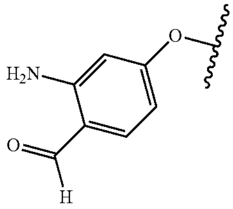
,
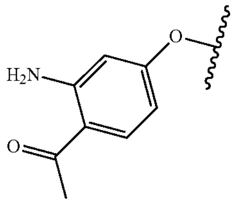
,
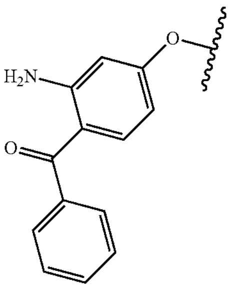
,
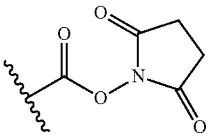
, or
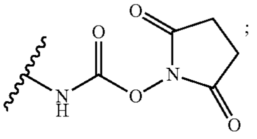
;

wherein $R^{13}$ is independently selected for each occasion from H and $C_1$-$C_6$ alkyl;

$R^{14}$ is $-S(CH_2)_nCHR^{15}NHC(=O)R^{13}$;

$R^{15}$ is $R^{13}$ or $-C(=O)OR^{13}$;

$R^{16}$ is independently selected for each occasion from H, $C_1$-$C_6$ alkyl, F, Cl, and —OH;

$R^{17}$ is independently selected for each occasion from H, $C_1$-$C_6$ alkyl, F, Cl, $-NH_2$, $-OCH_3$, $-OCH_2CH_3$, $-N(CH_3)_2$, —CN, $-NO_2$ and —OH; and $R^{18}$ is independently selected for each occasion from H, $C_1$-$C_6$ alkyl, F, benzyloxy substituted with —C(=O)OH, benzyl substituted with —C(=O)OH, $C_1$-$C_4$ alkoxy substituted with —C(=O)OH, and $C_1$-$C_4$ alkyl substituted with —C(=O)OH;

m is independently selected for each occasion from 1, 2, 3, 4, 5, 6, 7, 8, 9 and 10; and n is independently selected for each occasion from 1, 2, 3, 4, 5, 6, 7, 8, 9, 10, 11, 12, 13 and 14.

As depicted in Table 2, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i) N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z' attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z'. For instance, Z' may be a Michael acceptor (e.g., maleimide), activated ester, electron-deficient carbonyl compound, and aldehyde, among others.

For instance, linkers suitable for the synthesis of ADCs include, without limitation, reactive substituents Z' such as maleimide or haloalkyl groups. These may be attached to the linker by reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (het-ero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

Non-limiting examples of amatoxin-linker conjugates containing a reactive substituent Z' suitable for reaction with a reactive residue on the antibody or antigen-binding fragment thereof include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl) cyclohexanecarbonyl)piperazin-1-yl)-amatoxin; 7'C-(4-(6-(4-((maleimido)methyl)cyclohexanecarboxamido) hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido) ethyl)piperidin-1-yl)-amatoxin; 7'C-(4-(2-(4-((maleimido) methyl)cyclohexanecarboxamido)ethyl)piperidin-1-yl)-amatoxin; 7'C-(4-(2-(6-(4-((maleimido)methyl) cyclohexanecarboxamido)hexanamido)ethyl)piperidin-1-yl)-amatoxin; 7'C-(4-(2-(3-carboxypropanamido)ethyl) piperidin-1-yl)-amatoxin; 7'C-(4-(2-(2-bromoacetamido) ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl) cyclohexanecarboxamido)hexanamido)ethyDpiperidin-1-yl)-amatoxin; 7'C-(3-((6-(maleimido)hexanamido)methyl) pyrrolidin-1-yl)-amatoxin; 7'C-(3-((6-(6-(maleimido) hexanamido)hexanamido)methyl)pyrrolidin-1-yl)-amatoxin; 7'C-(3-((4-((maleimido)methyl) cyclohexanecarboxamido)methyl)pyrrolidin-1-yl)-amatoxin; 7'C-(3-((6-((4-(maleimido)methyl) cyclohexanecarboxamido)hexanamido)methyl)pyrrolidin-1-yl)-amatoxin; 7'C-(4-(2-(6-(2-(aminooxy)acetamido) hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl) piperazin-1-yl)-amatoxin; 7'C-(4-(6-(2-(aminooxy) acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)

methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyDpiperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1-yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; (2-(aminooxy)acetylamido)hexyl)-amatoxin; 6'O-((6-aminooxy)hexyl)-amatoxin; and 6'O-(6-(2-iodoacetamido)hexyl)-amatoxin.

In some embodiments, an amatoxin as disclosed herein is conjugated to a linker-reactive moiety -L-Z' having the following formula:

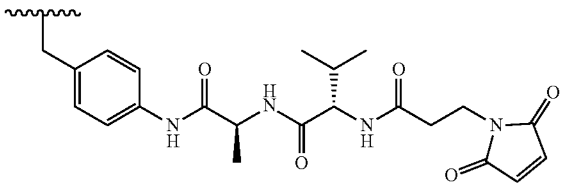 [SMILES: *Cc1ccc(NC(=O)[C@H](C)NC(=O)[C@@H](NC(=O)CCN2C(=O)C=CC2=O)C(C)C)cc1]

In some embodiments, an amatoxin as disclosed herein is conjugated to a linker-reactive moiety -L-Z' having the following formula:

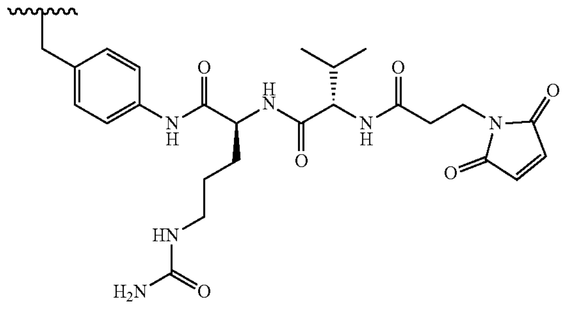 [SMILES: *Cc1ccc(NC(=O)[C@H](CCCNC(N)=O)NC(=O)[C@@H](NC(=O)CCN2C(=O)C=CC2=O)C(C)C)cc1]

The foregoing linker moieties and amatoxin-linker conjugates, among others useful in conjunction with the compositions and methods described herein, are described, for example, in U.S. Patent Application Publication No. 2015/

0218220 and Patent Application Publication No. WO2017/149077, the disclosure of each of which is incorporated herein by reference in its entirety.

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

Preparation of Antibody-Drug Conjugates

In the ADCs of formula I as disclosed herein, an anti-CD45 antibody, or antigen binding fragment thereof, can be conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z', followed by reaction with a reactive substituent of an antibody or antigen binding fragment thereof as described herein above. Additional methods for preparing ADC are described herein.

In another aspect, the anti-CD45 antibody, or antigen binding fragment thereof, has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the anti-CD45 antibody, or antigen binding fragment thereof, can have one or more carbohydrate groups that can be chemically modified to have one or more sulfhydryl groups. The ADC is then formed by conjugation through the sulfhydryl group's sulfur atom as described herein above.

In yet another aspect, the anti-CD45 antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), which is incorporated herein by reference in its entirety.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

Methods of Treatment

CD45 is an important cell surface molecule broadly expressed throughout the hematopoietic and immune systems. Described herein are anti-CD45 antibodies and anti-CD45 ADCs that can be used to treat patients with autoimmune diseases such as arthritis (or diseases represented by proteoglycan-induced arthritis (PGIA)), autoimmune encephalitis, sclerodermatous graft-vs-host disease, multiple sclerosis, or scleroderma. Furthermore, there is currently a need for compositions and methods for promoting the engraftment of exogenous hematopoietic stem cell grafts such that the multi-potency and hematopoietic functionality of these cells is preserved following transplantation. The compositions disclosed herein further provide a solution to this challenging problem.

Thus, disclosed herein are methods of treating a variety of autoimmune diseases, such as rheumatoid arthritis (represented by PGIA in a mouse model), autoimmune encephalitis, type 1 diabetes, or sclerodermatous graft-vs-host disease. The compositions and methods described herein may (i) directly deplete a population of cells that give rise to a pathology, such as a population of autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an ADC, antibody, or antigen-binding fragment thereof, capable of binding an antigen expressed by an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. The invention is based in part on the discovery that ADCs, antibodies, or antigen-binding fragments thereof, capable of binding CD45 expressed by hematopoietic stem cells can be administered to a patient to affect both of the above activities. ADCs, antibodies, or antigen-binding fragments thereof, that bind an antigen expressed by hematopoietic stem cells and/or autoimmune cells (e.g., CD45) can be administered to a patient suffering from an autoimmune disease (e.g., rheumatoid arthritis (represented by PGIA in a mouse model), autoimmune encephalitis, type 1 diabetes, or scleroderma) to directly deplete a population of autoimmune cells. The foregoing agent(s) can also condition the patient for receipt of a transplant comprising hematopoietic stem cells, and be administered to a patient in need of hematopoietic stem cell transplant therapy in order to promote the survival and engraftment potential of transplanted hematopoietic stem cells.

As described herein, hematopoietic stem cell transplant therapy can be administered to a subject in need of treatment (e.g., for an autoimmune disease or disorder) so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

The compositions and methods described herein can be used to treat autoimmune disorders, such as rheumatoid arthritis (represented by PGIA in a mouse model), autoimmune encephalitis, type 1 diabetes, or scleroderma. For instance, an antibody, or antigen-binding fragment thereof, can be administered to a subject, such as a human patient suffering from an autoimmune disorder, so as to kill a CD45+ immune cell. For example, a CD45+ immune cell may be an autoreactive lymphocyte, such as a T-cell that expresses a T-cell receptor that specifically binds, and mounts an immune response against, a self antigen. By depleting self-reactive, CD45+, the compositions and methods described herein can be used to treat autoimmune pathologies, such as those described herein. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can reconstitute a population of cells depleted during autoimmune cell eradication.

In some embodiments, an anti-CD45 antibody or ADC can be administered to the subject in conjunction with a second therapeutic agent.

Autoimmune diseases that can be treated using the compositions and methods described herein include, without limitation, PGIA, autoimmune encephalitis, scleroderma, psoriasis, psoriatic arthritis, Type 1 diabetes mellitus (Type 1 diabetes), rheumatoid arthritis (RA), human systemic lupus erythematosus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis. In certain embodiments, the autoimmune disease is rheumatoid arthritis (represented by PGIA in a mouse model). In certain embodiments, the autoimmune disease is an inflammatory arthritis. Non-limiting examples of an inflammatory arthritis include rheumatoid arthritis, psoriatic arthritis, ankylosing spondylitis, juvenile idiopathic arthritis, and systemic lupus erythematosus. In other embodiments, the autoimmune disease is autoimmune encephalitis. In yet further embodiments, the autoimmune disease is sclerodermatous graft-vs-host disease.

In some embodiments, the transplant is allogeneic. In some embodiments, the transplant is autologous.

In some embodiments, the transplant is a bone marrow transplant, a peripheral blood transplant, or a cord blood transplant.

In some embodiments, the transplant includes hematopoietic cells (e.g., hematopoietic stem cells).

In any of the embodiments described herein, the transplant may be any solid organ or skin transplant. In some embodiments, the transplant is selected from the group consisting of kidney transplant, heart transplant, liver transplant, pancreas transplant, lung transplant, intestine transplant and skin transplant.

In some embodiments, the compositions and methods described herein may be effective to cause immune reset in patients having an autoimmune disease. In some such embodiments, a patient having an autoimmune disease who undergoes treatment in accordance with the present methods does not require additional treatment (e.g., chronic treatment) for the autoimmune disease following transplantation. For example, in some embodiments, the patient has multiple sclerosis, and the patient does not require treatment with natalizumab, dimethyl fumarate, or monomethyl fumarate following treatment with an anti-CD45 ADC and transplantation in accordance with the methods herein. In other embodiments, the patient has arthritis, and the patient does not require treatment with a TNF inhibitor (e.g., anti-TNFα antibody, such as etanercept, infliximab, adalimumab, certolizumab pegol, or golimumab) following treatment with an anti-CD45 ADC and transplantation in accordance with the methods herein. In certain embodiments, a single dose of the anti-CD45 ADC is effective to achieve immune reset.

A patient having an autoimmune disease who undergoes treatment in accordance with the methods provided herein may, in some instances, enter remission, such as clinical remission, biochemical remission, or histologic remission. For example, in some embodiments, the patient enters remission for at least 1 year, at least 2 years, at least 3 years, at least 4 years, at least 5 years, at least 6 years, at least 7 years, at least 8 years, at least 9 years, or at least 10 years. In some embodiments, the patient enters remission for at least 1-3 years, at least 3-5 years, at least 5-7 years, at least 7-9 years, or at least 8-10 years.

Routes of Administration and Dosing

Antibodies, antigen-binding fragments thereof, or ADCs described herein can be administered to a patient (e.g., a human patient suffering from an autoimmune disease, or in need of hematopoietic stem cell transplant therapy) in a variety of dosage forms. For instance, ADCs described herein can be administered to a patient suffering from an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

Some embodiments comprise administering to a subject an anti-CD45 antibody, or antigen binding portion thereof. Some embodiments comprise administering to a subject an ADC that includes an anti-CD45 antibody, or an antigen binding portion thereof.

Some embodiments comprise administering to a subject a combination of an anti-CD45 antibody (or an antigen binding portion thereof) and a second therapeutic agent. Some embodiments comprise administering to a subject a combination of an ADC comprising an anti-CD45 antibody (or an antigen binding portion thereof) and a second therapeutic agent. Some embodiments comprise administering to a subject a bispecific antibody, antigen-binding portion thereof, or ADC that specifically binds CD45 and a second antigen. Some aspects comprise administering to a subject a combination of an anti-CD45 antibody (or an antigen binding portion thereof) or ADC and two or more additional therapeutic agents.

Pharmaceutical formulations comprising an anti-CD45 antibody, or conjugates thereof (e.g., ADCs as described herein) are prepared by mixing such antibody or ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The ADCs described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and/or the patient's excretion rate.

The effective dose of an antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 μg/mL) of the antibody, or antigen-binding fragment thereof. The dose may be administered one or more times (e.g., 2-10 times) per day, week, or month to a subject (e.g., a human) suffering from an autoimmune disease, or undergoing conditioning therapy in preparation for receipt of a hematopoietic stem cell transplant.

In certain embodiments, the anti-CD45 antibody or ADC is administered to the patient as a single dose. In other embodiments, the anti-CD45 antibody or ADC is administered to the patient as a fractionated dose, in which the dose of the anti-CD45 antibody or ADC is divided and administered to the subject at spaced intervals. For example, in a fractionated dosing regimen, the dose of the anti-CD45 antibody or ADC can be divided into two, three, four, five, six, seven, eight, nine or ten fractions, and each fraction is administered to the subject at spaced intervals. In some embodiments, the intervals are spaced by 1 hour, 3 hours, 6 hours, 9 hours, 12 hours, 15 hours, 18 hours, 21 hours, 24 hours, 36 hours, 48 hours, 72 hours, 96 hours, 120 hours, 1 week, 1.5 weeks, 2 weeks, 2.5 weeks, 3 weeks, 4 weeks, 5 weeks, 6 weeks, 7 weeks, or 8 weeks. In one embodiment, an anti-CD45 antibody or ADC described herein is administered to the patient as a fractionated dose, in which two fractions are administered to the patient. In one embodiment, an anti-CD45 antibody or ADC described herein is administered to the patient as a fractionated dose, in which three fractions are administered to the patient.

In some embodiments, the dose of an antibody or ADC described herein administered to the human patient is about 0.001 mg/kg to 10 mg/kg, about 0.01 mg/kg to 9.5 mg/kg, about 0.1 mg/kg to 9 mg/kg, about 0.1 mg/kg to 8.5 mg/kg, about 0.1 mg/kg to 8 mg/kg, about 0.1 mg/kg to 7.5 mg/kg, about 0.1 mg/kg to 7 mg/kg, about 0.1 mg/kg to 6.5 mg/kg, about 0.1 mg/kg to 6 mg/kg, about 0.1 mg/kg to 5.5 mg/kg, about 0.1 mg/kg to 5 mg/kg, about 0.1 mg/kg to 4.5 mg/kg, about 0.1 mg/kg to 4 mg/kg, about 0.5 mg/kg to 3.5 mg/kg, about 0.5 mg/kg to 3 mg/kg, about 1 mg/kg to 10 mg/kg, about 1 mg/kg to 9 mg/kg, about 1 mg/kg to 8 mg/kg, about 1 mg/kg to 7 mg/kg, about 1 mg/kg to 6 mg/kg, about 1 mg/kg to 5 mg/kg, about 1 mg/kg to 4 mg/kg, or about 1 mg/kg to 3 mg/kg.

In some embodiments, the dose of an antibody or ADC administered to the human patient is about 0.1 mg/kg to about 0.3 mg/kg.

In some embodiments, the dose of an antibody or ADC administered to the human patient is about 0.15 mg/kg to about 0.3 mg/kg.

In some embodiments, the dose of an antibody or ADC administered to the human patient is about 0.15 mg/kg to about 0.25 mg/kg.

In some embodiments, the dose of an antibody or administered to the human patient is about 0.2 mg/kg to about 0.3 mg/kg.

In some embodiments, the dose of an antibody or ADC administered to the human patient is about 0.25 mg/kg to about 0.3 mg/kg.

In some embodiments, the dose of an antibody or ADC administered to the human patient is about 1 mg/kg to about 3 mg/kg.

In some embodiments, the dose of an antibody or ADC administered to the human patient is about 0.1 mg/kg.

In some embodiments, the dose of an antibody or ADC administered to the human patient is about 0.2 mg/kg.

In some embodiments, the dose of an antibody or ADC administered to the human patient is about 0.3 mg/kg.

In some embodiments, the dose of an antibody or ADC administered to the human patient is about 1 mg/kg.

In some embodiments, the dose of an antibody or ADC administered to the human patient is about 2 mg/kg.

In some embodiments, the dose of an antibody or ADC administered to the human patient is about 3 mg/kg.

In the case of a conditioning procedure prior to hematopoietic stem cell transplantation, the antibody, or antigen-binding fragment thereof can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Using the methods disclosed herein, a physician of skill in the art can administer to a human patient in need of hematopoietic stem cell transplant therapy an ADC, an antibody or an antigen-binding fragment thereof capable of binding CD45 expressed by hematopoietic stem cells. In this fashion, a population of endogenous hematopoietic stem cells can be depleted prior to administration of an exogenous hematopoietic stem cell graft so as to promote engraftment of the hematopoietic stem cell graft. The antibody may be covalently conjugated to a toxin, such as a cytotoxic molecule described herein or known in the art. For instance, an anti-CD45 antibody or antigen-binding fragment thereof can be covalently conjugated to a cytotoxin, such as pseudomonas exotoxin A, deBouganin, diphtheria toxin, an amatoxin, such as α-amanitin, β-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or drug-antibody conjugate can subsequently be administered to the patient, for example, by intravenous administration, prior to transplantation of exogenous hematopoietic stem cells (such as autologous, syngeneic, or allogeneic hematopoietic stem cells) to the patient.

The anti-CD45 antibody, antigen-binding fragment thereof, or ADC can be administered in an amount sufficient to reduce the quantity of endogenous hematopoietic stem cells, for example, by 10%, 20%, 30%, 40%, 50%, 60%, 70%, 80%, 90%, 95%, or more prior to hematopoietic stem cell transplant therapy. The reduction in hematopoietic stem cell count can be monitored using conventional techniques known in the art, such as by FACS analysis of cells expressing characteristic hematopoietic stem cell surface antigens in a blood sample withdrawn from the patient at varying intervals during conditioning therapy. For instance, a physician of skill in the art can withdraw a blood sample from the patient at various time points during conditioning therapy and determine the extent of endogenous hematopoietic stem cell reduction by conducting a FACS analysis to elucidate the relative concentrations of hematopoietic stem cells in the sample using antibodies that bind to hematopoietic stem cell marker antigens. According to some embodiments, when the concentration of hematopoietic stem cells has reached a minimum value in response to conditioning therapy with an anti-CD45 antibody, antigen-binding fragment thereof, or ADC, the physician may conclude the conditioning therapy, and may begin preparing the patient for hematopoietic stem cell transplant therapy.

The anti-CD45 antibody, antigen-binding fragment thereof, or ADC can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or drug-antibody conjugate can be administered to the patient at a dosage of, for example, from 0.001 mg/kg to 100 mg/kg prior to administration of a hematopoietic stem cell graft to the patient. The anti-CD45 antibody, antigen-binding fragment thereof, or ADC can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from $1\times10^3$ to $1\times10^9$ hematopoietic stem cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from 1 hour to 6 months, or more, following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that treatment with the anti-CD45 antibody, or antigen-binding fragment thereof, or ADC has successfully promoted engraftment of the transplanted hematopoietic stem cell graft.

Engraftment of hematopoietic stem cell transplants due to the administration of an anti-CD45 antibody, antigen-binding fragments thereof, or ADCs, can manifest in a variety of empirical measurements. For instance, engraftment of transplanted hematopoietic stem cells can be evaluated by assessing the quantity of competitive repopulating units (CRU) present within the bone marrow of a patient following administration of an anti-CD45 antibody or antigen-binding fragment thereof, and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Anti-CD45 ADC Successfully Conditions Mice for Congenic Transplant To address challenges associated with autologous HSC transplantation, antibody drug conjugates (ADCs) were developed targeting CD45, a target expressed throughout the hematopoietic system to enable simultaneous myelo- and lympho-depletion prior to autologous transplant in autoimmune diseases. To model this strategy, an anti-mouse CD45-ADC containing an anti-CD45 antibody conjugated to pyrrolobenzodiazepine (PBD) was developed that achieved full myeloablation with single dose administration in mice.

C57BL/6 (CD45.2) and C57BL/6 (CD45.1) mice were purchased from the Jackson Laboratories. C57BL/6 (CD45.2) mice were conditioned with a single intravenous dose administration of anti-mouse CD45-ADC (0.3, 1, or 3 mg/kg) or Isotype-ADC (isotype control mAb conjugated to PBD) (3 mg/kg) 48 h prior to transplant (see FIG. 1A for depiction of study design). 5 Gy TBI was used as the conventional conditioning positive control administered 24 h prior to transplant. Conditioned mice were transplanted with $2\times10^7$ whole bone marrow cells harvested from pooled C57BL/6 CD45.1 congenic donor, and chimerism was assessed over 16 weeks. Peripheral blood was harvested at week 4, 8, 12, and 16, and assessed by flow cytometry.

Figure 1B:
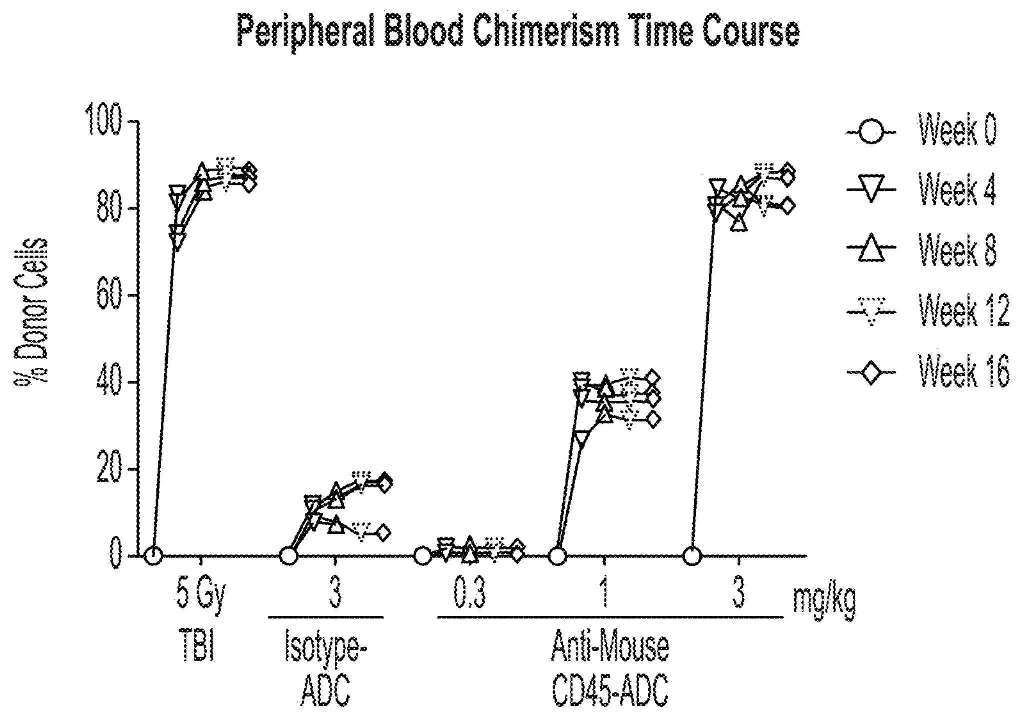
Figure 1C:
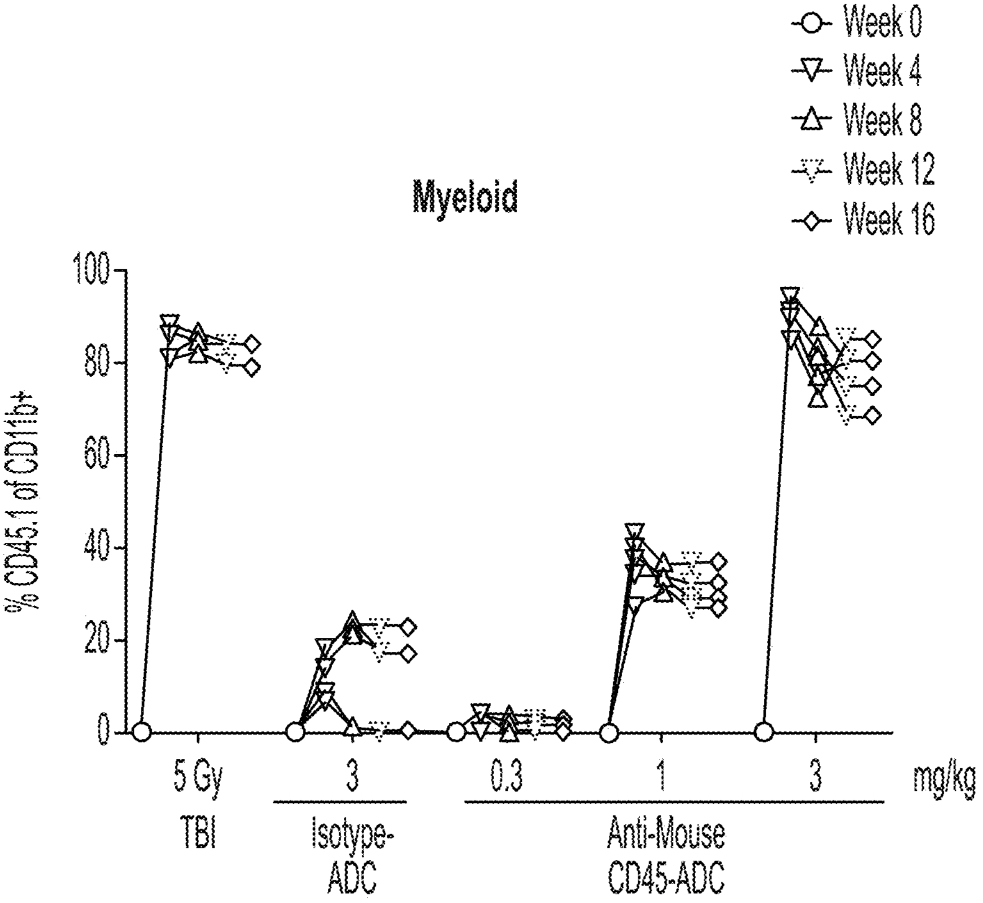
Figure 1D:
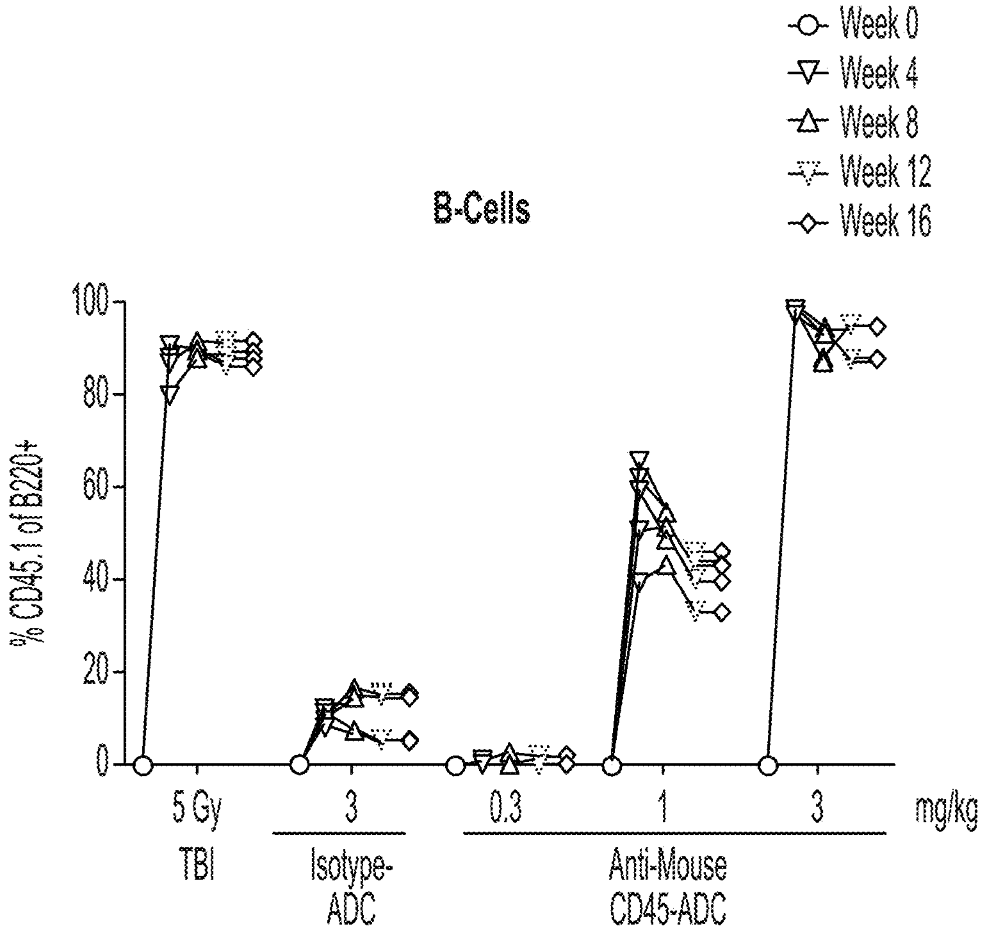
Figure 1E:
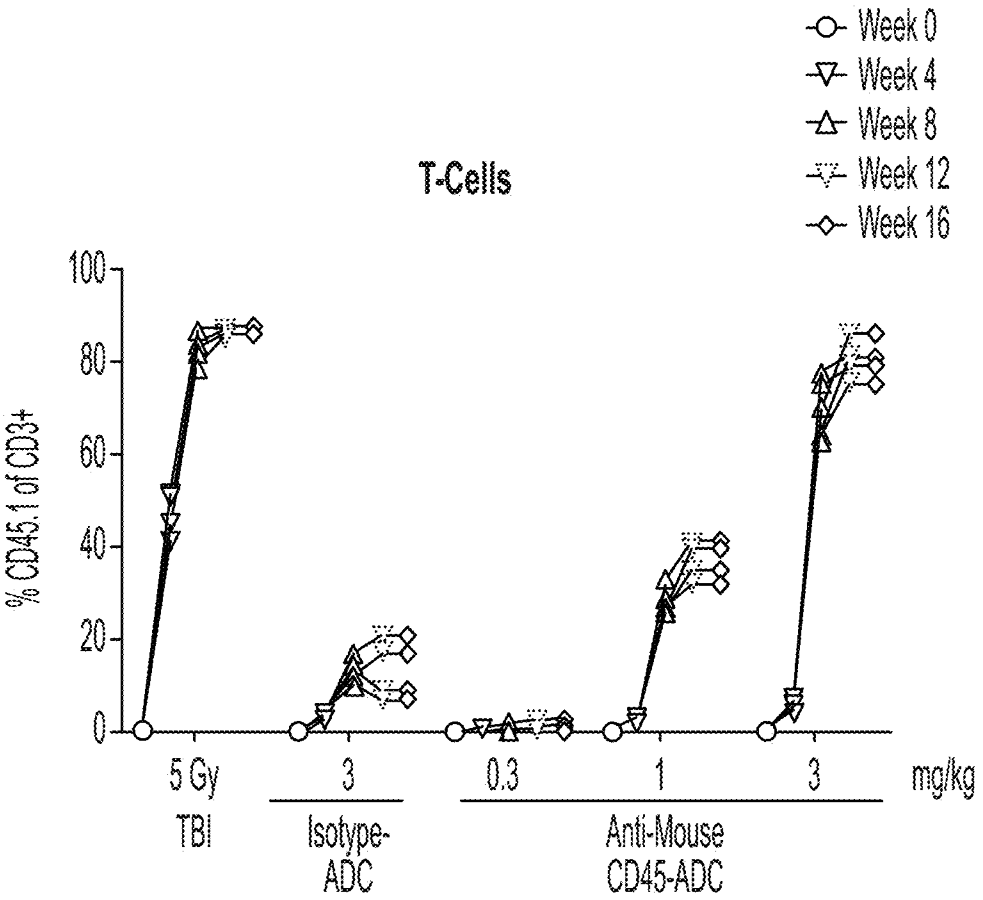

As shown in FIG. 1B, dose responsive donor chimerism was observed with CD45-ADC conditioning. Dose responsive donor myeloid, B-cells, and T-cells were observed over a 16 week time course with CD45-ADC conditioning (FIGS. 1C-1E). These results indicate that anti-CD45-ADC (3 mg/kg, iv, single dose) conditioning enables full donor chimerism following congenic transplant.

Example 2. Anti-CD45-ADC Preferentially Kills Proliferating T Cells In Vitro Mouse PBMCs were cultured with plate bound αCD3 clone 145-2C11C to promote survival and expansion of murine T cells. T cells were cultured with an anti-mouse CD45-ADC (anti-CD45 mAb conjugated to PBD) or an isotype-ADC, and total T cell number and percentage of proliferating (Ki67+) T cells were assessed.

Figure 2B:
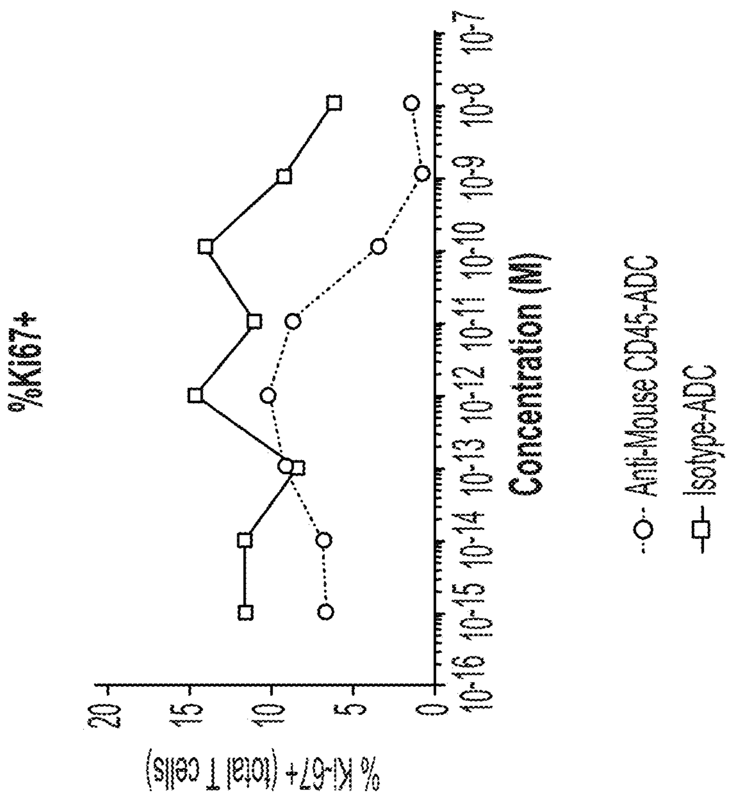
FIGS. 2A and 2B graphically depict the results of in vitro cell killing assays showing that anti-CD45 ADCs preferentially kills proliferating T cells in vitro. The total T cell number (FIG. 2A) or percentage of proliferating T cells (Ki67+.
Figure 2A:
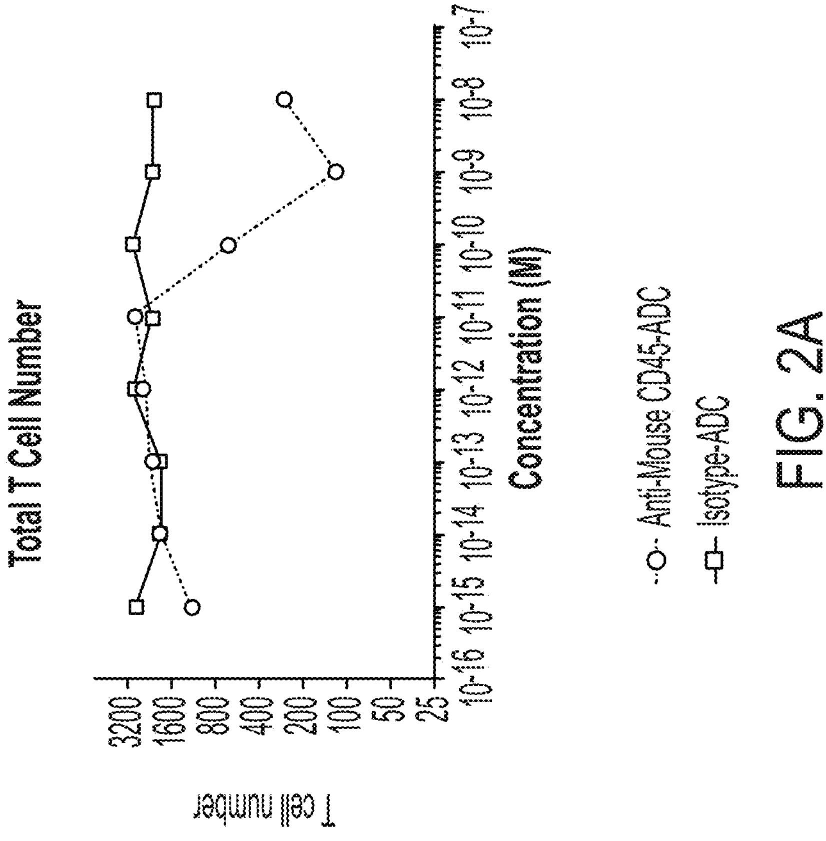

As shown in FIG. 2A, anti-mouse CD45-ADC (vs. Isotype-ADC) treatment substantially reduces the number of T cells. As shown in FIG. 2B, there was a dose responsive decrease of proliferating T cells (Ki67+) with increasing doses of anti-mouse CD45-ADC compared to Isotype-ADC. These results show that anti-mouse CD45-ADC preferentially kills cycling murine T cells in vitro.

Example 3. Anti-CD45-ADC Preferentially Kills Proliferating T Cells in an In Vivo Model of scGvDH Next, anti-CD45-ADC (anti-CD45 mAb conjugated to PBD) was assessed in the sclerodermatous Graft-vs-Host-Disease (scGVHD) model of scleroderma, also known as systemic sclerosis.

Figure 3A:
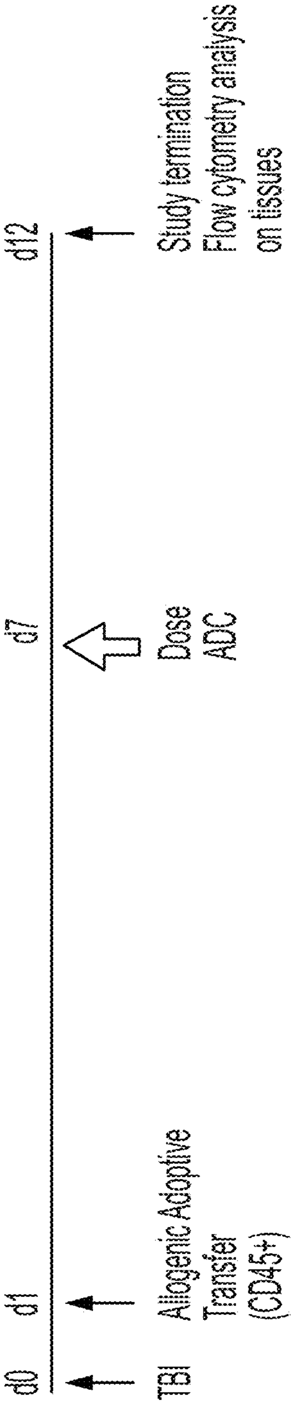
FIGS. 3A-3E graphically depict the results of an in vivo cell depletion assay showing that anti-CD45-ADC preferentially kills proliferating T cells in an in vivo model of sclerodermatous graft versus host disease (scGvDH), representative of scleroderma.

DBA/2 and Balb/c (CD45.1) mice were purchased from the Jackson Laboratories. Balb/c (CD45.1) mice were conditioned with 6.5 Gy total body irradiation (TBI) 24 h prior to allogeneic (Allo) adoptive cell transfer of DBA/2 (CD45.2) splenocytes (see study design in FIG. 3A).

Figure 3B:
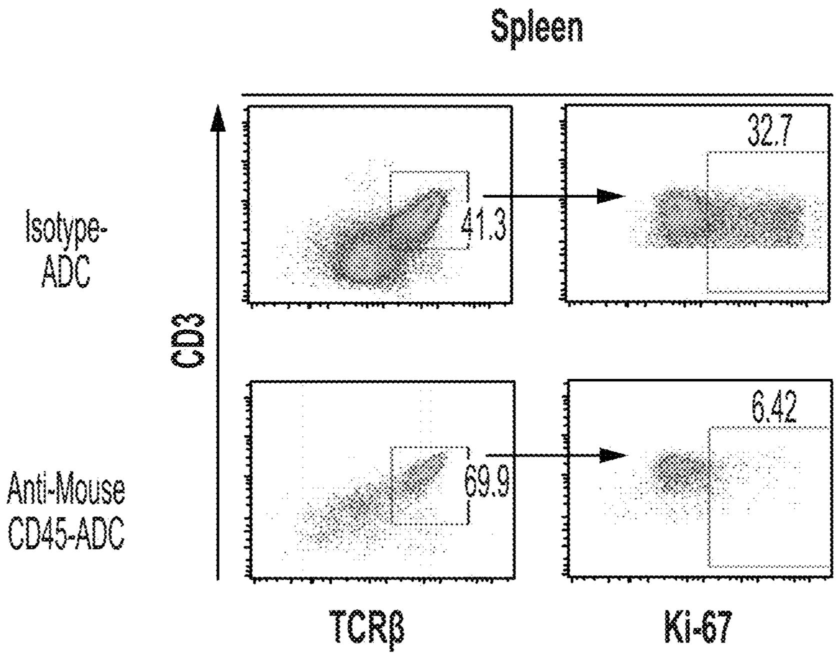
Figure 3C:
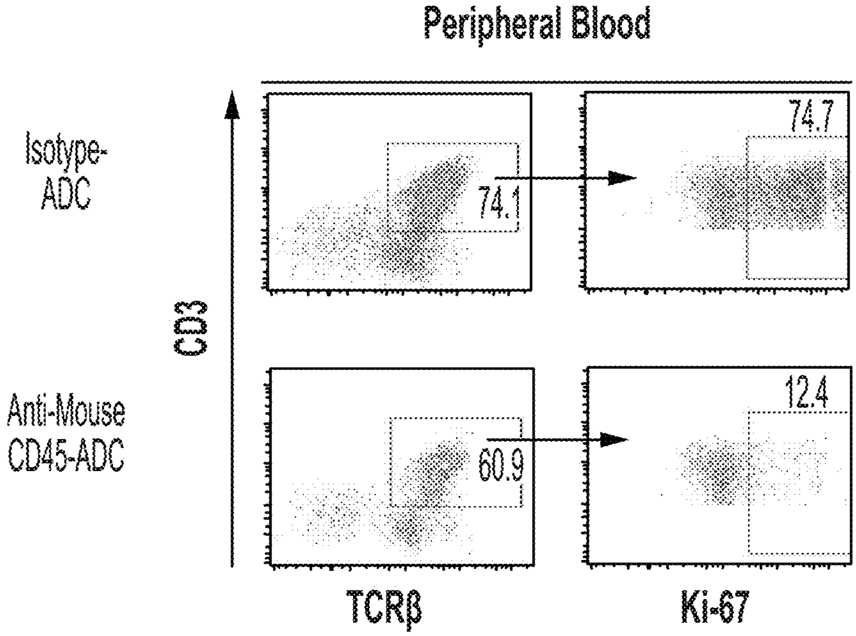
Figure 3D:
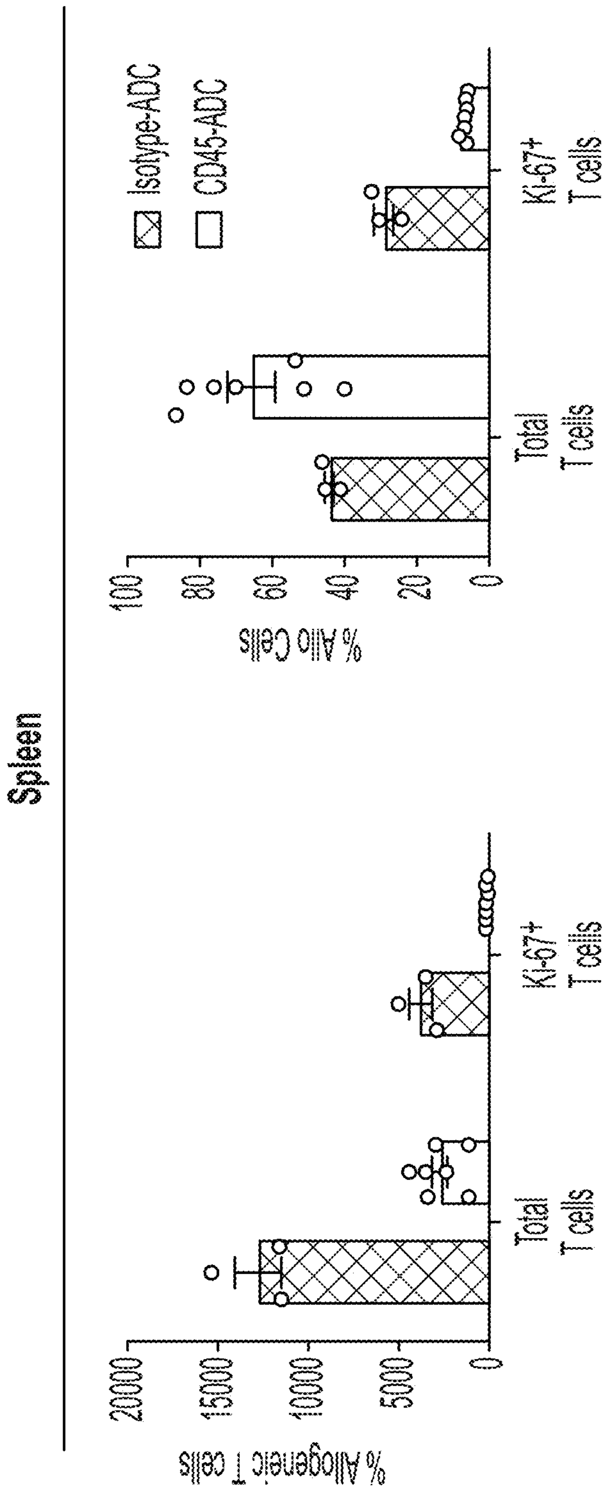
Figure 3E:
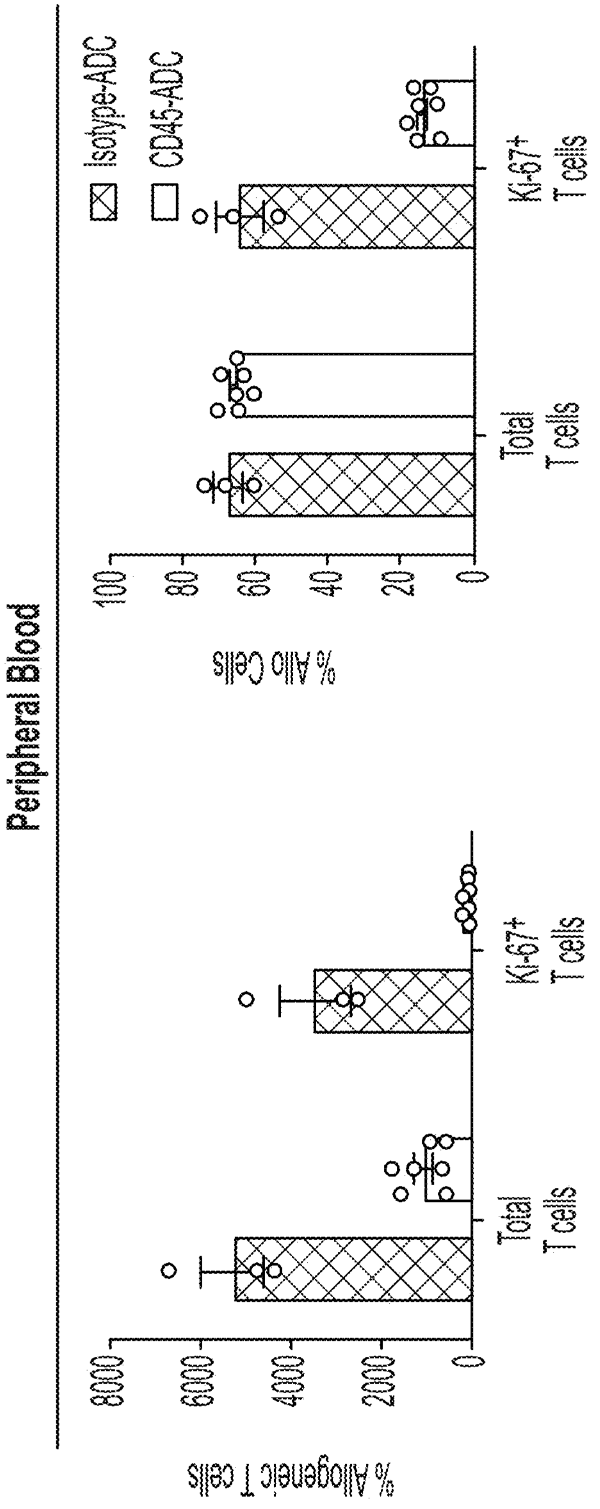

Host animals (CD45.1+) were treated with a single intravenous dose (3 mg/kg) administration of anti-mouse CD45-ADC, or isotype-ADC 7 days post initiation of scGvHD (CD45.2+ cells). Animals were euthanized on day 12 post initiation (5 days post ADC administration). Tissues (blood, spleen) were analyzed for allogeneic cells, T-cells, and proliferating T cells (FIGS. 3B and 3C). As shown in FIGS. 3D and 3E, greater depletion of T-cells was observed with CD45-ADC treatment in spleen or peripheral blood compared to Isotype-ADC. These results indicate that CD45-ADC selectively depletes a greater percentage of proliferating allogeneic T cells compared to isotype-ADC.

Example 4. Transient Amelioration of Murine EAE Disease Following Congenic Transplant Enabled by Total Body Irradiation (TBI)

Next, a murine experimental autoimmune encephalomyelitis (EAE) model of autoimmune disease was assessed. Conditioning by total body irradiation (TBI) was tested in the EAE model.

Experimental Autoimmune Encephalomyelitis (EAE) Model: C57BL/6 (CD45.2) mice were induced with MOG35-55 peptide in complete Freund's adjuvant, followed by the administration of pertussis toxin (PTX) at 4 h post MOG35-55 and 24 h post initial dose of PTX. Disease onset was around 9-12 days post induction. Animals were scored twice a day for a duration of 80 days post EAE induction. EAE Clinical Scoring Scale: 1-limp tail; 2-partial hind limb paralysis; 3-Complete hind limb paralysis; 4-Complete hind and partial front limb paralysis; 5-moribund bound. Animals were euthanized at 2 consecutive scores of 4. Terminal analysis of tissues (peripheral blood, lymph nodes) were evaluated to determine chimerism and immune component of the relapsing EAE mice. Lymph node cells were stimulated (S) with PMS/Ionomycin (50 ng/mL) and Brefeldin A (1 μg/mL) or not stimulated (NS) and evaluated for T cell chimerism (donor, host) and IL-17 production.

Figure 4A:
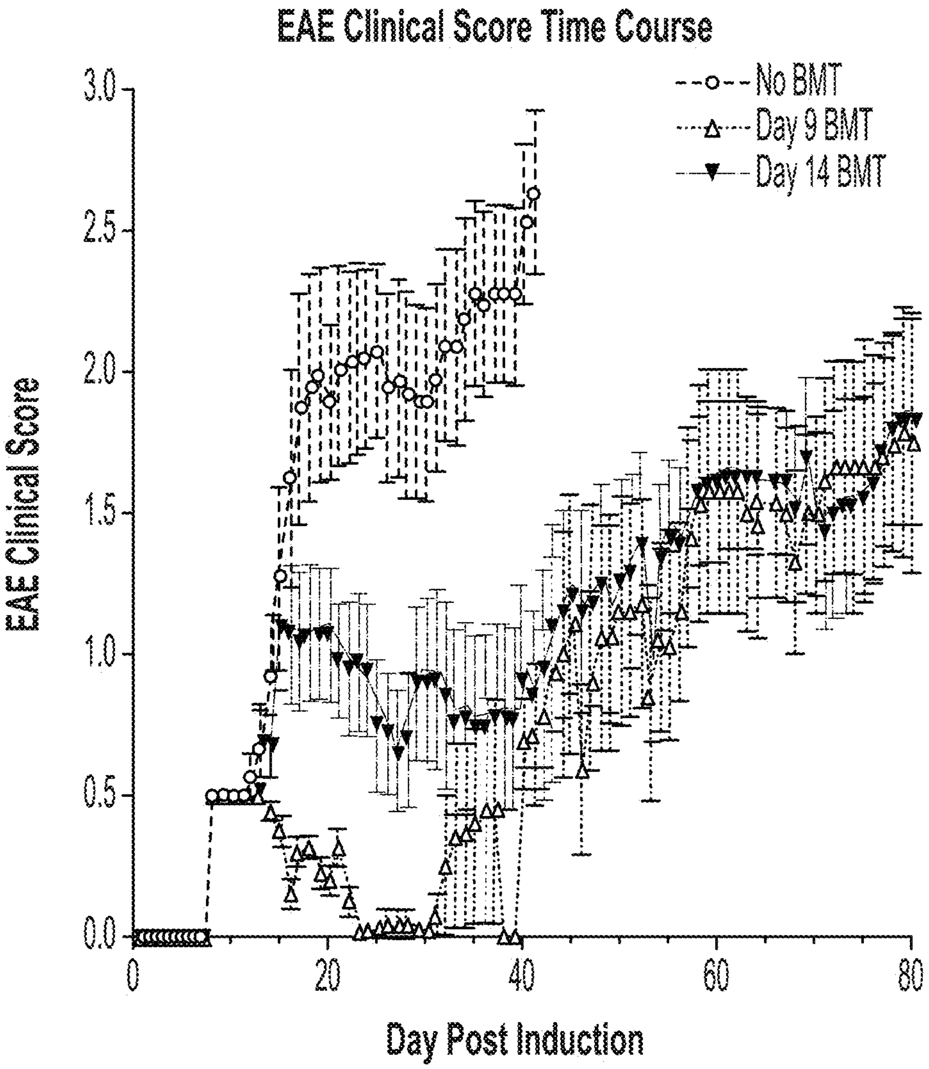
FIGS. 4A-4D graphically depict results of an in vivo study showing that an autologous bone marrow transplant (BMT) ameliorates murine experimental autoimmune encephalitis (EAE). Animals were conditioned with 9 Gy TBI on day 8 and 13 post EAE induction. Conditioned mice were transplanted with $10^7$ donor cells 24 h post TBI.
Figure 4B:
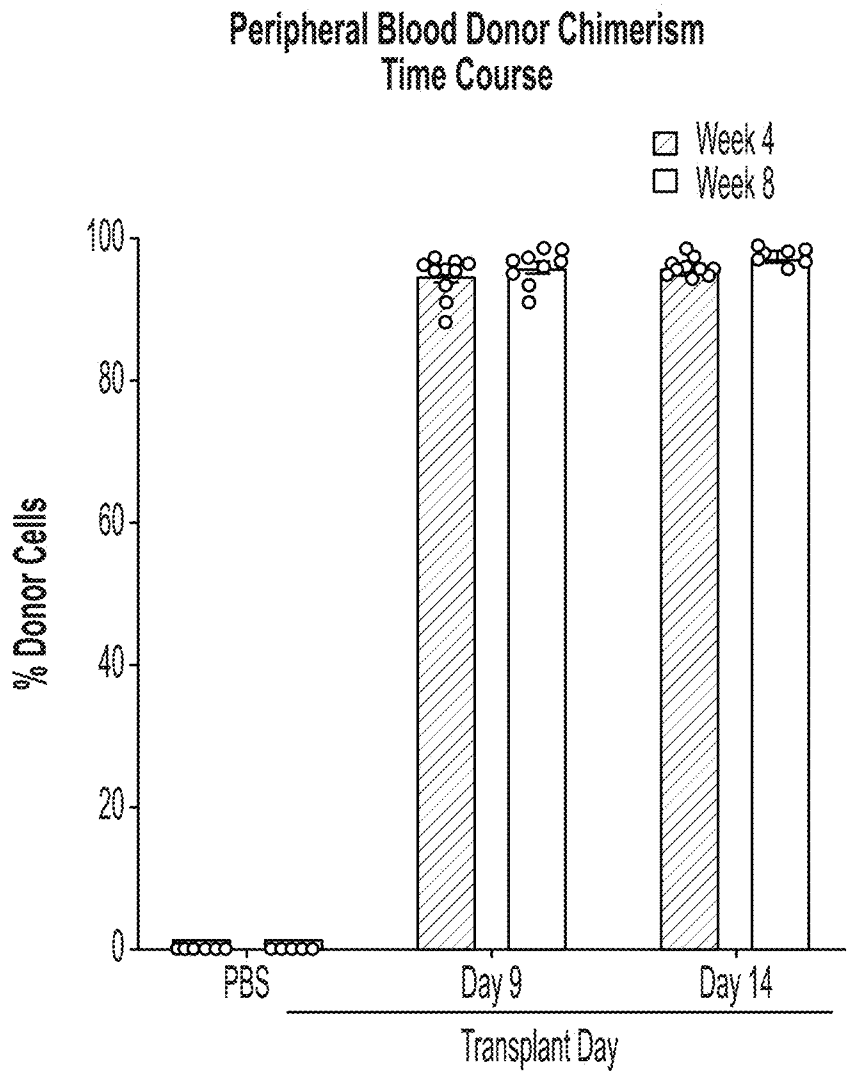
Figure 4C:
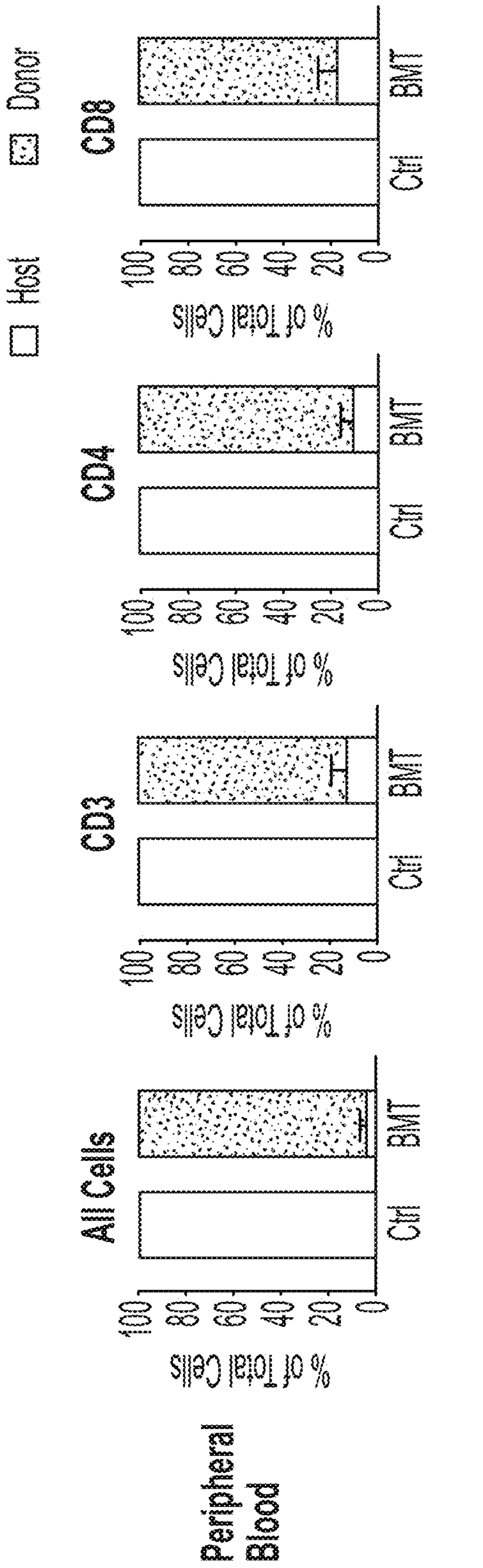
Figure 4D:
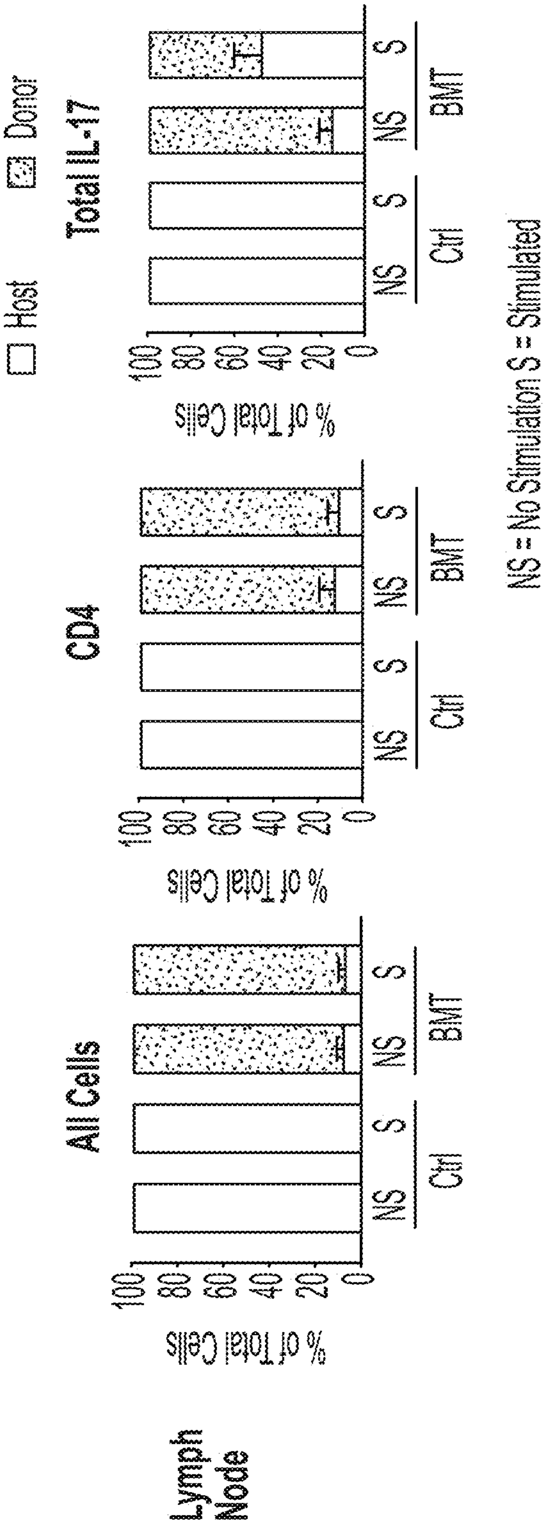

Animals were conditioned with 9 Gy TBI on day 8, and, 13 post EAE induction. Conditioned mice were transplanted with $10^7$ donor cells 24 h post TBI. The data show a correlation of transient disease amelioration or delayed disease progression when transplant occurred at lower clinical scores (FIG. 4A). The data also show full donor chimerism was achieved at 4 weeks post-transplant and maintained though 8 weeks (FIG. 4B). FIGS. 4C and 4D show a comparison of host and donor cells in the peripheral blood (FIG. 4C) and lymph node (FIG. 4D) harvested from control (no transplant) vs treated (day 9 BMT) mice. Greater than 95% donor chimerism was observed at terminal analysis of all cells and >90% of donor T cells in the peripheral blood or lymph node. IL-17 is a proinflammatory cytokine that plays a crucial role in the development of EAE. The residual host IL-17 producing CD4 T cells in the lymph node may drive relapse of disease.

In summary, these results indicated that in the EAE model, conditioning with irradiation (9 Gy) followed by congenic transplant resulted in transient amelioration of disease.

Example 5. A Single Dose of CD45-Targeted ADC Safely Conditions for Autologous Transplant and Ameliorates Disease in Multiple Models of Autoimmune Disease The following example describes use of a single dose of an anti-CD45 ADC for autologous transplantation, where the anti-CD45 ADC ameliorated disease in a number of mouse models for autoimmune disease.

To address challenges associated with autologous HSC transplantation, antibody drug conjugates (ADCs) that selectively target CD45 were tested to determine if an anti-CD45 ADC could eradicate autoimmune cells and enable autoHSCT as a potentially one-time curative treatment for patients with autoimmune disease.

To model this approach in mice, an ADC targeting murine CD45 (anti-CD45 mAb conjugated to PBD) was generated as a single conditioning agent for murine congenic transplant. The murine CD45 ADC specifically targets the CD45.2 isoform of mouse CD45, and is engineered to eliminate effector function, allow for site-specific conjugation of linker payload, and be rapidly cleared. The payload for this murine tool ADC is potent and preferentially kills dividing cells. The anti-mouse CD45 ADC was evaluated for the ability to condition recipients in a murine congenic transplant model following a single myeloablative dose. This ADC was further evaluated for its ability to eliminate pathogenic host-reactive cells and enable immune reset in recipients in the context of multiple murine models of autoimmune disease, including MOG-induced experimental autoimmune encephalitis (EAE; a murine model of multiple sclerosis (MS)), proteoglycan-induced arthritis (PGIA), type 1 diabetes, and sclerodermatous graft-vs-host disease (scGVHD).

Figure 5A:
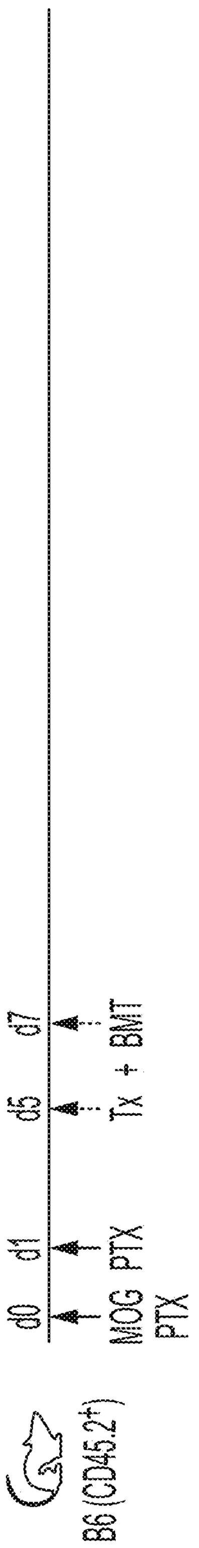
FIGS. 5A-5H graphically depict the results of in vivo and in vitro studies using a CD45-ADC in the context of experimental autoimmune encephalitis (EAE) and multiple sclerosis (MS).

To induce EAE in a murine model, C57BL/6 (CD45.2+) mice were induced with $MOG_{35\_55}$ peptide in complete Freund's adjuvant, followed by the administration of pertussis toxin (PTX). Immunized Mice were conditioned for CD45.1+ congenic transplant (B6.SJL donor) on day 5 post-immunization and transplanted 48 hours after conditioning. A schematic of the study design is shown in FIG. 5A.

Figure 5B:
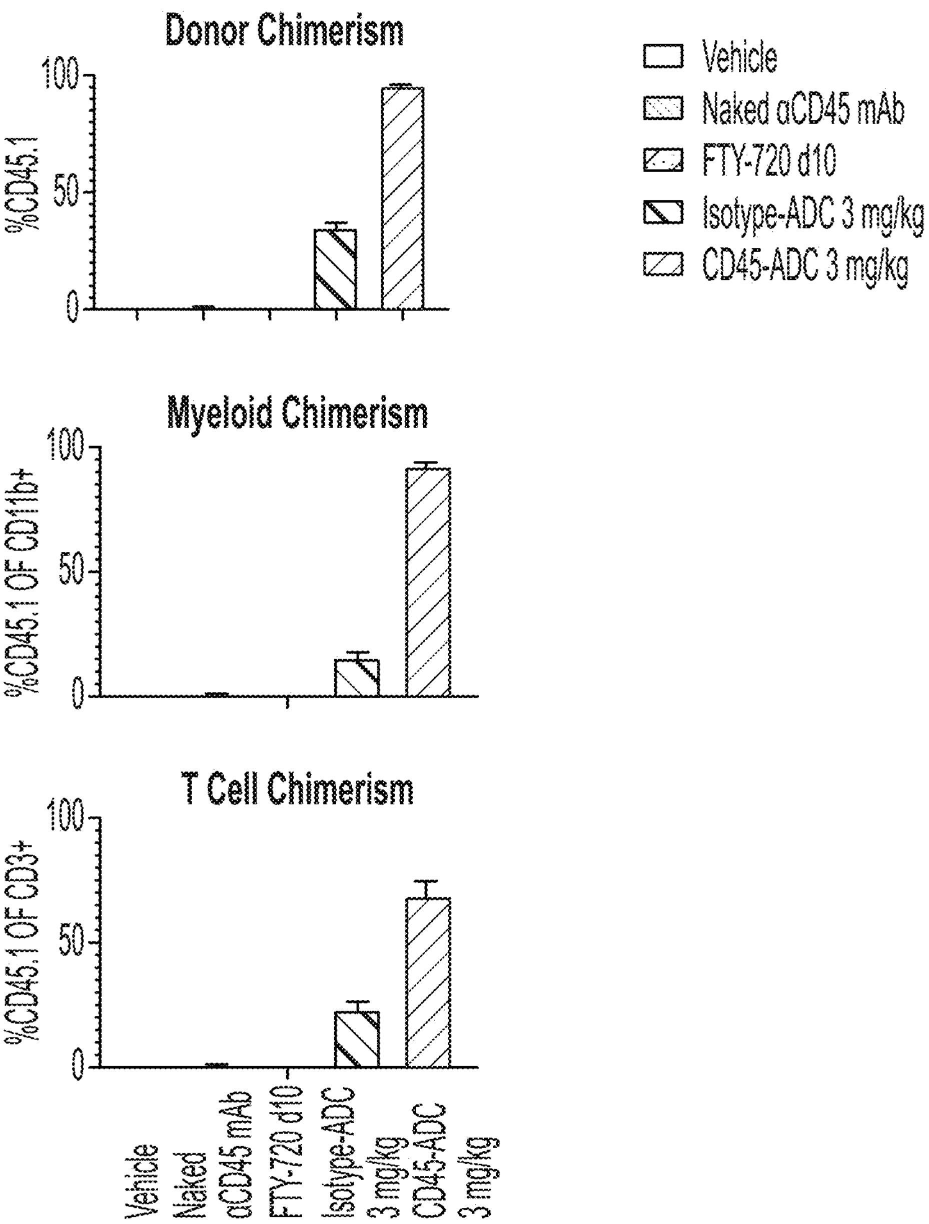
Figure 5D:
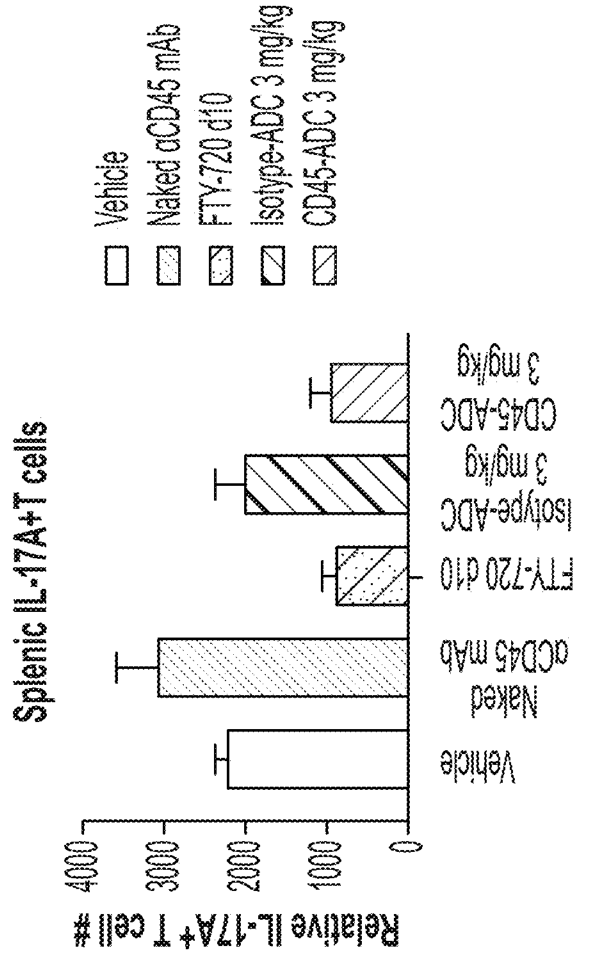
Figure 5C:
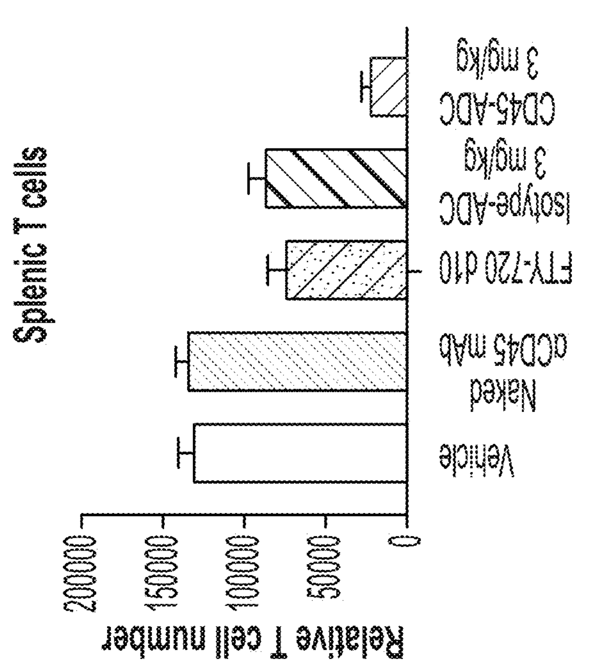

A single-dose of the tool anti-mouse CD45-ADC at 3 mg/kg achieved full myeloablation in recipient mice and enabled full donor chimerism (>99% depletion of LT-HSCs (Lin−Kit+Sca−1+CD150+CD48−) in a congenic mouse transplant model). Untransplanted mice were euthanized approximately 12 days after dosing due to expected hematopoietic failure. Transplanted mice achieved full engraftment with congenic BMT (>90% chimerism at 16 weeks). In particular, terminal analysis of tissues (bone marrow, peripheral blood, spleen, lymph nodes) demonstrated that conditioning with CD45-ADC enabled full donor chimerism (FIG. 5B). The disease modifying effects of the ADCs was associated with reductions in host splenic T cells in general (FIG. 5C), as well as splenic IL-17A-producing effector cells (FIG. 5D).

Figure 5F:
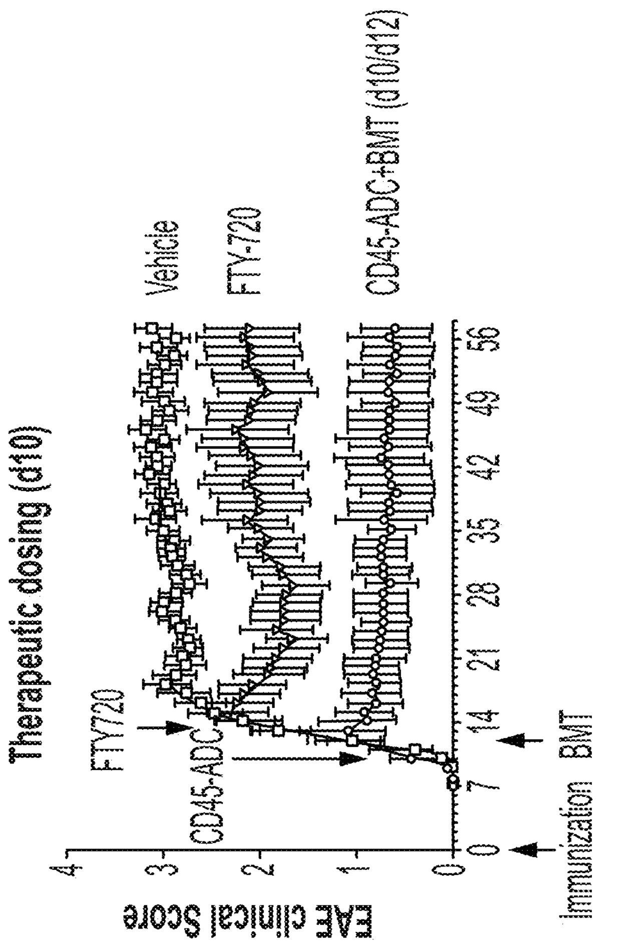
Figure 5E:
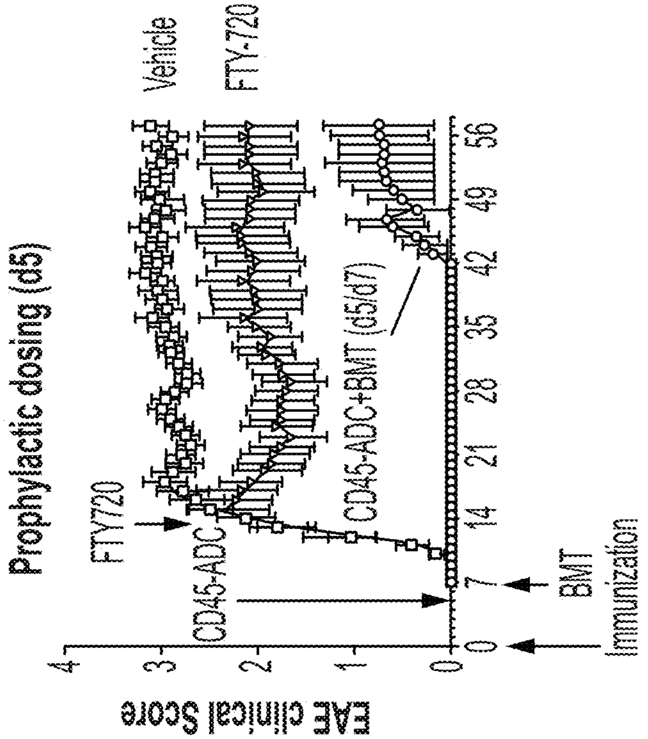
Figure 5G:
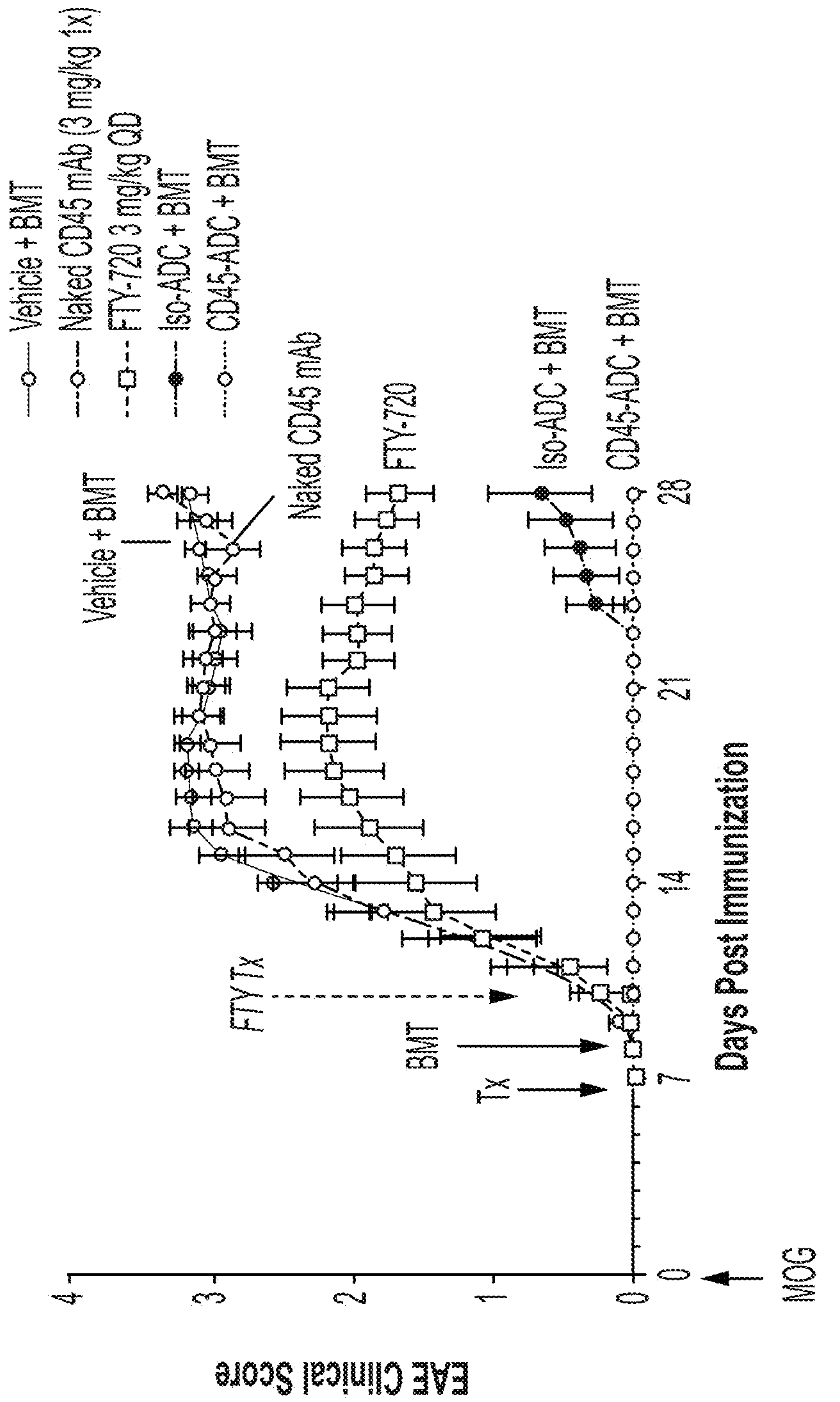

In EAE, conditioning with a myeloablative dose of the CD45-ADC followed by congenic transplant prior to disease onset led to full donor chimerism, significantly delayed disease onset (mean time to onset 38 days), reduced overall disease severity, and reduced disease incidence (3/12, 25%) (FIGS. 5E and 5G). In contrast, disease onset was around 9-12 days post induction for vehicle- or CD45 antibody-treated animals (FIGS. 5E and 5G).

FIG. 5E shows disease onset at 21 days with a peak disease score 2.1 following treatment with 1 mg/kg CD45-ADC; disease onset at 42 days with a peak disease score of 0.75 following treatment with 3 mg/kg CD45-ADC+BMT; and disease onset at 11 days with a peak disease score 3.1 for vehicle-treated mice. FIG. 5G shows similar findings with regard to treatment with 3 mg/kg CD45-ADC+BMT and additionally shows the effects of treatment with an isotype-ADC or naked CD45 antibody. A less substantial effect on donor chimerism and disease-modification was observed in animals treated with isotype-ADC (28 days to disease onset, 5/12 (40%) incidence), a result consistent with known platform toxicity of the murine ADC payload on rapidly dividing cells in an immunization model. The mean time to EAE onset and disease incidence in each treatment group in FIG. 5G is summarized in Table 3.

TABLE 3

Mean time to EAE Onset

| Group | Mean Time to EAE onset | Incidence |
|---|---|---|
| Vehicle + BMT | 11 | 100% |
| Naked CD45 mAb | 11 | 100% |
| FTY-720 | 12 | 100% |
| Isotype-ADC + BMT | 28 | 42% |
| CD45-ADC + BMT | 38 | 25% |

In active EAE, treatment with 3 mg/kg of anti-mouse CD45-ADC on day 10 or day 13 followed by congenic transplant halted progression of disease activity (FIG. 5F, no increase from disease score at time of treatment; peak disease scores of 0.75 and 2.3, respectively). The effect observed with CD45-ADC treatment at day 13 with congenic transplant was comparable to that achieved by treatment with a clinically validated standard of care, FTY-720 (approved S1P1 antagonist equivalent to Gilenya) at day 13, which also halted disease at a peak score of 2.3.

Disease control in this study compared favorably to a prior study where mice were treated with 9 Gy TBI and congenic BMT at day 9. These data show that CD45-ADC conditioning followed by congenic transplant is effective at immune reset, and ameliorated disease in an EAE model. In particular, immune reset via anti-mouse CD45 conditioning enabled congenic engraftment, delayed EAE onset, reduced EAE incidence, and killed disease-mediating effector T cells in vivo. Further, the disease modifying effect in EAE with anti-mouse CD45-ADC conditioning showed comparable efficacy to clinically validated conditioning therapies.

To translate these encouraging pre-clinical data, anti-human CD45 ADCs were generated that cross-react with nonhuman primates (NHP). The human-targeted CD45-ADC contains an affinity-matured mAb that targets an epitope present on all human CD45 isoforms, is cross-reactive with NHP CD45, and is conjugated to amatoxin, a payload that efficiently kills both quiescent and cycling cells. This ADC is engineered to eliminate Fc-mediated effector function, enable site-specific conjugation of linker/payload, and enable rapid clearance. These were evaluated for the ability to deplete hematopoietic and immune cells in vitro and in vivo in humanized NSG (hNSG) mice and NHPs.

Figure 5H:
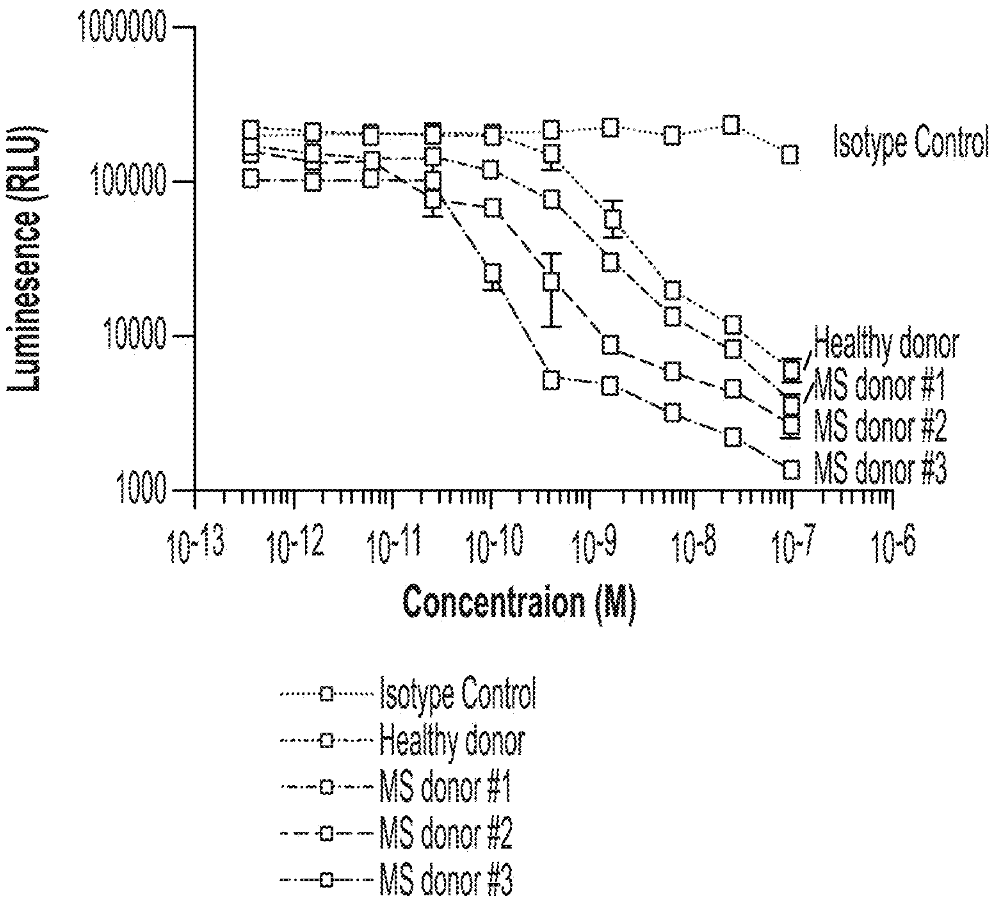
Figure 6A:
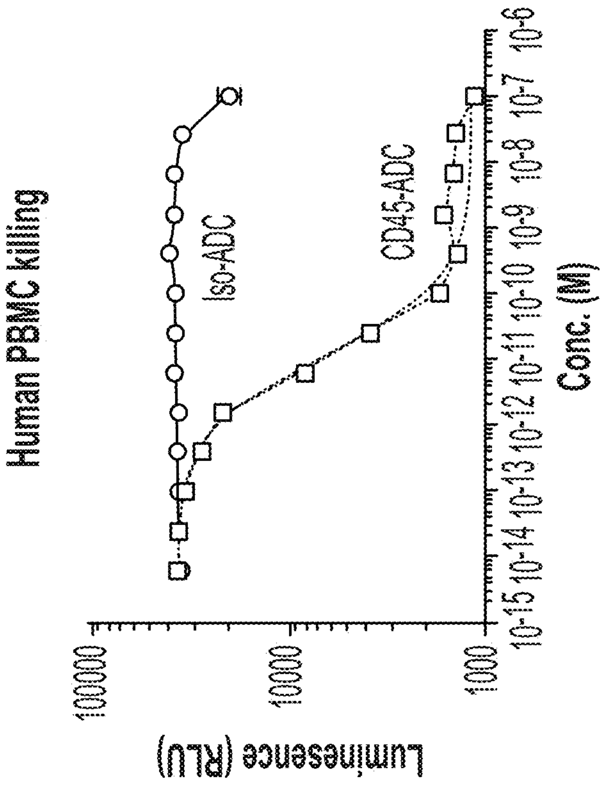
FIGS. 6A-6I graphically depict the results of in vitro and in vivo studies showing that an anti-human CD45-ADC potently kills primary human and cyno hematopoietic cells in vitro and in humanized NSG mice.
Figure 6B:
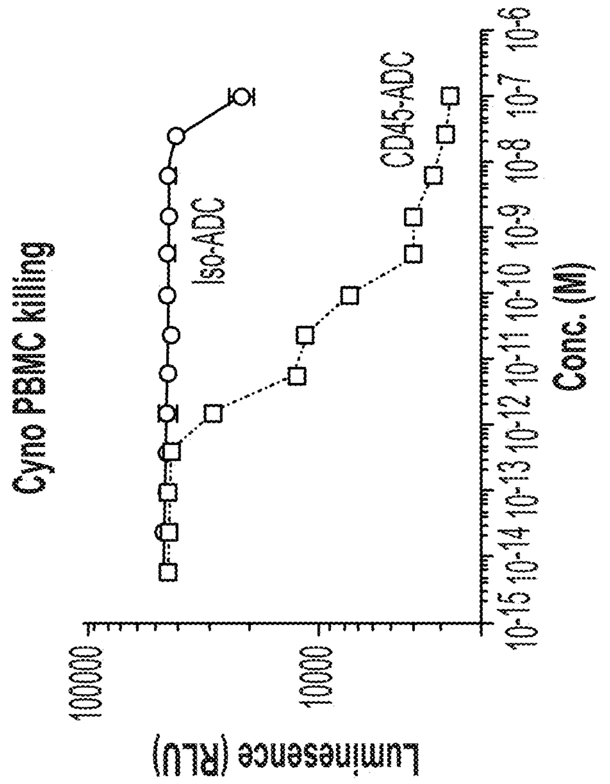
Figure 6C:
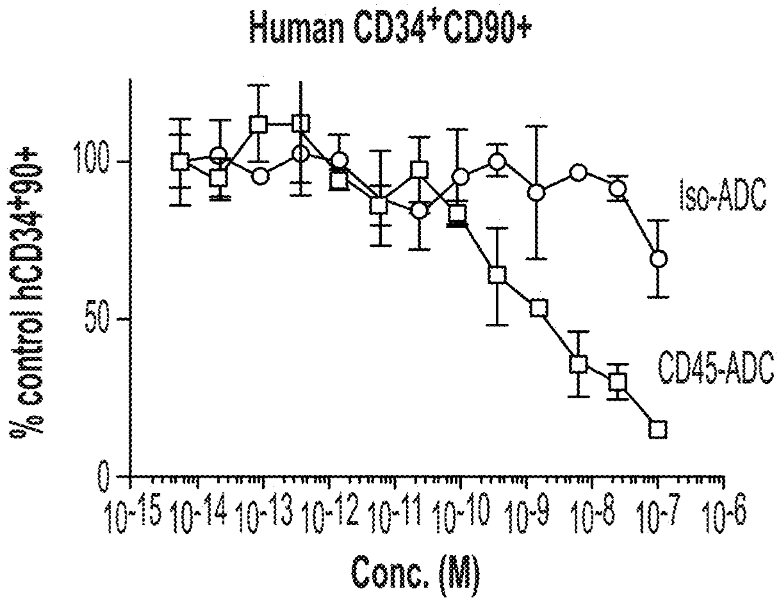
Figure 6D:
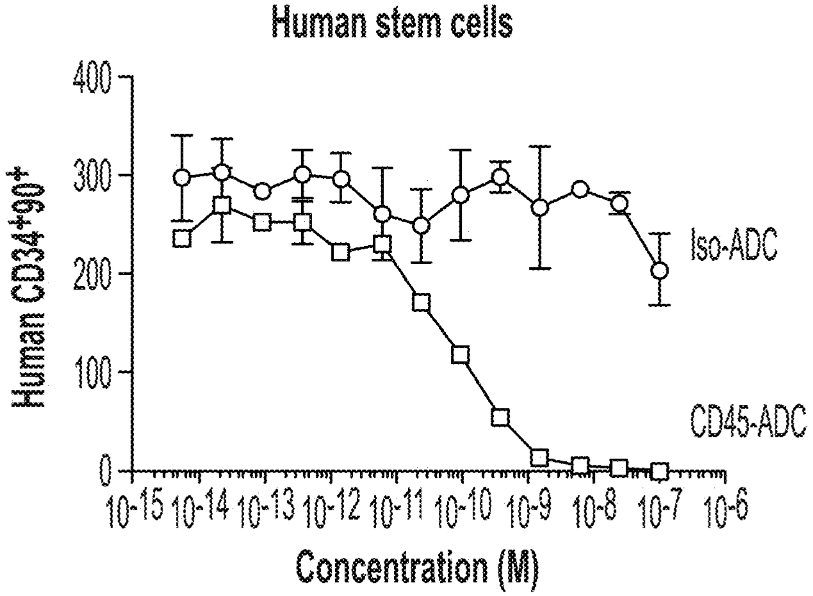
Figure 6E:
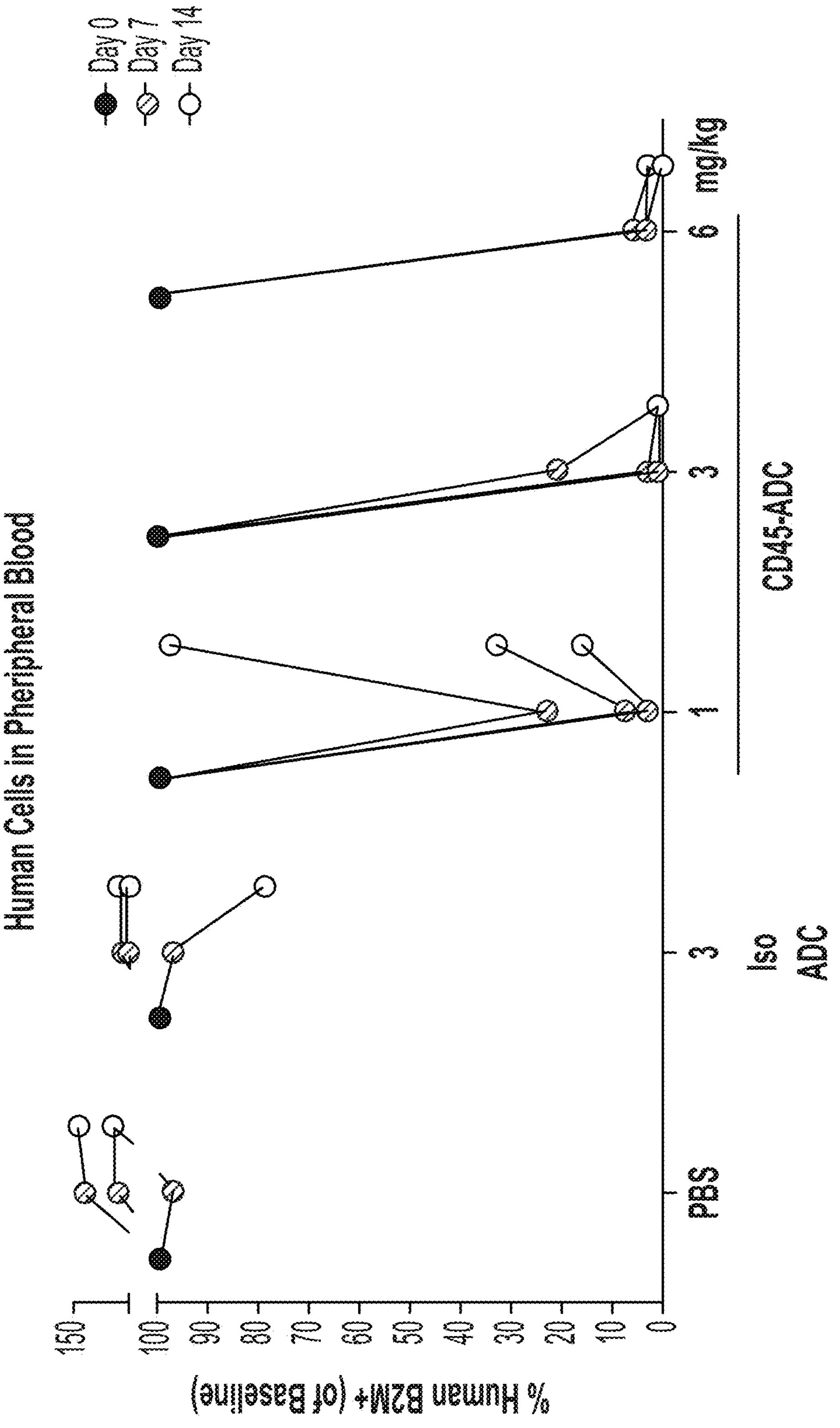
Figure 6F:
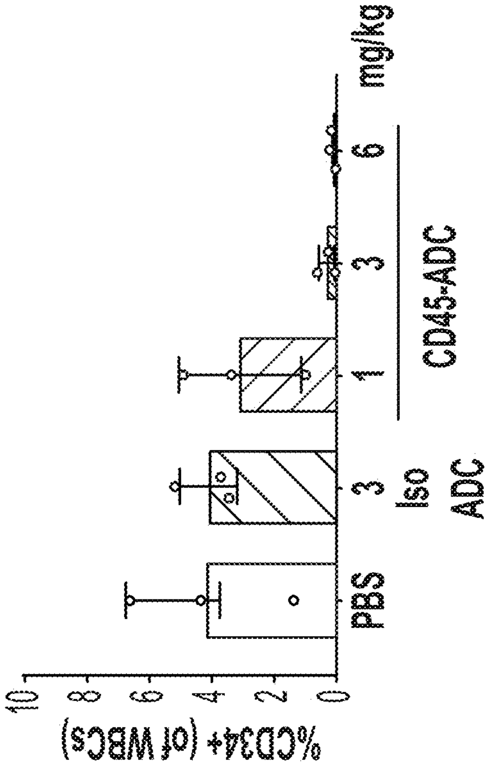
Figure 6G:
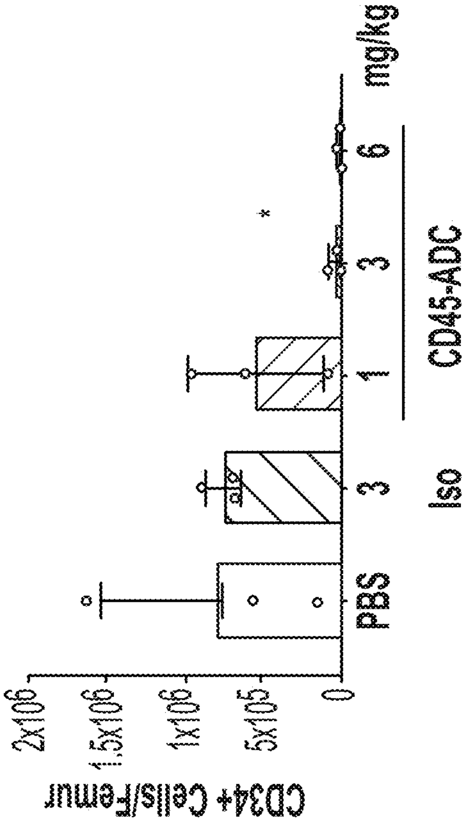
Figure 6I:
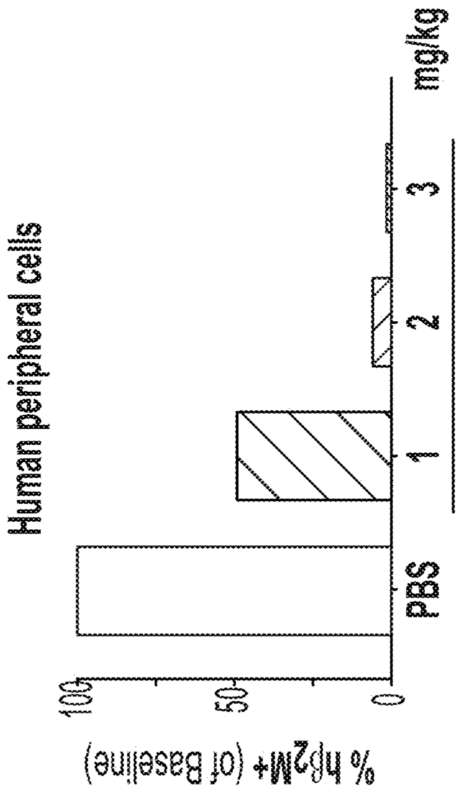
Figure 6H:
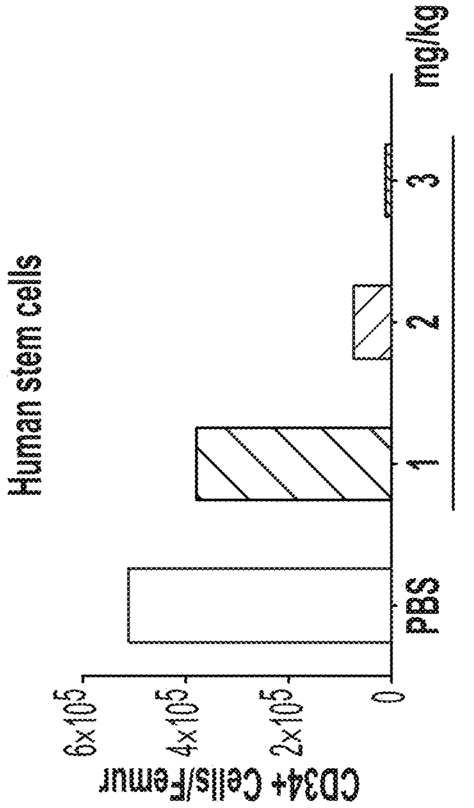

The anti-human CD45-ADC showed efficient killing of human BM CD34+ (EC50 $2.44\times10^{-9}$ M) and peripheral CD3+ cells from normal donor (EC50 $7.6\times10^{-10}$ M) and MS patients (EC50 $1.5\times10^{-10}$M) (FIG. 5H). Further, the anti-human CD45-ADC potently kills human and cynomolgus PBMCs (FIGS. 6A and 6B) and human CD34+CD90+ cells (FIG. 6C) in vitro. Anti-human CD45-amatoxin ADCs potently kill human CD34+CD90+ human stem cells (FIG. 6D). $EC_{50}$ values for CD45-ADC mediated killing from representative experiments are summarized in Table 4. These results indicate that the anti-human CD45-ADC potently kills primary human and cyno hematopoietic cell types in vitro, including CD34+ hematopoietic stem and progenitors (HSPC), and CD3+ T cells from both healthy donors and MS patients In vivo in hNSG, single doses of the CD45-ADCs were well-tolerated and led to substantial (>95%) depletion of human cells (see also Example 8). Single doses of CD45-ADC depleted human hematopoietically-derived cells in the periphery (FIG. 6E) and bone marrow (FIGS. 6F, 6G, 6H, and 6I) of humanized NSG mice in a dose-dependent manner.

TABLE 4

EC50 Values for the anti-human CD45-ADC

| Population | CD45-AM EC50 |
|---|---|
| Human PBMC | 0.5 pM |
| Cyno PBMC | 0.8 pM |
| $hCD34^{+}CD90^{+}$ | 254 pM |

Figure 7A:
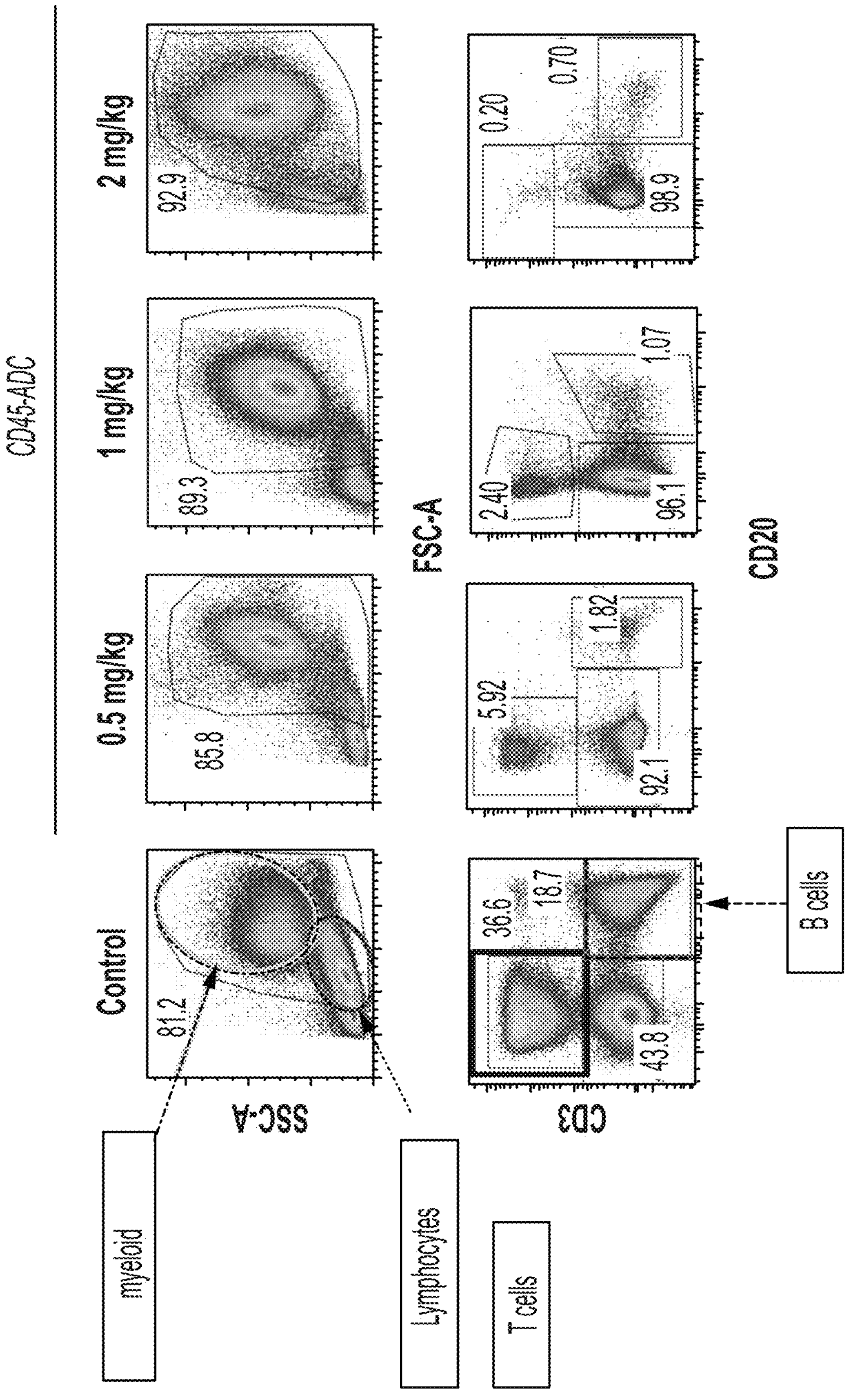
FIGS. 7A-7H graphically depict the results of an in vivo study showing that a single dose of an anti-human CD45-ADC is well-tolerated and leads to depletion of lymphocytes and HSCs in a non-human primate (NHP).
Figure 7B:
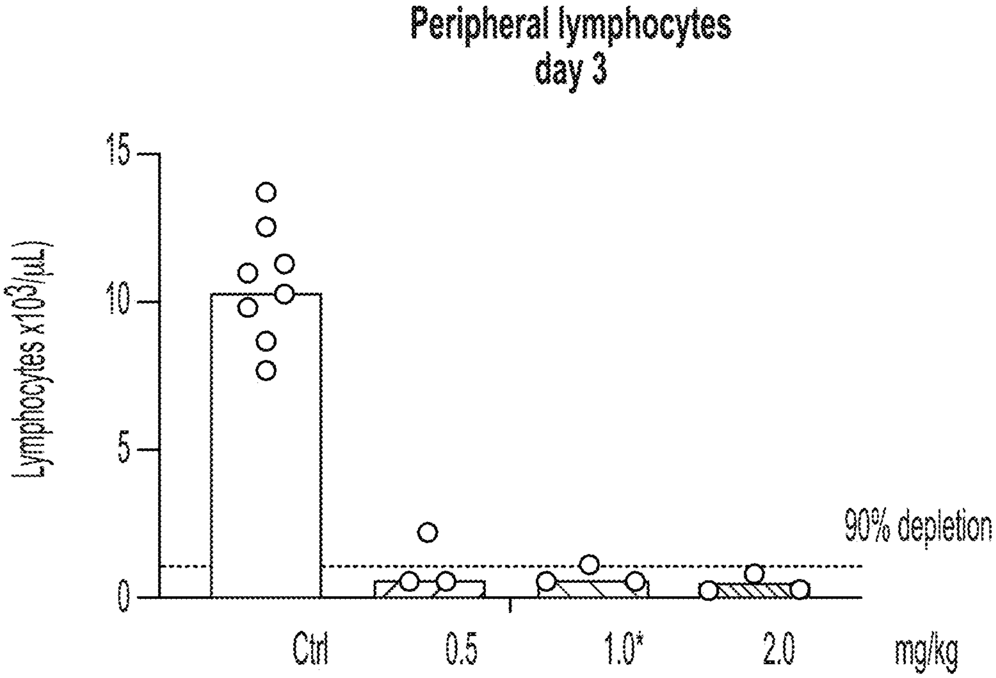
Figure 7C:
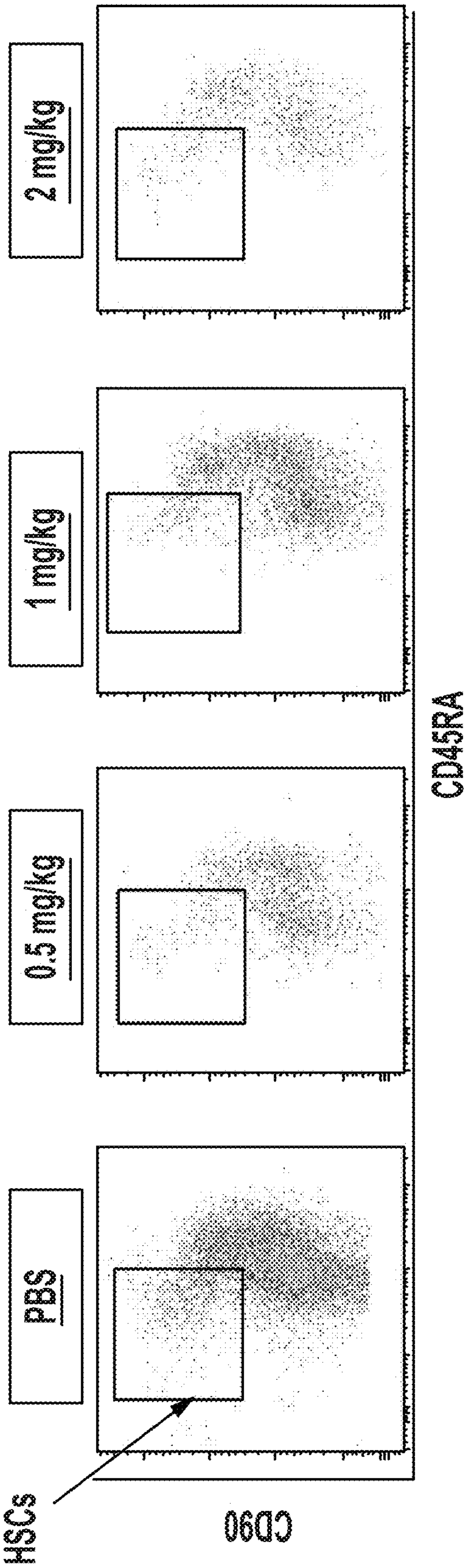
Figure 7D:
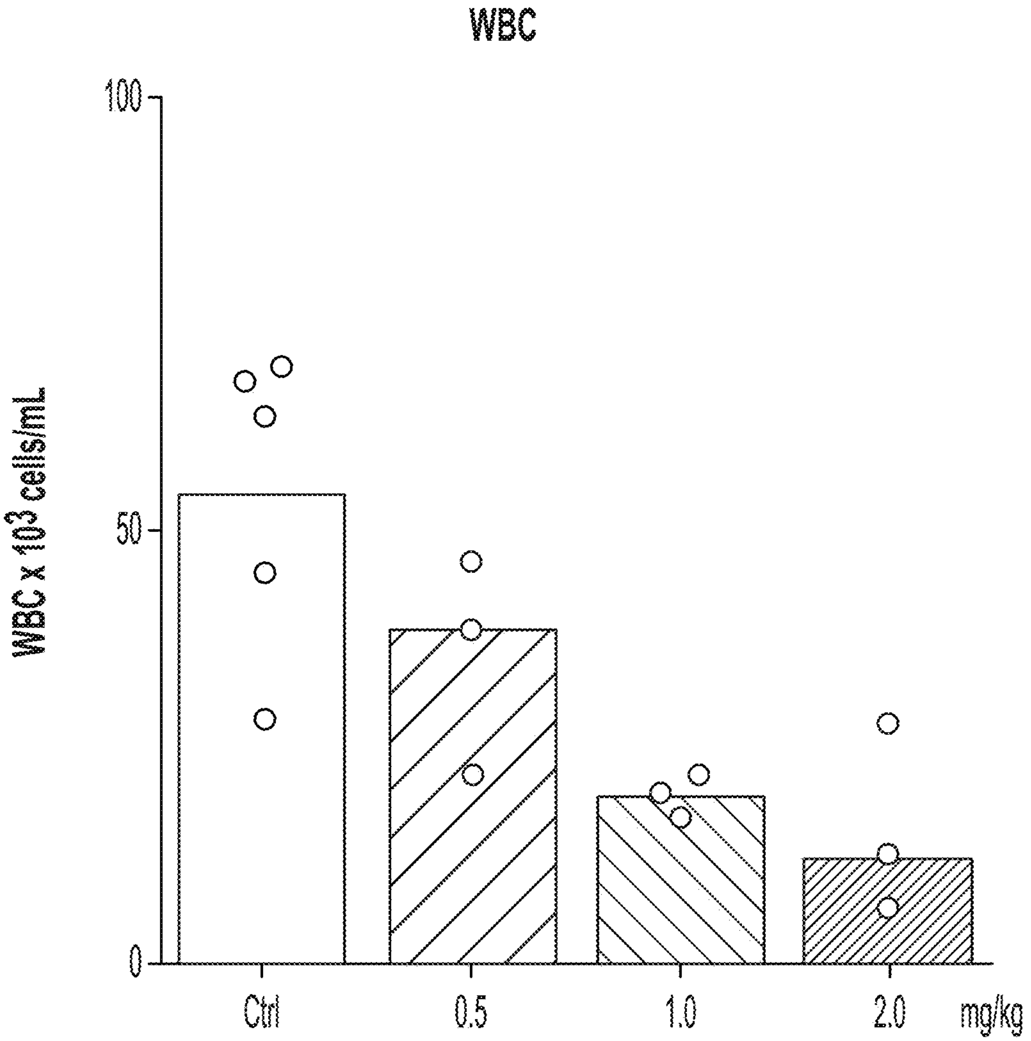
Figure 7D:
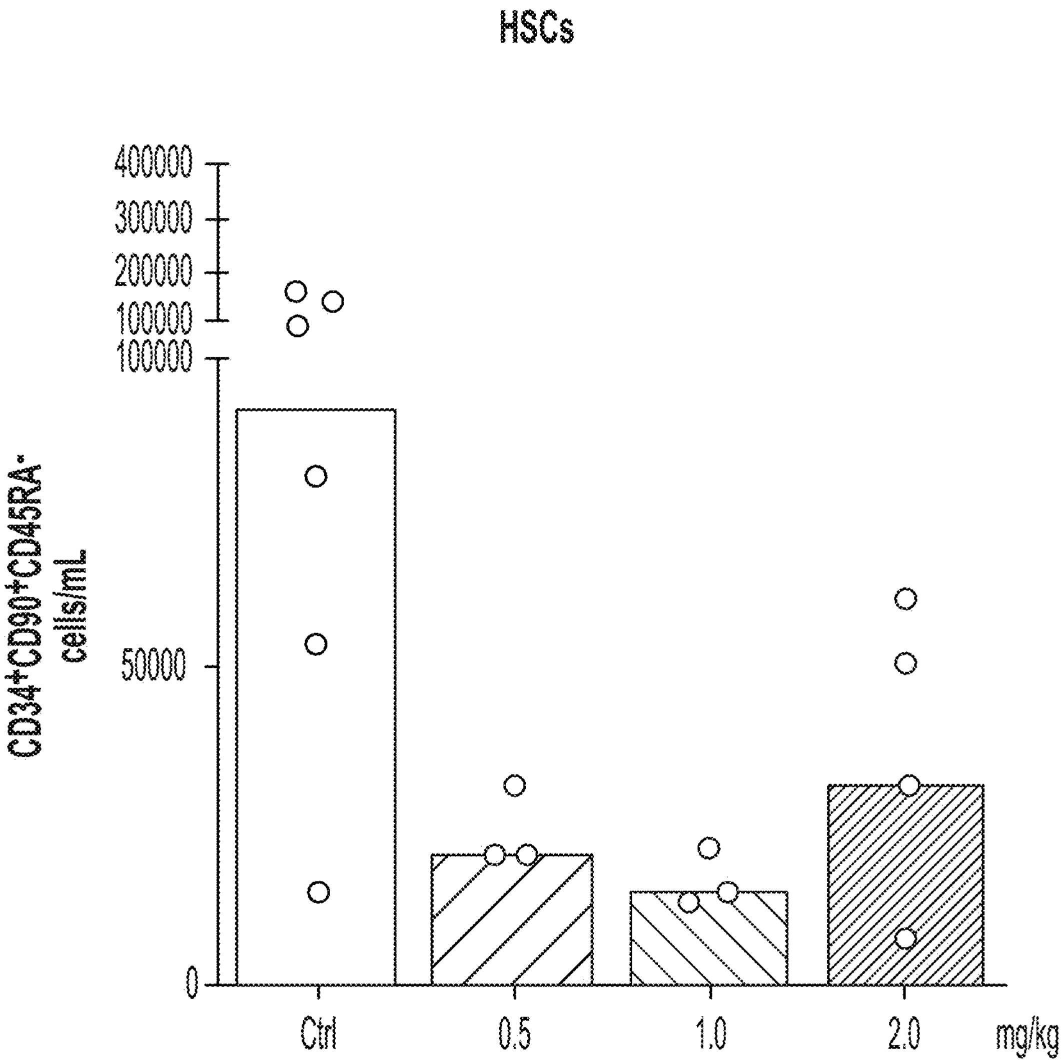
Figure 7D:
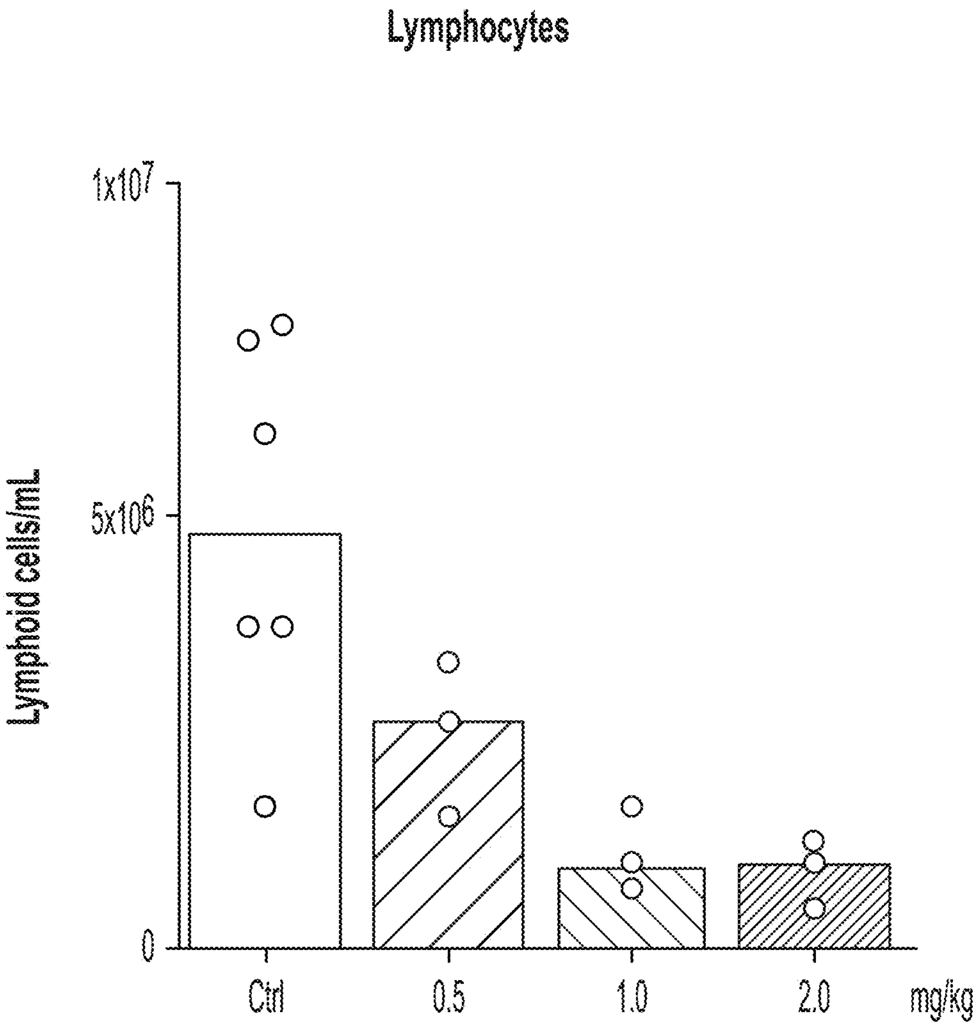
Figure 7E:
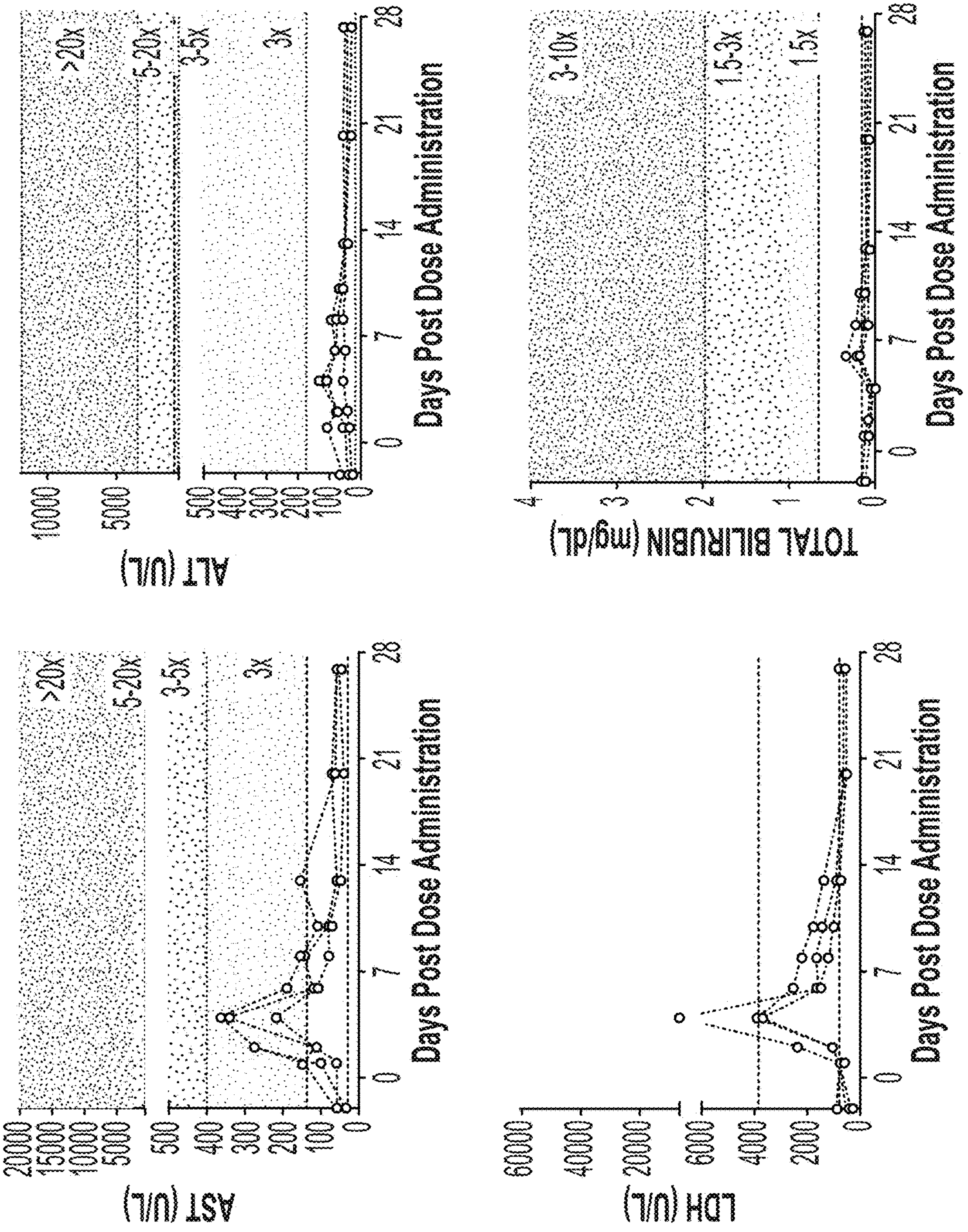
Figure 7F:
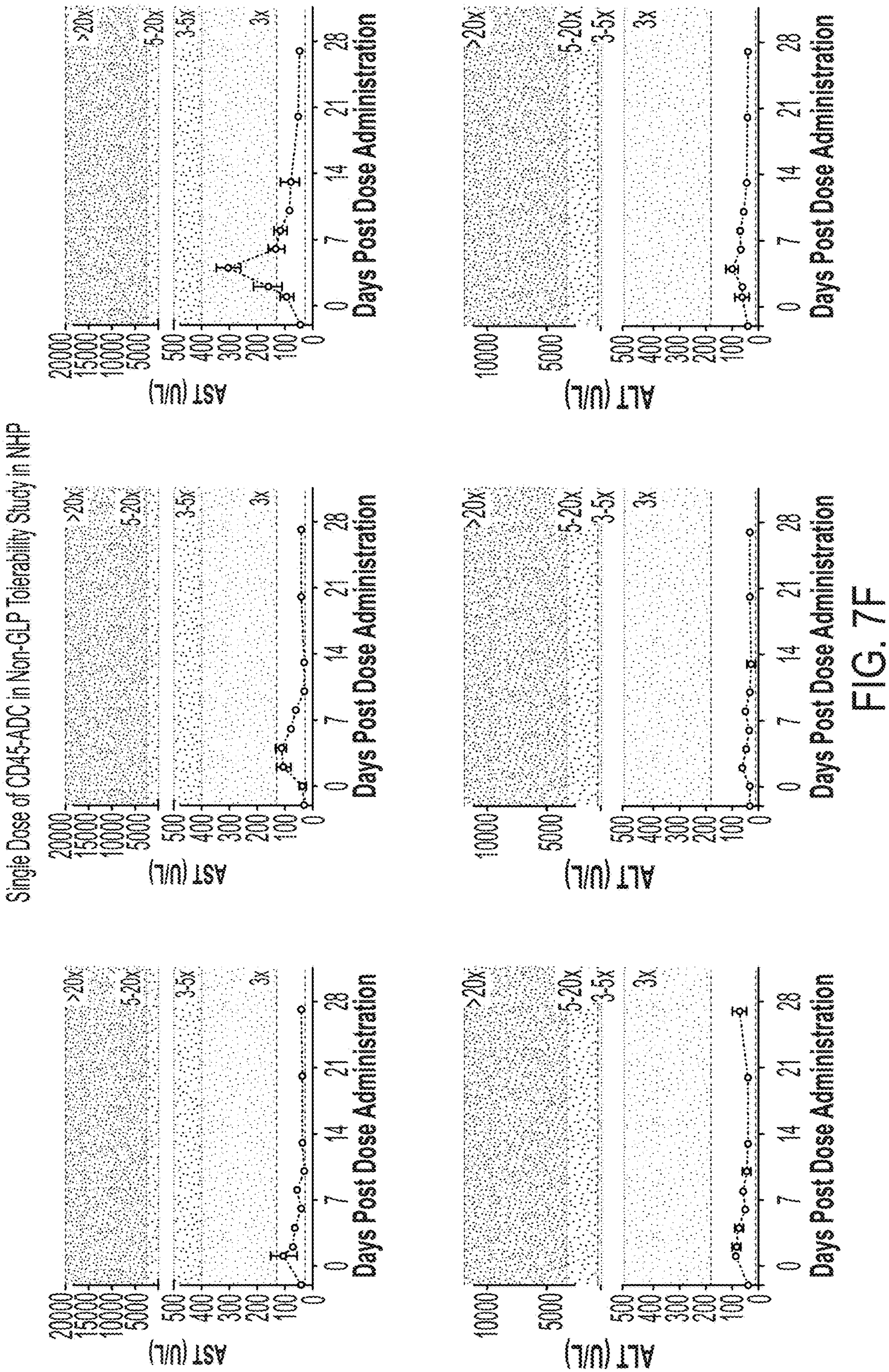
Figure 7F:
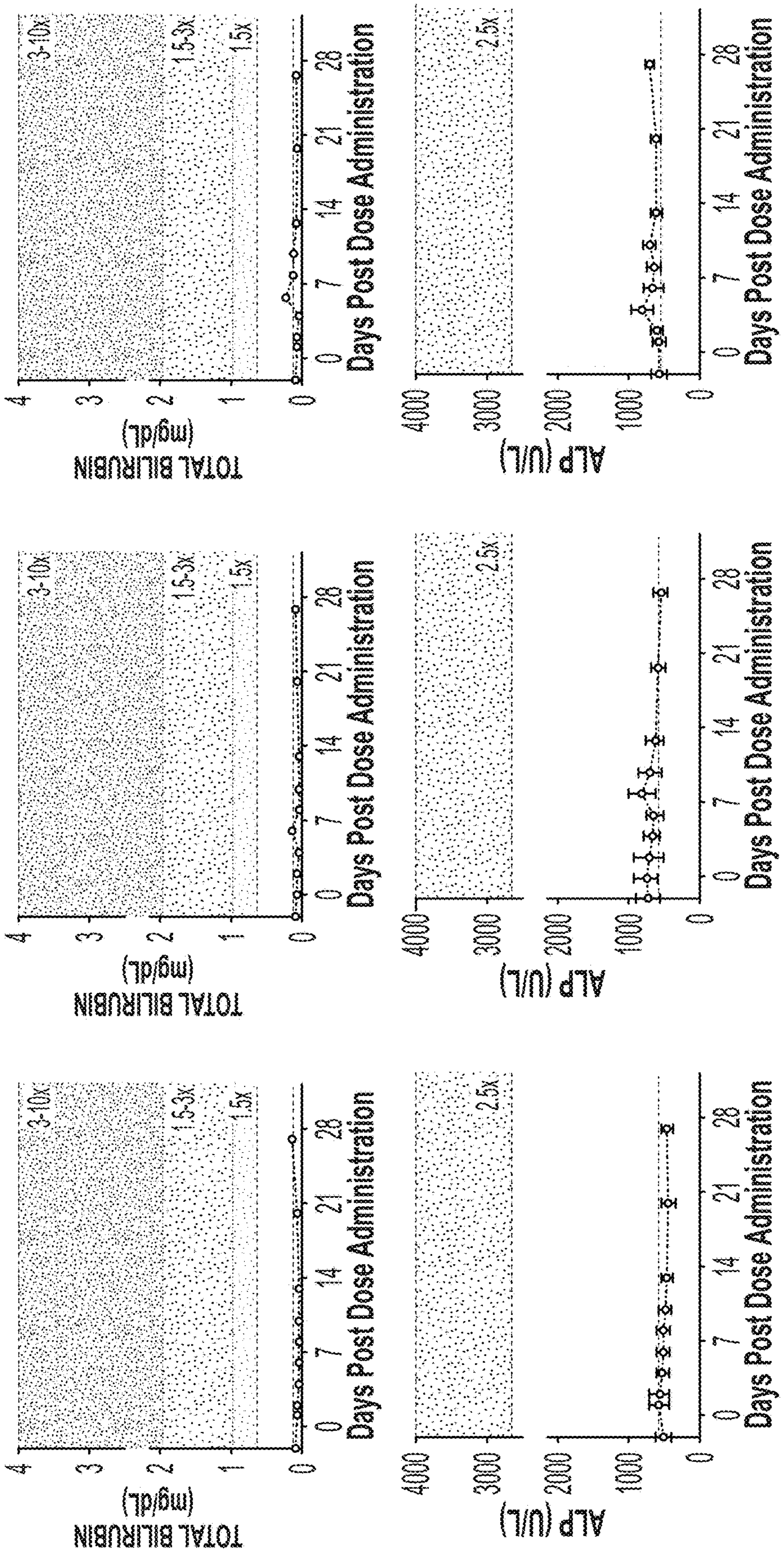
Figure 7H:
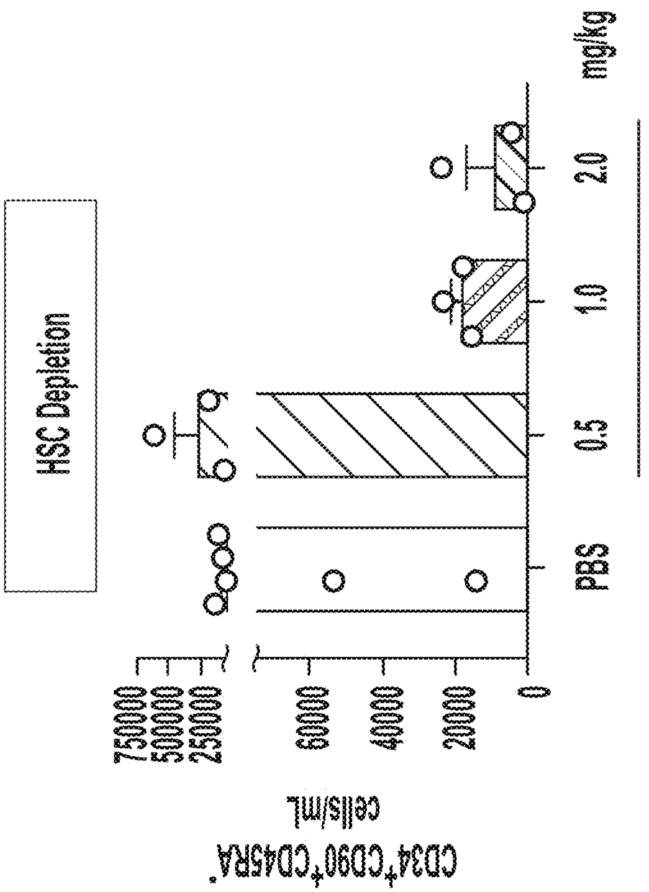
Figure 7G:
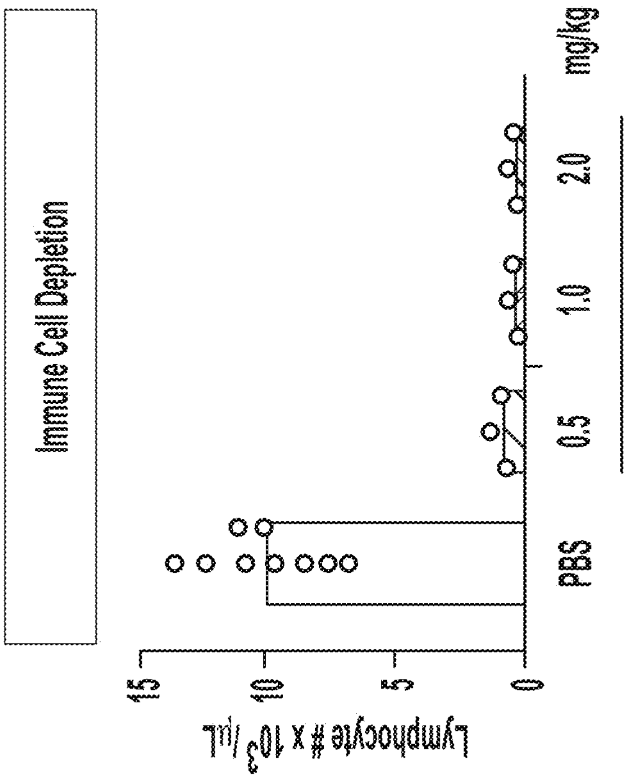

In NHPs, single doses of the anti-human CD45-ADC achieved >90% peripheral lymphocyte depletion (FIGS. 7A and 7B) and >80% depletion of hematopoietic stem cells (HSCs; FIGS. 7C and 7D). See also FIG. 7G, showing that single doses of the anti-human CD45-ADC result in immune cell depletion, and FIG. 7H, showing that single doses of the anti-human CD45-ADC result in CD34+CD90+CD45RA-HSC depletion. Further, as shown in FIGS. 7E and 7F, clinical chemistry values for alanine transaminase (ALT), total bilirubin (TBIL), alkaline phosphatase (ALP), and aspartate transaminase (AST) demonstrate that a single dose of the anti-human CD45-ADC was well-tolerated in NHPs. No changes were observed in clinical chemistry values for gamma glutamyltransferase (GGT), albumin, blood urea nitrogen (BUN), creatinine, glucose, and prothrombin (PT).

These results suggest that targeted immune depletion with a single treatment of CD45-ADC may be sufficient for auto-HSCT and allow immune reset and re-establishment of immune tolerance. Targeted CD45-ADCs may represent a safer and better tolerated approach for conditioning patients prior to immune reset through autoHSCT and may significantly reduce the side effects associated with current conditioning protocols.

Example 6. Treatment with a Murine CD45-ADC Renders Resting T Cells Incapable of Mounting an Allogeneic Response B6 mice (H-$2^{b}$) were treated with vehicle, Isotype-ADC, or CD45-ADC (anti-CD45 mAb conjugated to PBD). After 7 days, splenocytes were isolated, labelled with CellTrace Violet, and adoptively transferred into naïve, immunodeficient NSG hosts (H-$2^{g7}$, H-2d). Cells were isolated from peripheral blood (d2 and d7) and spleen (d7) at various times post transfer and assessed for CTV staining intensity (FIG. 8A), the absolute number of T cells in the peripheral blood as a function of days post-transfer (FIG. 8B), and the absolute number of T cells in the spleen seven days post-transfer (FIG. 8C).

Figure 8A:
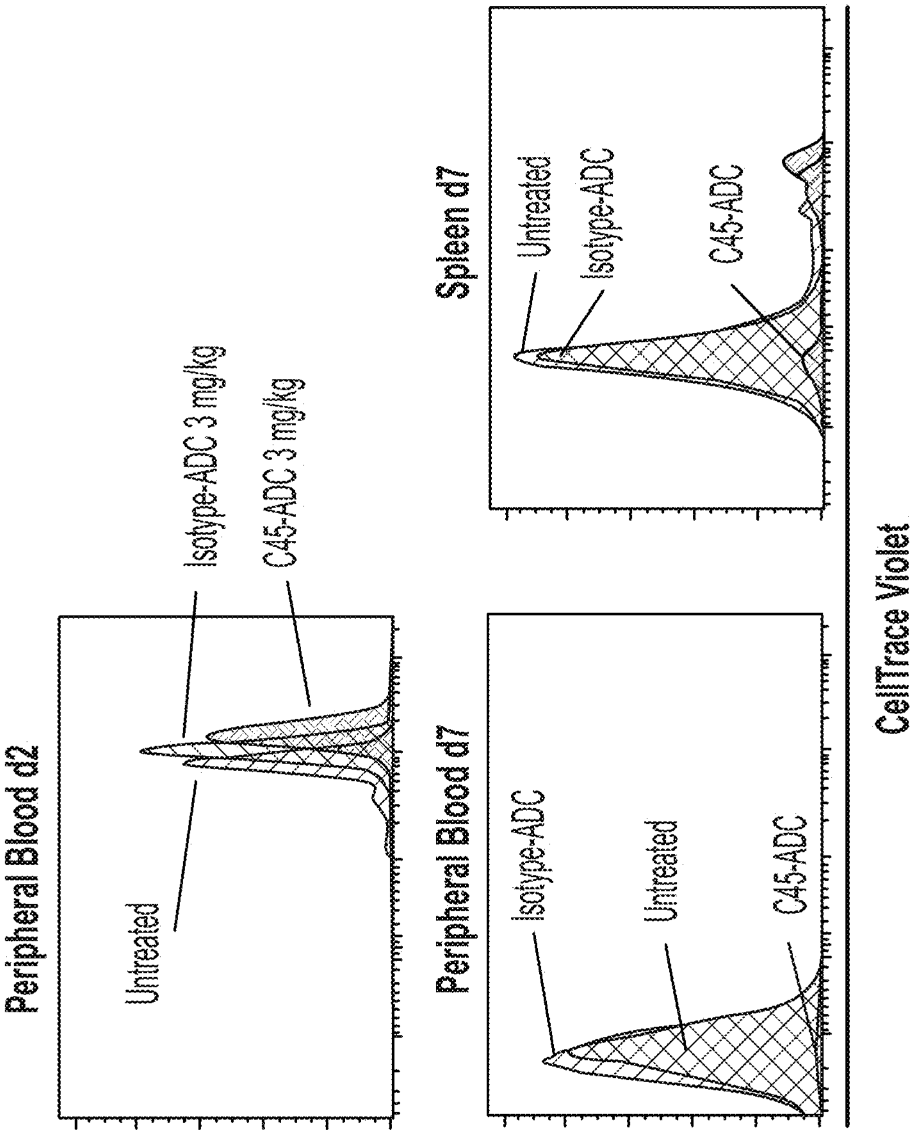
FIGS. 8A-8C graphically depict results of an in vivo study showing that treatment with a murine CD45-ADC renders resting T cells incapable of mounting an allogeneic response. Cells were isolated from peripheral blood (d2 and d7) and spleen (d7) at various times post transfer and assessed for CTV staining intensity (FIG. 8A), the absolute number of T cells in the peripheral blood as a function of days post-transfer (FIG. 8B), and the absolute number of T cells in the spleen (FIG. 8C) seven days post-transfer.
Figure 8B:
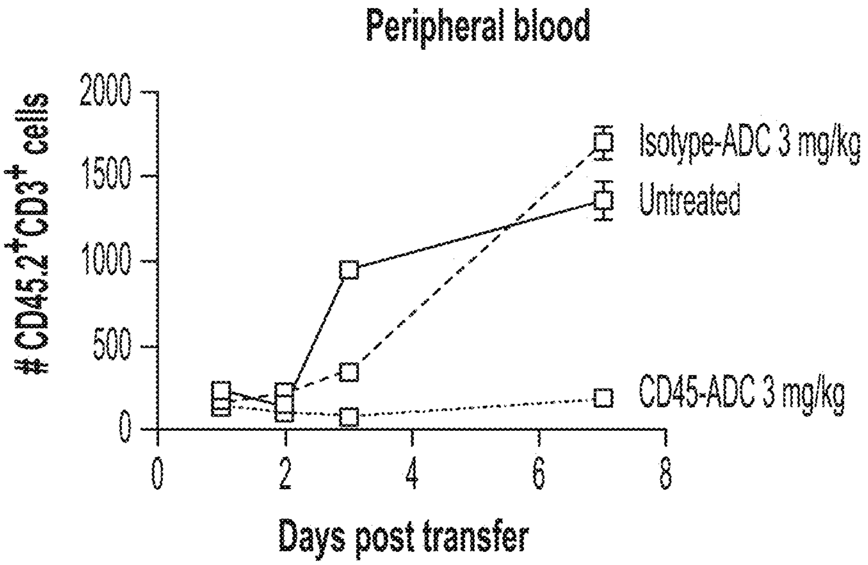
Figure 8C:
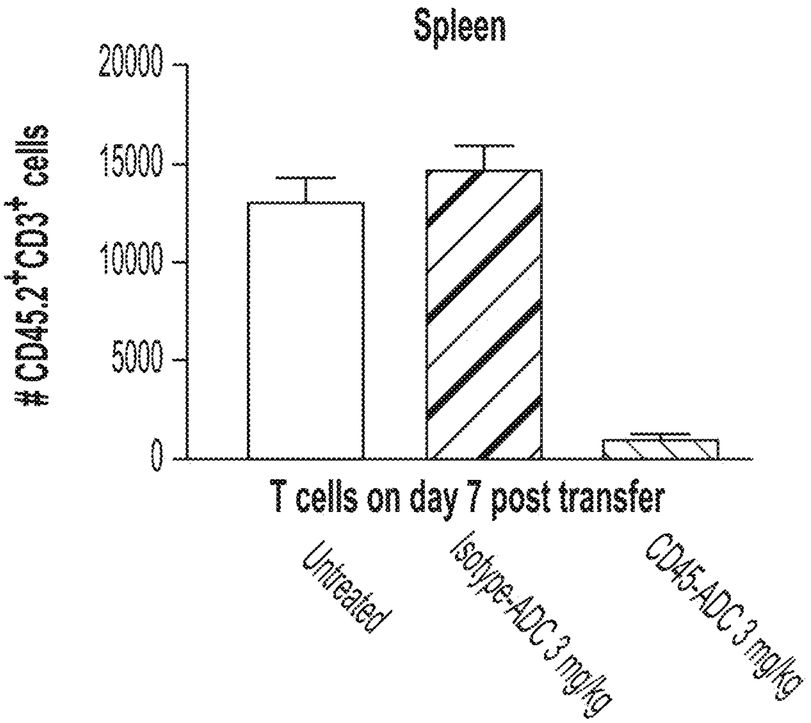

As shown in FIGS. 8A-8C, T cells from untreated or isotype-ADC-treated mice expand and accumulate after adoptive transfer into immunodeficient allogeneic transplant-recipients, while T cells from CD45-ADC treated mice could not proliferate. These results show that treatment with a murine CD45-ADC renders resting (i.e., quiescent) T cells incapable of mounting an allogeneic response.

These results indicate that the anti-mouse tool CD45-ADC has a dual mechanism of action in mouse models of autoimmune disease by (a) preferentially killing the proliferating allogeneic T cells in vivo compared to resting T cells (see Example 3) and (b) rendering the remaining T cells incapable of mounting an allogeneic response. These results establish that CD45-ADC mediates targeted elimination and neutralization of $CD45^{+}$ effector cells.

Figure 9A:
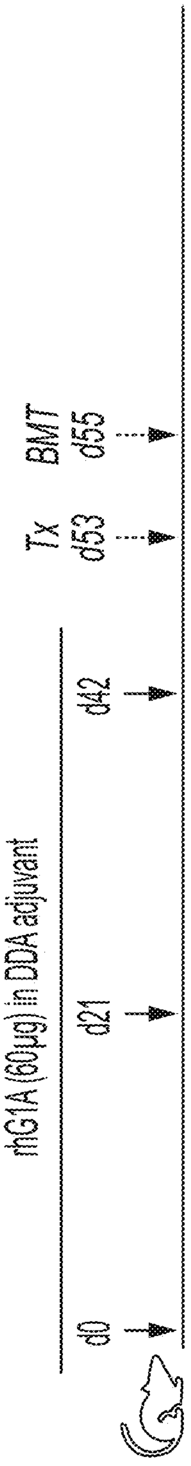
FIGS. 9A-9E graphically depict the results of an in vivo study showing that therapeutic treatment with CD45-ADC enables immune reset via congenic BMT and results in halt of disease progression in a murine model of rheumatoid arthritis (proteoglycan-induced arthritis).

Example 7. Immune Reset after Anti-Mouse CD45-ADC Conditioning and BMT Ameliorates Disease in a Murine Model of Rheumatoid Arthritis Conditioning with an anti-mouse CD45-ADC (anti-CD45 mAb conjugated to PBD) prior to bone marrow transplant was assessed in mouse proteoglycan-induced arthritis (PGIA), a murine model of rheumatoid arthritis. As depicted in FIG. 9A, Balb/c mice (CD45.2+) were given 3 immunizations (study day 0, 21, and 42) with recombinant human core G1 aggrecan (60 μg in 2 mg DDA). Animals were treated on day 11 post the final immunization (study day 53) and conditioned animals were transplanted with Balb/c CD45.1+ congenic BM 48 hours later. Animals treated with a neutralizing monoclonal antibody to murine TNFα received 500 μg/mouse IP weekly starting on study day 53.

Figure 9B:
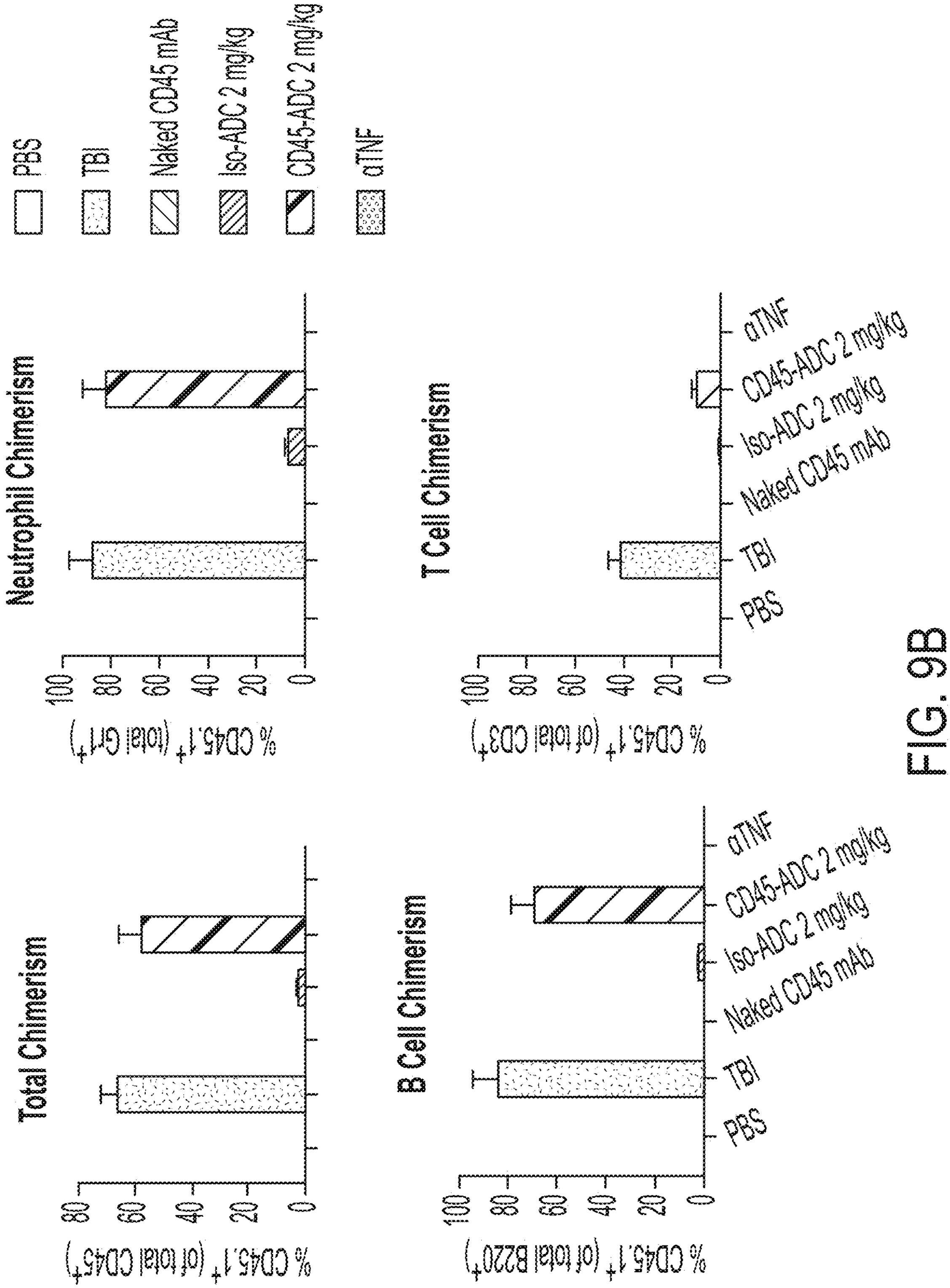
Figure 9C:
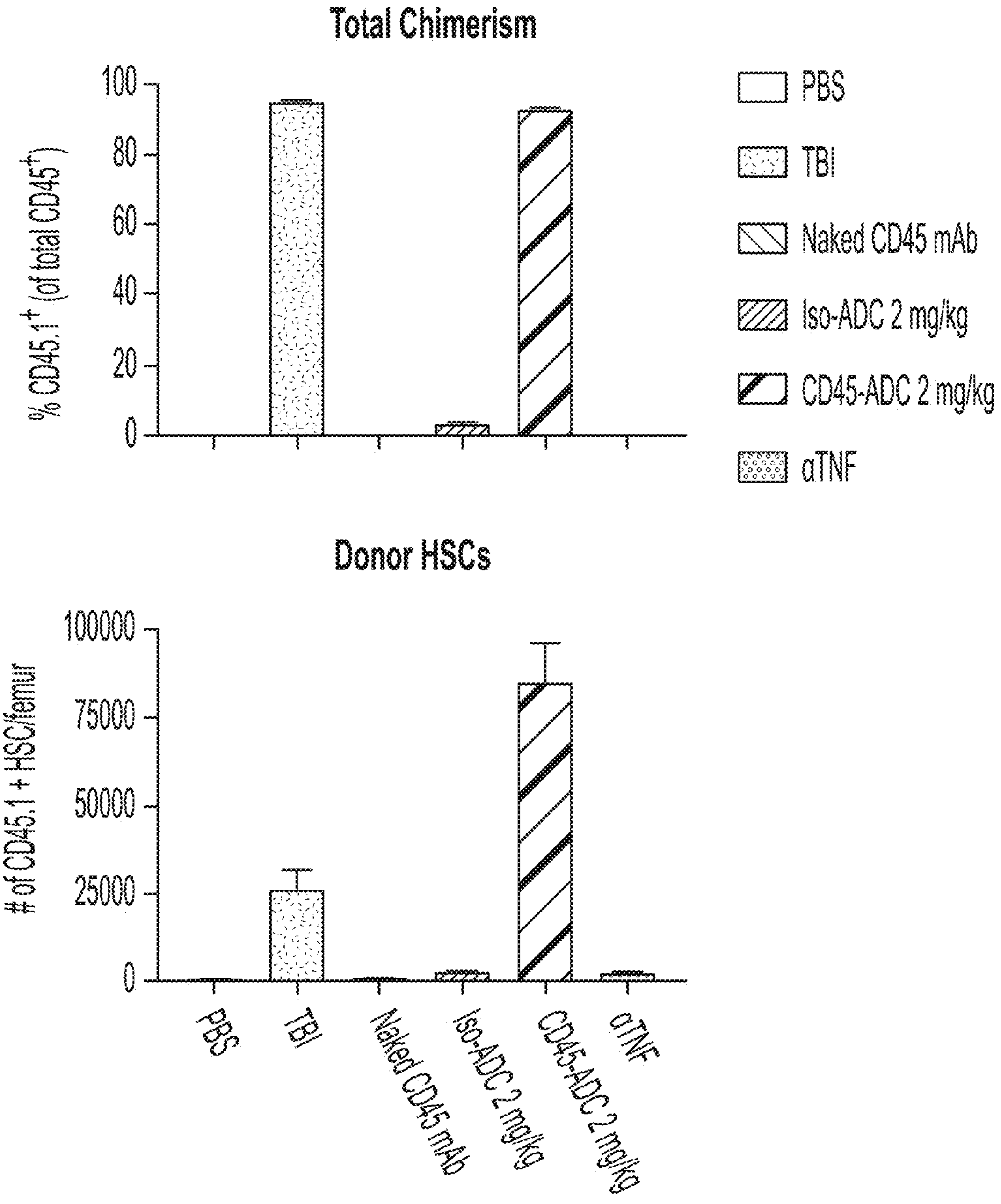
Figure 9D:
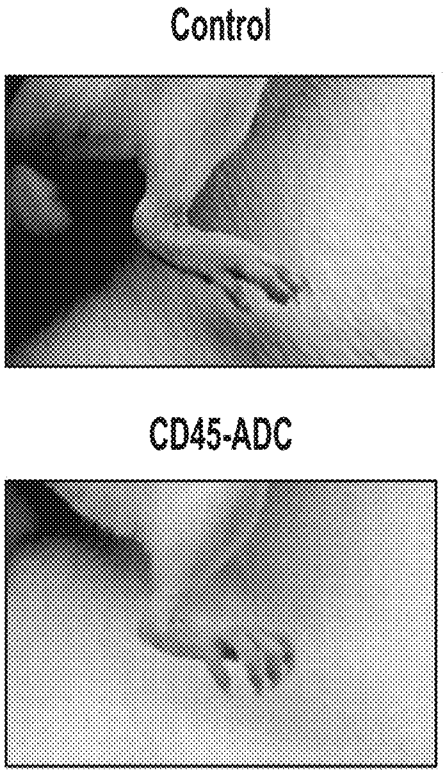
Figure 9E:
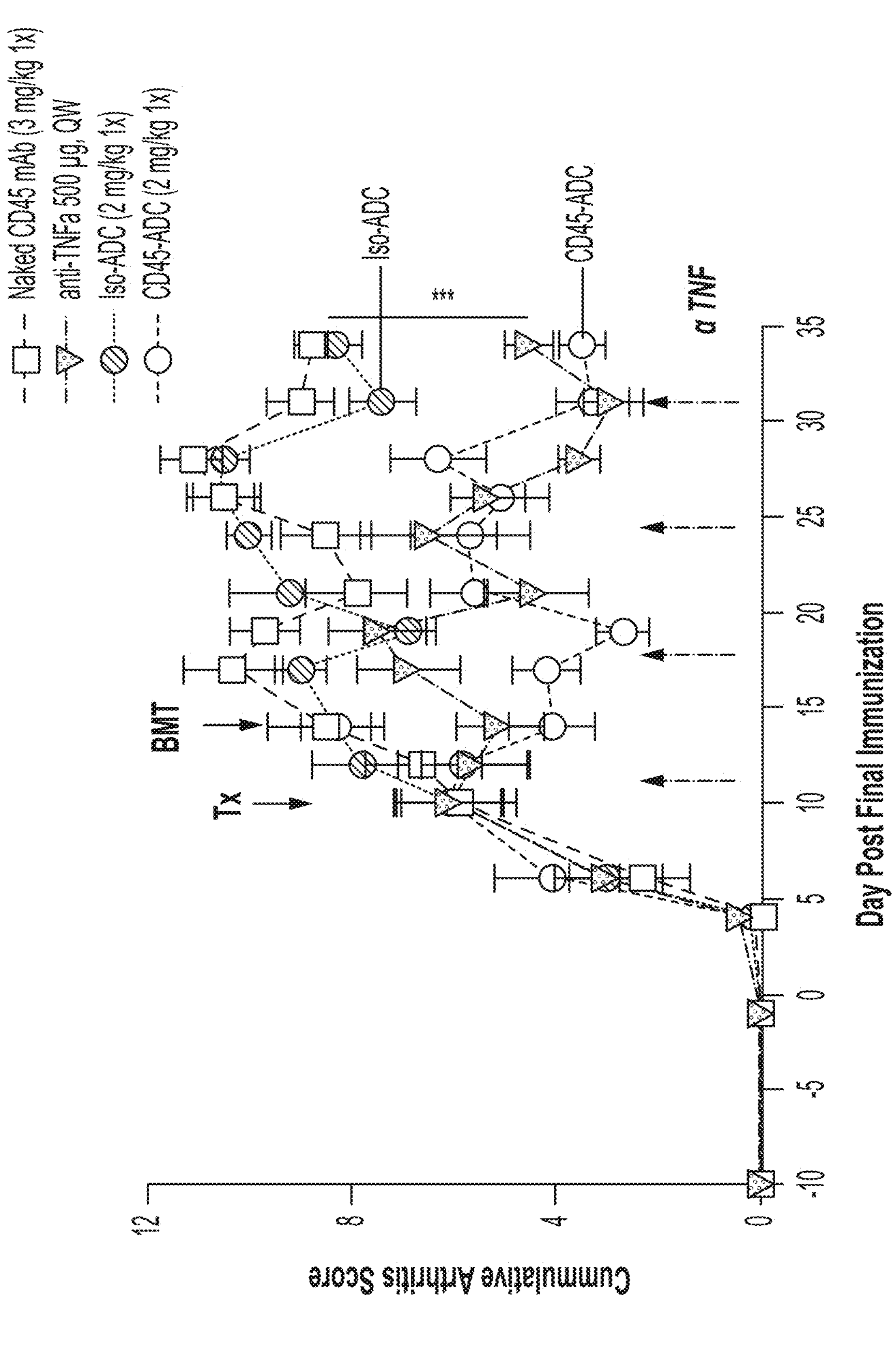

As shown in FIGS. 9B and 9C, treatment with 2 mg/kg of CD45-ADC, but not Isotype-ADC, enabled full congenic donor chimerism in peripheral blood (FIG. 9B) and bone marrow (FIG. 8C) at 3 weeks post-transplant. The clinical scoring system for the model as developed by Glantt and Mikecz (Methods in Molecular Medicine, Vol. 102 (17): 313-338) was used to score animals, with examples from control and CD45-ADC-treated animals shown in FIG. 9D. Scores for the treatment groups over time are shown in FIG. 9E.

In the PGIA model, therapeutic intervention (day 11 post $3^{rd}$ immunization) with CD45-ADC and BMT halted disease progression, similar to the clinically-validated approach of TNFα neutralization. These results indicate that therapeutic treatment with CD45-ADC enables immune reset via congenic BMT and results in halt of disease progression in a murine model of rheumatoid arthritis.

Figure 10A:
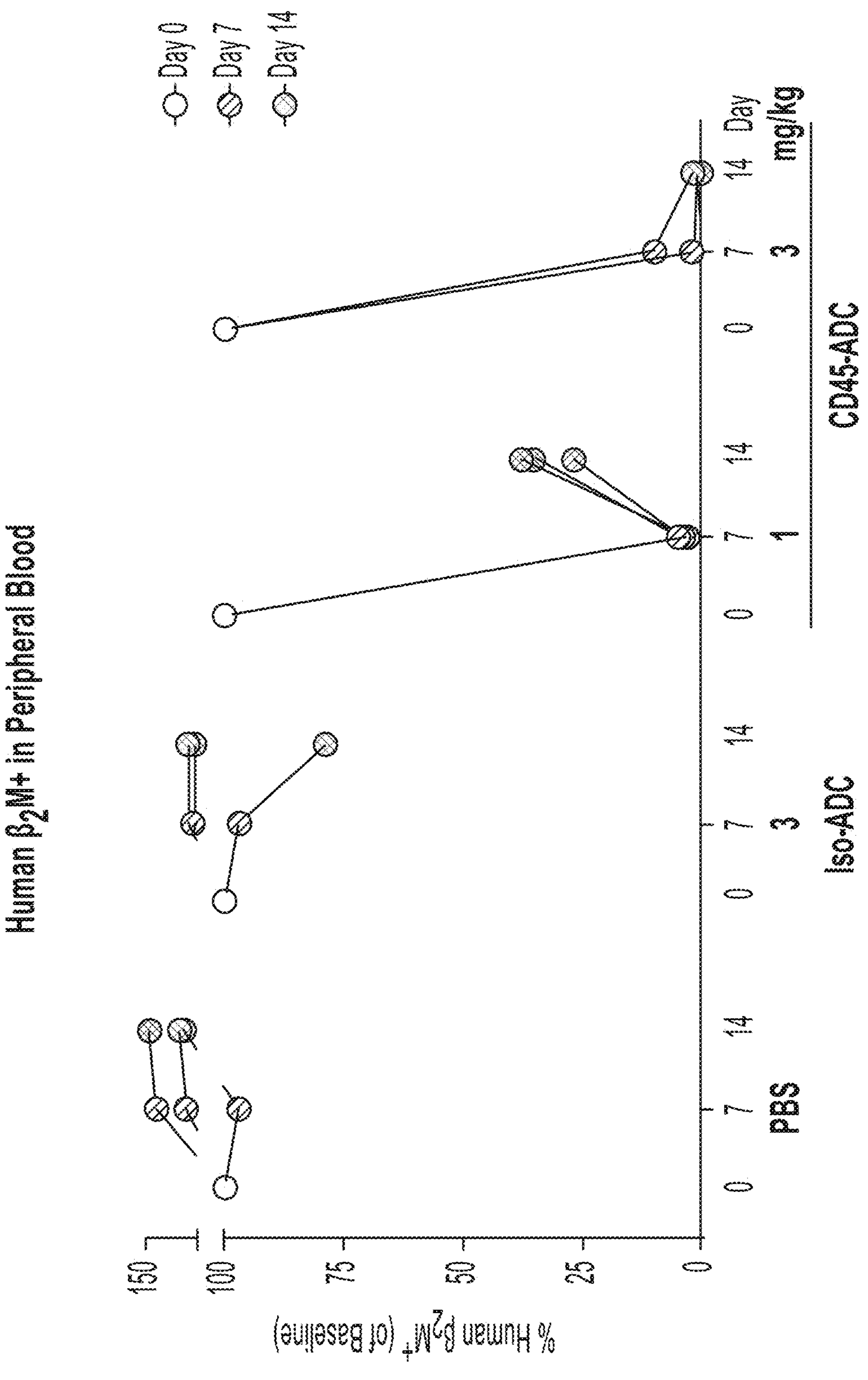
FIGS. 10A-10F graphically depict the results of an in vivo study showing that treatment with a single dose of an anti-human CD45 ADC results in elimination of human effector cells and amelioration of disease in a scleroderma-like model of xenoGVHD.
Figure 10B:
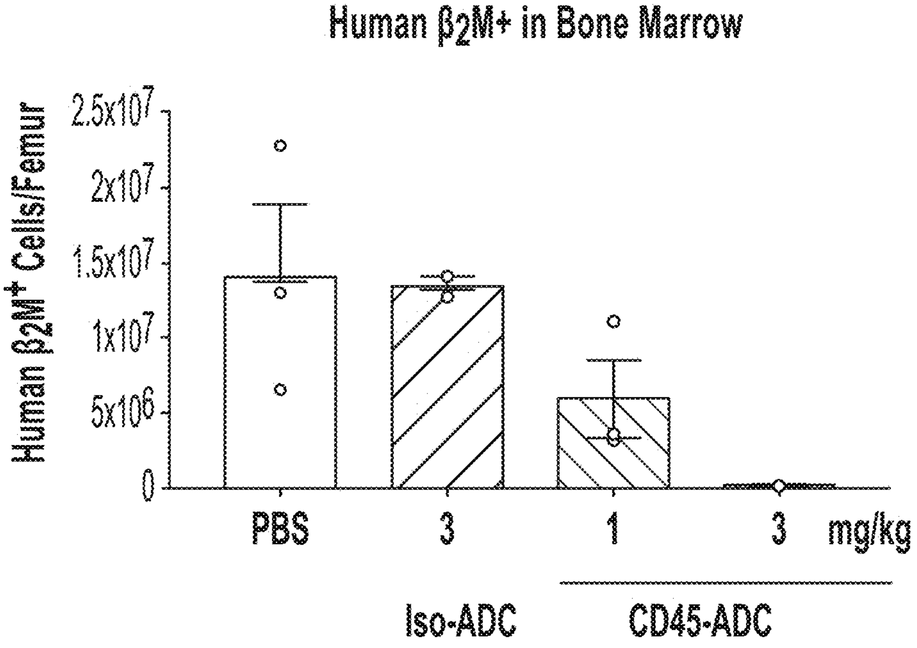
Figure 10C:
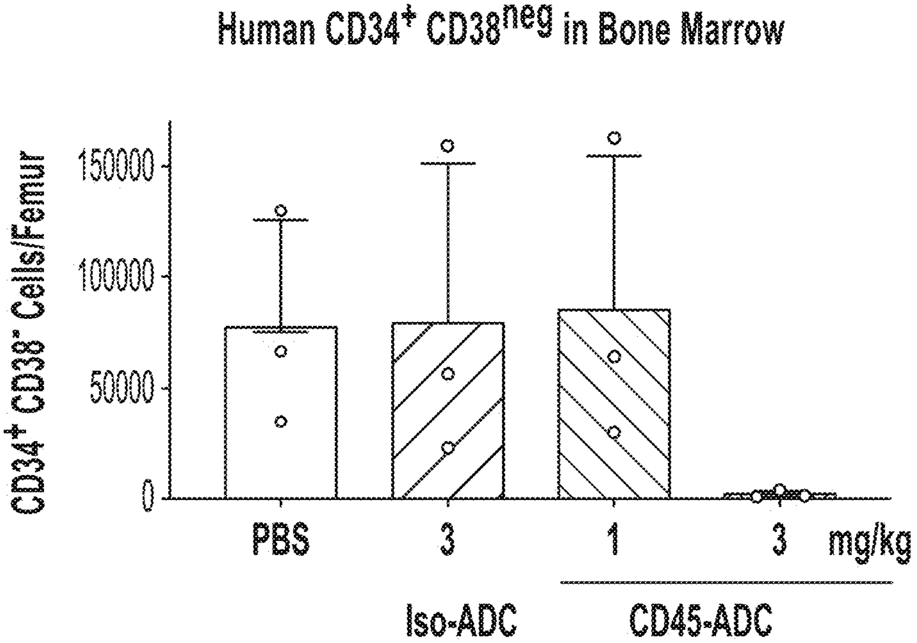
Figure 10D:
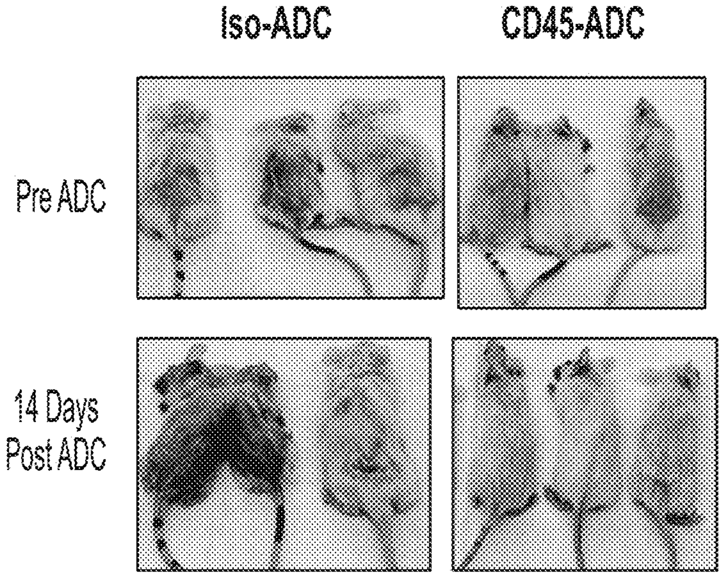
Figure 10E:
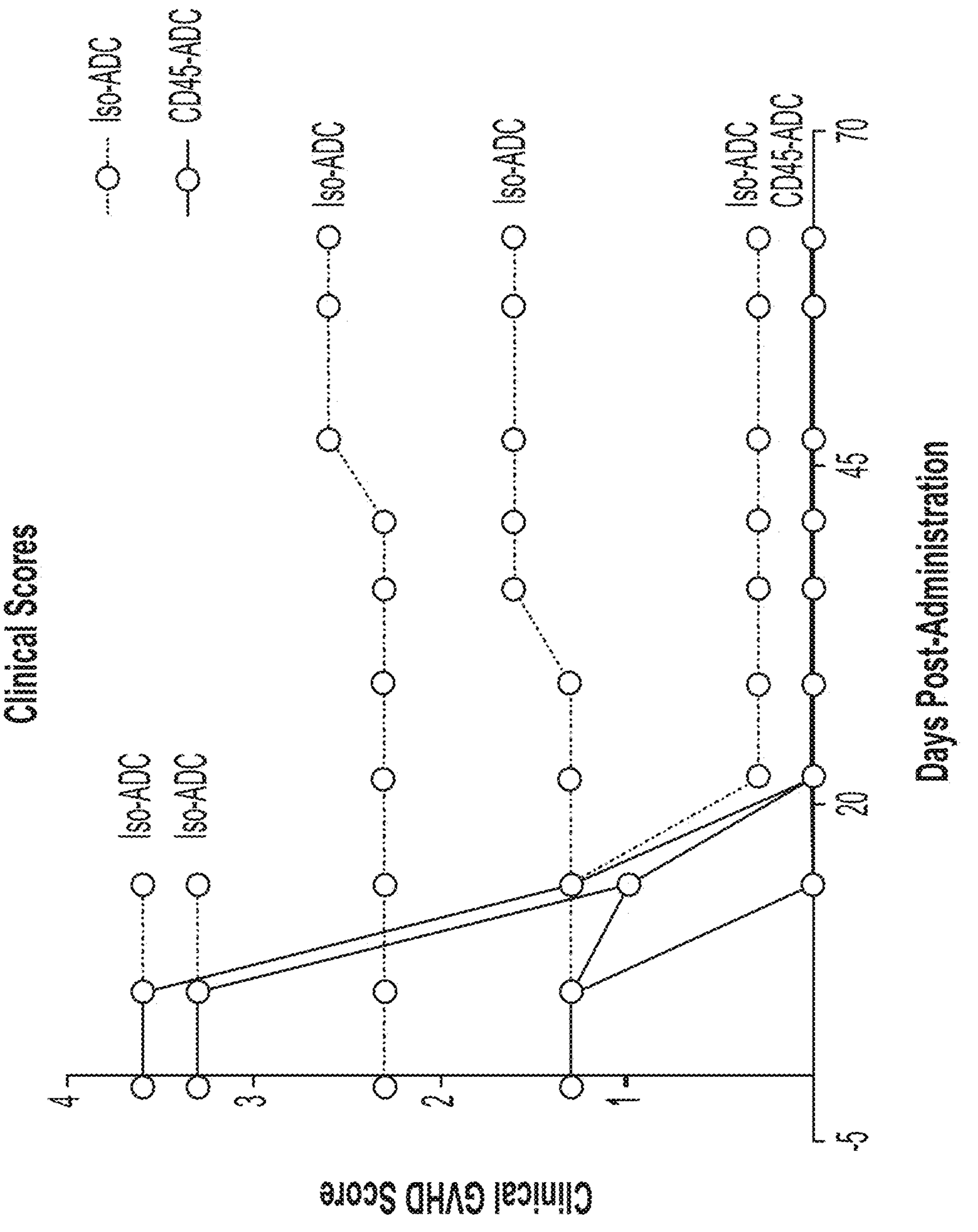
Figure 10F:
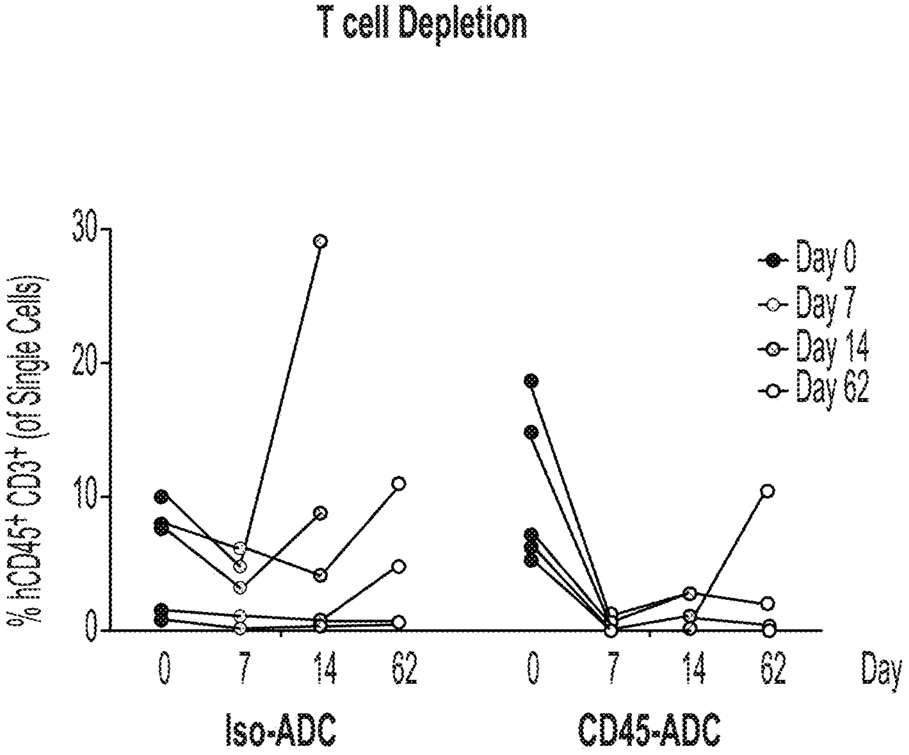

Example 8. An Anti-Human CD45-ADC Eliminates Effector Cells and Reduces Disease in a Scleroderma-Like Model of xenoGVHD An anti-human CD45 ADC (anti-CD45 mAb conjugated to amatoxin) was used in this study to evaluate its ability to deplete hematopoietic and immune cells in vivo in humanized NSG (hNSG) mice. hNSG mice that had developed a chronic, xenoGVHD with skin involvement after adoptive transfer of human PBMC were given a single dose of either an isotype ADC or an anti-human CD45-targeting ADC. A single dose of anti-human CD45-ADC was well tolerated and eliminated human hematopoietic cells in the periphery (FIG. 10A) and progenitor cells in BM (FIGS. 10B and 10C). As shown in FIG. 10D in images of selected animals, there was a clear resolution of skin pathology and regrowth of hair in animals administered CD45-ADC at 14 days post treatment, while isotype-ADC treated animals did not improve. Clinical scores for the animals based on the size and presentation of skin lesions are summarized in FIG. 10E. The top scoring animals in the isotype-ADC treated group had to be euthanized at day 14 due to their symptoms. Further, durable depletion of peripheral human T cells was achieved in animals treated with the anti-human CD45 ADC (FIG. 10F).

As described in Example 5 and FIG. 5H, in vitro, the CD45-ADC showed efficient killing of human peripheral $CD3^+$ cells from healthy donor (EC50 $7.6\times10^{-10}$ M) and MS patients (EC50 $1.5\times10^{-10}$ M). The present example demonstrates that, in vivo, a single dose of the CD45-ADC in hNSG was well-tolerated and led to substantial depletion of both lymphocytes and hematopoietic stem cells (HSCs). A single dose of CD45-ADC, but not Iso-ADC, resulted in elimination of disease-causing T cells and reversal of clinical symptoms in the scleroderma-like chronic xenoGVHD model. These results indicate that treatment with a single dose of an anti-human CD45 ADC results in elimination of human effector cells and amelioration of disease in a scleroderma-like model of xenoGVHD in hNSG mice.

Example 9. Treatment with a Single Dose of CD45-ADC and Congenic HSCT Leads to Disease Prevention in an Adoptive Transfer Model of Type I Diabetes Conditioning with a single dose of CD45-ADC (anti-CD45 mAb conjugated to PBD) followed by congenic HSC transplant was assessed in an adaptive transfer mouse model of Type I diabetes.

Figure 11A:
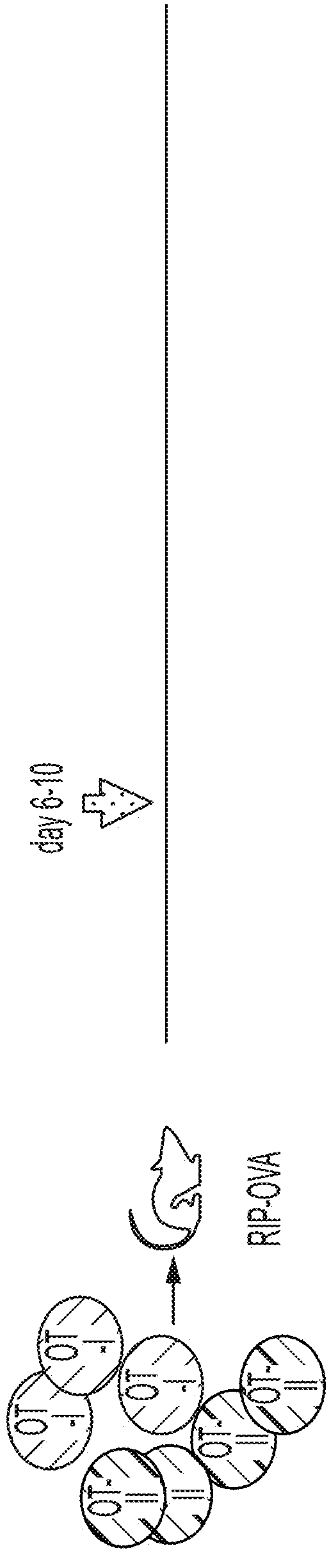
FIGS. 11A and 11B depict the study design and results of an in vivo study showing that treatment with a single dose of CD45-ADC and congenic HSC transplant leads to disease prevention in an adoptive transfer model of Type I Diabetes.

The design of the study, which utilized a RIP-OVA/OT-I/II system, is summarized in FIG. 11A and Table 5. RIP-OVA mice are B6 mice that express chicken ovalbumin in β-islet cells of pancreas. Central and peripheral tolerance mechanisms combine such that the adaptive immune system recognizes OVA as self. OT-I (MHC I-restricted) and OT-II (MHC II restricted) are two TCR Tg lines that specifically recognize epitopes of OVA. They were maintained on a B6 background.

Adoptive transfer of OT-I and OT-II into RIP-OVA mice led to destruction of β islet cells and onset of diabetes. Diabetes onset was monitored by blood glucose level (tail vein nick to test on strips; glucose >14.3 mmol/L). Mice became diabetic in this model 5-12 days after transfer of CD8+ OT-I cells (two consecutive measurements of 250 mg/dL, Drujont PLoS One 2014). Mice were peeled off on day 6 post adoptive transfer (n=4/treatment). Flow cytometry was performed on peripheral blood, spleen, dLN, and pancreas for Vβ5, Vα2 to measure transferred cells. Subsequently, mice (n=6 mice/group) were transplanted with $2\times10^7$ cells from B6 CD45.1 two days post-treatment. Body weight, BCS, and blood glucose 2× week were measured as endpoints.

TABLE 5

Study Design

| Mouse Strain | Treatment Group | # | CD8 Transfer | CD4 Transfer | Peel off | Transplant (2 days post tx) |
|---|---|---|---|---|---|---|
| RIP-mOVA | Vehicle | 10 | OT-I $1.0\times10^6$ (Actual input: $0.6\times10^6$) | OT-II $2\times10^6$ (Actual input: $1.2\times10^6$) | n = 4/ group on day 6 post adoptive transfer | — |
| | Anti-Thy1.2 (500 ug) | 10 | | | | — |
| | 9 Gy TBI | 10 | | | | $2\times10^7$ B6 CD45.1 |
| | 1 mg/kg Isotype PBD | 10 | | | | $2\times10^7$ B6 CD45.1 |
| | 3 mg/kg Isotype PBD | 10 | | | | $2\times10^7$ B6 CD45.1 |
| | 1 mg/kg CD45-PBD | 10 | | | | $2\times10^7$ B6 CD45.1 |
| | 3 mg/kg CD45-PBD | 10 | | | | $2\times10^7$ B6 CD45.1 |
| C57BI/6 | | 6 | | | | — |

Figure 11B:
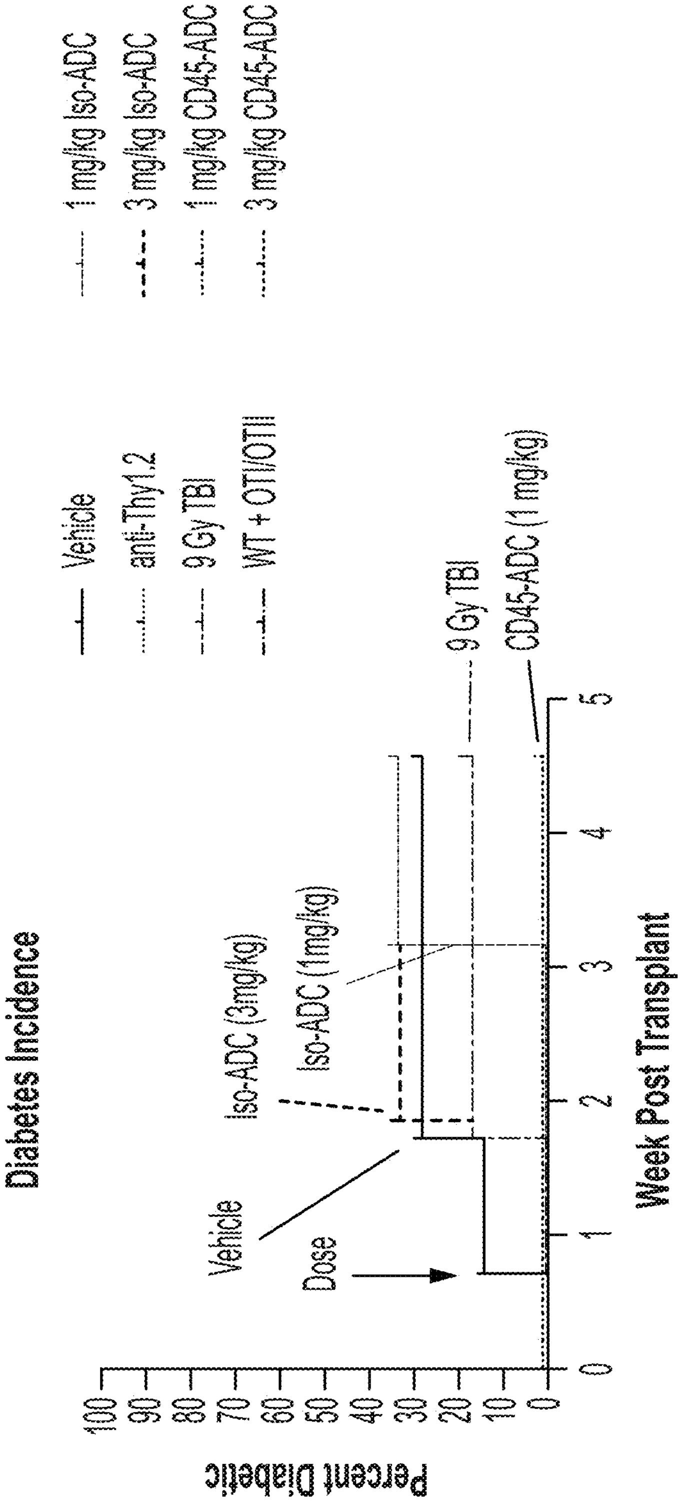

RIP-OVA mice were treated with either a vehicle control, anti-Thy1.2 (500 ug), 9 Gy TBI, 1 mg/kg or 3 mg/kg Isotype-ADC (Iso-PBD), or 1 mg/kg or 3 mg/kg CD45-ADC (CD45-PBD). As shown in FIG. 11B, diabetes incidence in vehicle-treated mice was approximately 40% through week 4 post-implantation. In contrast, zero out of the 6 mice had diabetes following treatment with the CD45-ADC at 1 or 3 mg/kg. These results indicate that treatment with a single dose of CD45-ADC and congenic HSC transplant leads to disease prevention in an adoptive transfer model of Type I Diabetes.

TABLE 6

SEQUENCE LISTING TABLE

| SEQ ID NO: | Description | Sequence |
|---|---|---|
| 1 | AbA heavy chain (HC) variable region (CDRs underlined) | EVQLVESGGDRVQPGRSLTLSCVTSGFTFNNYWMTWIRQVPG KGLEWVASISSSGGSIYYPDSVKGRFTISRDNAKNTLYLQMNSL RSEDTATYYCARDERWAGAMDAWGQGTSVTVSS |
| 2 | AbA HC CDR1 | FTFNNYWMT |
| 3 | AbA HC CDR2 | SISSSGGSIYYPDSVKG |

TABLE 6-continued

SEQUENCE LISTING TABLE

| SEQ ID NO: | Description | Sequence |
|---|---|---|
| 4 | AbA HC CDR3 | ARDERWAGAMDA |
| 5 | AbA light chain (LC) variable region (CDRs underlined) | DIQMTQSPPVLSASVGDRVTLSCKASQNINKNLDWYQQKHGEA PKLLIYETNNLQTGIPSRFSGSGSGTDYTLTISSLQPEDVATYYC YQHNSRFTFGSGTKLEIK |
| 6 | AbA LC CDR1 | KASQNINKNLD |
| 7 | AbA LC CDR2 | ETNNLQT |
| 8 | AbA LC CDR3 | YQHNSRFT |
| 9 | AbB heavy chain (HC) variable region (CDRs underlined) | EVQLVESGGDLVQPGRSLKLSCIASGFTFTNFWMTWIRQVSGK GLEWVASISSSGGSIYYPDSVKDRFTISRDNAKNTLYLQMNSLR SEDTATYYCVKLHYYSGGGDAWGQGTSVTVSS |
| 10 | AbB HC CDR1 | FTFTNFWMT |
| 11 | AbB HC CDR2 | SISSSGGSIYYPDSVKD |
| 12 | AbB HC CDR3 | VKLHYYSGGGDA |
| 13 | AbB light chain (LC) variable region (CDRs underlined) | DIQMTQSPSFLSASVGDRVTINCKASQNINKYLDWYQQKHGEAP KLLIHYTNNLHTGIPSRFSGSGSGTDYTLTISSLQPEDVATYFCLQ HSSRWTFGGGTKLELK |
| 14 | AbB LC CDR1 | KASQNINKYLD |
| 15 | AbB LC CDR2 | YTNNLHT |
| 16 | AbB LC CDR3 | LQHSSRWT |
| 17 | AbC heavy chain (HC) variable region | EVQLVESGGDLVQPGRSLKLSCVASGFTFNNYWMTWIRQVPG KGLEWVASISSSGGSIYYPDSVKDRFTISRDNAKNTLFLQMNSL RSEDTATYYCARLYYYSGGGDAWGQGTSVTVSS |
| 18 | AbC HC CDR1 | FTFNNYWMT |
| 19 | AbC HC CDR2 | SISSSGGSIYYPDSVKD |
| 20 | AbC HC CDR3 | ARLYYYSGGGDA |
| 21 | AbC light chain (LC) variable region (CDRs underlined) | DIQMTQSPSFLSASVGDRVTIICKASQDINKYLDWYQQKLGEAP KLLIYNTNNLHTGIPSRFSGSGSGTDYTLTISSLQPEDVATYFCLQ HISRWTFGGGTKLELK |
| 22 | AbC LC CDR1 | KASQDINKYLD |
| 23 | AbC LC CDR2 | NTNNLHT |
| 24 | AbC LC CDR3 | LQHISRWT |
| 25 | AbA LC variable DNA | GACATCCAGATGACCCAGTCTCCACCTGTGCTGTCTGCATCT GTAGGAGACAGAGTCACCCTTTCATGCAAGGCAAGTCAGAAT ATTAACAAAAATTTAGACTGGTATCAGCAGAAACATGGGGAA GCCCCTAAGCTCCTGATCTATGAGACAAATAATTTGCAAACG GGGATCCCATCAAGGTTCAGTGGCAGTGGATCTGGGACAGA TTACACTCTCACCATCAGCAGTCTGCAACCTGAAGATGTGGC AACTTACTACTGTTACCAGCACAACTCCAGATTCACTTTTGGC TCAGGGACCAAGCTGGAGATCAAA |
| 26 | AbA HC variable DNA | GAAGTGCAGCTGGTGGAGTCTGGGGGAGACAGGGTACAGCC TGGCAGGTCCCTGACACTCTCCTGTGTAACATCTGGATTCAC CTTTAACAACTATTGGATGACCTGGATCCGGCAAGTACCAGG GAAGGGCCTGGAGTGGGTCGCTTCTATTAGTTCCAGTGGCG GTAGCATATATTATCCCGACTCTGTGAAGGGCCGATTCACCA TCTCCAGAGACAACGCCAAGAACACCCTGTATCTGCAAATGA ACAGTCTGAGATCCGAGGACACGGCGACCTACTACTGCGCA AGAGACGAAAGATGGGCTGGCGCTATGGACGCCTGGGGGCA AGGGACCTCCGTCACCGTCTCCTCA |
| 27 | AbB LC variable DNA | GACATCCAGATGACCCAGTCTCCATCCTTCCTGTCTGCATCT GTAGGAGACAGAGTCACCATCAACTGCAAGGCGAGTCAGAA CATTAATAAATATTTAGATTGGTATCAGCAGAAACATGGGGAG GCCCCTAAGCTCCTGATCCATTACACCAATAATTTGCACACAG GGATACCATCAAGGTTCAGTGGAAGTGGATCTGGGACAGATT |

TABLE 6-continued

SEQUENCE LISTING TABLE

| SEQ ID NO: | Description | Sequence |
|---|---|---|
| | | ACACTTTGACCATCAGCAGCCTGCAGCCTGAAGATGTTGCAA<br>CATATTTCTGTCTGCAACATTCCAGCAGGTGGACCTTCGGCG<br>GAGGGACCAAGCTTGAGCTGAAA |
| 28 | AbB HC variable DNA | GGGAAGGGCCTGGAGTGGGTCGCTAGCATTAGTTCTAGTGG<br>AGGTAGCATATATTATCCCGACTCTGTGAAGGACCGATTCAC<br>CATCTCCAGAGACAACGCCAAGAACACACTGTATCTGCAAAT<br>GAACAGTCTGAGATCCGAGGACACGGCGACATACTACTGCG<br>TTAAGCTTCACTACTATTCCGGAGGGGGTGATGCTTGGGGCC<br>AAGGAACCTCCGTCACCGTCTCCTCA |
| 29 | AbC LC variable DNA | GACATCCAGATGACCCAGTCTCCATCCTTCCTGTCTGCATCT<br>GTAGGAGACAGAGTCACCATCATCTGCAAGGCGAGTCAGGA<br>CATTAACAAGTATTTAGACTGGTATCAGCAGAAATTGGGGGA<br>AGCCCCTAAGCTCCTGATCTACAATACAAATAATTTGCACACA<br>GGGATACCATCAAGGTTCAGTGGAAGTGGATCTGGGACAGAT<br>TACACTTTGACCATCAGCAGCCTGCAGCCTGAAGATGTCGCA<br>ACATATTTTTGTCTGCAGCACATTAGCAGATGGACCTTCGGC<br>GGAGGGACCAAGCTGGAGCTGAAA |
| 30 | AbC HC variable DNA | GAAGTGCAGCTGGTGGAGTCTGGGGGAGATTTGGTACAGCC<br>TGGCAGGTCCCTGAAACTCTCCTGTGTTGCCTCTGGATTCAC<br>CTTTAATAACTATTGGATGACATGGATTCGGCAAGTTCCAGG<br>GAAGGGCCTGGAGTGGGTCGCTTCCATTAGTAGTAGTGGTG<br>GTAGCATATATTATCCCGACTCTGTGAAGGATCGATTCACCAT<br>CTCCAGAGACAACGCCAAGAACACACTGTTTCTGCAAATGAA<br>CAGTCTGAGATCTGAGGACACGGCGACATACTACTGCGCGA<br>GACTGTATTACTATTCTGGTGGTGGCGATGCGTGGGGCCAAG<br>GAACCTCCGTCACCGTCTCCTCA |
| 31 | Human CD45RA Isoform (Uniprot Accession No: P08575-8) | MTMYLWLKLLAFGFAFLDTEVFVTGQSPTPSPTGLTTAKMPSVP<br>LSSDPLPTHTTAFSPASTFERENDFSETTTSLSPDNTSTQVSPD<br>SLDNASAFNTTDAYLNASETTTLSPSGSAVISTTTIATTPSKPTCD<br>EKYANITVDYLYNKETKLFTAKLNVNENVECGNNTCTNNEVHNL<br>TECKNASVSISHNSCTAPDKTLILDVPPGVEKFQLHDCTQVEKA<br>DTTICLKWKNIETFTCDTQNITYRFQCGNMIFDNKEIKLENLEPEH<br>EYKCDSEILYNNHKFTNASKIIKTDFGSPGEPQIIFCRSEAAHQGV<br>ITWNPPQRSFHNFTLCYIKETEKDCLNLDKNLIKYDLQNLKPYTK<br>YVLSLHAYIIAKVQRNGSAAMCHFTTKSAPPSQVWNMTVSMTS<br>DNSMHVKCRPPRDRNGPHERYHLEVEAGNTLVRNESHKNCDF<br>RVKDLQYSTDYTFKAYFHNGDYPGEPFILHHSTSYNSKALIAFLA<br>FLIIVTSIALLVVLYKIYDLHKKRSCNLDEQQELVERDDEKQLMNV<br>EPIHADILLETYKRKIADEGRLFLAEFQSIPRVFSKFPIKEARKPFN<br>QNKNRYVDILPYDYNRVELSEINGDAGSNYINASYIDGFKEPRKY<br>IAAQGPRDETVDDFWRMIWEQKATVIVMVTRCEEGNRNKCAEY<br>WPSMEEGTRAFGDVVVKINQHKRCPDYIIQKLNIVNKKEKATGR<br>EVTHIQFTSWPDHGVPEDPHLLLKLRRRVNAFSNFFSGPIVVHC<br>SAGVGRTGTYIGIDAMLEGLEAENKVDVYGYVVKLRRQRCLMV<br>QVEAQYILIHQALVEYNQFGETEVNLSELHPYLHNMKKRDPPSE<br>PSPLEAEFQRLPSYRSWRTQHIGNQEENKSKNRNSNVIPYDYN<br>RVPLKHELEMSKESEHDSDESSDDDSDSEEPSKYINASFIMSYW<br>KPEVMIAAQGPLKETIGDFWQMIFQRKVKVIVMLTELKHGDQEIC<br>AQYWGEGKQTYGDIEVDLKDTDKSSTYTLRVFELRHSKRKDSR<br>TVYQYQYTNWSVEQLPAEPKELISMIQVVKQKLPQKNSSEGNK<br>HHKSTPLLIHCRDGSQQTGIFCALLNLLESAETEEVVDIFQVVKAL<br>RKARPGMVSTFEQYQFLYDVIASTYPAQNGQVKKNNHQEDKIE<br>FDNEVDKVKQDANCVNPLGAPEKLPEAKEQAEGSEPTSGTEGP<br>EHSVNGPASPALNQGS |
| 32 | Human CD45RO Isoform (NCBI Accession No: NP_563578 .2) | MTMYLWLKLLAFGFAFLDTEVFVTGQSPTPSPTDAYLNASETTT<br>LSPSGSAVISTTTIATTPSKPTCDEKYANITVDYLYNKETKLFTAK<br>LNVNENVECGNNTCTNNEVHNLTECKNASVSISHNSCTAPDKTL<br>ILDVPPGVEKFQLHDCTQVEKADTTICLKWKNIETFTCDTQNITY<br>RFQCGNMIFDNKEIKLENLEPEHEYKCDSEILYNNHKFTNASKIIK<br>TDFGSPGEPQIIFCRSEAAHQGVITWNPPQRSFHNFTLCYIKETE<br>KDCLNLDKNLIKYDLQNLKPYTKYVLSLHAYIIAKVQRNGSAAMC<br>HFTTKSAPPSQVWNMTVSMTSDNSMHVKCRPPRDRNGPHERY<br>HLEVEAGNTLVRNESHKNCDFRVKDLQYSTDYTFKAYFHNGDY<br>PGEPFILHHSTSYNSKALIAFLAFLIIVTSIALLVVLYKIYDLHKKRS<br>CNLDEQQELVERDDEKQLMNVEPIHADILLETYKRKIADEGRLFL<br>AEFQSIPRVFSKFPIKEARKPFNQNKNRYVDILPYDYNRVELSEIN<br>GDAGSNYINASYIDGFKEPRKYIAAQGPRDETVDDFWRMIWEQ<br>KATVIVMVTRCEEGNRNKCAEYWPSMEEGTRAFGDVVVKINQH<br>KRCPDYIIQKLNIVNKKEKATGREVTHIQFTSWPDHGVPEDPHLL<br>LKLRRRVNAFSNFFSGPIVVHCSAGVGRTGTYIGIDAMLEGLEAE<br>NKVDVYGYVVKLRRQRCLMVQVEAQYILIHQALVEYNQFGETEV |

TABLE 6-continued

SEQUENCE LISTING TABLE

| SEQ ID NO: | Description | Sequence |
|---|---|---|
| | | NLSELHPYLHNMKKRDPPSEPSPLEAEFQRLPSYRSWRTQHIG NQEENKSKNRNSNVIPYDYNRVPLKHELEMSKESEHDSDESSD DDSDSEEPSKYINASFIMSYWKPEVMIAAQGPLKETIGDFWQMIF QRKVKVIVMLTELKHGDQEICAQYWGEGKQTYGDIEVDLKDTDK SSTYTLRVFELRHSKRKDSRTVYQYQYTNWSVEQLPAEPKELIS MIQVVKQKLPQKNSSEGNKHHKSTPLLIHCRDGSQQTGIFCALL NLLESAETEEVVDIFQVVKALRKARPGMVSTFEQYQFLYDVIAST YPAQNGQVKKNNHQEDKIEFDNEVDKVKQDANCVNPLGAPEKL PEAKEQAEGSEPTSGTEGPEHSVNGPASPALNQGS |
| 33 | Human CD45RB Isoform (NCBI Accession No: XP_006711537.1) | MTMYLWLKLLAFGFAFLDTEVFVTGQSPTPSPTGVSSVQTPHLP THADSQTPSAGTDTQTFSGSAANAKLNPTPGSNAISDAYLNASE TTTLSPSGSAVISTTTIATTPSKPTCDEKYANITVDYLYNKETKLFT AKLNVNENVECGNNTCTNNEVHNLTECKNASVSISHNSCTAPD KTLILDVPPGVEKFQLHDCTQVEKADTTICLKWKNIETFTCDTQNI TYRFQCGNMIFDNKEIKLENLEPEHEYKCDSEILYNNHKFTNASK IIKTDFGSPGEPQIIFCRSEAAHQGVITWNPPQRSFHNFTLCYIKE TEKDCLNLDKNLIKYDLQNLKPYTKYVLSLHAYIIAKVQRNGSAA MCHFTTKSAPPSQVWNMTVSMTSDNSMHVKCRPPRDRNGPH ERYHLEVEAGNTLVRNESHKNCDFRVKDLQYSTDYTFKAYFHN GDYPGEPFILHHSTSYNSKALIAFLAFLIIVTSIALLVVLYKIYDLHK KRSCNLDEQQELVERDDEKQLMNVEPIHADILLETYKRKIADEG RLFLAEFQSIPRVFSKFPIKEARKPFNQNKNRYVDILPYDYNRVE LSEINGDAGSNYINASYIDGFKEPRKYIAAQGPRDETVDDFWRMI WEQKATVIVMVTRCEEGNRNKCAEYWPSMEEGTRAFGDVVVKI NQHKRCPDYIIQKLNIVNKKEKATGREVTHIQFTSWPDHGVPED PHLLLKLRRRVNAFSNFFSGPIVVHCSAGVGRTGTYIGIDAMLEG LEAENKVDVYGYVVKLRRQRCLMVQVEAQYILIHQALVEYNQFG ETEVNLSELHPYLHNMKKRDPPSEPSPLEAEFQRLPSYRSWRT QHIGNQEENKSKNRNSNVIPYDYNRVPLKHELEMSKESEHDSD ESSDDDSDSEEPSKYINASFIMSYWKPEVMIAAQGPLKETIGDF WQMIFQRKVKVIVMLTELKHGDQEICAQYWGEGKQTYGDIEVDL KDTDKSSTYTLRVFELRHSKRKDSRTVYQYQYTNWSVEQLPAE PKELISMIQVVKQKLPQKNSSEGNKHHKSTPLLIHCRDGSQQTGI FCALLNLLESAETEEVVDIFQVVKALRKARPGMVSTFEQYQFLY DVIASTYPAQNGQVKKNNHQEDKIEFDNEVDKVKQDANCVNPL GAPEKLPEAKEQAEGSEPTSGTEGPEHSVNGPASPALNQGS |
| 34 | Human CD45RAB Isoform (NCBI Accession No: XP_006711535.1) | MTMYLWLKLLAFGFAFLDTEVFVTGQSPTPSPTGLTTAKMPSVP LSSDPLPTHTTAFSPASTFERENDFSETTTSLSPDNTSTQVSPD SLDNASAFNTTGVSSVQTPHLPTHADSQTPSAGTDTQTFSGSA ANAKLNPTPGSNAISDAYLNASETTTLSPSGSAVISTTTIATTPSK PTCDEKYANITVDYLYNKETKLFTAKLNVNENVECGNNTCTNNE VHNLTECKNASVSISHNSCTAPDKTLILDVPPGVEKFQLHDCTQV EKADTTICLKWKNIETFTCDTQNITYRFQCGNMIFDNKEIKLENLE PEHEYKCDSEILYNNHKFTNASKIIKTDFGSPGEPQIIFCRSEAAH QGVITWNPPQRSFHNFTLCYIKETEKDCLNLDKNLIKYDLQNLKP YTKYVLSLHAYIIAKVQRNGSAAMCHFTTKSAPPSQVWNMTVSM TSDNSMHVKCRPPRDRNGPHERYHLEVEAGNTLVRNESHKNC DFRVKDLQYSTDYTFKAYFHNGDYPGEPFILHHSTSYNSKALIAF LAFLIIVTSIALLVVLYKIYDLHKKRSCNLDEQQELVERDDEKQLM NVEPIHADILLETYKRKIADEGRLFLAEFQSIPRVFSKFPIKEARKP FNQNKNRYVDILPYDYNRVELSEINGDAGSNYINASYIDGFKEPR KYIAAQGPRDETVDDFWRMIWEQKATVIVMVTRCEEGNRNKCA EYWPSMEEGTRAFGDVVVKINQHKRCPDYIIQKLNIVNKKEKAT GREVTHIQFTSWPDHGVPEDPHLLLKLRRRVNAFSNFFSGPIVV HCSAGVGRTGTYIGIDAMLEGLEAENKVDVYGYVVKLRRQRCL MVQVEAQYILIHQALVEYNQFGETEVNLSELHPYLHNMKKRDPP SEPSPLEAEFQRLPSYRSWRTQHIGNQEENKSKNRNSNVIPYD YNRVPLKHELEMSKESEHDSDESSDDDSDSEEPSKYINASFIMS YWKPEVMIAAQGPLKETIGDFWQMIFQRKVKVIVMLTELKHGDQ EICAQYWGEGKQTYGDIEVDLKDTDKSSTYTLRVFELRHSKRKD SRTVYQYQYTNWSVEQLPAEPKELISMIQVVKQKLPQKNSSEG NKHHKSTPLLIHCRDGSQQTGIFCALLNLLESAETEEVVDIFQVV KALRKARPGMVSTFEQYQFLYDVIASTYPAQNGQVKKNNHQED KIEFDNEVDKVKQDANCVNPLGAPEKLPEAKEQAEGSEPTSGTE GPEHSVNGPASPALNQGS |
| 35 | Human CD45RBC Isoform (NCBI Accession No: XP_006711536.1) | MTMYLWLKLLAFGFAFLDTEVFVTGQSPTPSPTGVSSVQTPHLP THADSQTPSAGTDTQTFSGSAANAKLNPTPGSNAISDVPGERST ASTFPTDPVSPLTTTLSLAHHSSAALPARTSNTTITANTSDAYLN ASETTTLSPSGSAVISTTTIATTPSKPTCDEKYANITVDYLYNKET KLFTAKLNVNENVECGNNTCTNNEVHNLTECKNASVSISHNSCT APDKTLILDVPPGVEKFQLHDCTQVEKADTTICLKWKNIETFTCD TQNITYRFQCGNMIFDNKEIKLENLEPEHEYKCDSEILYNNHKFT NASKIIKTDFGSPGEPQIIFCRSEAAHQGVITWNPPQRSFHNFTL |

TABLE 6-continued

SEQUENCE LISTING TABLE

| SEQ ID NO: | Description | Sequence |
|---|---|---|
| | | CYIKETEKDCLNLDKNLIKYDLQNLKPYTKYVLSLHAYIIAKVQRN GSAAMCHFTTKSAPPSQVWNMTVSMTSDNSMHVKCRPPRDR NGPHERYHLEVEAGNTLVRNESHKNCDFRVKDLQYSTDYTFKA YFHNGDYPGEPFILHHSTSYNSKALIAFLAFLIIVTSIALLVVLYKIY DLHKKRSCNLDEQQELVERDDEKQLMNVEPIHADILLETYKRKIA DEGRLFLAEFQSIPRVFSKFPIKEARKPFNQNKNRYVDILPYDYN RVELSEINGDAGSNYINASYIDGFKEPRKYIAAQGPRDETVDDF WRMIWEQKATVIVMVTRCEEGNRNKCAEYWPSMEEGTRAFGD VVVKINQHKRCPDYIIQKLNIVNKKEKATGREVTHIQFTSWPDHG VPEDPHLLLKLRRRVNAFSNFFSGPIVVHCSAGVGRTGTYIGIDA MLEGLEAENKVDVYGYVVKLRRQRCLMVQVEAQYILIHQALVEY NQFGETEVNLSELHPYLHNMKKRDPPSEPSPLEAEFQRLPSYR SWRTQHIGNQEENKSKNRNSNVIPYDYNRVPLKHELEMSKESE HDSDESSDDDSDSEEPSKYINASFIMSYWKPEVMIAAQGPLKETI GDFWQMIFQRKVKVIVMLTELKHGDQEICAQYWGEGKQTYGDI EVDLKDTDKSSTYTLRVFELRHSKRKDSRTVYQYQYTNWSVEQ LPAEPKELISMIQVVKQKLPQKNSSEGNKHHKSTPLLIHCRDGSQ QTGIFCALLNLLESAETEEVVDIFQVVKALRKARPGMVSTFEQYQ FLYDVIASTYPAQNGQVKKNNHQEDKIEFDNEVDKVKQDANCV NPLGAPEKLPEAKEQAEGSEPTSGTEGPEHSVNGPASPALNQG S |
| 36 | Human CD45RABC Isoform (NCBI Accession No. NP_002829 .3) | MTMYLWLKLLAFGFAFLDTEVFVTGQSPTPSPTGLTTAKMPSVP LSSDPLPTHTTAFSPASTFERENDFSETTTSLSPDNTSTQVSPD SLDNASAFNTTGVSSVQTPHLPTHADSQTPSAGTDTQTFSGSA ANAKLNPTPGSNAISDVPGERSTASTFPTDPVSPLTTTLSLAHHS SAALPARTSNTTITANTSDAYLNASETTTLSPSGSAVISTTTIATTP SKPTCDEKYANITVDYLYNKETKLFTAKLNVNENVECGNNTCTN NEVHNLTECKNASVSISHNSCTAPDKTLILDVPPGVEKFQLHDCT QVEKADTTICLKWKNIETFTCDTQNITYRFQCGNMIFDNKEIKLE NLEPEHEYKCDSEILYNNHKFTNASKIIKTDFGSPGEPQIIFCRSE AAHQGVITWNPPQRSFHNFTLCYIKETEKDCLNLDKNLIKYDLQN LKPYTKYVLSLHAYIIAKVQRNGSAAMCHFTTKSAPPSQVWNMT VSMTSDNSMHVKCRPPRDRNGPHERYHLEVEAGNTLVRNESH KNCDFRVKDLQYSTDYTFKAYFHNGDYPGEPFILHHSTSYNSKA LIAFLAFLIIVTSIALLVVLYKIYDLHKKRSCNLDEQQELVERDDEK QLMNVEPIHADILLETYKRKIADEGRLFLAEFQSIPRVFSKFPIKEA RKPFNQNKNRYVDILPYDYNRVELSEINGDAGSNYINASYIDGFK EPRKYIAAQGPRDETVDDFWRMIWEQKATVIVMVTRCEEGNRN KCAEYWPSMEEGTRAFGDVVVKINQHKRCPDYIIQKLNIVNKKE KATGREVTHIQFTSWPDHGVPEDPHLLLKLRRRVNAFSNFFSGP IVVHCSAGVGRTGTYIGIDAMLEGLEAENKVDVYGYVVKLRRQR CLMVQVEAQYILIHQALVEYNQFGETEVNLSELHPYLHNMKKRD PPSEPSPLEAEFQRLPSYRSWRTQHIGNQEENKSKNRNSNVIPY DYNRVPLKHELEMSKESEHDSDESSDDDSDSEEPSKYINASFIM SYWKPEVMIAAQGPLKETIGDFWQMIFQRKVKVIVMLTELKHGD QEICAQYWGEGKQTYGDIEVDLKDTDKSSTYTLRVFELRHSKRK DSRTVYQYQYTNWSVEQLPAEPKELISMIQVVKQKLPQKNSSE GNKHHKSTPLLIHCRDGSQQTGIFCALLNLLESAETEEVVDIFQV VKALRKARPGMVSTFEQYQFLYDVIASTYPAQNGQVKKNNHQE DKIEFDNEVDKVKQDANCVNPLGAPEKLPEAKEQAEGSEPTSG TEGPEHSVNGPASPALNQGS |
| 37 | Human CD45RABC Antigen (Fragment of Human CD45RABC Isoform) | QSPTPSPTGLTTAKMPSVPLSSDPLPTHTTAFSPASTFERENDF SETTTSLSPDNTSTQVSPDSLDNASAFNTTGVSSVQTPHLPTHA DSQTPSAGTDTQTFSGSAANAKLNPTPGSNAISDVPGERSTAST FPTDPVSPLTTTLSLAHHSSAALPARTSNTTITANTSDAYLNASE TTTLSPSGSAVISTTTIATTPSKPTCDEKYANITVDYLYNKETKLFT AKLNVNENVECGNNTCTNNEVHNLTECKNASVSISHNSCTAPD KTLILDVPPGVEKFQLHDCTQVEKADTTICLKWKNIETFTCDTQNI TYRFQCGNMIFDNKEIKLENLEPEHEYKCDSEILYNNHKFTNASK IIKTDFGSPGEPQIIFCRSEAAHQGVITWNPPQRSFHNFTLCYIKE TEKDCLNLDKNLIKYDLQNLKPYTKYVLSLHAYIIAKVQRNGSAA MCHFTTKSAPPSQVWNMTVSMTSDNSMHVKCRPPRDRNGPH ERYHLEVEAGNTLVRNESHKNCDFRVKDLQYSTDYTFKAYFHN GDYPGEPFILHHSTSYNSK |
| 38 | CD45 Fragment | RNGPHERYHLEVEAGNT |
| 39 | CD45 Fragment | CRPPRDRNGPHERYHLEVEAGNTLVRNESHK |

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of depleting a population of CD45+ cells in a human patient having an autoimmune disease, the method comprising administering to the patient having the autoimmune disease an effective amount of an antibody-drug conjugate (ADC) comprising an anti-CD45 antibody, or antigen binding portion thereof, conjugated to a cytotoxin via a linker, wherein the cytotoxin is a pyrrolobenzodiazepine dimer, or an indolinobenzodiazepine pseudodimer, wherein:

i) the pyrrolobenzodiazepine dimer has a structure of formula:

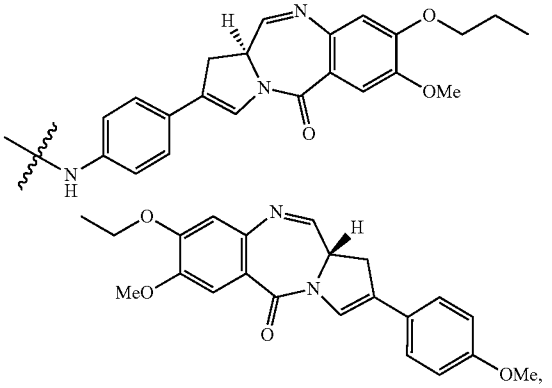

or

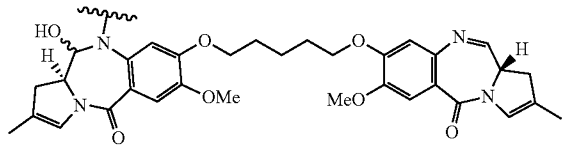

wherein the wavy line indicates the attachment point of the linker; or ii) the indolinobenzodiazepine pseudodimer has a structure of formula:

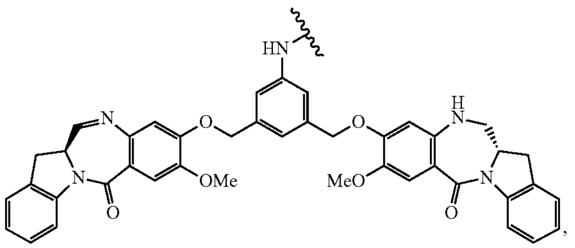 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker.

2. A method of conditioning a human patient having an autoimmune disease for receiving a hematopoietic stem cell (HSC) transplant, the method comprising administering to the human patient having the autoimmune disease an antibody-drug conjugate (ADC) comprising an anti-CD45 antibody, or antigen binding portion thereof, conjugated to a cytotoxin via a linker, wherein the cytotoxin is a pyrrolobenzodiazepine dimer, or an indolinobenzodiazepine pseudodimer, wherein:

i) the pyrrolobenzodiazepine dimer has a structure of formula:

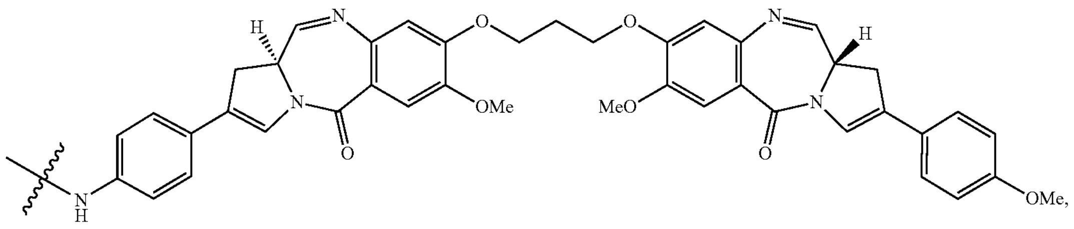

or

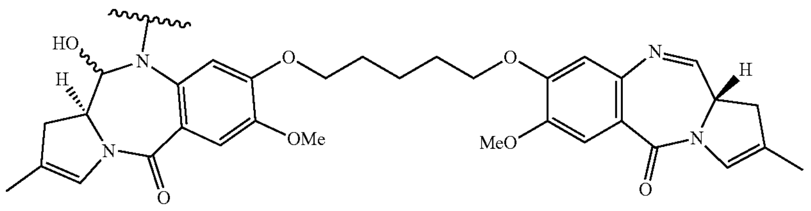

wherein the wavy line indicates the attachment point of the linker; or ii) the indolinobenzodiazepine pseudodimer has a structure of formula:

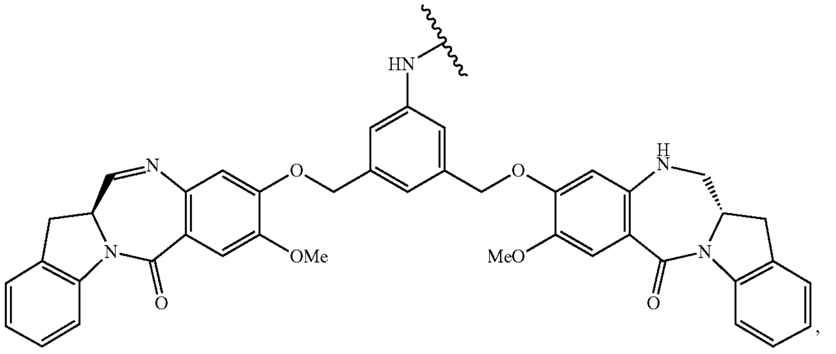 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker.

3. The method of claim 1, wherein the autoimmune disease is an inflammatory arthritis, autoimmune encephalitis, scleroderma, multiple sclerosis, type 1 diabetes, or systemic sclerosis.

4. The method of claim 2, further comprising administering a transplant comprising hematopoietic stem cells (HSCs) to the patient.

5. The method of claim 4, wherein the HSC transplant is an autologous HSC transplant (autoHSCT).

6. The method of claim 4, wherein the anti-CD45 ADC is administered to the patient about three days prior to the patient receiving the transplant comprising HSCs.

7. The method of claim 4, wherein the HSC transplant is administered to the patient after the anti-CD45 ADC has substantially cleared from the blood of the human patient.

8. A method of treating a patient having scleroderma or multiple sclerosis, said method comprising administering an anti-CD45 antibody drug conjugate (ADC) to a patient having a sclerodermatous graft-vs-host disease (scGVHD), such that the scGVHD is treated, wherein the anti-CD45 ADC comprises an anti-CD45 antibody, or fragment thereof, conjugated to a cytotoxin via a linker;

wherein the cytotoxin is a pyrrolobenzodiazepine dimer, or an indolinobenzodiazepine pseudodimer, wherein:

i) the pyrrolobenzodiazepine dimer has a structure of formula:

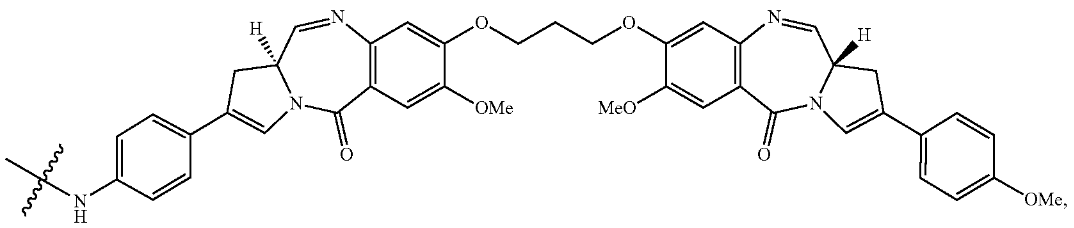

or

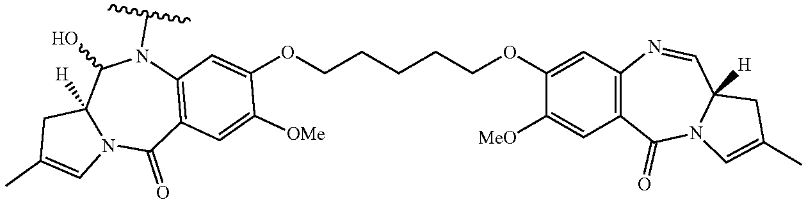

wherein the wavy line indicates the attachment point of the linker; or ii) the indolinobenzodiazepine pseudodimer has a structure of formula:

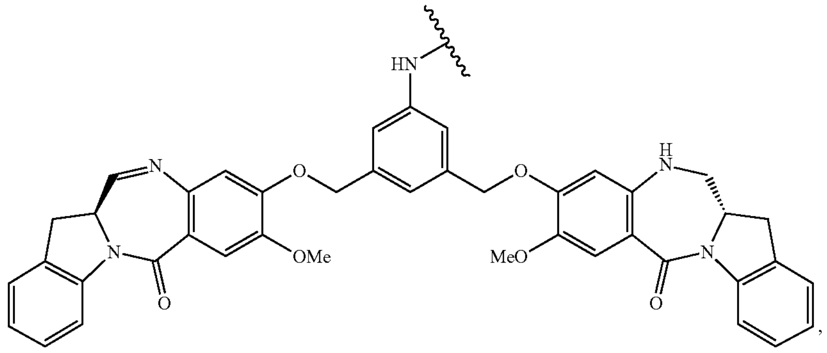 [SMILES: *Nc1cc(COc2cc3c(cc2OC)C(=O)N2c4ccccc4C[C@H]2C=N3)cc(COc2cc3c(cc2OC)C(=O)N2c4ccccc4C[C@H]2CN3)c1]

wherein the wavy line indicates the attachment point of the linker.

9. The method of claim 1, wherein the anti-CD45 ADC is administered to the patient as a single dose or as a fractionated dose.

10. The method of claim 2, wherein the patient does not require treatment for the autoimmune disease following the HSC transplant.

11. The method of claim 2, wherein the patient has multiple sclerosis, and wherein the patient does not require treatment with natalizumab, dimethyl fumarate, or monomethyl fumarate following the HSC transplant.

12. The method of claim 2, wherein the patient has arthritis, and wherein the patient does not require treatment with a Tumor Necrosis Factor (TNF) inhibitor following the HSC transplant.

13. The method of claim 12, wherein the TNF inhibitor is an anti-Tumor Necrosis Factor-alpha (TNFα) antibody.

14. The method of claim 2, wherein the patient enters a remission for at least 1 year following the HSC transplant.

15. The method of claim 14, wherein the remission is clinical remission, biochemical remission, or histologic remission.

16. The method of claim 1, wherein the anti-CD45 antibody is a chimeric antibody or a humanized antibody.

17. The method of claim 1, wherein the anti-CD45 antibody is a human antibody.

18. The method of claim 1, wherein the anti-CD45 antibody is intact.

19. The method claim 1, wherein the anti-CD45 antibody or antigen-binding portion thereof is selected from the group consisting of a monoclonal antibody or antigen-binding portion thereof, a bispecific antibody or antigen-binding portion thereof, a dual-variable immunoglobulin domain, a single-chain Fv molecule (scFv), a diabody, a triabody, a nanobody, an antibody-like protein scaffold, a Fv fragment, a Fab fragment, a F(ab')2 molecule, and a tandem di-scFv.

20. The method of claim 1, wherein the anti-CD45 antibody has an isotype selected from the group consisting of IgG, IgA, IgM, IgD, and IgE.

21. The method of claim 20, wherein the anti-CD45 antibody contains a human IgG1, IgG2, IgG3, or IgG4 isotype Fc domain.

22. The method of claim 1, wherein the anti-CD45 antibody, or antigen binding portion thereof, comprises an Fc domain, and wherein the anti-CD45 antibody, or antigen binding portion thereof, is conjugated to the cytotoxin by way of a cysteine residue in the Fc domain.

23. The method of claim 22, wherein the cysteine residue is introduced by way of an amino acid substitution in the Fc domain.

24. The method of claim 23, wherein the amino acid substitution is D265C (EU numbering).

* * * * *